United States Patent
Carpenedo et al.

(10) Patent No.: US 12,338,460 B2
(45) Date of Patent: Jun. 24, 2025

(54) METHOD FOR GENERATING T CELL LINEAGE POPULATIONS FROM STEM/PROGENITOR CELLS

(71) Applicant: Notch Therapeutics (Canada), Inc., Vancouver (CA)

(72) Inventors: Richard Carpenedo, Vancouver (CA); Alessia Pallaoro, Vancouver (CA); Steven Woodside, Calgary (CA)

(73) Assignee: Notch Therapeutics (Canada), Inc., Vancouver (CA)

( * ) Notice: Subject to any disclaimer, the term of this patent is extended or adjusted under 35 U.S.C. 154(b) by 0 days.

(21) Appl. No.: 18/424,664

(22) Filed: Jan. 26, 2024

(65) Prior Publication Data

US 2024/0254442 A1 Aug. 1, 2024

Related U.S. Application Data

(60) Provisional application No. 63/466,465, filed on May 15, 2023, provisional application No. 63/441,718, filed on Jan. 27, 2023.

(51) Int. Cl.
| | |
|---|---|
| *C12N 5/0783* | (2010.01) |
| *A61K 39/00* | (2006.01) |
| *A61K 40/11* | (2025.01) |
| *A61K 40/31* | (2025.01) |
| *A61K 40/42* | (2025.01) |

(52) U.S. Cl.
CPC ............ *C12N 5/0636* (2013.01); *A61K 40/11* (2025.01); *A61K 40/31* (2025.01); *A61K 40/4211* (2025.01); *C12N 2501/42* (2013.01); *C12N 2501/58* (2013.01); *C12N 2506/45* (2013.01); *C12N 2510/00* (2013.01); *C12N 2513/00* (2013.01)

(58) Field of Classification Search
None
See application file for complete search history.

(56) References Cited

U.S. PATENT DOCUMENTS

2022/0403326 A1  12/2022 Zandstra et al.

FOREIGN PATENT DOCUMENTS

| WO | WO-2017173551 A1 | 10/2017 |
| WO | WO-2018146297 A1 | 8/2018 |
| WO | WO-2019157597 A1 | 8/2019 |
| WO | WO-2021150919 A1 | 7/2021 |

OTHER PUBLICATIONS

Corning. Surface Areas and Guide for Recommended Medium Volumes for Corning® Cell Culture Vessels. Corning CLS-AN-209 product info sheet, published 2020, p. 1-4. (Year: 2020).*

Woodside et al. Controlled and Scalable T Cell Differentiation from Induced Pluripotent Stem Cell Cell-Derived Blood Progenitor Cells Using the Engineered Thymic Niche Technology. ISSCR 2021 Annual Meeting poster and abstract. Jun. 21-26, 2021, p. 1-3. (Year: 2021).*

Rasaiyaah et al. TCRαβ/CD3 disruption enables CD3-specific antileukemic T cell immunotherapy. JCI Insight. 2018;3(13):e99442, p. 1-13 and Fig S1-S8. (Year: 2018).*

Dongre et al. Non-canonical Notch signaling drives activation and differentiation of peripheral CD4C T cells. Front Immunol. 2014;5: 54, p. 1-14 and Fig S1. (Year: 2014).*

Andreatta et al., "Interpretation of T cell states from single-cell transcriptomics data using reference atlases." Nat Commun. May 20, 2021; 12(1): 2965. doi: 10.1038/s41467-021-23324-4. 19 pages.

Awong et al., "Characterization in vitro and engraftment potential in vivo of human progenitor T cells generated from hematopoietic stem cells." Blood. Jul. 30, 2009; 114(5): 972-82. Epub Jun. 2, 2009. 11 pages.

Bai, Z et al. "Single-cell antigen-specific landscape of CAR T infusion product identifies determinants of CD19-positive relapse in patients with ALL." Sci Adv. Jun. 10, 2022; 8(23): eabj2820. Epub Jun. 8, 2022. 16 pages.

Baulu et al., "TCR-engineered T cell therapy in solid tumors: State of the art and perspectives." Sci Adv. Feb. 15, 2023; 9(7): eadf3700. Epub Feb. 15, 2023. 15 pages.

Blassberg, Robert, "Genome Editing of Pluripotent Stem Cells for Adoptive and Regenerative Cell Therapies." GEN Biotechnology 1(1): 77-90 Feb. 2022. 14 pages.

Dos Santos Schiavinato et al., "TNF-alpha and Notch signaling regulates the expression of HOXB4 and GATA3 during early T lymphopoiesis." In Vitro Cell Dev Biol Anim. Oct. 2016; 52(9): 920-934.

Drougkas et al., "Comprehensive clinical evaluation of CAR-T cell immunotherapy for solid tumors: a path moving forward or a dead end?" J Cancer Res Clin Oncol. Jun. 2023; 149(6): 2709-2734. Epub Dec. 24, 2022.

Guha et al., "Assessing the Future of Solid Tumor Immunotherapy." Biomedicines. Mar. 11, 2022; 10(3): 655. 19 pages.

Hafemeister and Satija, "Normalization and variance stabilization of single-cell RNA-seq data using regularized negative binomial regression." Genome Biol. Dec. 23, 2019; 20(1): 296. 15 pages.

Hanzelmann et al., "GSVA: gene set variation analysis for microarray and RNA-seq data." BMC Bioinformatics. Jan. 16, 2013: 14: 7. 15 pages.

Haradhvala et al., "Distinct cellular dynamics associated with response to CAR-T therapy for refractory B-cell lymphoma." Nature Medicine Sep. 2022; 28(9): 1848-1859. Author manuscripts; available in Pub Med Central (PMC), Mar. 12, 2023. 45 pages.

(Continued)

*Primary Examiner* — Taeyoon Kim
*Assistant Examiner* — Jianjian Zhu

(57) ABSTRACT

The present disclosure provides a method for generating a T cell lineage population from progenitor T cells. The method comprises culturing the progenitor cells in the presence of Notch signalling ligand, such as Delta-like-4 (DL4), provided on a surface area of at least 7 square centimetres per millilitre culture volume (7 cm$^2$/mL). Population of cells produced using the method are provided as well as methods of using same. Further provided is a method of differentiating a progenitor T cell population enriched for CD4−CD8+ TCRγδ+ cells comprising culturing progenitor T cells in the presence of Notch signalling ligand, such as DL4, provided on a surface area of 0.78 to 4.7 cm$^2$/mL.

24 Claims, 90 Drawing Sheets

Specification includes a Sequence Listing.

(56) References Cited

OTHER PUBLICATIONS

Ikawa et al., "An Essential Developmental Checkpoint for Production of the T Cell Lineage." Science, Jul. 2, 2010, vol. 329, pp. 93-96.

Iriguchi et al., "A clinically applicable and scalable method to regenerate T-cells from iPSCs for off-the-shelf T-cell immunotherapy." Nat Commun. Jan. 18, 2021; 12(1): 430. 15 pages.

Kirouac, D. C. et al., "Deconvolution of clinical variance in CAR-T cell pharmacology and response." Nat Biotechnol. Nov. 2023; 41(11): 1606-1617. doi: 10.1038/s41587-023-01687-x. Epub Feb. 27, 2023. 19 pages.

La Motte-Mohs et al., "Induction of T-cell development from human cord blood hematopoietic stem cells by Delta-like 1 in vitro." Blood, Feb. 15, 2005, vol. 105, No. 4, pp. 1431-1439.

Michaels et al., "DLL4 and VCAMI enhance the emergence of T cell-competent hematopoietic progenitors from human pluripotent stem cells." Sci Adv. Aug. 26, 2022; 8(34): eabn5522. Epub Aug. 24, 2022. 17 pages.

Minagawa et al., "Enhancing T Cell Receptor Stability in Rejuvenated iPSC-Derived T Cells Improves Their Use in Cancer Immunotherapy", Cell Stem Cell. Dec. 6, 2018; 23(6): 850-858.e4. Epub Nov. 15, 2018.

Montel-Hagen et al. "Generation of Artificial Thymic Organoids from Human and Murine Hematopoietic Stem and Progenitor Cells." Curr Protoc. Apr. 2022; 2(4): e403. 26 pages.

Park et al., "A cell atlas of human thymic development defines T cell repertoire formation." Science. Feb. 21, 2020; 367(6480): eaay3224. 12 pages.

Qu et al., "Tumor buster—where will the CAR-T cell therapy 'missile' go?" Mol Cancer. Oct. 19, 2022; 21(1): 201. 53 pages.

Rahman et al., "Controlled Generation of Hematopoietic Progenitor Cells from Human Pluripotent Stem Cells." Doctorate of Philosophy Thesis, University of Toronto, 2017, 175 pages.

Sataija, R., et al., "Spatial reconstruction of single-cell gene expression data." Nat Biotechnol. May 2015; 33(5): 495-502. Epub Apr. 13, 2015.

Shukla et al., "Progenitor T-cell differentiation from hematopoietic stem cells using Delta-like-4 and VCAM-1." Nature Methods, vol. 14, No. 5, May 2017, pp. 531-538.

Sjoukje et al., "Generation of T-cell-receptor-negative CD8αβ-positive CAR T cells from T-cell-derived induced pluripotent stem cells." Nat Biomed Eng. Nov. 2022; 6(11): 1284-1297. Author manuscript; available in PMC May 1, 2023. 44 pages.

Smits et al., "Tumor necrosis factor promotes T-cell at the expense of B-cell lymphoid development from cultured human CD34+ cord blood cells." Experimental Hematology 35 (2007) 1272-1278.

Street, K., et al., "Slingshot: cell lineage and pseudotime inference for single-cell transcriptomics." BMC Genomics. Jun. 19, 2018; 19(1): 477. 16 pages.

Sun et al., "Evolution of CD8+ T Cell Receptor (TCR) Engineered Therapies for the Treatment of Cancer." Cells. Sep. 10, 2021; 10(9): 2379. 19 pages.

Taqvi et al., "Biomaterial-based notch signaling for the differentiation of hematopoietic stem cells into T cells." J Biomed Mater Res A., Dec. 1, 2006; 79(3): 689-97.

Trotman-Grant et al., "DL4-μbeads induce T cell lineage differentiation from stem cells in a stromal cell free system." Nat Commun. Aug. 18, 2021; 12(1): 5023. 11 pages.

Van De Walle et al., "An early decrease in Notch activation is required for human TCR-alpha beta lineage differentiation at the expense of TCR-gamma delta T cells." Blood, Mar. 26, 2009, vol. 113, No. 13, pp. 2988-2998.

Van Gassen et al., "FlowSOM: Using self-organizing maps for visualization and interpretation of cytometry data." Cytometry A. Jul. 2015; 87(7): 636-45. Epub Jan. 8, 2015.

Want et al., "T Cell Based Immunotherapy for Cancer: Approaches and Strategies." Vaccines (Basel). Apr. 13, 2023; 11(4): 835. 19 pages.

Weber et al., "The Emerging Landscape of Immune Cell Therapies." Cell. 2020 181(1): 46-62.

Weekx et al., "Generation of T cells from adult human hematopoietic stem cells and progenitors in a fetal thymic organ culture system: stimulation by tumor necrosis factor-alpha." Blood, May 1, 2000, vol. 95, No. 9, pp. 2806-2812.

Zheng et al. "Massively parallel digital transcriptional profiling of single cells." Nat Commun. Jan. 16, 2017: 8: 14049. 12 pages.

Zuniga-Pflucker et al., "Requirement for TNF-alpha and IL-1 alpha in fetal thymocyte commitment and differentiation." Science, vol. 268, Jun. 30, 1995, pp. 1906-1909.

\* cited by examiner

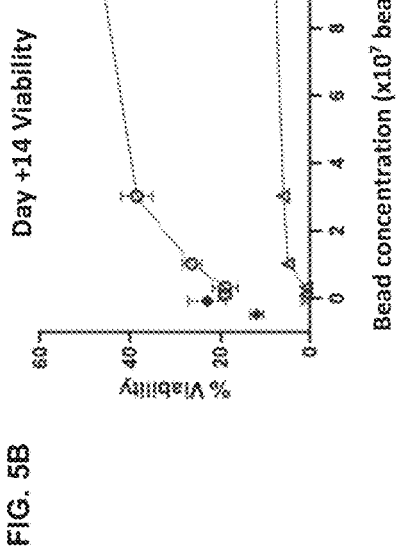
FIG. 5A
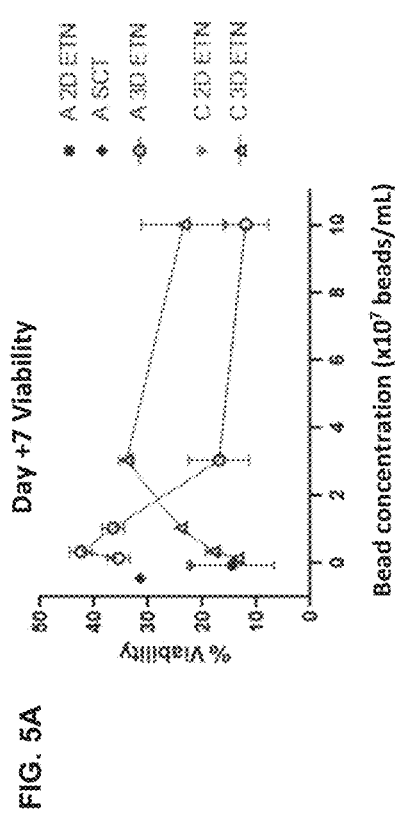
FIG. 5C
FIG. 5B
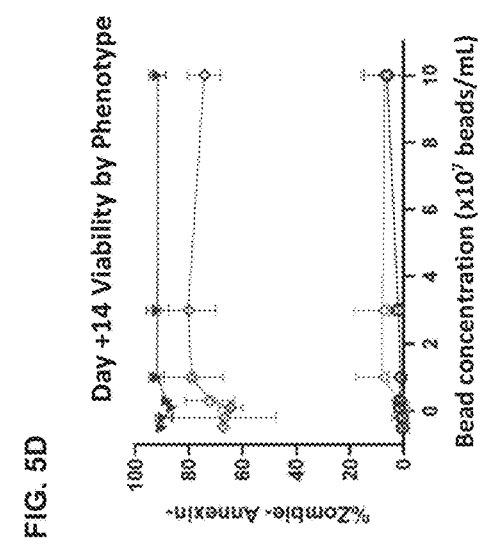
FIG. 5D
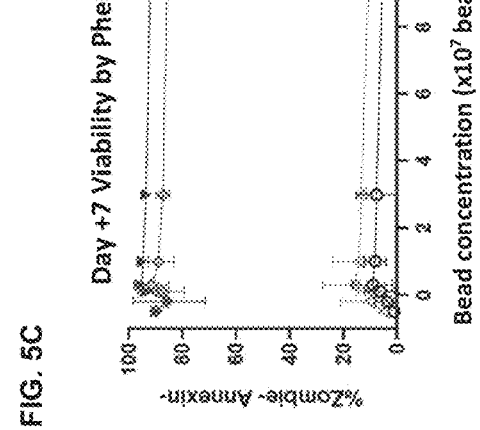

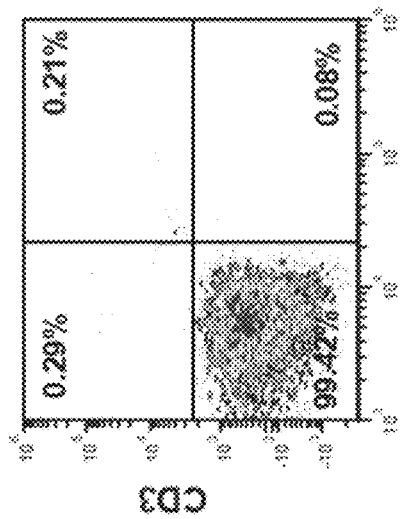
FIG. 9A
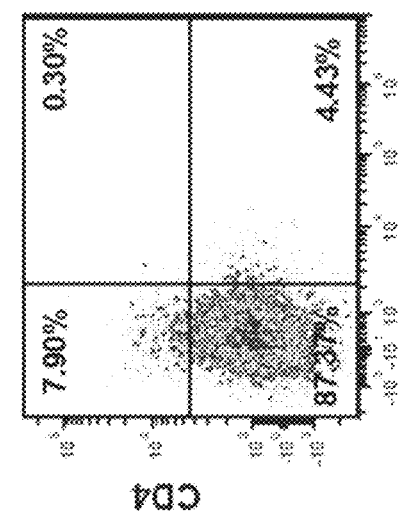
FIG. 9B
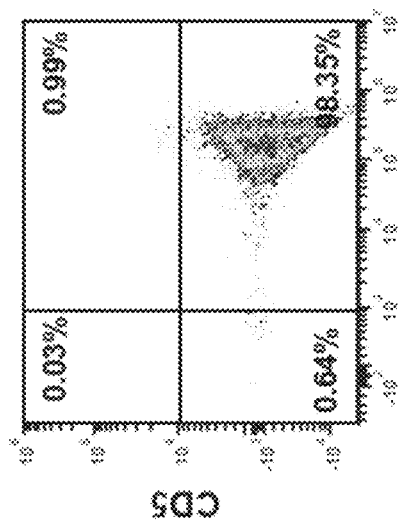
FIG. 9C
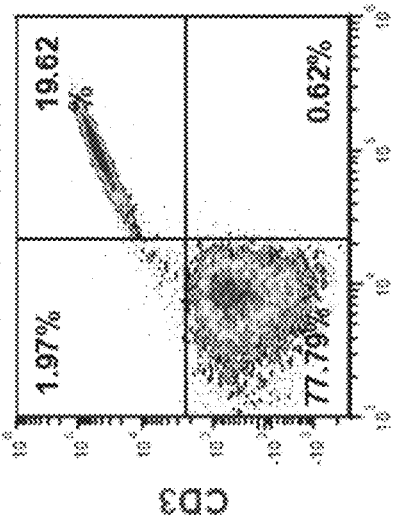
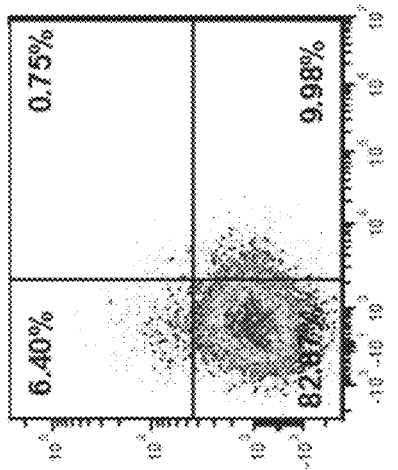
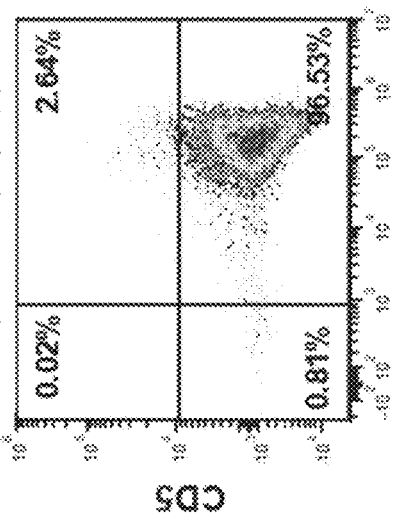

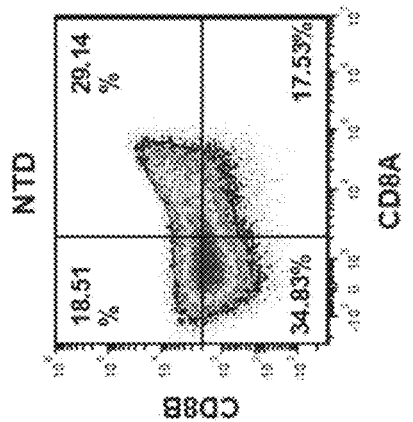
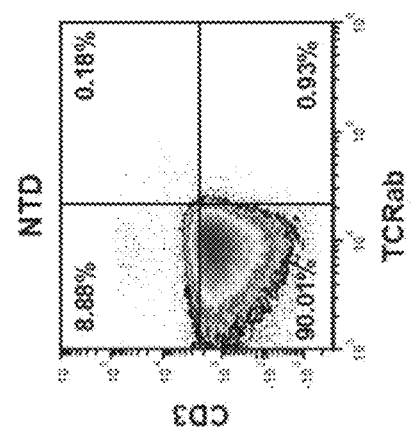
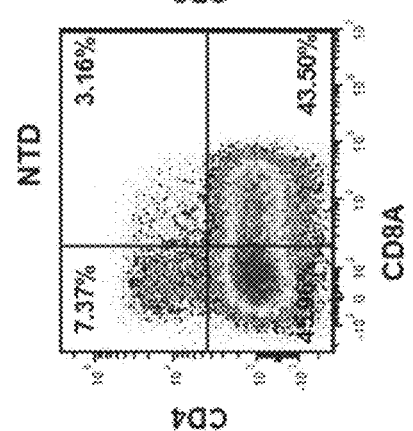
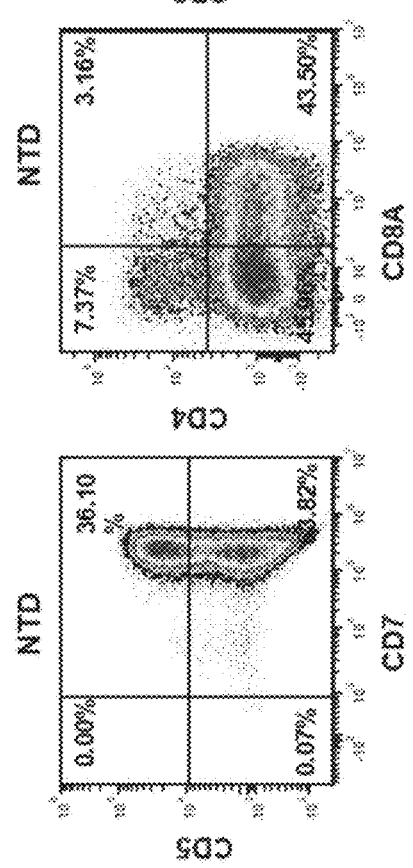
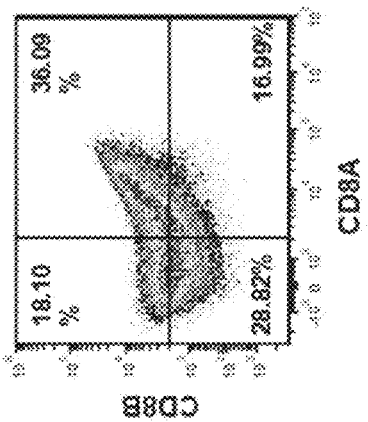
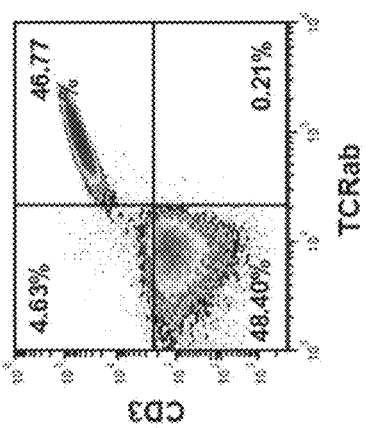
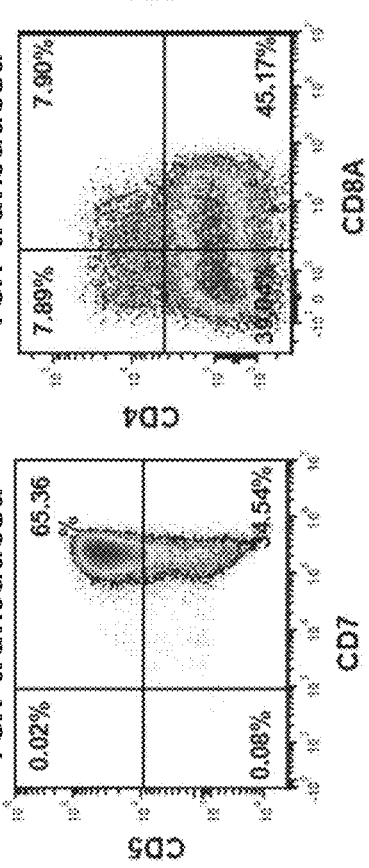

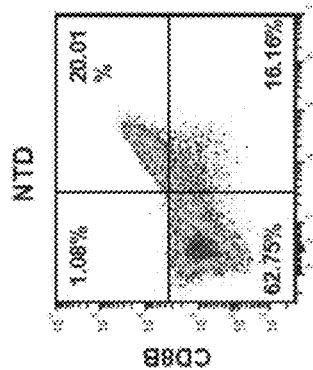
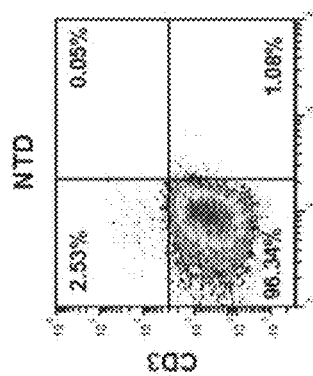
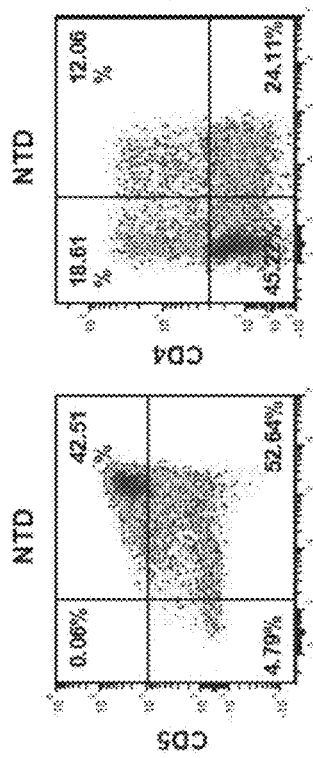

FIG. 13A
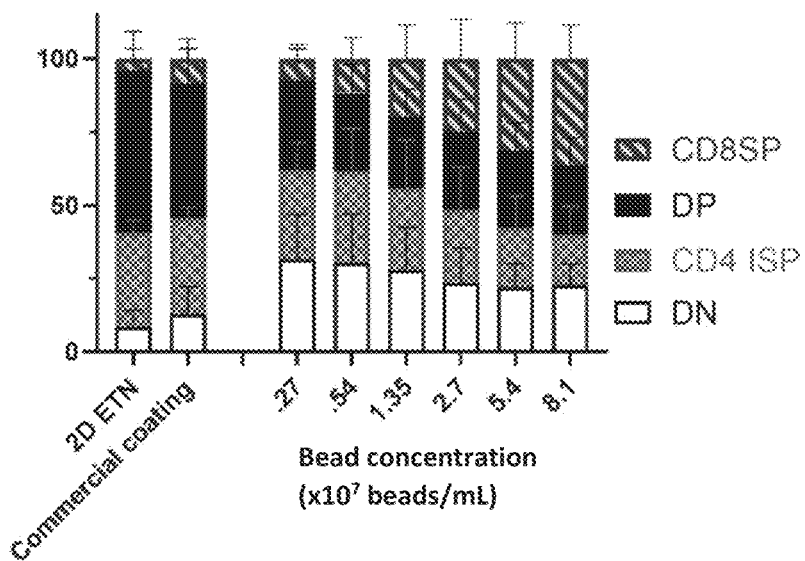
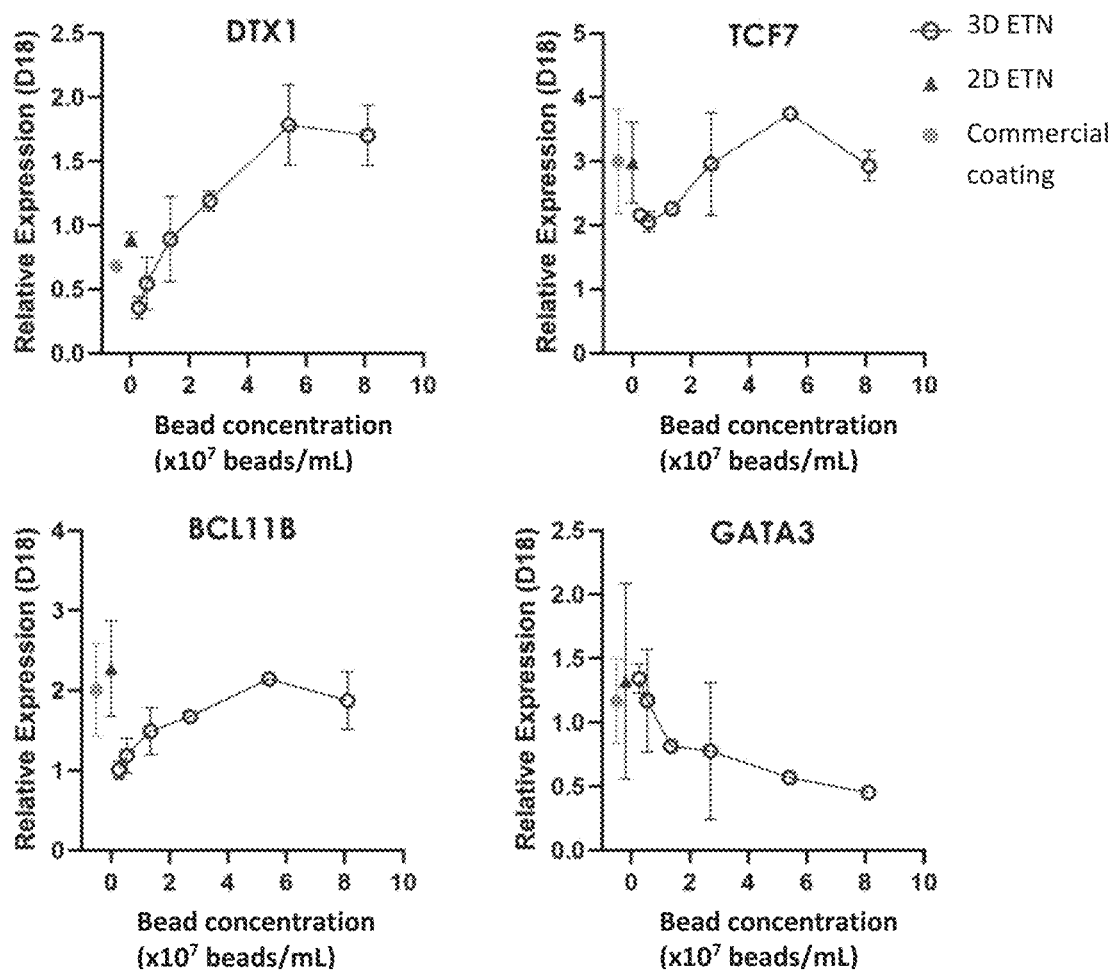
FIG. 13B

FIG. 13E
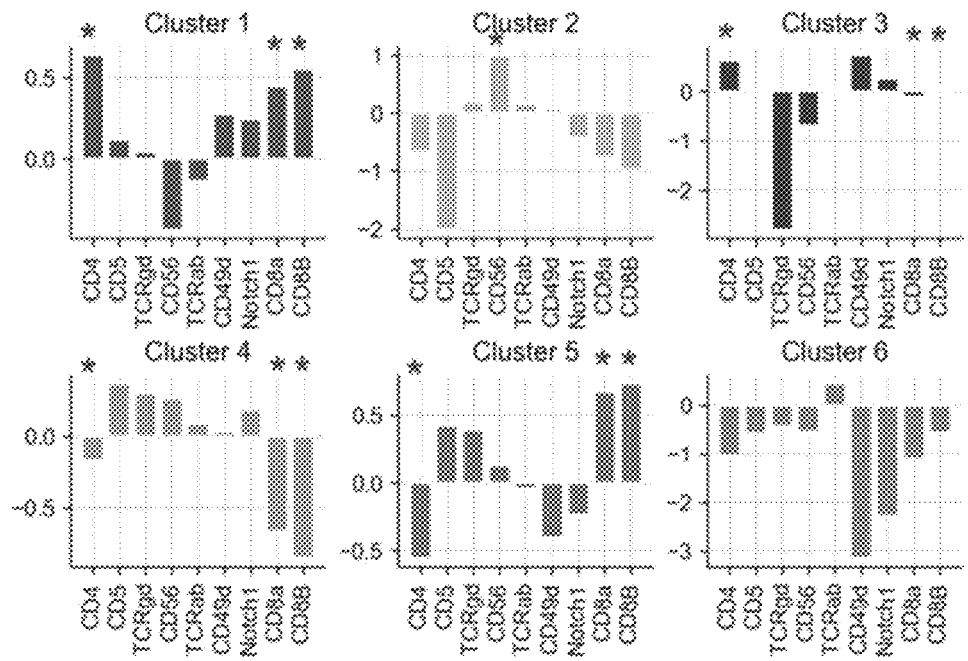
Cluster 1: DP  Cluster 4: DN
Cluster 2: NK cells  Cluster 5: CD8 SP
Cluster 3: CD4 ISP  Cluster 6: Other
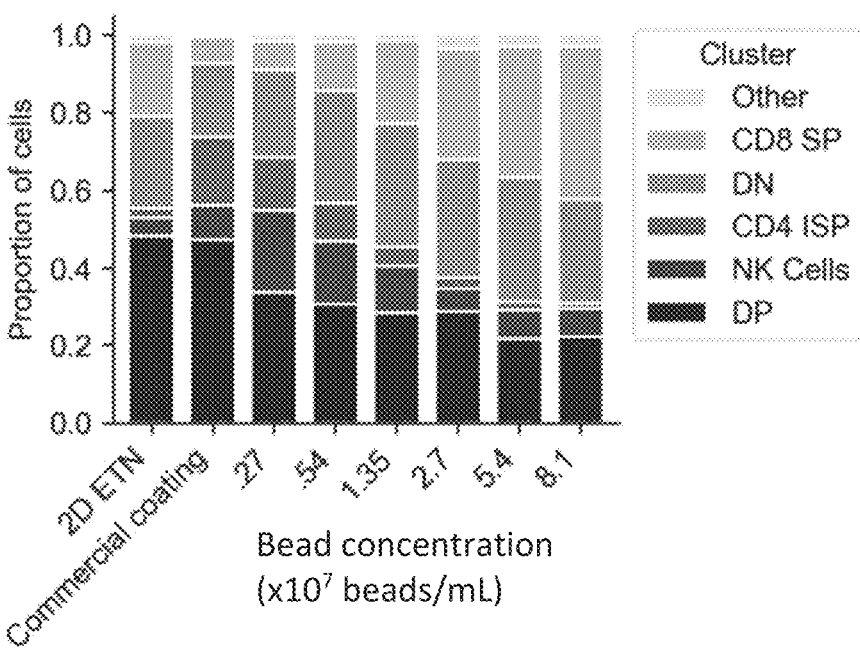
FIG. 13F FIG. 15 A
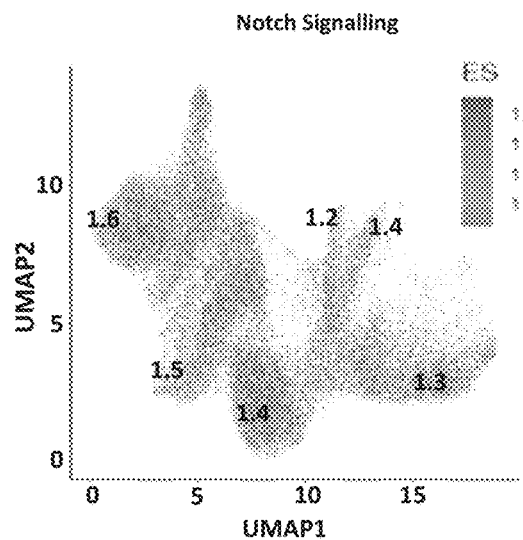
FIG. 15B
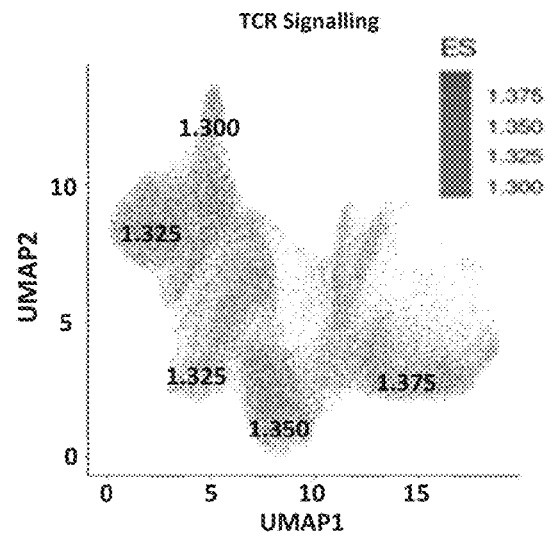
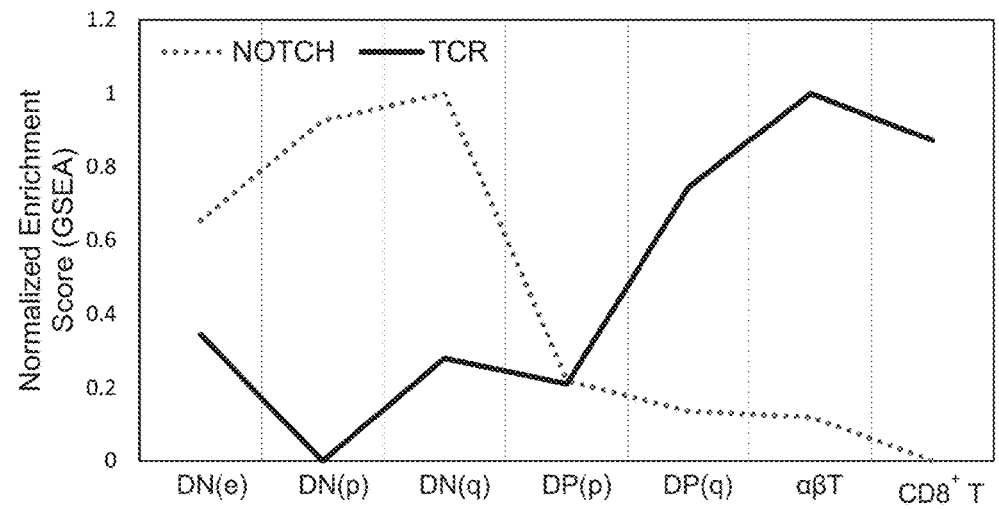
FIG. 15C

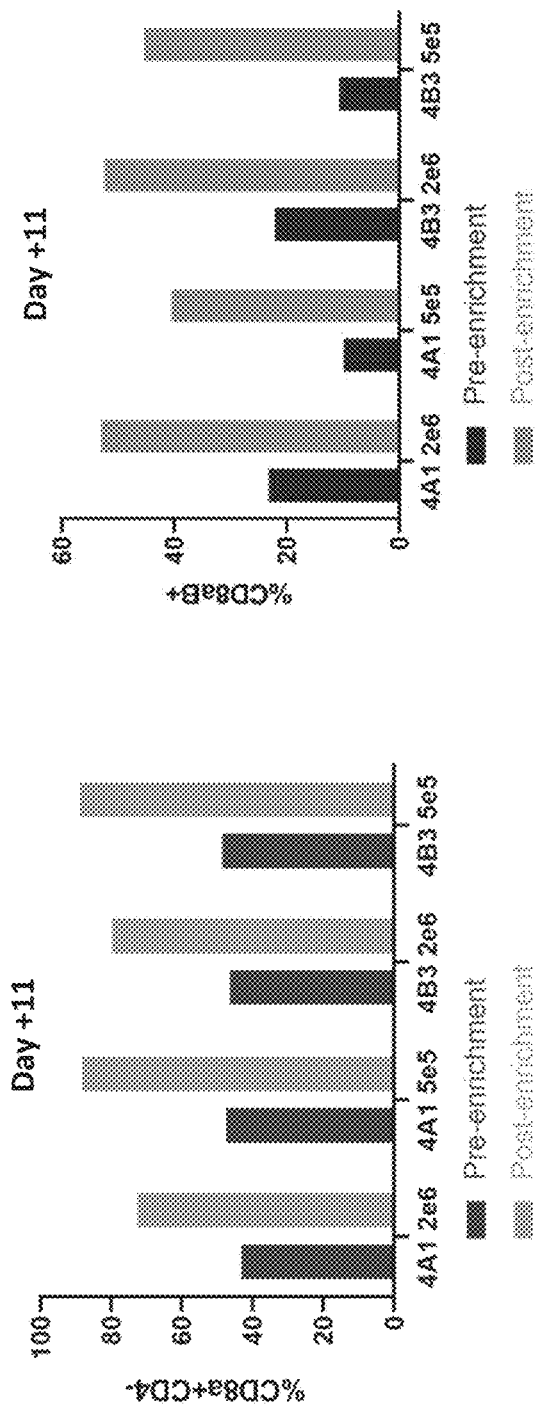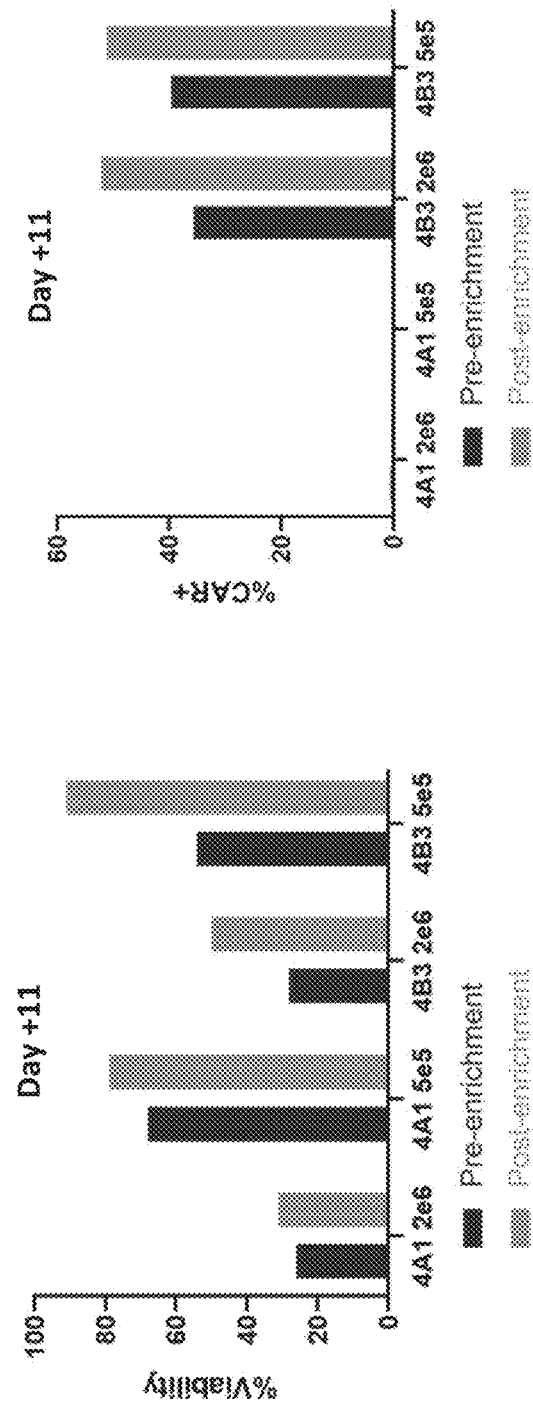

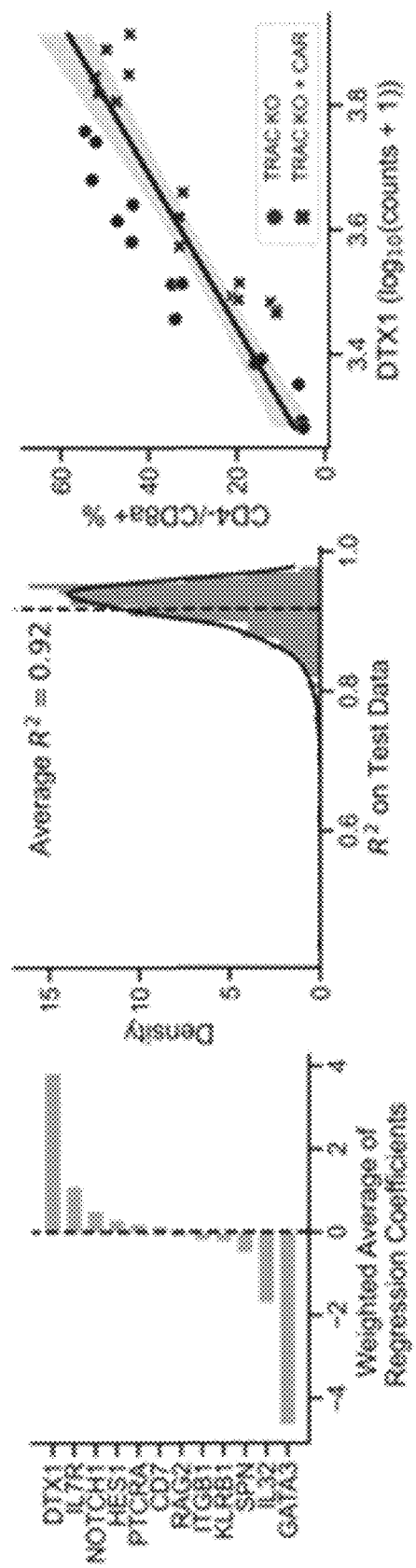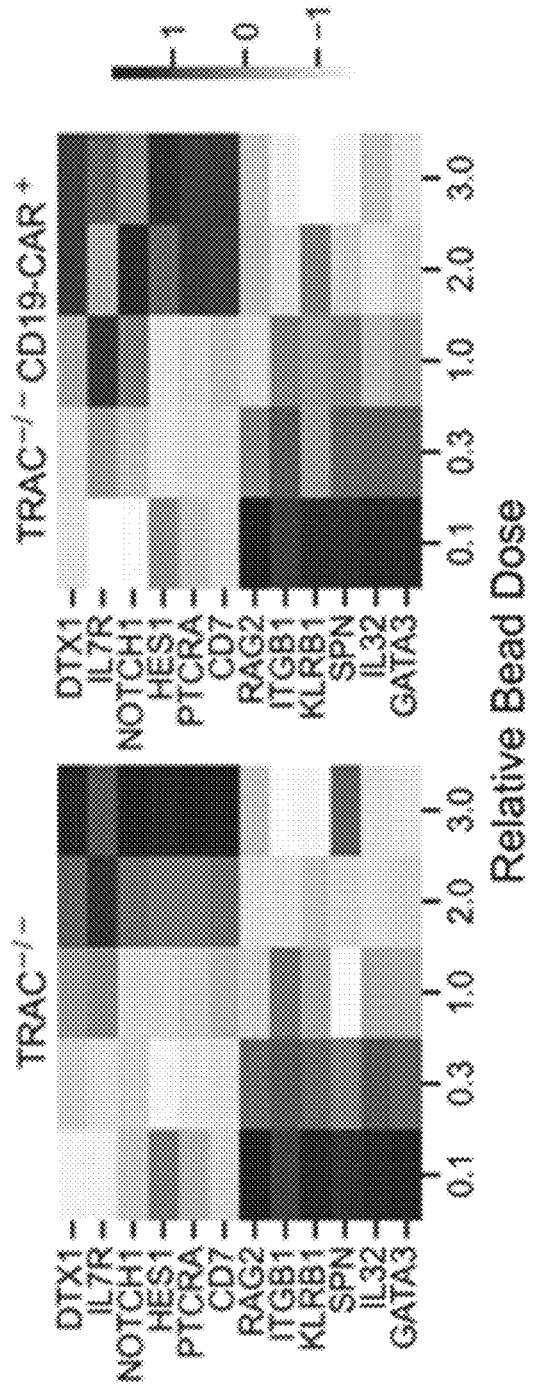

FIG. 28I
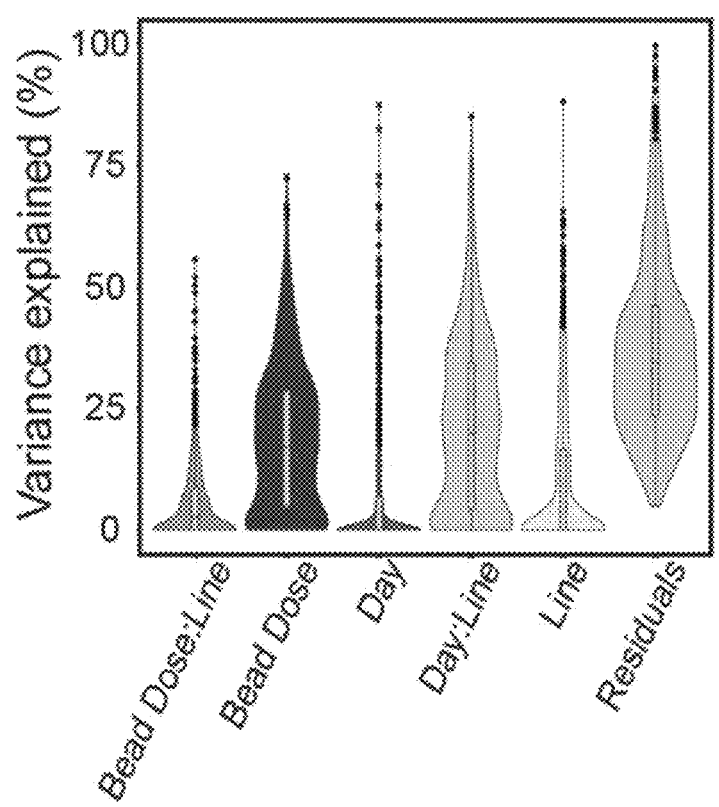
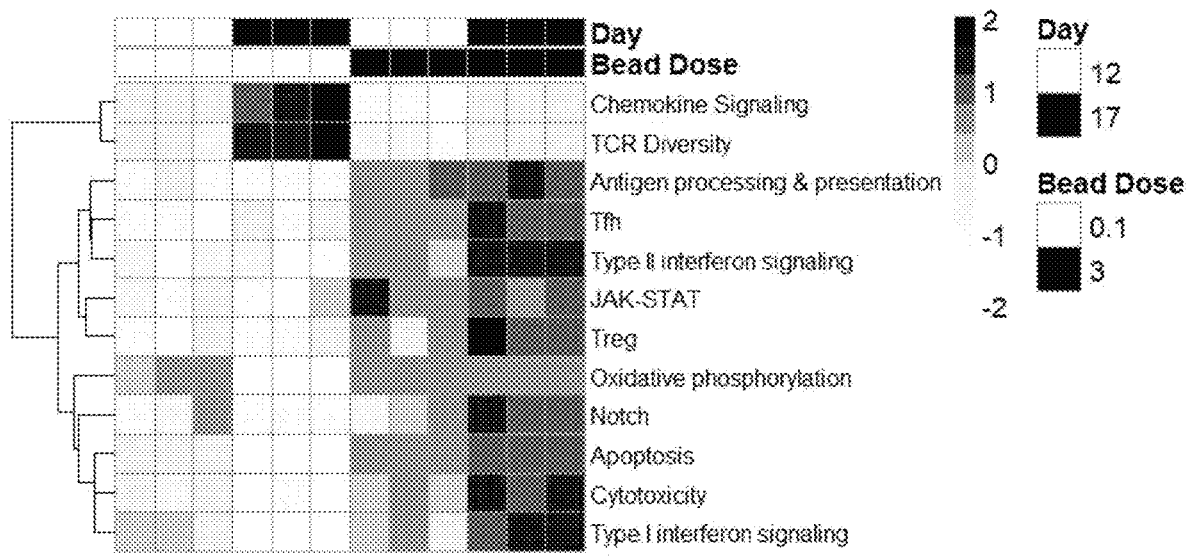
FIG. 28J

FIG. 29J
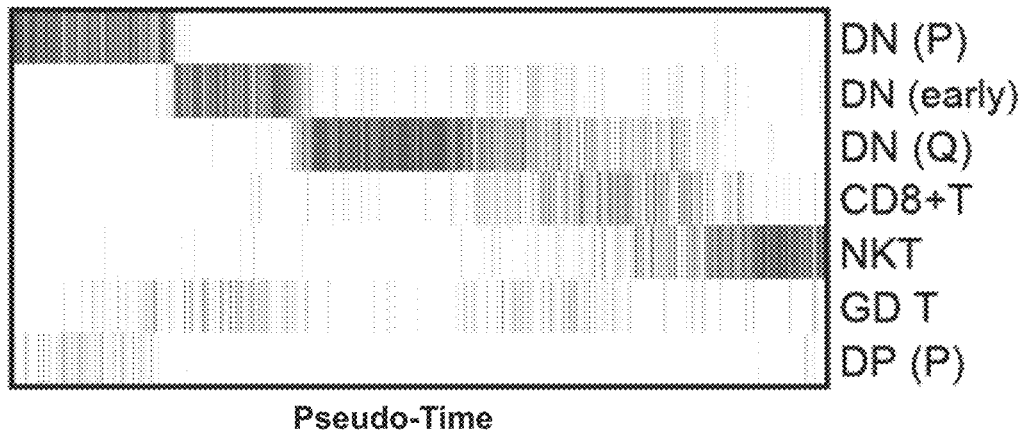
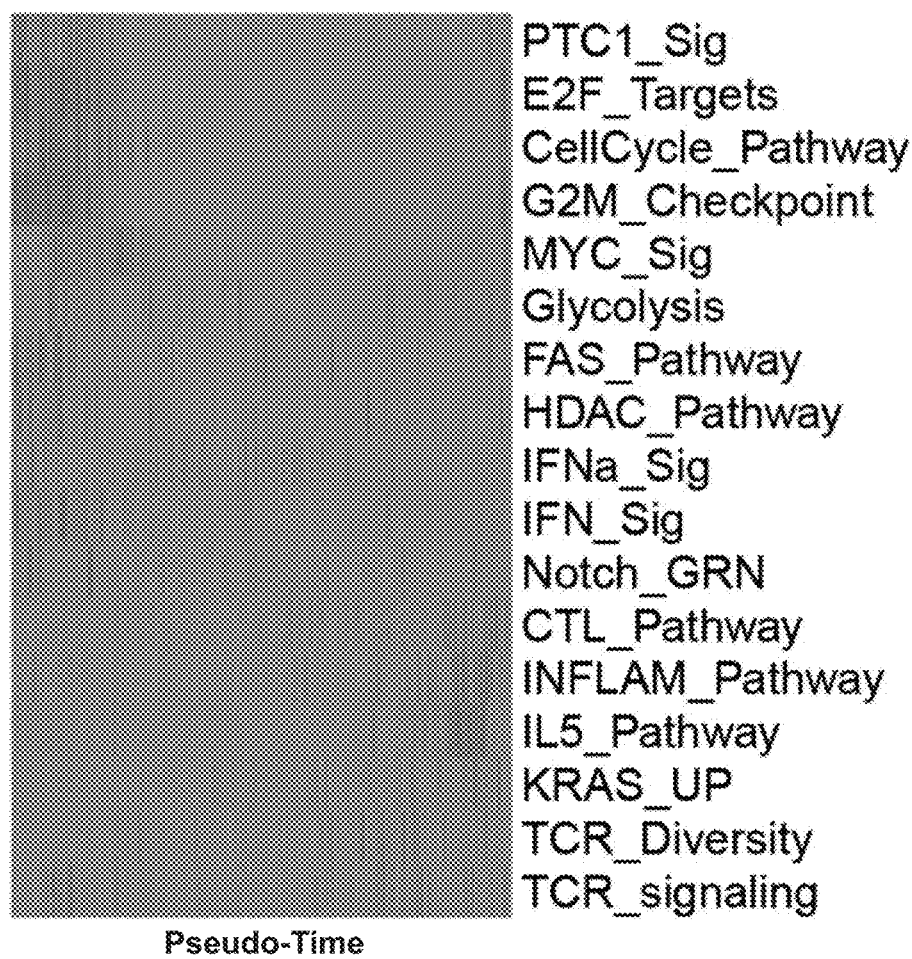
FIG. 29K

FIG. 31A
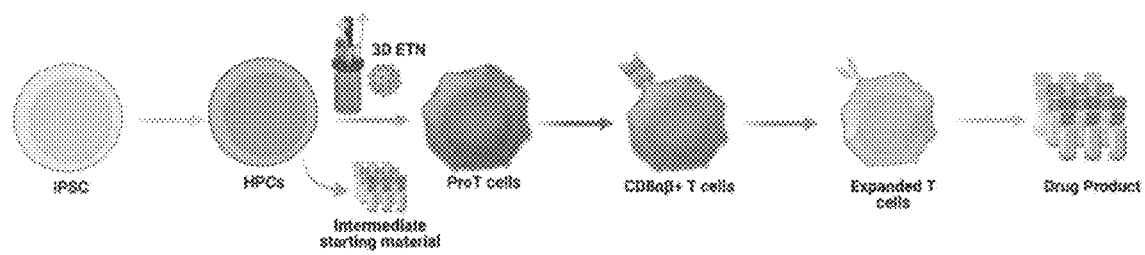
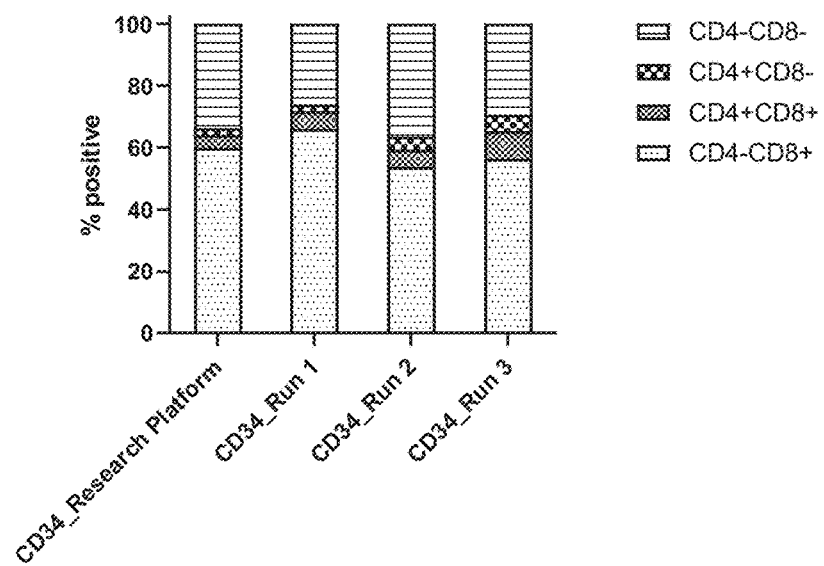
FIG. 31B

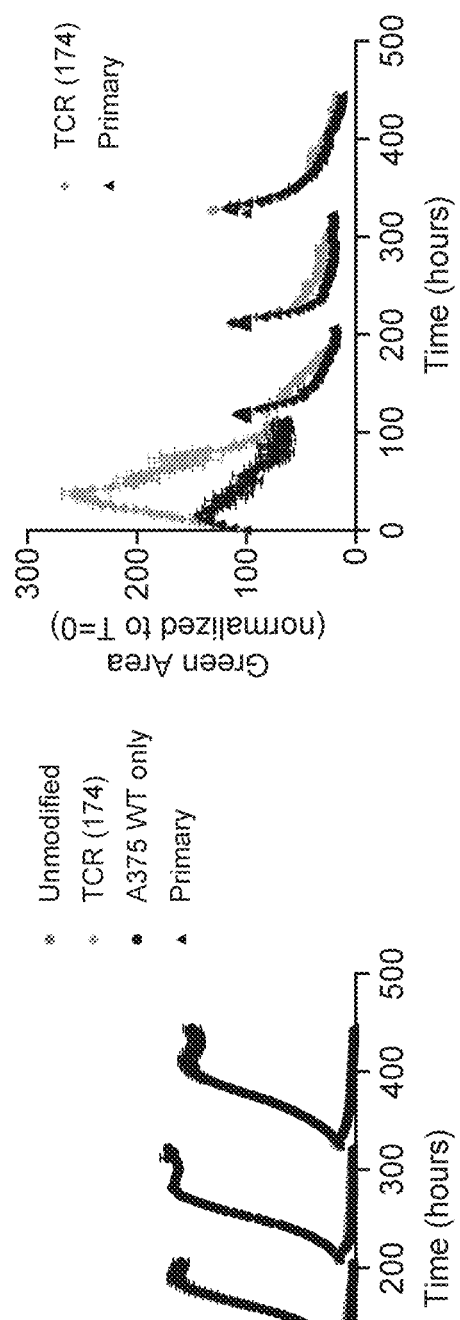
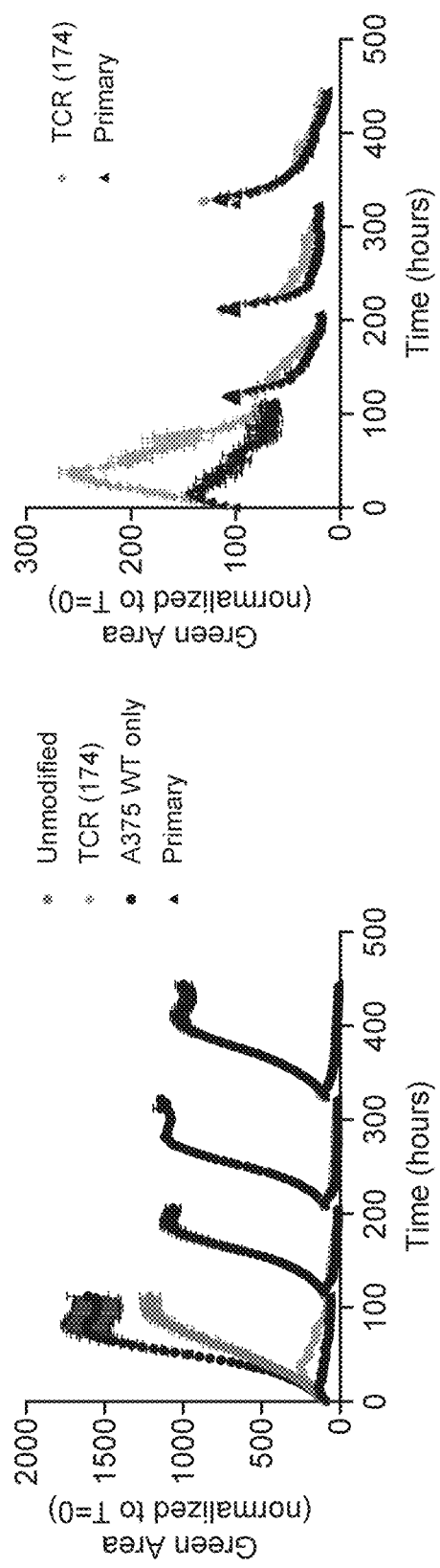
FIG. 44A
FIG. 44B
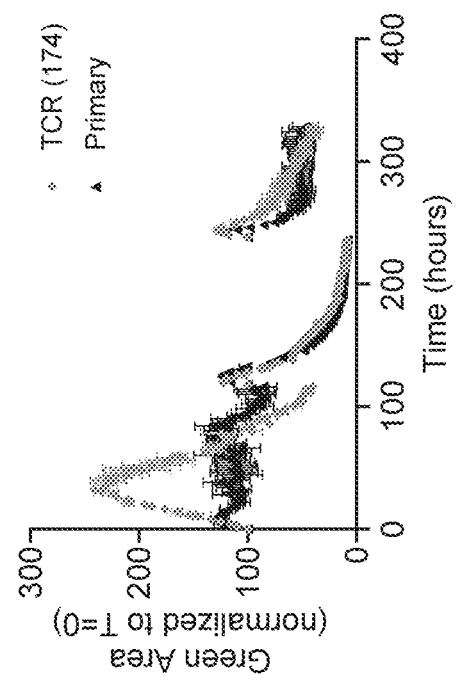
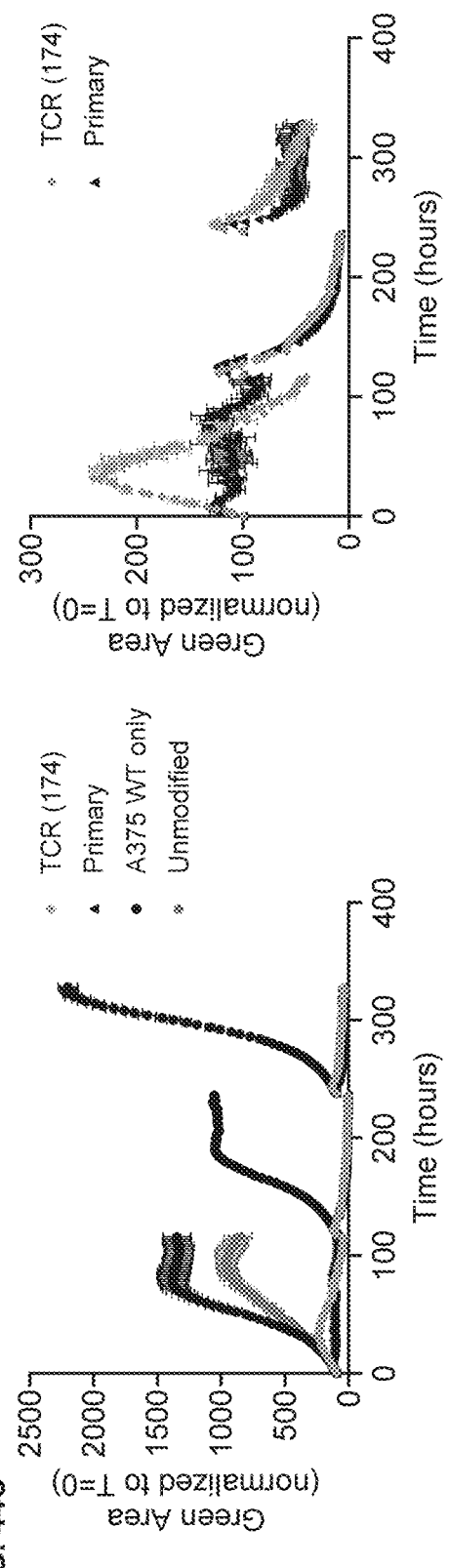
FIG. 44C
FIG. 44D FIG. 46B
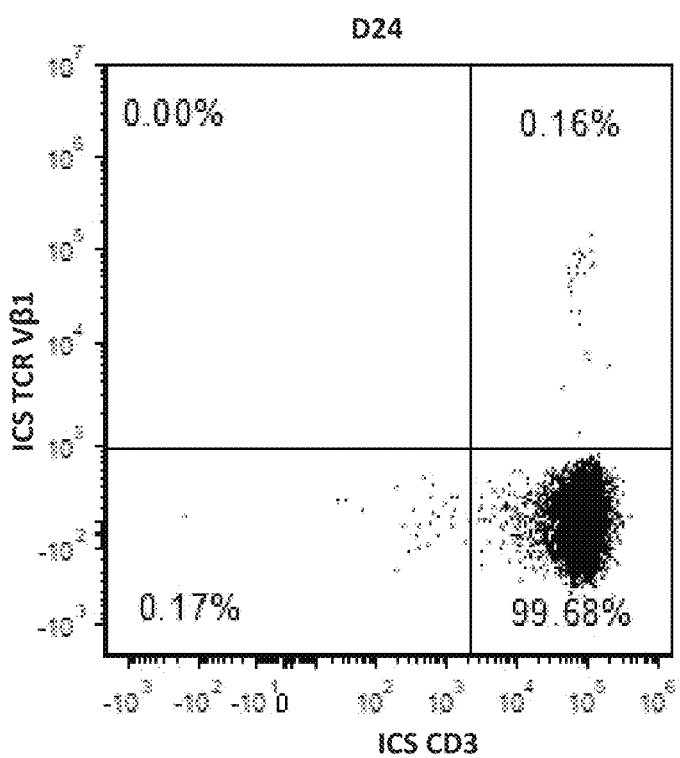
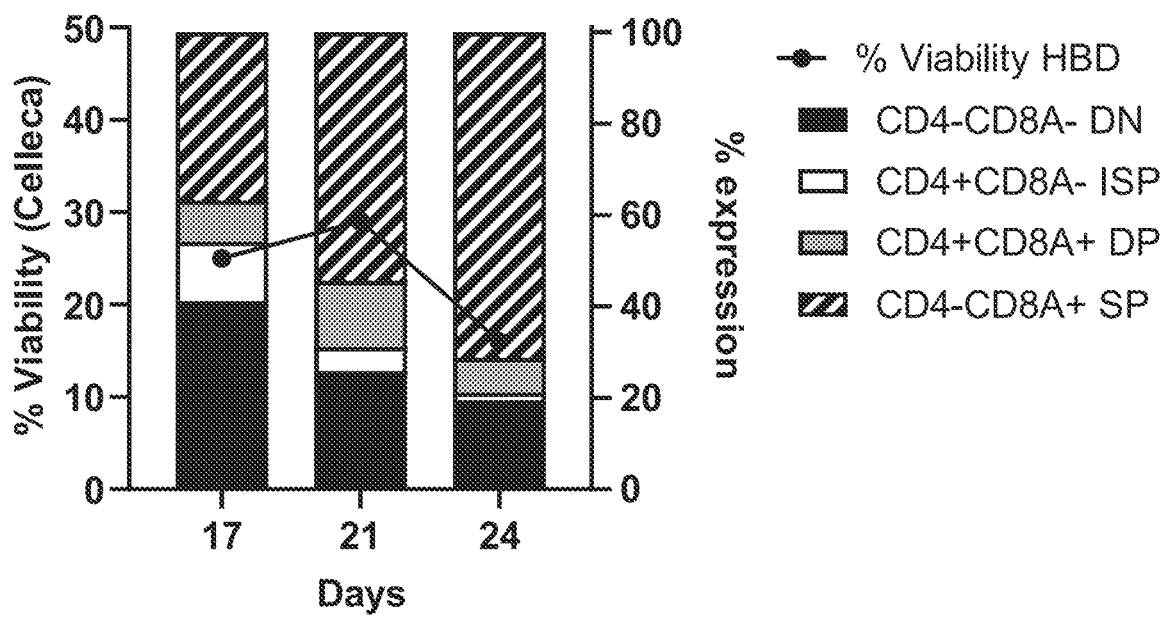
FIG. 46C

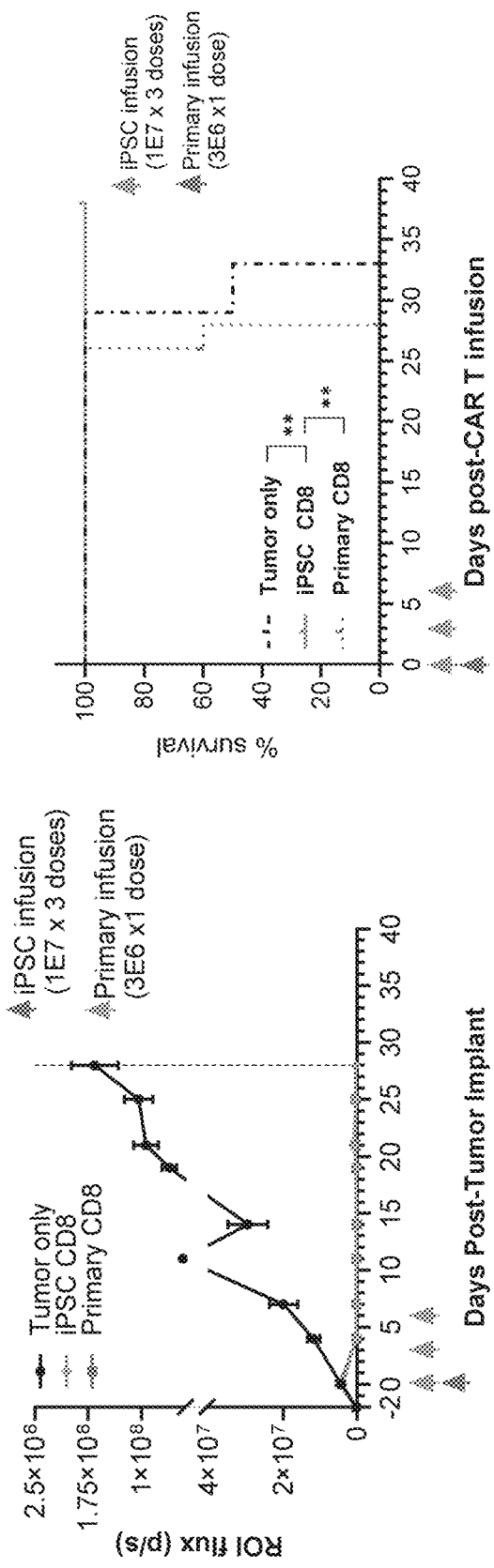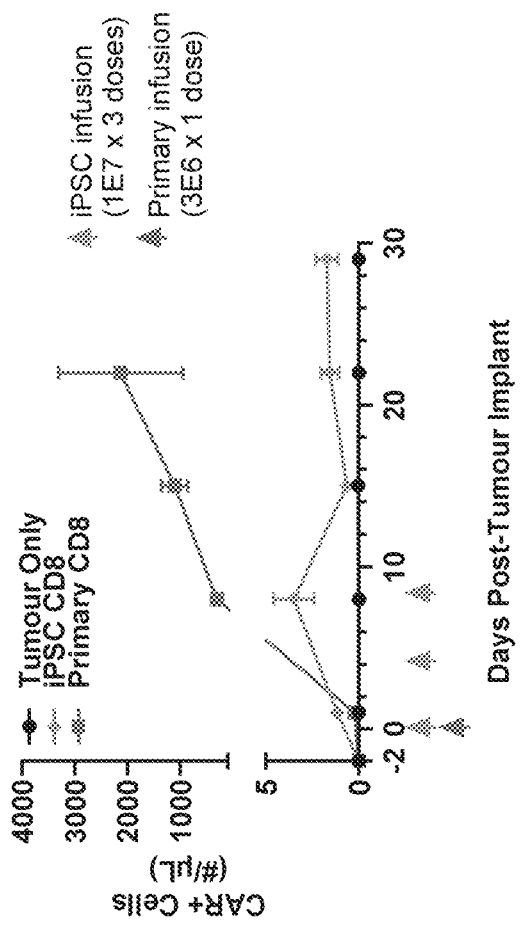

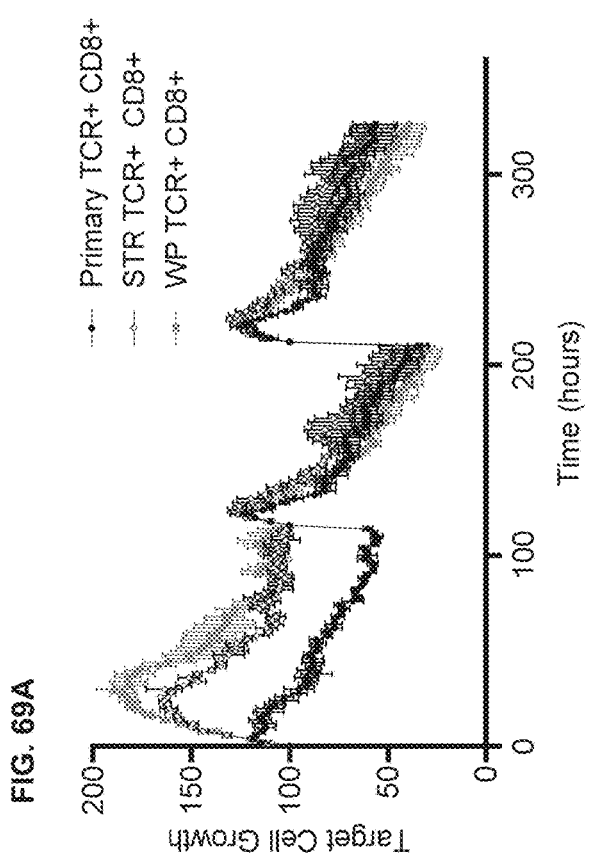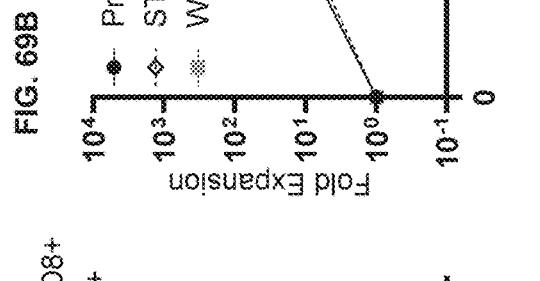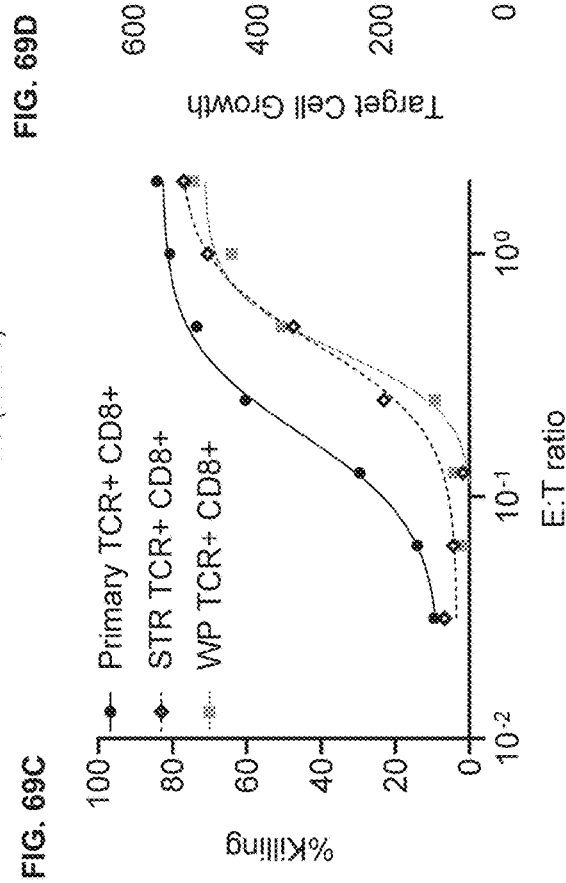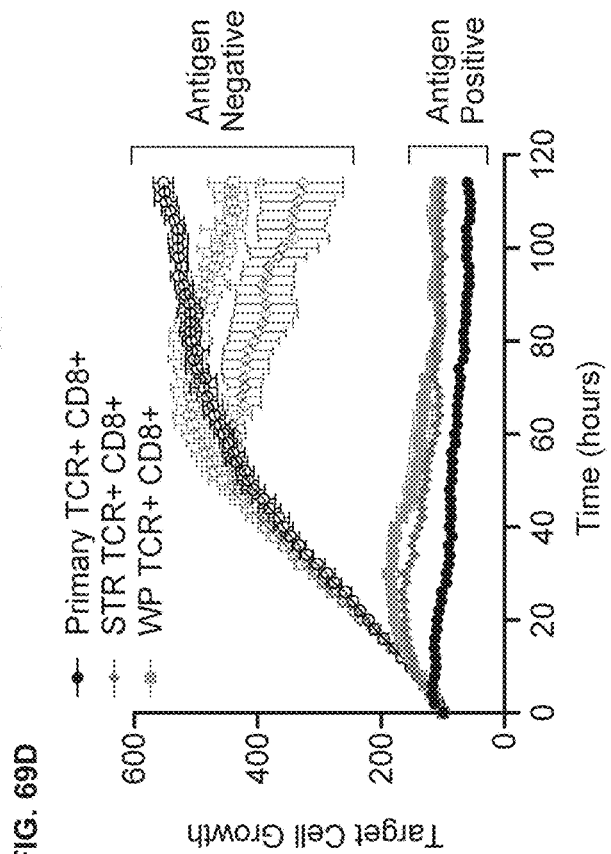
FIG. 69A
FIG. 69B
FIG. 69C
FIG. 69D

SEQUENCE LISTING

```
Sequence total quantity: 5
SEQ ID NO: 1              moltype = AA  length = 685
FEATURE                   Location/Qualifiers
source                    1..685
                          mol_type = protein
                          organism = Homo sapiens
SEQUENCE: 1
MAAASRSASG WALLLLVALW QQRAAGSGVF QLQLQEFINE RGVLASGRPC EPGCRTFFRV  60
CLKHFQAVVS PGPCTFGTVS TPVLGTNSFA VRDDSSGGGR NPLQLPFNFT WPGTFSLIIE  120
AWHAPGDDLR PEALPPDALI SKIAIQGSLA VGQNWLLDEQ TSTLTRLRYS YRVICSDNYY  180
GDNCSRLCKK RNDHFGHYVC QPDGNLSCLP GWTGEYCQQP ICLSGCHEQN GYCSKPAECL  240
CRPGWQGRLC NECIPHNGCR HGTCSTPWQC TCDEGWGGLF CDQDLNYCTH HSPCKNGATC  300
SNSGQRSYTC TCRPGYTGVD CELELSECDS NPCRNGGSCK DQEDGYHCLC PPGYYGLHCE  360
HSTLSCADSP CFNGGSCRER NQGANYACEC PPNFTGSNCE KKVDRCTSNP CANGGQCLNR  420
GPSRMCRCRP GFTGTYCELH VSDCARNPCA HGGTCHDLEN GLMCTCPAGF SGRRCEVRTS  480
IDACASSPCF NRATCYTDLS TDTFVCNCPY GFVGSRCEFP VGLPPSFPWV AVSLGVGLAV  540
LLVLLGMVAV AVRQLRLRRP DDGSREAMNN LSDFQKDNLI PAAQLKNTNQ KKELEVDCGL  600
DKSNCGKQQN HTLDYNLAPG PLGRGTMPGK FPHSDKSLGE KAPLRLHSEK PECRISAICS  660
PRDSMYQSVC LISEERNECV IATEV                                       685

SEQ ID NO: 2              moltype = AA  length = 6
FEATURE                   Location/Qualifiers
source                    1..6
                          mol_type = protein
                          organism = Homo sapiens
SEQUENCE: 2
QIDSPL                                                            6

SEQ ID NO: 3              moltype = AA  length = 8
FEATURE                   Location/Qualifiers
source                    1..8
                          mol_type = protein
                          organism = Homo sapiens
SEQUENCE: 3
TQIDSPLN                                                          8

SEQ ID NO: 4              moltype = AA  length = 739
FEATURE                   Location/Qualifiers
source                    1..739
                          mol_type = protein
                          organism = Mus musculus
SEQUENCE: 4
MPVKMVAVLG ASTVLWILFA VSQAFKIEIS PEYKTIAQIG DSMALTCSTT GCESPLFSWR  60
TQIDSPLNAK VRTEGSKSVL TMEPVSFENE HSYLCTATCG SGKLERSIHV DIYSFPKDPE  120
IQFSGPLEVG KPVTVKCLAP DIYPVYRLEI DLFKGDQLMN RQEFSSEEMT KSLETKSLEV  180
TFTPVIEDIG KALVCRAKLH IDQIDSTLKE RETVKELQVY ISPRNTTISV HPSTRLQEGG  240
AVTMTCSSEG LPAPEIFWGR KLDNEVLQLL SGNATLTLIA MRMEDSGVYV CEGVNLIGRD  300
KAEVELVVQE KPFIVDISPG SQVAAQVGDS VVLTCAAIGC DSPSFSWRTQ TDSPLNGVVR  360
NEGAKSTLVL SSVGFEDEHS YLCAVTCLQR TLEKRTQVEV YSFPEDPVIK MSGPLVHGRP  420
VTVNCTVPNV YPFDHLEIEL LKGETTLMKK YFLEEMGIKS LETKILETTF IPTIEDTGKS  480
LVCLARLHSG EMESEPKQRQ SVQPLYVNVA PKETTIWVSP SPILEEGSPV NLTCSSDGIP  540
APKILWSRQL NNGELQPLSE NTTLTFMSTK RDDSGIYVCE GINEAGISRK SVELIIQVSP  600
KDIQLTVFPS KSVKEGDTVI ISCTCGNVPE TWIILKKKAK TGDMVLKSVD GSYTIRQAQL  660
QDAGIYECES KTEVGSQLRS LTLDVKGKEH NKDYFSPELL ALYCASSLVI PAIGMIVYFA  720
RKANMKGSYS LVEAQKSKV                                              739

SEQ ID NO: 5              moltype = AA  length = 739
FEATURE                   Location/Qualifiers
source                    1..739
                          mol_type = protein
                          organism = Homo sapiens
SEQUENCE: 5
MPGKMVVILG ASNILWIMFA ASQAFKIETT PESRYLAQIG DSVSLTCSTT GCESPFFSWR  60
TQIDSPLNGK VTNEGTTSTL TMNPVSFGNE HSYLCTATCE SRKLEKGIQV EIYSFPKDPE  120
```

-continued

```
IHLSGPLEAG KPITVKCSVA DVYPFDRLEI DLLKGDHLMK SQEFLEDADR KSLETKSLEV  180
TFTPVIEDIG KVLVCRAKLH IDEMDSVPTV RQAVKELQVY ISPKNTVISV NPSTKLQEGG  240
SVTMTCSSEG LPAPEIFWSK KLDNGNLQHL SGNATLTLIA MRMEDSGIYV CEGVNLIGKN  300
RKEVELIVQE KPFTVEISPG PRIAAQIGDS VMLTCSVMGC ESPSFSWRTQ IDSPLSGKVR  360
SEGTNSTLTL SPVSFENEHS YLCTVTCGHK KLEKGIQVEL YSFPRDPEIE MSGGLVNGSS  420
VTVSCKVPSV YPLDRLEIEL LKGETILENI EFLEDTDMKS LENKSLEMTF IPTIEDTGKA  480
LVCQAKLHID DMEFEPKQRQ STQTLYVNVA PRDTTVLVSP SSILEEGSSV NMTCLSQGFP  540
APKILWSRQL PNGELQPLSE NATLTLISTK MEDSGVYLCE GINQAGRSRK EVELIIQVTP  600
KDIKLTAFPS ESVKEGDTVI ISCTCGNVPE TWIILKKKAE TGDTVLKSID GAYTIRKAQL  660
KDAGVYECES KNKVGSQLRS LTLDVQGREN NKDYFSPELL VLYFASSLII PAIGMIIYFA  720
RKANMKGSYS LVEAQKSKV                                              739
```

METHOD FOR GENERATING T CELL LINEAGE POPULATIONS FROM STEM/PROGENITOR CELLS

This application claims priority to and benefit of U.S. Provisional Patent Application 63/441,718, filed Jan. 27, 2023 and U.S. Provisional Patent Application 63/466,465, filed May 15, 2023, which are incorporated herein by reference as if set forth in their entirety.

STATEMENT REGARDING SEQUENCE LISTING

The Sequence Listing XML associated with this application is provided in XML file format and is hereby incorporated by reference into the specification. The name of the XML file containing the Sequence Listing XML is TORY_002_02US_ST26.xml. The XML file is 7,527 bytes, and created on Jan. 26, 2024, and is being submitted electronically via USPTO Patent Center.

FIELD

The present invention relates generally to in vitro methods of generating T cell lineage populations from progenitor cells and use of same.

BACKGROUND OF THE DISCLOSURE

Various feeder cell-based methods are available for the in vitro generation of T lineage cells. However, the expression of cell surface proteins by the supportive stromal cells in feeder cell-based systems is heterogenous, leading to diverse outcomes. Further, feeder cell-based systems are not easily scalable to meet the needs of clinical manufacturing.

Immobilized Notch signalling ligands, such as DL4, in combination with VCAM-1, have been shown to promote in vitro generation of progenitor T cells in a feeder-free and serum-free culture system (Shukla et al., 2017). Microbeads modified to present DL4 have also been shown to support in vitro differentiation of T-lineage cells, albeit with limited progression to mature lineages such as CD4−CD8+ cells (Trotman-Grant et al., 2021). TCR stimulation of T cell progenitors through an anti-CD3 antibody, in the absence of Notch signalling, has been shown to promote maturation into CD4− CD8αβ+ T cells (Iriguchi et al., 2021). Engagement of a chimeric antigen receptor (CAR), in the absence of Notch signalling, has also been shown to induce generation of CD4−CD8αβ+ cells from CD4+CD8+ cells in a TRAC−/− cell line (Sjoukje, et al., 2022). Currently, there are no reports of a method of controlling in vitro emergence of mature T cell lineage populations via Notch signalling. There are also no reports of the unique phenotype of cells that would emerge from such a process.

SUMMARY OF THE DISCLOSURE

In a first aspect of the disclosure, a method of generating a T cell lineage cell population from progenitor T cells is provided. The method comprises providing a population of progenitor T cells and culturing the progenitor T cells in the presence of a Notch signalling ligand provided on a surface area of at least 7 square centimetres per millilitre culture volume (7 cm$^2$/mL).

In an embodiment, the T cell lineage cell population is enriched for CD4−CD8+ cells.

In an embodiment, culturing the progenitor T cells in the presence of increasing concentrations of the Notch signalling ligand increases the absolute number and/or the relative number of CD4−CD8+ cells in the cell population.

In an embodiment, the Notch signalling ligand is provided on a surface area of 7 to 56 cm$^2$/mL, 7.8 to 55.2 cm$^2$/mL, or 15.7 to 55.2 cm$^2$/mL.

In an embodiment, the Notch signalling ligand is provided on a three-dimensional substrate.

In an embodiment, the three-dimensional substrate is one or more beads.

In an embodiment, the one or more beads is comprised of a material selected from a group consisting of polystyrene, iron oxide and gold.

In an embodiment, the one or more beads is comprised of polystyrene.

In an embodiment, the Notch signalling ligand is covalently conjugated to the one or more beads.

In an embodiment, the Notch signalling ligand comprises Notch ligand Delta-like-4 (DL4) or a variant thereof.

In an embodiment, the concentration of DL4 is $7.89 \times 10^{10}$ to $1.66 \times 10^{13}$ molecules/mL.

In an embodiment, the Notch signalling ligand is DL4 and wherein the step of culturing the progenitor T cells further comprises culturing in the presence of surface-bound vascular cell adhesion molecule 1 (VCAM-1).

In an embodiment, the DL4 and the VCAM-1 are provided on a surface area of 7.8 to 55.2 cm$^2$/mL.

In an embodiment, the concentration of DL4 is $7.89 \times 10^{10}$ to $1.66 \times 10^{13}$ molecules/mL and the concentration of VCAM-1 is $7.89 \times 10^{10}$ to $1.66 \times 10^{13}$ molecules/mL.

In an embodiment, the cell density is $5 \times 10^5$ to $2 \times 10^6$ cells/mL.

In an embodiment, the progenitor T cells are cultured for at least 3 days, at least 7 days, at least 11 days, or at least 14 days.

In an embodiment, the progenitor T cells are cultured for at least 14 days.

In an embodiment, the progenitor T cells are re-cultured at least once during or after the progenitor T cells are cultured for the at least 3 days, at least 7 days, at least 11 days, or at least 14 days, in the presence of a surface-bound Notch signalling ligand.

In an embodiment, the CD4−CD8+ cells are CD8αβ+ cells.

In an embodiment, the CD4−CD8+ cells are T cell receptor (TCR)− cells, surface CD3 negative (sCD3−) cells, or TCR−/sCD3− cells.

In an embodiment, the CD8αβ+ cells are T cell receptor (TCR)− cells, surface CD3 negative (sCD3−) cells, or TCR−/sCD3− cells.

In an embodiment, the progenitor T cells are derived from pluripotent stem cells.

In an embodiment, the progenitor T cells are derived from induced pluripotent stem cells (iPSC).

In an embodiment, the progenitor T cells comprise a nucleic acid encoding a chimeric antigen receptor (CAR) or an exogenous T cell receptor (TCR).

In an embodiment, the pluripotent stem cells comprise a nucleic acid encoding a chimeric antigen receptor (CAR) or an exogenous T cell receptor (TCR).

In a second aspect of the disclosure, a population of CD4−CD8+ cells made according to the method of the first aspect is provided.

In an embodiment, the CD4−CD8+ cells are CD8αβ+ cells.

In an embodiment, the CD4−CD8+ cells are T cell receptor (TCR)− cells, surface CD3 negative (sCD3−) cells, or TCR−/sCD3− cells.

In an embodiment, the CD8αβ+ cells are T cell receptor (TCR)− cells, surface CD3 negative (sCD3−) cells, or TCR−/sCD3− cells.

In an embodiment, the CD4−CD8+ cells express a chimeric antigen receptor (CAR).

In an embodiment, the CD4−CD8+ cells express an exogenous T cell receptor (TCR).

In a third aspect of the disclosure, a pharmaceutical composition comprising CD4−CD8+ cells and a pharmaceutically acceptable carrier is provided. The CD4−CD8+ cells are T cell receptor (TCR)− cells, surface CD3 negative (sCD3−) cells, or TCR−/sCD3− cells.

In an embodiment, the CD4−CD8+ cells are derived in vitro from progenitor T cells by culturing in the presence of a surface-bound Notch signalling ligand on a surface area of at least 7 square centimetres per millilitre culture volume (7 cm$^2$/mL).

In an embodiment, the progenitor T cells are derived in vitro from pluripotent stem cells.

In a fourth aspect of the disclosure, a method of treating a disease or condition in a subject is provided. The method comprises culturing a cell population comprising progenitor T cells in the presence of a surface-bound Notch signalling ligand provided on a surface area of at least 7 square centimetres per millilitre culture volume (7 cm$^2$/mL); and administering an effective amount of the T cell lineage cell population to a subject in need thereof.

In an embodiment of the method of treating a disease or condition in a subject provided herein, the T cell lineage cell population is enriched for CD4−CD8+ cells.

In an embodiment of the method of treating a disease or condition in a subject provided herein, the CD4−CD8+ cells are CD8αβ+ cells.

In an embodiment of the method of treating a disease or condition in a subject provided herein, the CD4−CD8+ cells are T cell receptor (TCR)− cells, CD3− cells, or TCR−/CD3− cells.

In an embodiment of the method of treating a disease or condition in a subject provided herein, the CD4−CD8αβ+ cells are T cell receptor (TCR)− cells, CD3− cells, or TCR−/CD3− cells.

In an embodiment of the method of treating a disease or condition in a subject provided herein, the T cell lineage cell population comprise a nucleic acid encoding a chimeric antigen receptor (CAR) or an exogenous T cell receptor (TCR).

In an embodiment of the method of treating a disease or condition in a subject provided herein, the Notch signalling ligand is provided on a three-dimensional substrate.

In an embodiment of the method of treating a disease or condition in a subject provided herein, the Notch signalling ligand comprises the Notch ligand Delta-like-4 (DL4), or a variant thereof.

In an embodiment of the method of treating a disease or condition in a subject provided herein, the Notch signalling ligand is DL4 and wherein the step of culturing the progenitor T cells further comprises culturing in the presence of surface-bound vascular cell adhesion molecule 1 (VCAM-1).

In an embodiment of the method of treating a disease or condition in a subject provided herein, the disease is cancer.

In a fifth aspect of the disclosure, a use of a T cell lineage cell population in the manufacture of a medicament for the treatment of a disease or condition is provided. The T cell lineage cell population is generated by a method comprising culturing a cell population comprising progenitor T cells in the presence of a surface-bound Notch signalling ligand provided on a surface area of at least 7 square centimetres per millilitre culture volume (7 cm$^2$/mL).

In an embodiment of the use of a T cell lineage cell population in the manufacture of a medicament for the treatment of a disease or condition provided herein, the T cell lineage cell population is enriched for CD4−CD8+ cells.

In an embodiment of the use of a T cell lineage cell population in the manufacture of a medicament for the treatment of a disease or condition provided herein, the CD4−CD8+ cells are CD8αβ+ cells.

In an embodiment use of a T cell lineage cell population in the manufacture of a medicament for the treatment of a disease or condition provided herein, the CD4−CD8+ cells are T cell receptor (TCR)− cells, surface CD3 negative (sCD3−) cells, or TCR−/sCD3− cells.

In an embodiment of the use of a T cell lineage cell population in the manufacture of a medicament for the treatment of a disease or condition provided herein, the CD4−CD8αβ+ cells are T cell receptor (TCR)− cells, surface CD3 negative (sCD3−) cells, or TCR−/sCD3− cells.

In an embodiment of the use of a T cell lineage cell population in the manufacture of a medicament for the treatment of a disease or condition provided herein, the T cell lineage cell population comprise a nucleic acid encoding a chimeric antigen receptor (CAR) or an exogenous T cell receptor (TCR).

In an embodiment of the use of a T cell lineage cell population in the manufacture of a medicament for the treatment of a disease or condition provided herein, the Notch signalling ligand is provided on a three-dimensional substrate.

In an embodiment of the use of a T cell lineage cell population in the manufacture of a medicament for the treatment of a disease or condition provided herein, the Notch signalling ligand comprises Notch ligand Delta-like-4 (DL4), or a variant thereof.

In an embodiment of the use of a T cell lineage cell population in the manufacture of a medicament for the treatment of a disease or condition provided herein, the Notch signalling ligand is DL4 and wherein the step of culturing the progenitor T cells further comprises culturing in the presence of surface-bound vascular cell adhesion molecule 1 (VCAM-1).

In an embodiment of the use of a T cell lineage cell population in the manufacture of a medicament for the treatment of a disease or condition provided herein, the disease is cancer.

In a sixth aspect of the disclosure, a method of differentiating a progenitor T cell population to generate a differentiated cell population enriched for CD4−CD8+TCRγδ+ cells is provided. The method comprises providing a population of progenitor T cells; and culturing the progenitor T cells in the presence of a surface-bound Notch signalling ligand provided on a surface area of 0.78 to 4.7 cm$^2$/mL.

In an embodiment of the method of differentiating a progenitor T cell population to generate a differentiated cell population enriched for CD4−CD8+TCRγδ+ cells provided herein, the Notch signalling ligand is provided on a three-dimensional substrate.

In an embodiment of the method of differentiating a progenitor T cell population to generate a differentiated cell population enriched for CD4−CD8+TCRγδ+ cells provided herein, the three-dimensional substrate is one or more beads.

In an embodiment of the method of differentiating a progenitor T cell population to generate a differentiated cell population enriched for CD4−CD8+TCRγδ+ cells provided herein, the one or more beads is comprised of a material selected from a group consisting of polystyrene, iron oxide and gold.

In an embodiment of the method of differentiating a progenitor T cell population to generate a differentiated cell population enriched for CD4−CD8+TCRγδ+ cells provided herein, the one or more beads is comprised of polystyrene.

In an embodiment of the method of differentiating a progenitor T cell population to generate a differentiated cell population enriched for CD4−CD8+TCRγδ+ cells provided herein, the Notch signalling ligand is covalently conjugated to the one or more beads.

In an embodiment of the method of differentiating a progenitor T cell population to generate a differentiated cell population enriched for CD4−CD8+TCRγδ+ cells provided herein, the Notch signalling ligand comprises Notch ligand Delta-like-4 (DL4), or a variant thereof.

In an embodiment of the method of differentiating a progenitor T cell population to generate a differentiated cell population enriched for CD4−CD8+TCRγδ+ cells provided herein, the Notch signalling ligand is DL4 and wherein the step of culturing the progenitor T cells further comprises culturing in the presence of surface-bound vascular cell adhesion molecule 1 (VCAM-1).

In a seventh aspect of the disclosure, a population of CD4−CD8+ TCRγδ+ cells generated in vitro according to the method of the sixth aspect is provided.

In an eighth aspect of the disclosure, a method of generating a cell population enriched for CD4−CD8+ cells is provided. The method comprises providing a population of progenitor T cells; and culturing the progenitor T cells in the presence of a surface-bound Notch signalling ligand provided on a surface area of at least 7 cm$^2$/mL, generating a cell population enriched for CD4−CD8+ cells.

In a ninth aspect of the disclosure, a method of differentiating a progenitor T cell population is provided. The method comprises providing a population of progenitor T cells; and culturing the progenitor T cells in the presence of a surface-bound Notch signalling ligand provided on a surface area of at least 7 cm$^2$/mL, where the differentiated cell population is enriched for CD4−CD8+ cells.

In a tenth aspect of the disclosure, a method of generating a T cell lineage cell population from progenitor T cells is provided. The method comprises providing a population of progenitor T cells and culturing the progenitor T cells in the presence of a Notch signalling ligand provided on a substrate, and the ratio of the surface area of the substrate to a culturing surface area of the culture vessel is at least 1.77 to 1.

In an embodiment, the T cell lineage cell population is enriched for CD4−CD8+ cells.

In an embodiment, culturing the progenitor T cells in the presence of increasing ratio of the surface of the substrate to a culturing surface area of the culture vessel increases the absolute number and/or the relative number of CD4−CD8+ cells in the cell population.

In an embodiment, the ratio of the surface area of the substrate to a culturing surface area of the culture vessel is 1.77:1 to 14:1, 2:1 to 14:1, or 4:1 to 14:1.

In an embodiment, the Notch signalling ligand is provided on a three-dimensional substrate.

In an embodiment, the three-dimensional substrate is one or more beads.

In an embodiment, the one or more beads is comprised of a material selected from a group consisting of polystyrene, iron oxide and gold.

In an embodiment, the one or more beads is comprised of polystyrene.

In an embodiment, the Notch signalling ligand is covalently conjugated to the one or more beads.

In an embodiment, the Notch signalling ligand comprises Notch ligand Delta-like-4 (DL4) or a variant thereof.

In an embodiment, the concentration of DL4 is $7.89 \times 10^{10}$ to $1.66 \times 10^{13}$ molecules/mL.

In an embodiment, the Notch signalling ligand is DL4 and wherein the step of culturing the progenitor T cells further comprises culturing in the presence of surface-bound vascular cell adhesion molecule 1 (VCAM-1).

In an embodiment, the DL4 and the VCAM-1 are provided on a substrate and the ratio of the surface area of the substrate to a culturing surface area of the culture vessel is 1.77:1 to 14:1, 2:1 to 14:1, or 4:1 to 14:1.

In an embodiment, the concentration of DL4 is $7.89 \times 10^{10}$ to $1.66 \times 10^{13}$ molecules/mL and the concentration of VCAM-1 is $7.89 \times 10^{10}$ to $1.66 \times 10^{13}$ molecules/mL.

In an embodiment, the cell density is $5 \times 10^5$ to $2 \times 10^6$ cells/mL.

In an embodiment, the progenitor T cells are cultured for at least 3 days, at least 7 days, at least 11 days, or at least 14 days.

In an embodiment, the progenitor T cells are cultured for at least 14 days.

In an embodiment, the progenitor T cells are re-cultured at least once during or after the progenitor T cells are cultured for the at least 3 days, at least 7 days, at least 11 days, or at least 14 days, in the presence of a surface-bound Notch signalling ligand.

In an embodiment, the CD4−CD8+ cells are CD8αβ+ cells.

In an embodiment, the CD4−CD8+ cells are T cell receptor (TCR)− cells, surface CD3 negative (sCD3−) cells, or TCR−/sCD3− cells.

In an embodiment, the CD8αβ+ cells are T cell receptor (TCR)− cells, surface CD3 negative (sCD3−) cells, or TCR−/sCD3− cells. In an embodiment, the progenitor T cells are derived from pluripotent stem cells.

In an embodiment, the progenitor T cells are derived from induced pluripotent stem cells (iPSC).

In an embodiment, the progenitor T cells comprise a nucleic acid encoding a chimeric antigen receptor (CAR) or an exogenous T cell receptor (TCR).

In an embodiment, the pluripotent stem cells comprise a nucleic acid encoding a chimeric antigen receptor (CAR) or an exogenous T cell receptor (TCR).

In an eleventh aspect of the disclosure, a method of generating a T cell lineage cell population from progenitor T cells is provided. The method comprises providing a population of progenitor T cells and culturing the progenitor T cells in the presence of a Notch signaling ligand and in the absence of a T cell receptor stimulator, where the T cell lineage cell population comprises CD4−CD8+ cells.

In an embodiment, the CD4−CD8+ cells are surface CD3 negative (sCD3−).

In an embodiment, the CD4−CD8+ cells are T cell receptor negative (TCR−) cells.

In an embodiment, the progenitor T cells comprise a nucleic acid encoding a CAR, and the step of culturing the progenitor T cells further comprises culturing in the absence of a CAR activator.

In an embodiment, the Notch signalling ligand is surface-bound, and the surface-bound Notch signalling ligand is provided on a surface area of at least 7 square centimetres per millilitre culture volume (7 cm$^2$/mL).

In an embodiment, the Notch signalling ligand is surface-bound, and the surface-bound Notch signalling ligand is provided on a surface area of between 7 square centimetres per millilitre culture volume (7 cm$^2$/mL) and 56 cm$^2$/mL.

In an embodiment, the Notch signalling ligand is provided on a three-dimensional substrate, and the ratio of the surface area of the substrate to a culturing surface area of the culture vessel is at least 1.77 to 1 (1.77:1).

In an embodiment, the ratio of the surface area of the substrate to a culturing surface area of the culture vessel is between 1.77 to 1 (1.77:1) and 14 to 1 (14:1).

In an embodiment, the three-dimensional substrate is one or more beads.

In a twelfth aspect of the disclosure, a method of generating a T cell lineage cell population from hematopoietic stem and/or progenitor cells is provided. The method comprises providing a population of hematopoietic stem and/or progenitor cells and culturing the hematopoietic stem/progenitor cells in the presence of a Notch signaling ligand and in the absence of a T cell receptor stimulator, where the T cell lineage cell population comprises CD4−CD8+ cells.

In an embodiment, the CD4−CD8+ cells are surface CD3 negative (sCD3−).

In an embodiment, the CD4−CD8+ cells are T cell receptor negative (TCR−) cells.

In an embodiment, the hematopoietic stem and/or progenitor cells comprise a nucleic acid encoding a CAR, and the step of culturing the hematopoietic stem and/or progenitor cells further comprises culturing in the absence of a CAR activator.

In an embodiment, the Notch signalling ligand is surface-bound.

In an embodiment, the Notch signalling ligand is provided on a three-dimensional substrate.

In an embodiment, the three-dimensional substrate is one or more beads.

In an embodiment, the Notch signalling ligand comprises Notch ligand Delta-like-4 (DL4) or a variant thereof.

In a thirteenth aspect of the disclosure, a method of generating a T cell lineage cell population from progenitor T cells is provided. The method comprises providing a population of progenitor T cells and culturing the progenitor T cells in the presence of a surface-bound Notch signalling ligand, where the Notch signalling ligand is provided on a surface area of between 7 square centimetres per millilitre culture volume (7 cm$^2$/mL) and 56 cm$^2$/mL, and where the T cell lineage cell population comprises CD4−CD8+ cells.

In a fourteenth aspect of the disclosure, a method of generating a T cell lineage cell population from progenitor T cells is provided. The method comprises providing a population of progenitor T cells and culturing the progenitor T cells in a culture vessel in the presence of a Notch signalling ligand, where the Notch signalling ligand is provided on a three-dimensional substrate, and where the ratio of the surface area of the substrate to a culturing surface area of the culture vessel is between 1.77 to 1 (1.77:1) and 14 to 1 (14:1), and where the T cell lineage cell population comprises CD4−CD8+ cells.

BRIEF DESCRIPTION OF THE DRAWINGS

In order that the subject matter may be readily understood, embodiments are illustrated by way of non-limiting examples in the accompanying drawings.

FIG. 5A is a graph depicting the percentage of viable cells as a function of 3D ETN bead concentration after 7 days of culture. Cell viability was determined by Acridine Orange+/Propidium Iodide− using the Cellaca® automated cell counter.

FIG. 5B is a graph depicting the percentage of viable cells as a function of 3D ETN bead concentration after 14 days of culture. Cell viability was determined by Acridine Orange+/Propidium Iodide using the Cellaca® automated cell counter.

FIG. 5C is a graph depicting the viability of the cells of 4 cell populations illustrated in FIG. 3A: CD4−CD8+ (CD8SP), CD4+CD8+ (DP), CD4+CD8− (CD4 ISP), and CD4−CD8− (DN), after culturing progenitor T cells for 7 days with increasing 3D ETN bead concentrations ($1.08 \times 10^7$ beads/mL-$10.8 \times 10^7$ beads/mL (0.02×-2× bead dose)).

FIG. 5D is a graph depicting the viability of the cells of 4 cell populations illustrated in FIG. 3A: CD4−CD8+ (CD8SP), CD4+CD8+ (DP), CD4+CD8− (CD4 ISP), and CD4−CD8− (DN), after culturing progenitor T cells for 14 days with increasing 3D ETN bead concentrations ($1.08 \times 10^7$ beads/mL-$10.8 \times 10^7$ beads/mL (0.02×-2× bead dose)).

FIG. 9A is flow cytometry plots of CD5 and CD7 expression in untransduced (top, NTD) and TCR-transduced (bottom) progenitor T cells.

FIG. 9B is flow cytometry plots of CD4 and CD8α (CD8A) expression in untransduced (top, NTD) and TCR-transduced (bottom) progenitor T cells.

FIG. 9C is flow cytometry plots of CD3 and TCR expression in untransduced (top, NTD) and TCR-transduced (bottom) progenitor T cells.

FIG. 10A is flow cytometry plots of CD5 and CD7 expression in untransduced (top, NTD) and TCR-transduced (bottom) cells following 7 days of culture of a progenitor T cell population with 3D ETN bead concentration of $1.08 \times 10^8$ beads/mL (2× bead dose).

FIG. 10B is flow cytometry plots of CD4 and CD8α (CD8A) expression in untransduced (top, NTD) and TCR-transduced (bottom) cells following 7 days of culture of a progenitor T cell population with 3D ETN bead concentration of $1.08 \times 10^8$ beads/mL (2× bead dose).

FIG. 10C is flow cytometry plots of CD3 and TCRαβ (TCRab) expression in untransduced (top, NTD) and TCR-transduced (bottom) cells following 7 days of culture of a progenitor T cell population with 3D ETN bead concentration of $1.08 \times 10^8$ beads/mL (2× bead dose).

FIG. 10D is flow cytometry plots of CD8β (CD8B) and CD8α (CD8A) expression in untransduced (top, NTD) and TCR-transduced (bottom) cells following 7 days of culture of a progenitor T cell population with 3D ETN bead concentration of $1.08 \times 10^8$ beads/mL (2× bead dose).

FIG. 11A is flow cytometry plots of CD5 and CD7 expression in untransduced (top, NTD), TCR-transduced (middle), and CD8β-enriched, TCR-transduced (bottom) cells following 11 days of culture of a progenitor T cell population with 3D ETN bead concentration of $1.08 \times 10^8$ beads/mL (2× bead dose).

FIG. 11B is flow cytometry plots of CD4 and CD8α (CD8A) expression in untransduced (top, NTD), TCR-transduced (middle), and CD8β-enriched, TCR-transduced (bottom) cells following 11 days of culture of a progenitor T cell population with 3D ETN bead concentration of $1.08 \times 10^8$ beads/mL (2× bead dose).

FIG. 11C is flow cytometry plots of CD3 and TCRαβ (TCRab) expression in untransduced (top, NTD), TCR-transduced (middle), and CD8β-enriched, TCR-transduced (bottom) cells following 11 days of culture of a progenitor T cell population with 3D ETN bead concentration of $1.08 \times 10^8$ beads/mL (2× bead dose).

FIG. 11D is flow cytometry plots of and CD8β (CD8B) and CD8α (CD8A) expression in untransduced (top, NTD), TCR-transduced (middle), and CD8β-enriched, TCR-transduced (bottom) cells following 11 days of culture of a progenitor T cell population with 3D ETN bead concentration of $1.08 \times 10^8$ beads/mL (2× bead dose).

FIG. 13A is a graph depicting the proportion of cells comprising 4 cell populations: CD4−CD8+(CD8SP), CD4+ CD8+ (DP), CD4+CD8− (CD4 ISP), and CD4−CD8− (DN), after progenitor T cells were cultured for 7 days with 2D ETN, SCT (Commercial Coating), and 3D ETN with increasing bead concentrations ($0.27 \times 10^7$ beads/mL-$8.1 \times 10^7$ beads/mL (0.5×-1.5× bead dose)).

FIG. 13B is graphs depicting expression of the genes DTX1, TCF7, BCL11B, and GATA3 after progenitor T cells were cultured for 3 days with 2D ETN, SCT (Commercial Coating), and 3D ETN with increasing bead concentrations ($0.27 \times 10^7$ beads/mL-$8.1 \times 10^7$ beads/mL (0.5×-1.5× bead dose)).

FIG. 13E is bar graphs depicting the relative levels of cell surface proteins expressed in each cluster depicted in FIG. 13D (e.g., cluster 1 was identified as describing CD4+CD8+ (DP) cells).

FIG. 13F is a bar graph depicting the proportion of each cluster identified in FIG. 13D as a function of cell culture with 2D ETN, SCT (Commercial Coating), and 3D ETN with increasing bead concentrations ($0.27 \times 10^7$ beads/mL-$8.1 \times 10^7$ beads/mL (0.5×-1.5× bead dose)).

FIG. 15A is a UMAP plot depicting Notch and TCR signalling enrichment, respectively, through T cell maturation in the thymus. Data was sourced from Park et al., 2020.

FIG. 15B is a UMAP plot depicting Notch and TCR signalling enrichment, respectively, through T cell maturation in the thymus. Data was sourced from Park et al., 2020.

FIG. 15C is a graph depicting the enrichment of Notch and TCR signalling at various T cell development stages in the thymus (Single Sample Gene Set Enrichment Analysis, ssGSEA). Developmental stages are designated as: early DN cells, DNI; proliferating DN cells, DN(p); quiescent DN cells, DN(q); proliferating DP cells, DP(p); quiescent DP cells, DP(q); alpha-beta T entry-stage cells, αβT; and CD8+ T cells, CD8+T. Data and cell labels were sourced from Park et al., 2020.

Figure 20A:
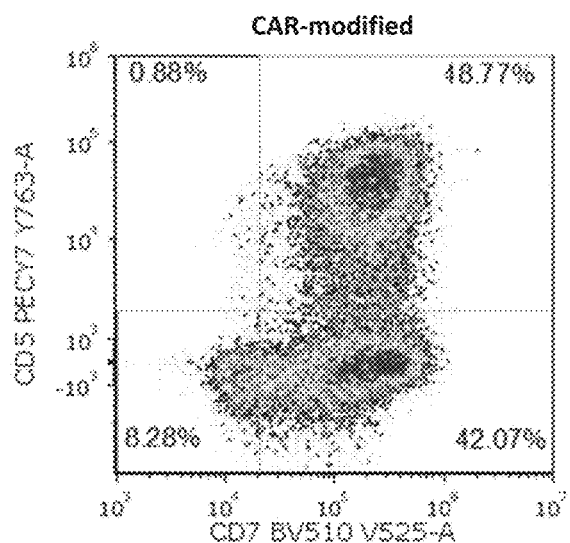

FIG. 20A is a flow cytometry plot of CD5 and CD7 expression for CAR-modified iPSC-derived cells following 10 days of culture of an iPSC-derived hematopoietic stem/progenitor cell population comprising CD34+ cells with 3D ETN bead concentration of $2.7 \times 10^7$ beads/mL (0.5× bead dose).

Figure 20B:
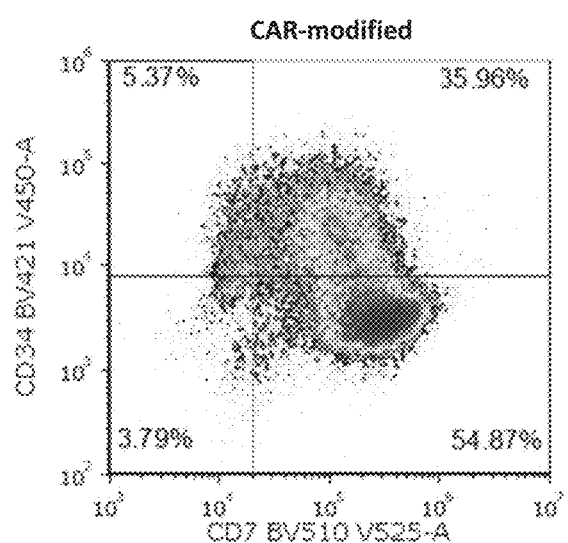

FIG. 20B is a flow cytometry plot of CD34 and CD7 expression for CAR-modified iPSC-derived cells following 10 days of culture of an iPSC-derived hematopoietic stem/progenitor cell population comprising CD34+ cells with 3D ETN bead concentration of $2.7 \times 10^7$ beads/mL (0.5× bead dose).

Figure 20C:
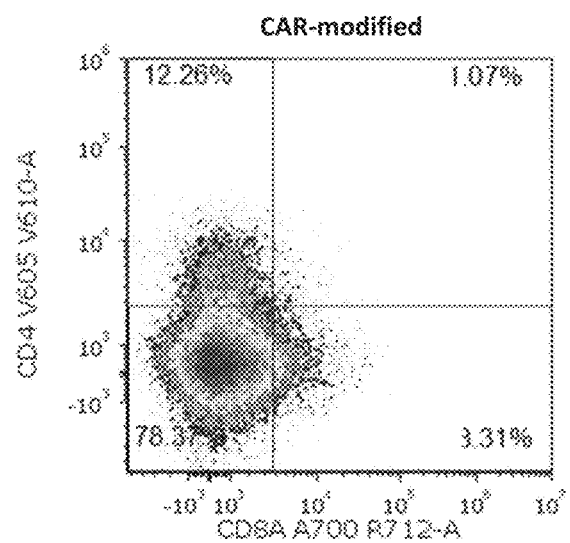

FIG. 20C is a flow cytometry plot of CD4 and CD8α (CD8A) expression for CAR-modified iPSC-derived cells following 10 days of culture of an iPSC-derived hematopoietic stem/progenitor cell population comprising CD34+ cells with 3D ETN bead concentration of $2.7 \times 10^7$ beads/mL (0.5× bead dose).

Figure 20D:
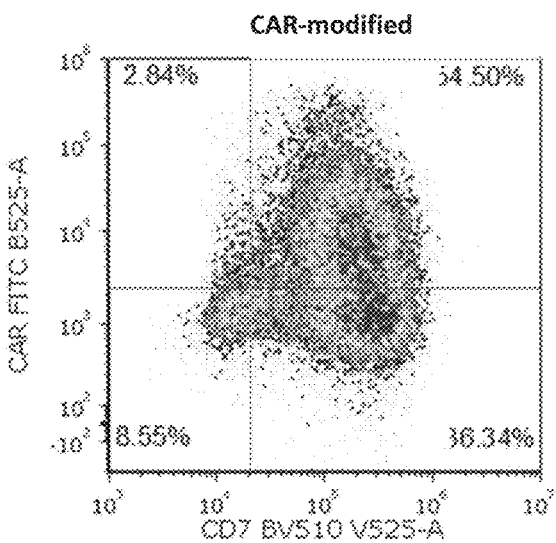

FIG. 20D is a flow cytometry plot of CAR and CD7 expression for CAR-modified iPSC-derived cells following 10 days of culture of an iPSC-derived hematopoietic stem/progenitor cell population comprising CD34+ cells with 3D ETN bead concentration of $2.7 \times 10^7$ beads/mL (0.5× bead dose).

Figure 21A:
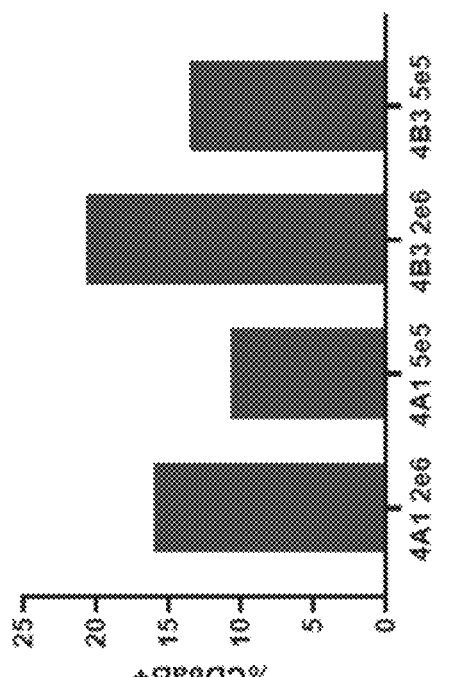

FIG. 21A is a graph quantifying the proportion of CD4–CD8α+ (CD8SP) cells for unmodified iPSC-derived cells ("4A1") or CAR-modified iPSC-derived cells ("4B3") following 7 days of culture of progenitor T cells at densities of $2 \times 10^7$ cells/mL or $5 \times 10^5$ cells/mL with 3D ETN bead concentration of $1.08 \times 10^8$ beads/mL (2× bead dose) (17 days of culture with 3D ETN from a hematopoietic stem/progenitor cell starting population).

Figure 21B:
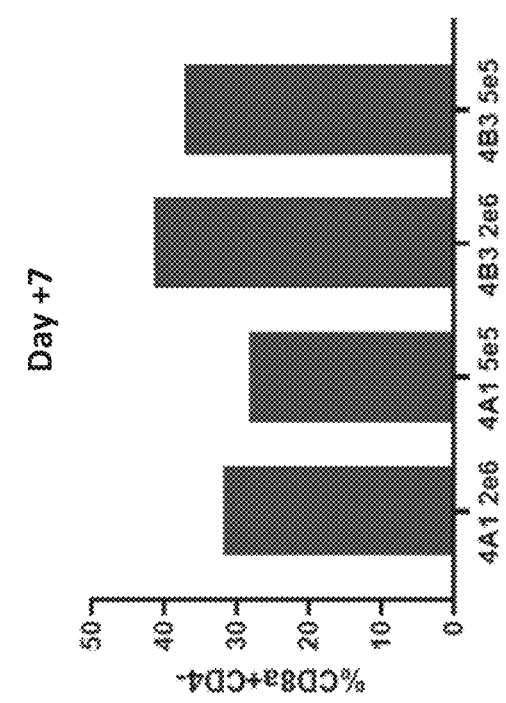

FIG. 21B is a graph quantifying the proportion of CD8αβ+ (CD8ab+) cells for unmodified iPSC-derived cells ("4A1") or CAR-modified iPSC-derived cells ("4B3") following 7 days of culture of progenitor T cells at densities of $2 \times 10^6$ cells/mL or $5 \times 10^5$ cells/mL with 3D ETN bead concentration of $1.08 \times 10^8$ beads/mL (2× bead dose) (17 days of culture with 3D ETN from a hematopoietic stem/progenitor cell starting population).

Figure 21C:
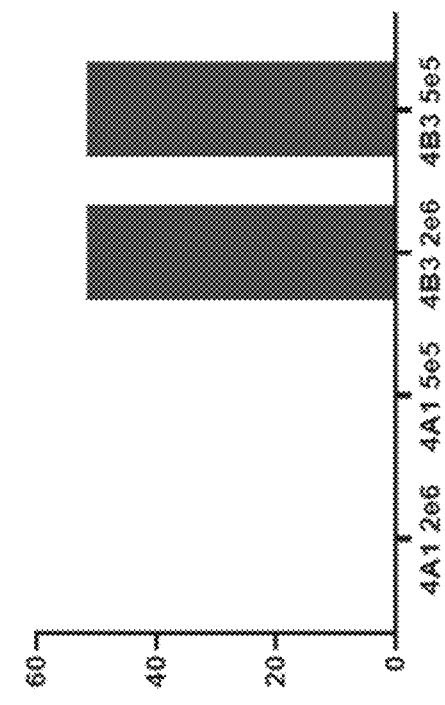

FIG. 21C is a graph quantifying the cell viability for unmodified iPSC-derived cells ("4A1") or CAR-modified iPSC-derived cells ("4B3") following 7 days of culture of progenitor T cells at densities of $2 \times 10^6$ cells/mL or $5 \times 10^5$ cells/mL with 3D ETN bead concentration of $1.08 \times 10^8$ beads/mL (2× bead dose) (17 days of culture with 3D ETN from a hematopoietic stem/progenitor cell starting population).

Figure 21D:
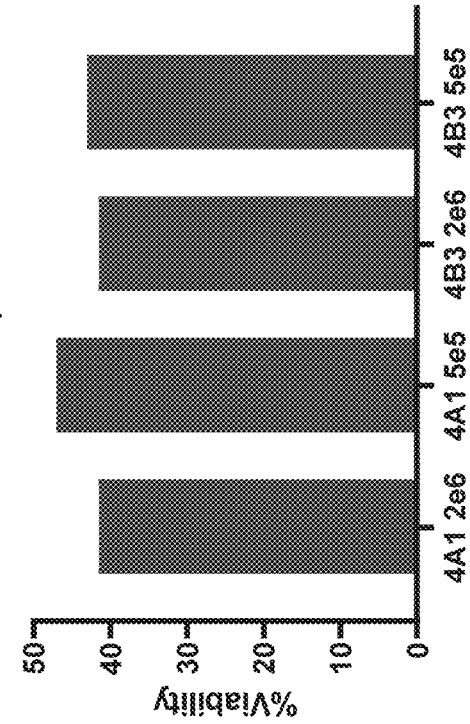

FIG. 21D is a graph quantifying the proportion of CAR+ cells for unmodified iPSC-derived cells ("4A1") or CAR-modified iPSC-derived cells ("4B3") following 7 days of culture of progenitor T cells at densities of $2 \times 10^6$ cells/mL or $5 \times 10^5$ cells/mL with 3D ETN bead concentration of $1.08 \times 10^8$ beads/mL (2× bead dose) (17 days of culture with 3D ETN from a hematopoietic stem/progenitor cell starting population).

FIG. 22A is a graph quantifying the percentage of CD4–CD8α+ (CD8SP) cells for unmodified iPSC-derived cells ("4A1") and CAR-modified iPSC-derived cells ("4B3") pre- and post-CD8α enrichment following 11 days of culture of cells at densities $2 \times 10^6$ cells/mL or $5 \times 10^5$ cells/mL with 3D ETN bead concentration of $1.08 \times 10^8$ beads/mL (2× bead dose) (21 days of culture with 3D ETN from a hematopoietic stem/progenitor cell starting population).

FIG. 22B is a graph quantifying the percentage of CD8αβ+ (CD8ab+) cells for unmodified iPSC-derived cells ("4A1") and CAR-modified iPSC-derived cells ("4B3") pre- and post-CD8α enrichment following 11 days of culture of cells at densities $2 \times 10^6$ cells/mL or $5 \times 10^5$ cells/mL with 3D ETN bead concentration of $1.08 \times 10^8$ beads/mL (2× bead dose) (21 days of culture with 3D ETN from a hematopoietic stem/progenitor cell starting population).

FIG. 22C is a graph quantifying the percentage of cell viability for unmodified iPSC-derived cells ("4A1") and CAR-modified iPSC-derived cells ("4B3") pre- and post-CD8α enrichment following 11 days of culture of cells at densities $2 \times 10^6$ cells/mL or $5 \times 10^5$ cells/mL with 3D ETN bead concentration of $1.08 \times 10^8$ beads/mL (2× bead dose) (21 days of culture with 3D ETN from a hematopoietic stem/progenitor cell starting population).

FIG. 22D is a graph quantifying the percentage of CAR expression for unmodified iPSC-derived cells ("4A1") and CAR-modified iPSC-derived cells ("4B3") pre- and post-CD8α enrichment following 11 days of culture of cells at densities $2 \times 10^6$ cells/mL or $5 \times 10^5$ cells/mL with 3D ETN bead concentration of $1.08 \times 10^8$ beads/mL (2× bead dose) (21 days of culture with 3D ETN from a hematopoietic stem/progenitor cell starting population).

Figure 23A:
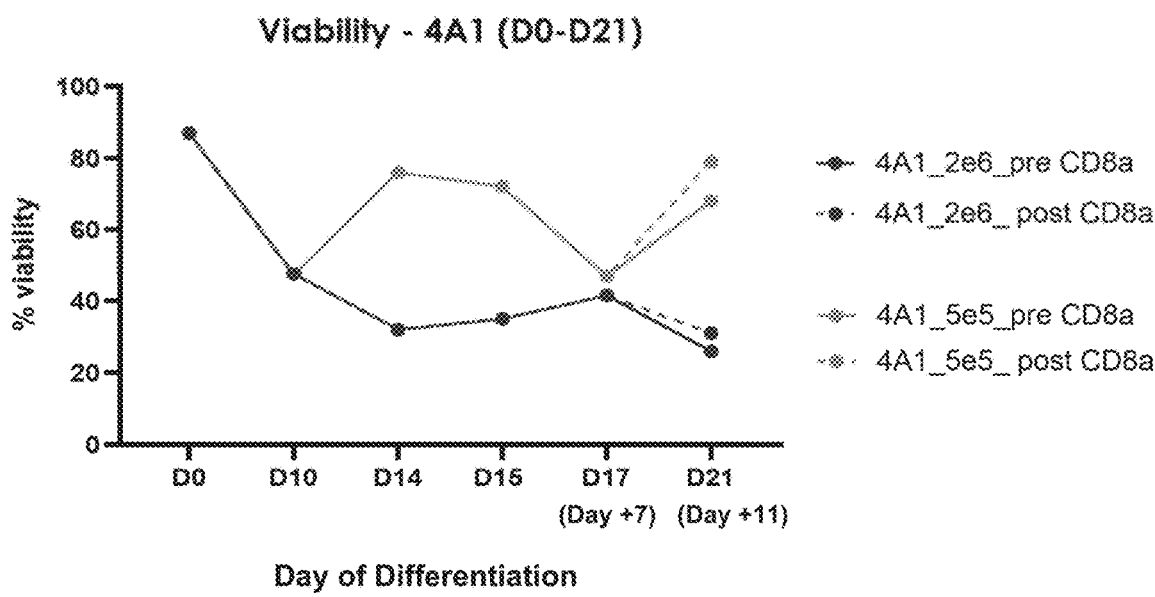

FIG. 23A is a graph depicting cell viability over time for unmodified iPSC-derived cells ("4A1").

Figure 23B:
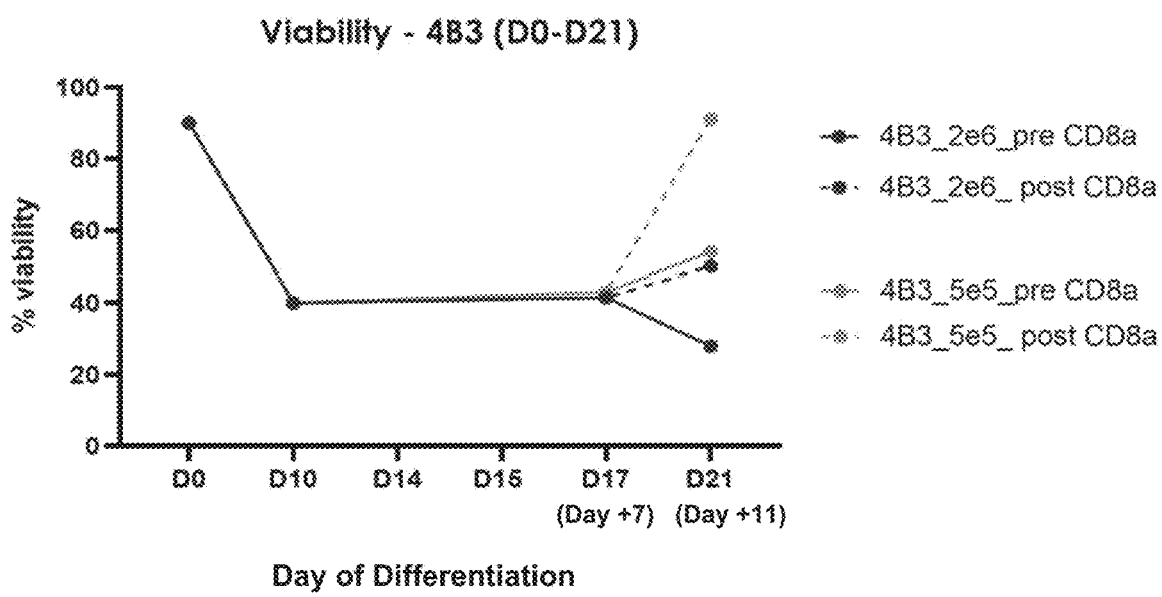

FIG. 23B is a graph depicting cell viability over time for CAR-modified iPSC-derived cells ("4B3").

Figure 24A:
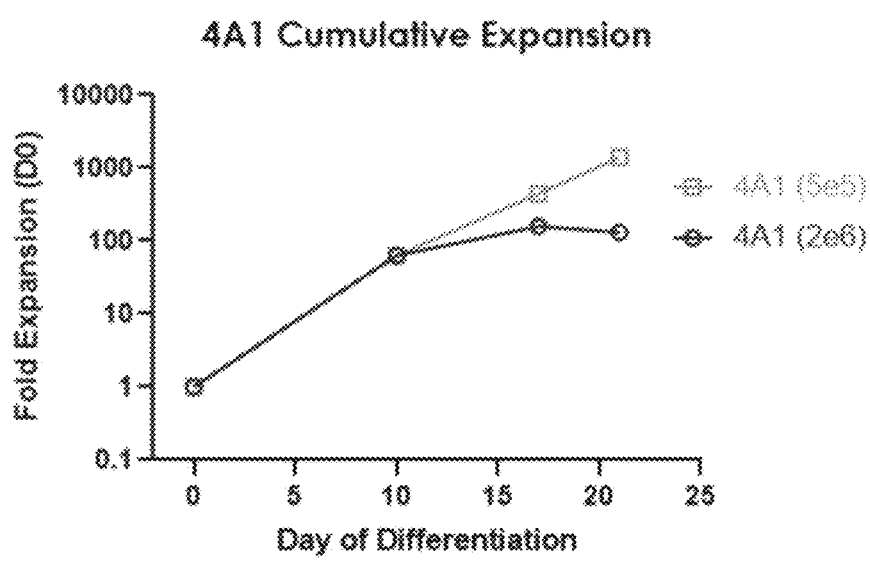

FIG. 24A is a graph depicting fold expansion over time for unmodified iPSC-derived cells ("4A1").

Figure 24B:
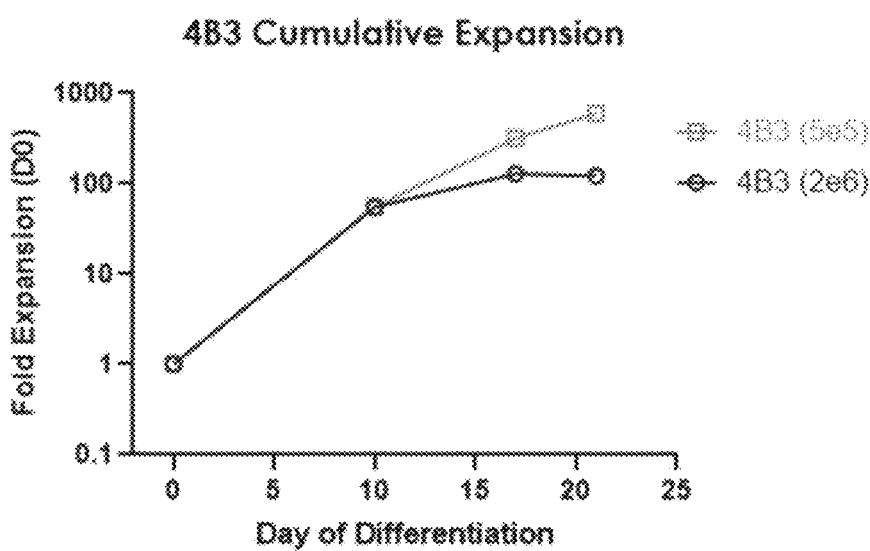

FIG. 24B is a graph depicting fold expansion over time for CAR-modified iPSC-derived cells ("4B3").

Figure 25:
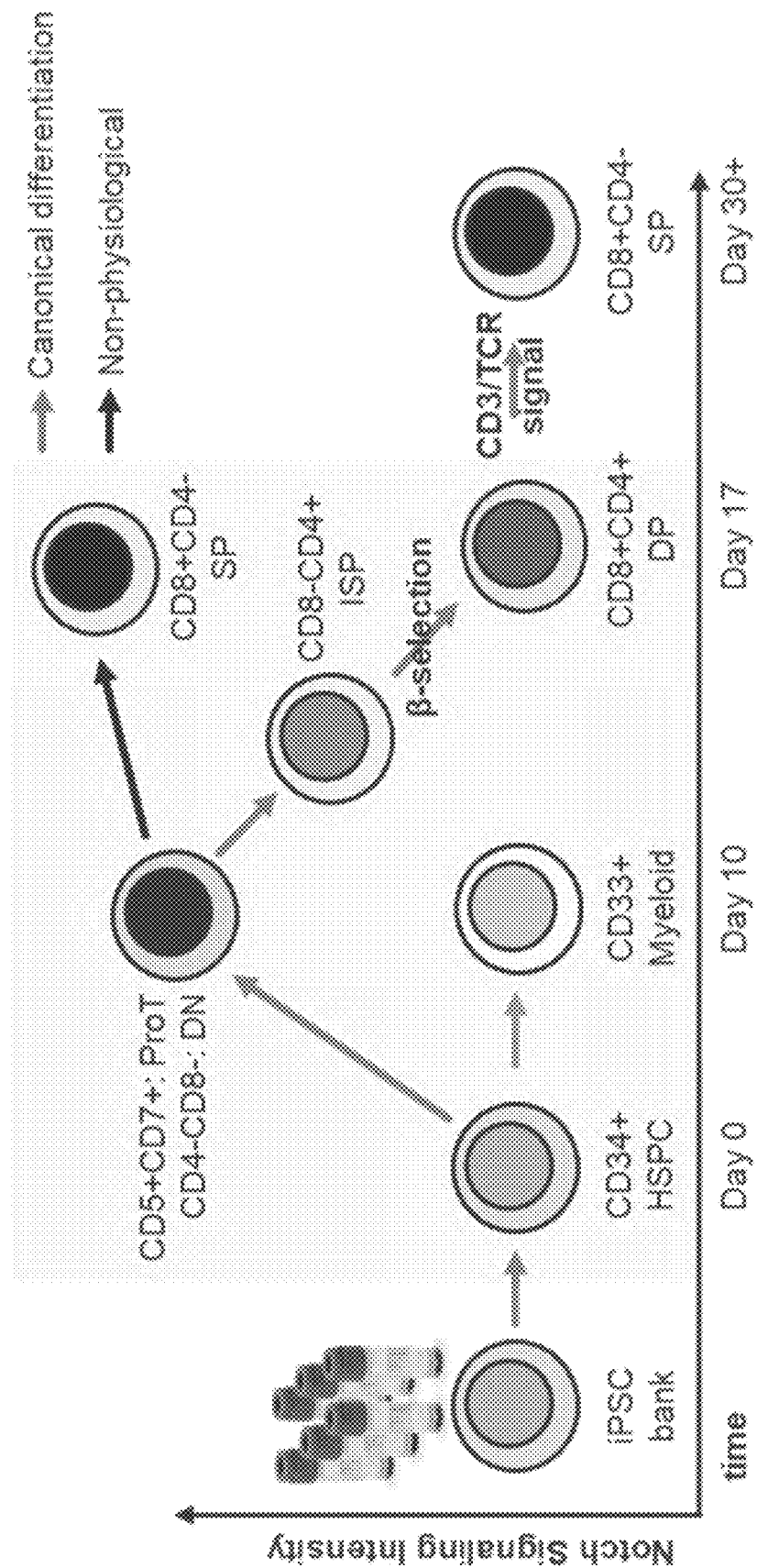

FIG. 25 is a schematic depicting canonical (gray arrows) and non-physiological (black arrows) differentiation of pluripotent stem cells (e.g. induced pluripotent stem cells, iPSCs) to CD8+CD4-cells. HSPC, hematopoietic stem/progenitor cell; DN, double negative cell; ISP, intermediate single positive cell; DP, double-positive cell; SP, single-positive cell.

Figure 26A:
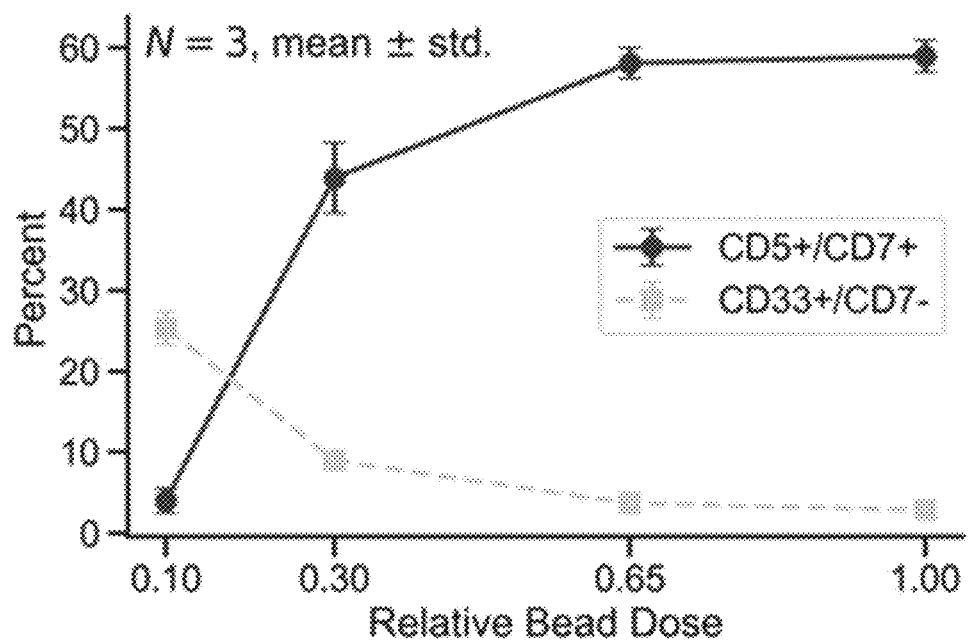

FIG. 26A is a graph quantifying the percentage of progenitor T cells (CD5+CD7+) and myeloid cells (CD33+CD7–) following differentiation of iPSC-derived HSPCs with varying concentrations of ETN.

Figure 26B:
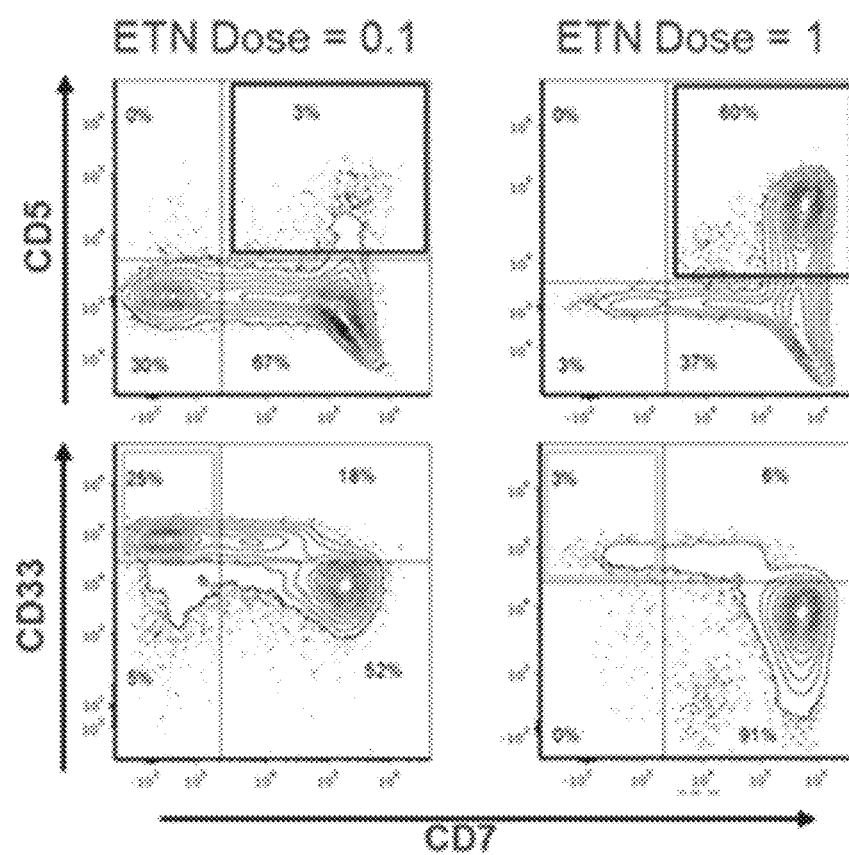

FIG. 26B is representative flow cytometry plots for the differentiation of iPSC-derived HSPCs at an ETN dose of $5.4 \times 10^6$ beads/mL (0.1× bead dose) or $5.4 \times 10^7$ beads/mL (1× bead dose) with progenitor T cell populations (CD5+CD7+) and myeloid cell populations (CD33+CD7–) outlined.

Figure 27A:
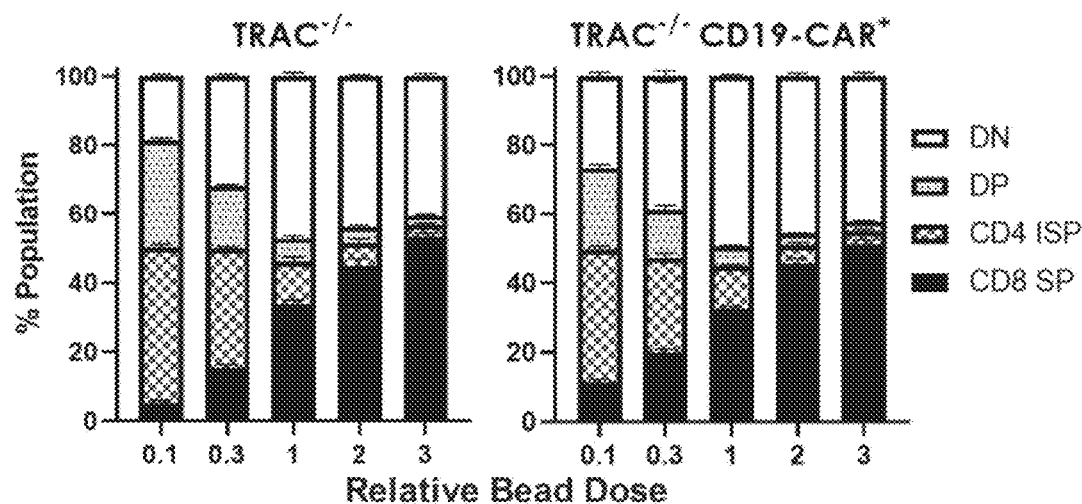

FIG. 27A is graphs depicting quantification of flow cytometry data showing percentage of CD4–CD8– (double-negative, DN), CD4+CD8+ (double-positive, DP), CD4+CD8– (CD4 ISP), and CD4–CD8+(CD8 single-positive, CD8SP) cells after two cell lines, TRAC-deficient (TRAC$^{-/-}$, left plot) and TRAC-deficient, CD19-CAR-engineered (TRAC$^{-/-}$ CD19-CAR$^+$, right plot) were cultured with 3D ETN at a range of bead doses.

Figure 27B:
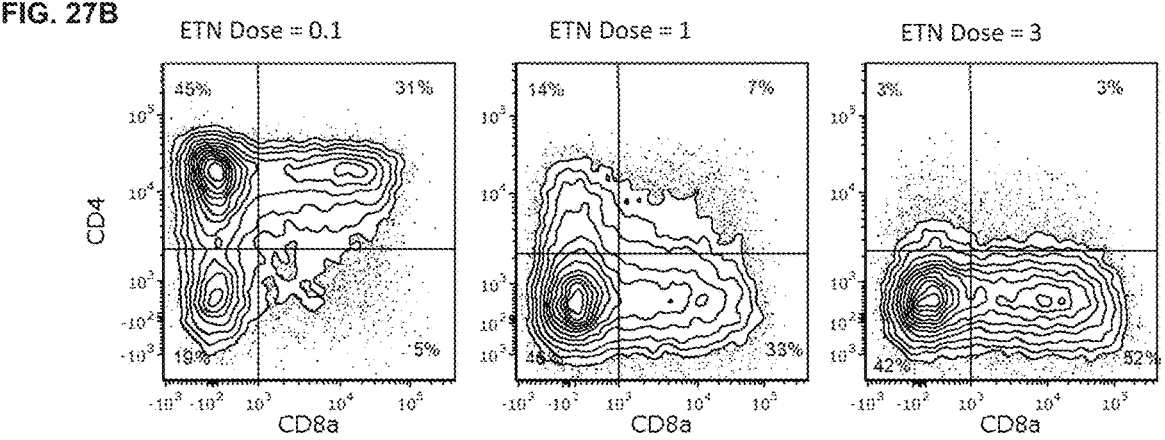

FIG. 27B is flow cytometry plots of CD4 and CD8α (CD8a) expression in TRAC-deficient, CD19-CAR-engineered cells after culture with 3D ETN at three doses. Annotated boxes on left-hand plot indicate populations as quantified in FIG. 26A.

FIG. 28A is a graph depicting changes in gene expression following 2 days of culture with 3D ETN that are positively or negatively associated with CD8 SP phenotype, as identified by a machine learning workflow (see FIG. 28B).

FIG. 28B is a graph depicting the accuracy distribution of the models used in the machine learning workflow.

FIG. 28C is a graph depicting correlation of the expression of the gene DTX1, identified as the most positively predictive feature, with the percentage of CD4−CD8a+ (CD8 SP) cells for both TRAC-deficient (TRAC KO, circles) and TRAC-deficient, CD19-CAR-engineered (TRAC KO+ CAR, x's) cell lines.

FIG. 28D is graphs depicting expression of select genes in TRAC-deficient (TRAC$^{-/-}$) and TRAC-deficient, CD19-CAR-engineered (TRAC$^{-/-}$ CD19-CAR$^+$) cell lines across a range of bead doses (z-score normalized mean expression shown, n=3).

Figure 28E:
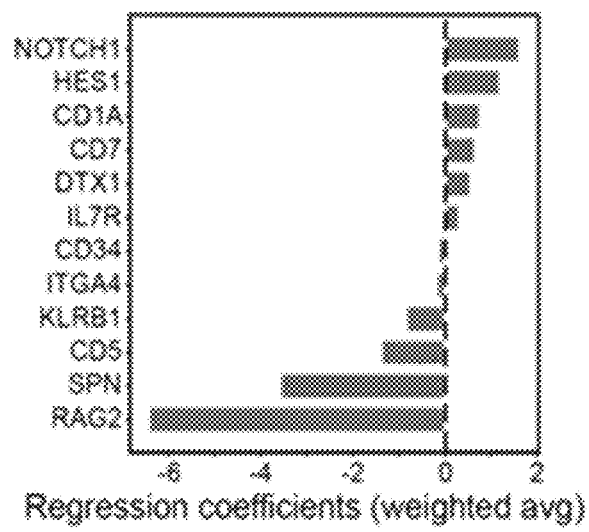
Figure 28F:
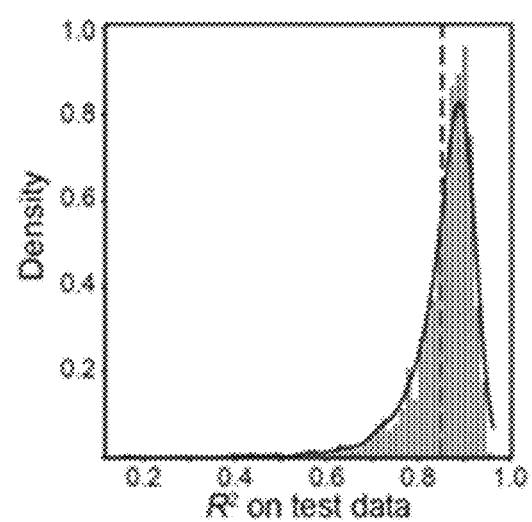

FIG. 28E is a graph depicting changes in gene expression following 2 days of culture with 3D ETN that are positively or negatively associated with CD8 SP phenotype, as identified by a machine learning workflow (see FIG. 28F). Mean weighted regression coefficients for the top 12 predictive features are shown.

FIG. 28F is a graph depicting the accuracy distribution of the models used in the machine learning workflow. CD8α SP phenotype at day-17 is predicted with good accuracy (85% cross-validation) independent of cell line using a machine learning workflow trained on gene expression at day-12.

Figure 28G:
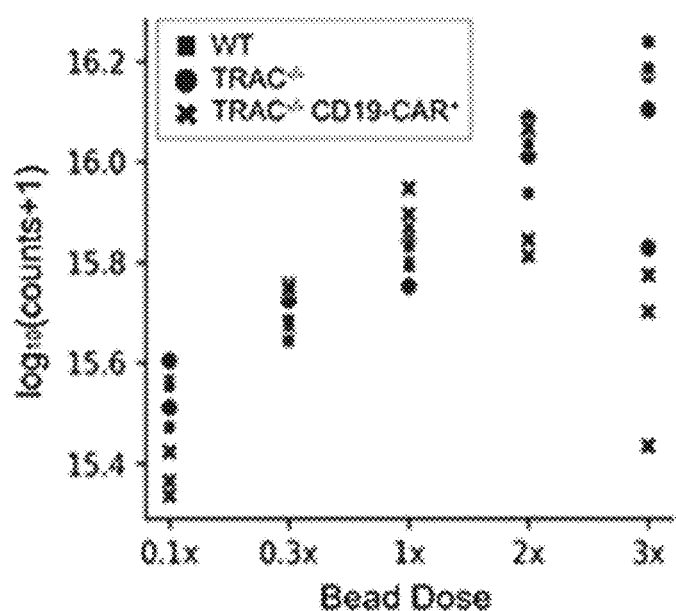

FIG. 28G is a graph depicting correlation of the expression of the gene NOTCH1, identified as the most positively predictive feature, with bead dose for wild-type (WT, squares), TRAC-deficient (TRAC$^{-/-}$, circles) and TRAC-deficient, CD19-CAR-engineered (TRAC$^{-/-}$ CD19-CAR$^+$, x's) cell lines.

Figure 28H:
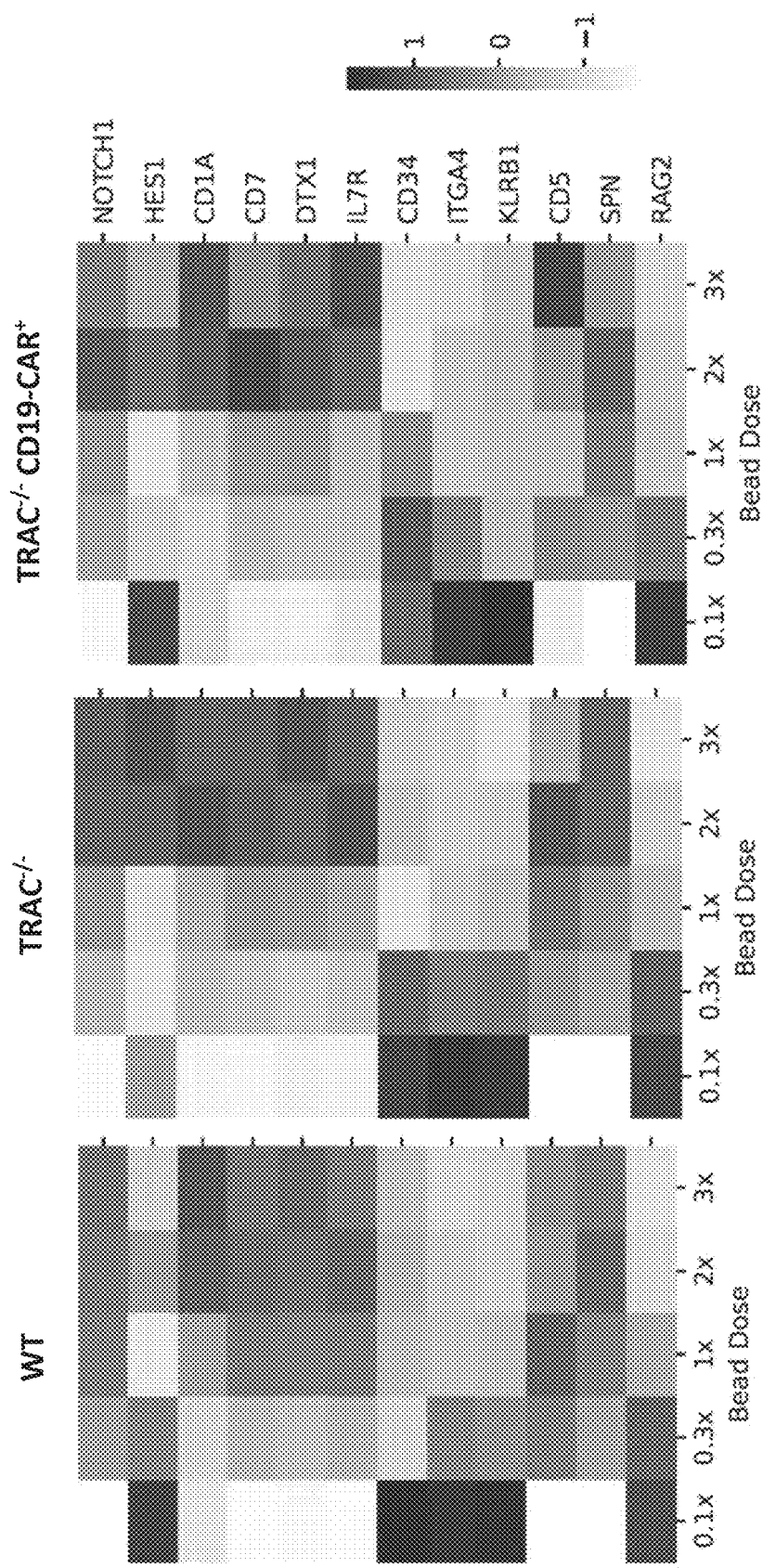

FIG. 28H is graphs depicting expression of select genes in wild-type (WT, left), TRAC-deficient (TRAC$^{-/-}$, middle) and TRAC-deficient, CD19-CAR-engineered (TRAC$^{-/-}$ CD19-CAR$^+$, right) cell lines across a range of bead doses (z-score normalized mean expression shown, n=3 or 6).

FIG. 28I is a graph depicting a variance partition analysis demonstrating that both bead dose and the interaction between day and cell line effects account for the majority of transcriptional variance.

FIG. 28J is a graph depicting differentially expressed pathways (using ssGSEA scores) across low and high bead dose and culture time (day 12 and day 17) in the TRAC-deficient, CD19-CAR-engineered cell line (TRAC$^{-/-}$ CD19-CAR$^+$).

Figure 29A:
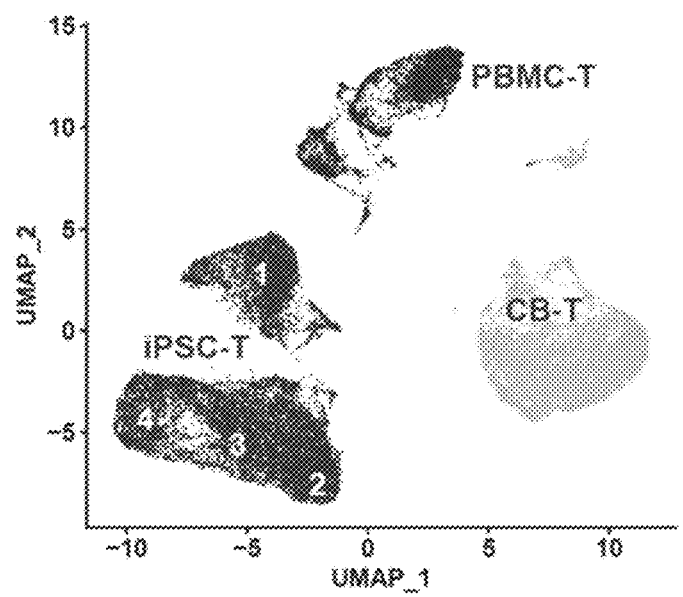

FIG. 29A is a UMAP plot of single cell transcriptomes for iPSC-derived T cells, CD8+ T cells from peripheral blood (PBMC-T) & cord blood (CB-T).

Figure 29B:
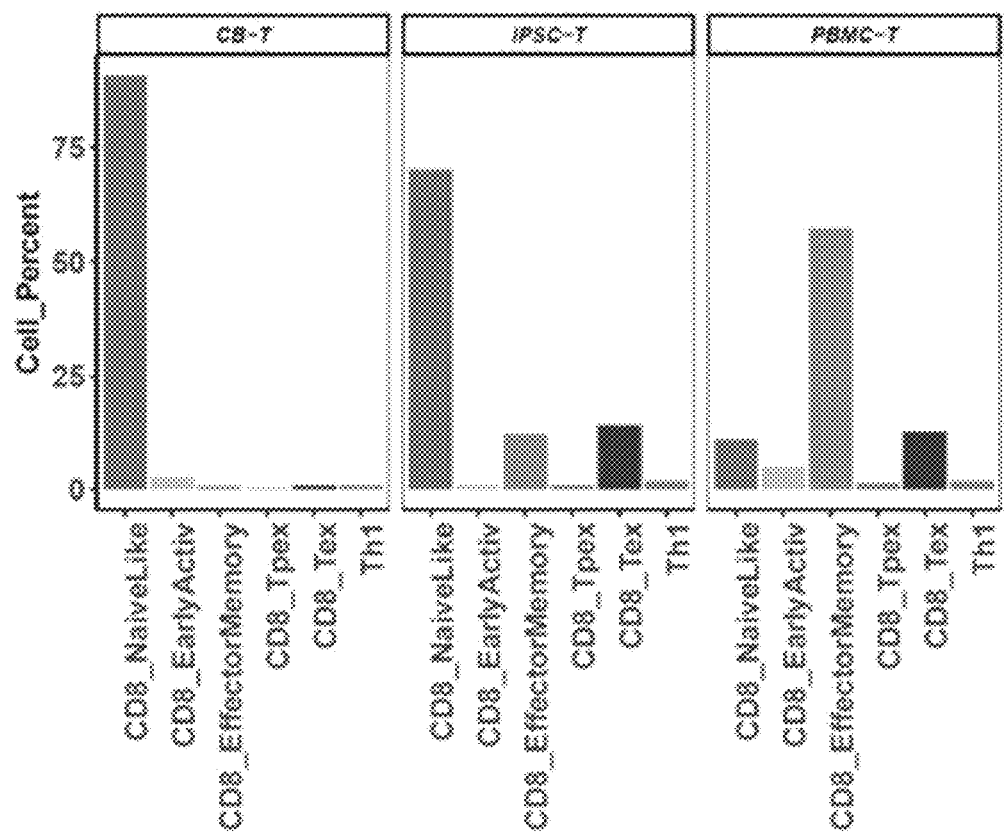

FIG. 29B is graphs depicting cell populations for iPSC-derived T cells, CD8+ T cells from peripheral blood (PBMC-T) & cord blood (CB), classified using an algorithm derived from ProjecTILs (Haradhvala et al., 2022).

Figure 29C:
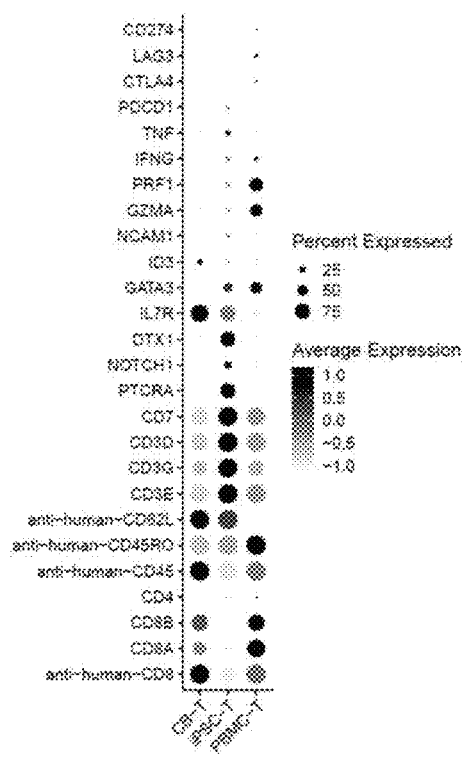

FIG. 29C is a graph depicting gene expression of markers for T cells, Notch response-genes, Innate lymphoid cells (ILCs), T cell activation and exhaustion transcripts for iPSC-derived T cells, CD8+ T cells from peripheral blood (PBMC-T) & cord blood (CB-T).

Figure 29D:
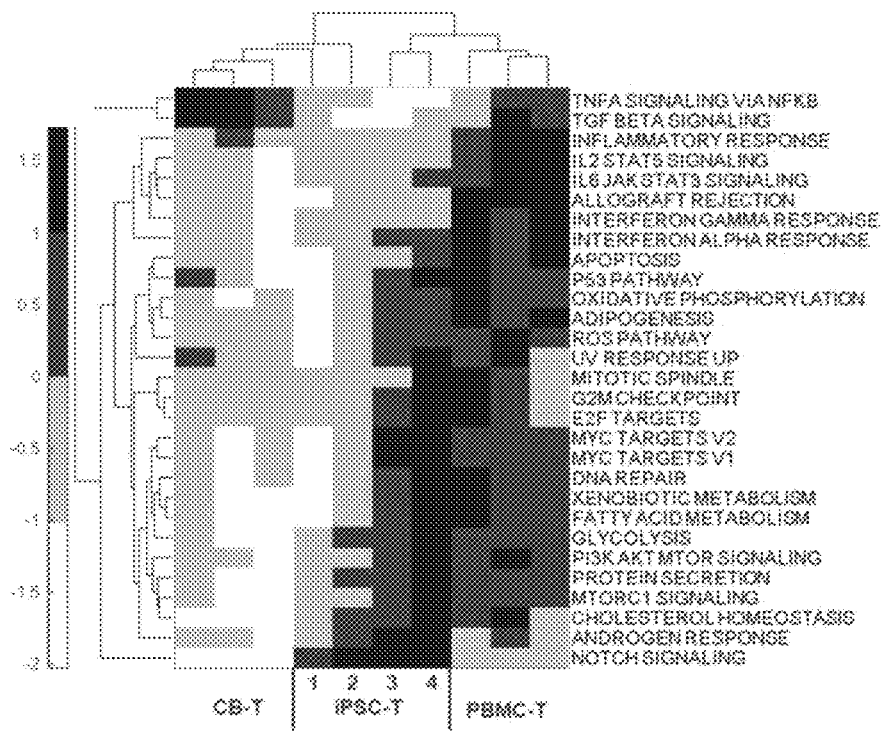

FIG. 29D is a graph depicting differential enrichment of select gene signatures in each cell cluster for iPSC-derived T cells (iPSC-T, numbered 1-4), CD8+ T cells from peripheral blood (PBMC-T) & cord blood (CB-T) by single-sample gene set enrichment analysis (GSEA).

Figure 29E:
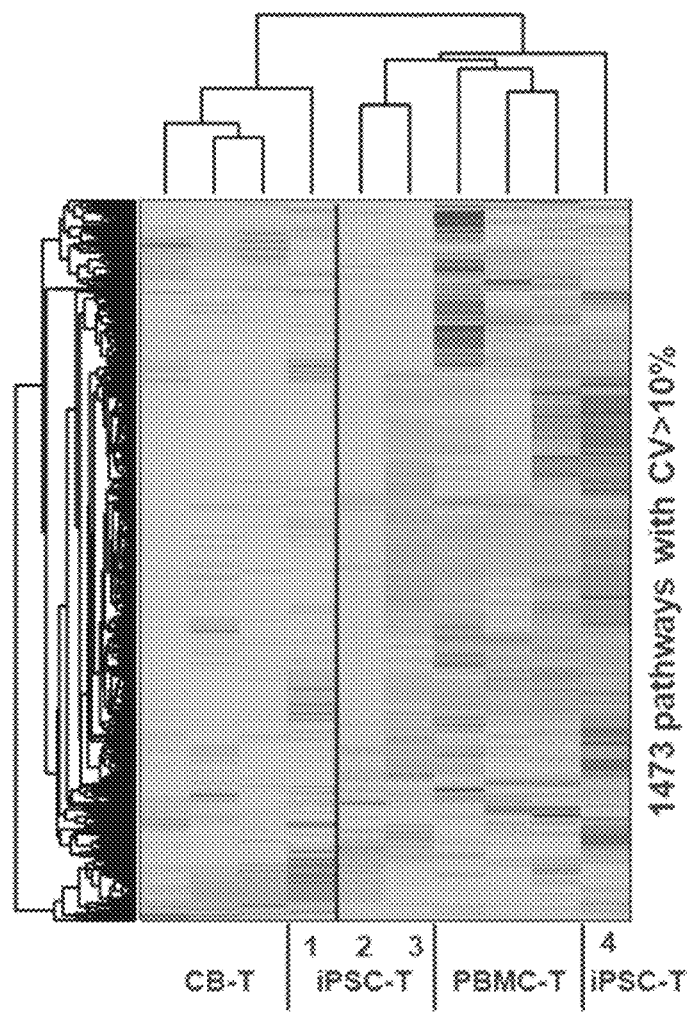

FIG. 29E is a graph depicting 1473 gene signatures differentially enriched in each cell cluster for iPSC-derived T cells (iPSC-T, numbered 1-4), CD8+ T cells from peripheral blood (PBMC-T) & cord blood (CB-T) by single-sample gene set enrichment analysis (GSEA).

Figure 29F:
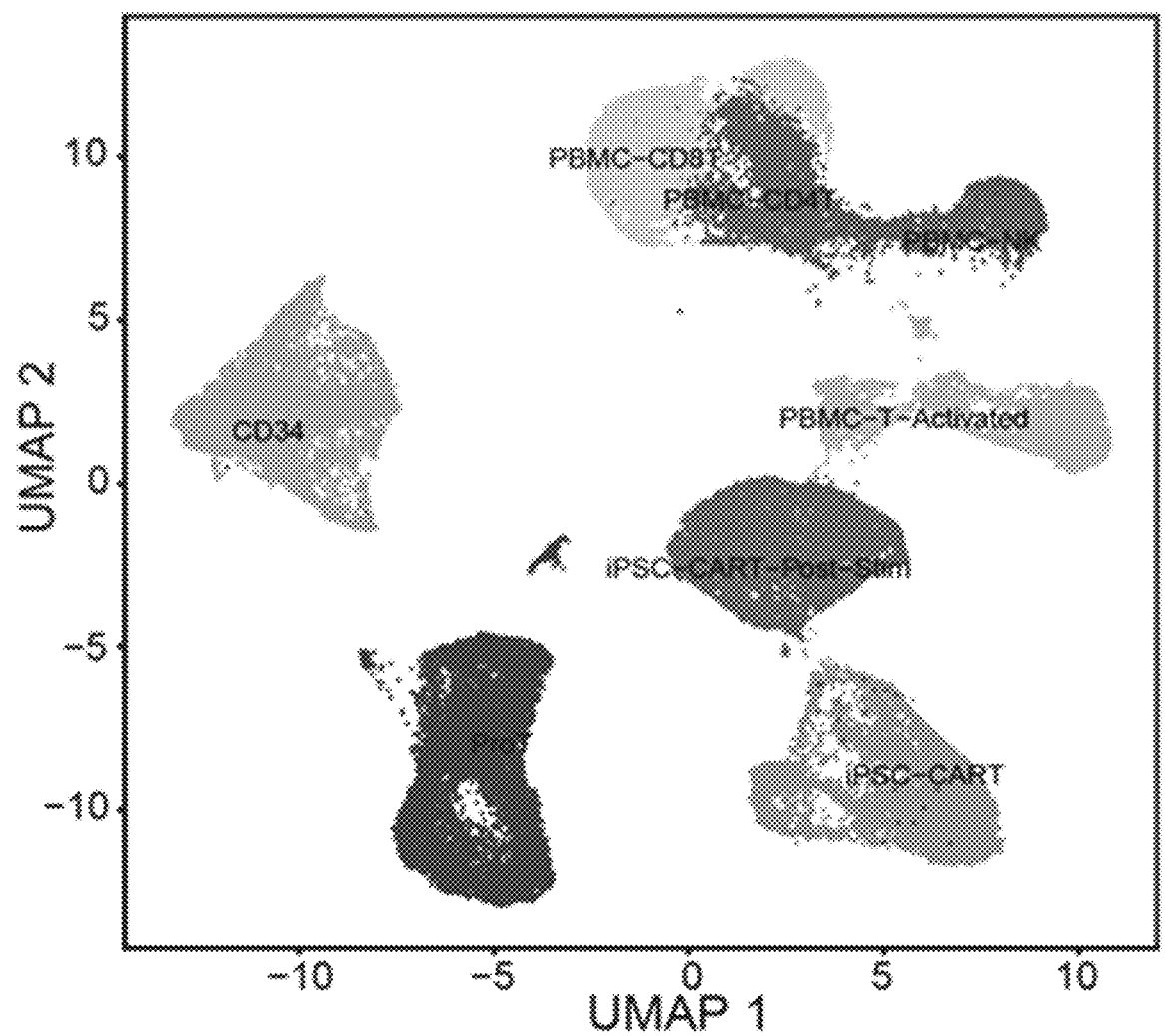

FIG. 29F is a UMAP of single cell transcriptomes for: iPSC-derived T cells through differentiation (CD34+, ProT, CD8+SP stage, and following CD19-antigen stimulation) vs. primary lymphocytes (CD4+ T cells, CD8+ T cells, CD56+ NK cells, and T cells activated by Dynabeads (CD3/CD28-stimulated).

Figure 29G:
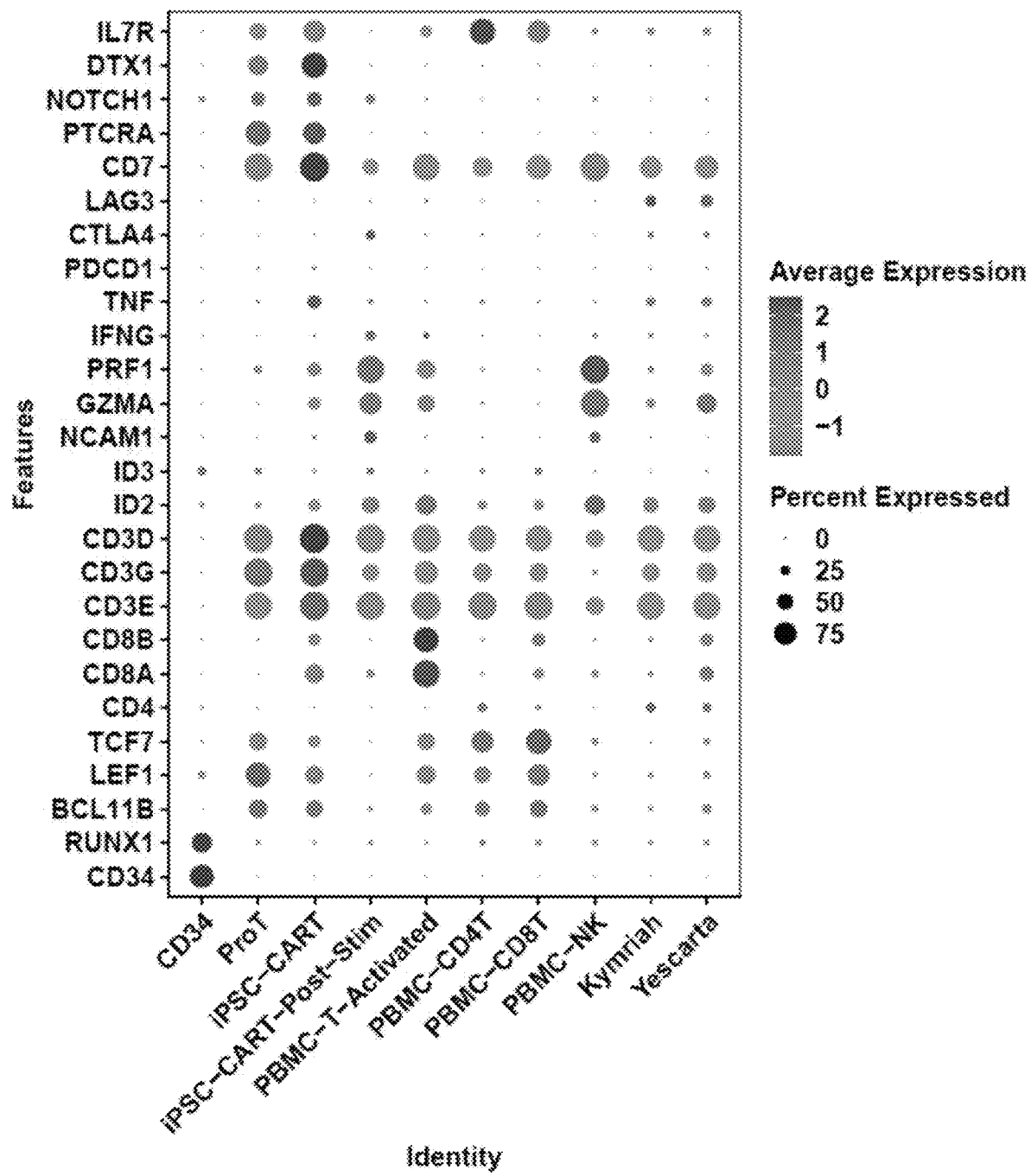

FIG. 29G is a bubble plot of select genes associated with blood progenitors, T cell lineage commitment, canonical T cell function, innate lymphocytes, cytotoxic T cells, exhausted T cells, and Notch-response elements.

Figure 29H:
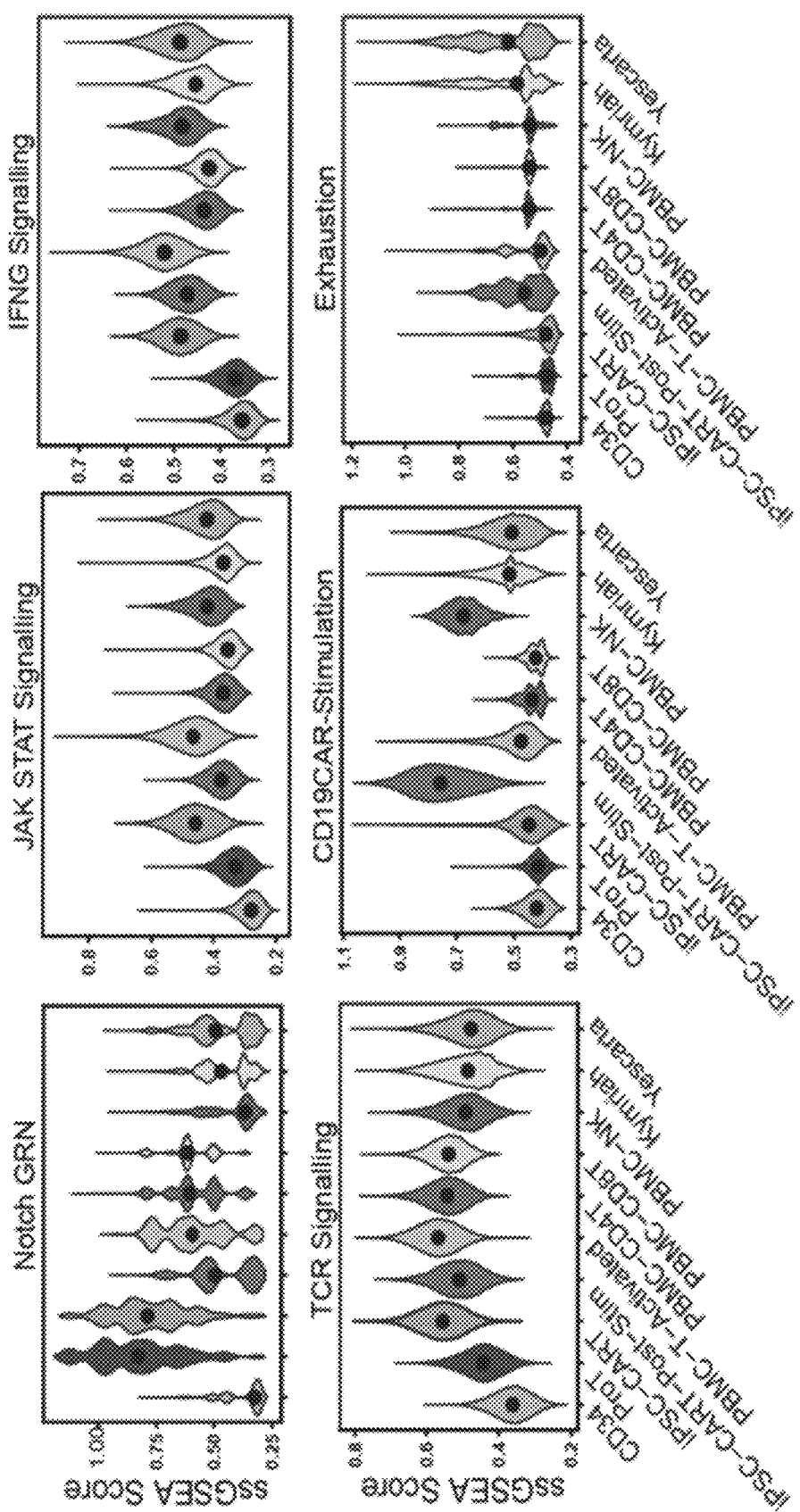

FIG. 29H are graphs depicting expression of transcriptional pathway signatures (ssGSEA scores) as noted across samples.

Figure 29I:
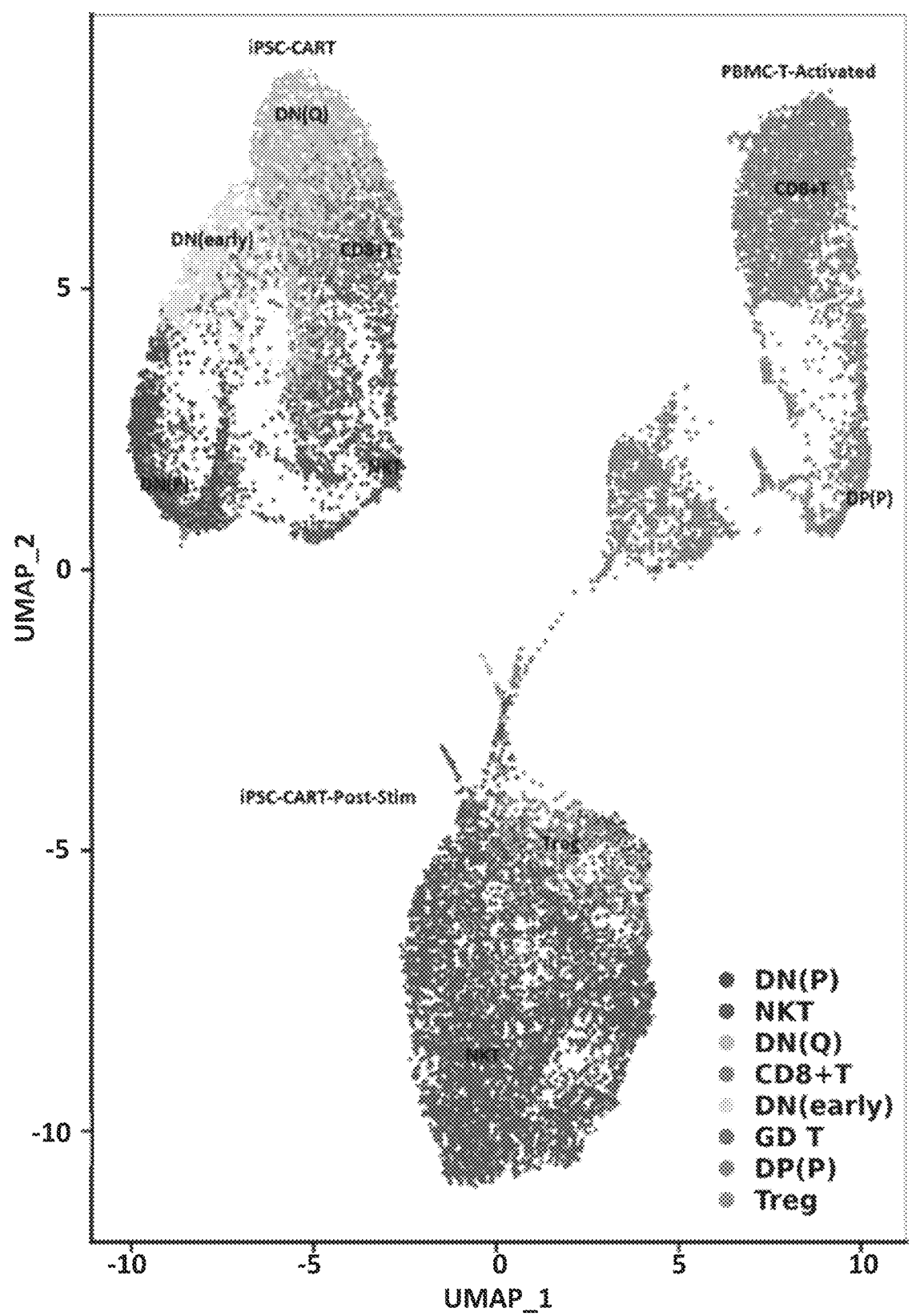

FIG. 29I is a UMAP plot of single cell transcriptomes focused on iPSC-CD8+ cells, iPSC-CD8+ cells post antigen stimulation, and activated T cells, annotated by transcriptional similarity to developing thymocytes (DN-proliferation, DN-early, DN-quiescent, CD8+T, NKT, gamma-delta T (GDT), DP-proliferating, and Treg).

FIG. 29J is a plot of emergence of different cell phenotypes in CAR-iPSC-derived cells as determined by single cell lineage inference and pseudo-time organization.

FIG. 29K is a plot of emergence of transcriptional pathways in CAR-iPSC-derived cells as determined by single cell lineage inference and pseudo-time organization.

Figure 30A:
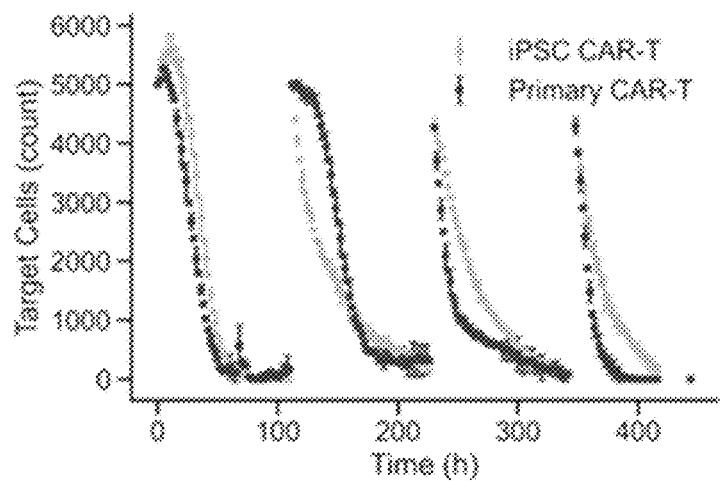

FIG. 30A is a graph depicting target cell (CD19-expressing A549) dynamics over four rounds of in vitro killing assay with primary CAR-Ts vs. iPSC-CD8 cells. Cell density readout using Incucyte® live cell imaging, wherein Effector T cells were added at 2:1 E:T ratios (mean±standard deviation, n=3).

Figure 30B:
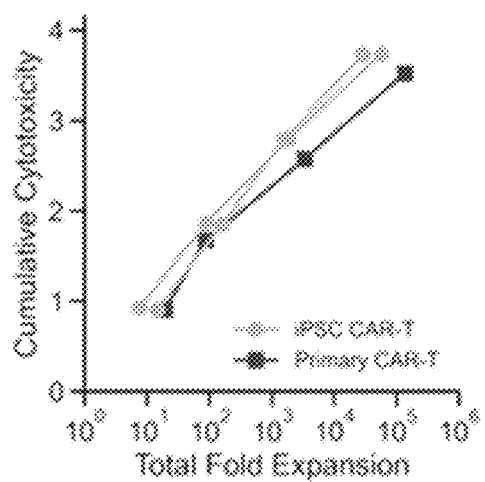

FIG. 30B is a graph depicting in vitro cytotoxicity vs. Effector cell expansion for primary CARTs vs. iPSC-CARTs (n=2 replicates). Cumulative cytotoxicity is the sum of relative change in AUC from a target cell only control on each stimulation (not shown).

Figure 30C:
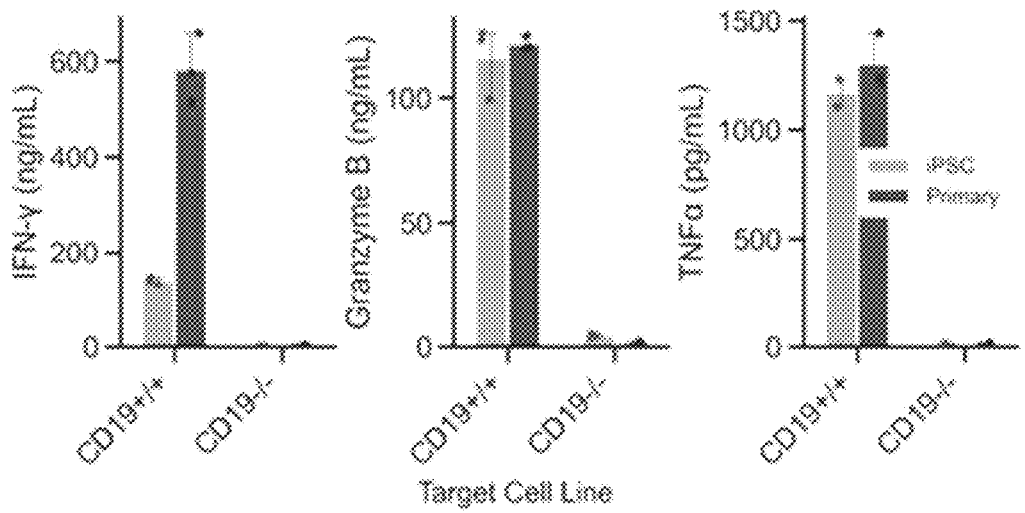

FIG. 30C is graphs depicting secretion of inflammatory cytokines IFN-γ, granzyme B, and tumour necrosis factor α (TNFα) by iPSC-derived T cells and primary CAR-T cells upon co-culture with antigen expressing target cells.

FIG. 31A is a schematic of the 3D Engineered Thymic Niche (ETN) platform for scalable T-cell manufacturing using iPSC derived CD34+ HPCs.

FIG. 31B is a graph depicting quantification of flow cytometry data showing percentage of CD4−CD8− (double-negative, DN), CD4+CD8− (CD4 ISP), CD4+CD8+ (double-positive, DP), and CD4−CD8+(CD8 single-positive, CD8SP) cells following microplate culture differentiation of iPSC-derived CD34+ HPCs generated in the STR, with differentiation of iPSC-derived HPCs generated in microplate culture as a reference (mean±SEM, 3 independent STR runs, n=6 bioreactors).

Figure 31C:
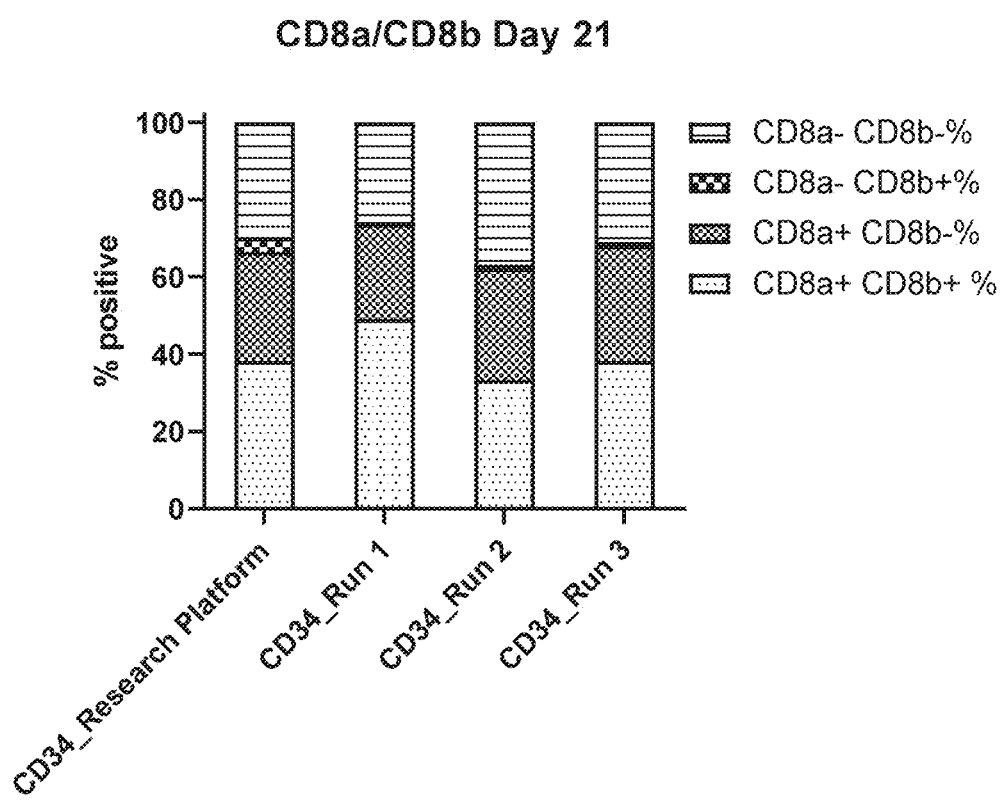

FIG. 31C is a graph depicting quantification of flow cytometry data showing percentage of CD8α (CD8a)− and CD8β (CD8b)-expressing cells following microplate culture differentiation of iPSC-derived CD34+ HPCs (mean±SEM, 3 independent STR runs, n=6 bioreactors).

Figure 32A:
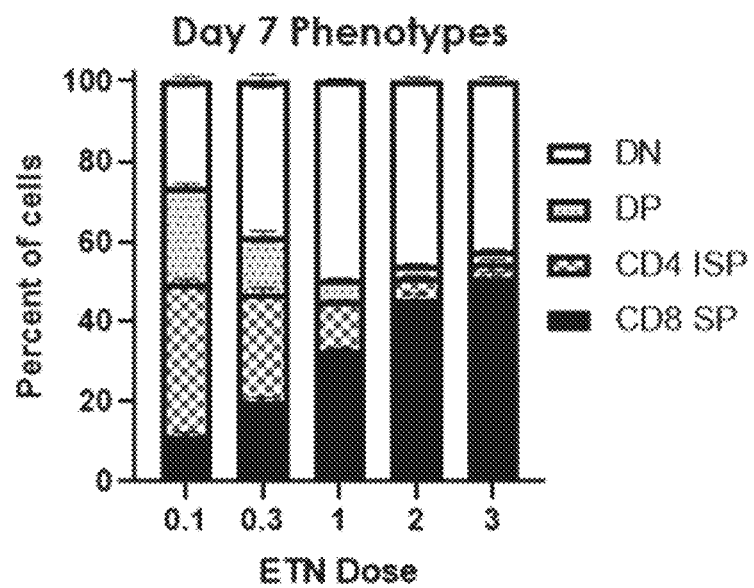

FIG. 32A is a graph depicting quantification of flow cytometry data showing percentage of CD4−CD8− (double-negative, DN), CD4+CD8− (CD4 ISP), CD4+CD8+ (double-positive, DP), and CD4−CD8+(CD8 single-positive, CD8SP) cells following microplate culture of iPSC-derived ProT cells for 7 days with 30-fold range of ETN dose (from 0.1× to 3× bead dose, or 5.4×10$^6$ beads/mL to 1.62×10$^8$ beads/mL).

Figure 32B:
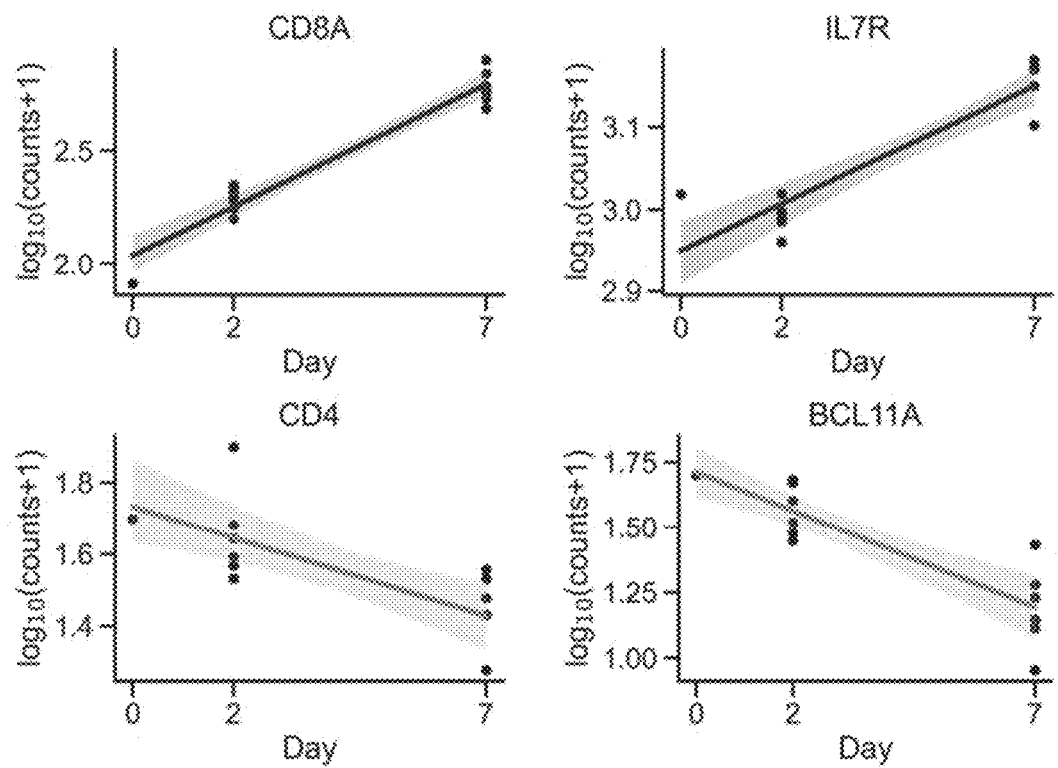

FIG. 32B is graphs depicting the expression of CDBA, IL7R, CD4, and BCL11A genes over 7 days following culture with ETN at a bead dose of 2× or 3× (1.08×10$^8$ beads/mL or 1.62×10$^8$ beads/mL).

Figure 33A:
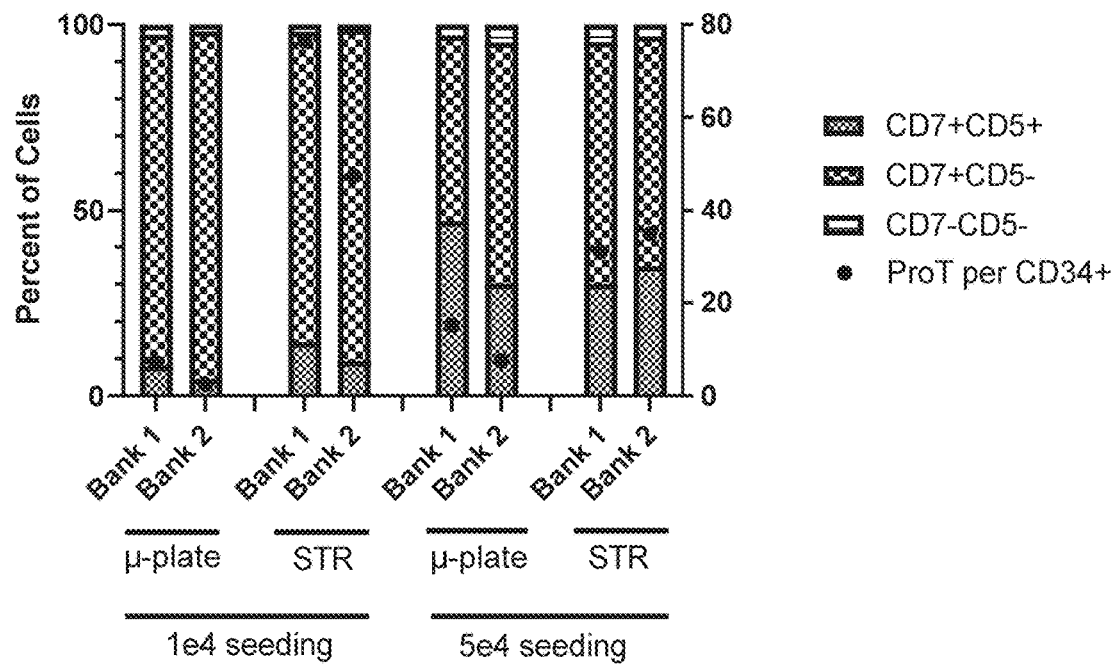

FIG. 33A is a graph depicting quantification of flow cytometry data showing CD7 and CD5 expression and percentage of total ProT cell population following 10 days of culture of iPSC-derived CD34+ cells in microplates and STR with the 3D ETN. Two (2) CD34+ cell banks were seeded in duplicate at 1×10$^4$ and 5×10$^4$ cells/mL in DAS-box® bioreactors (Eppendorf) and in 24-well plates.

Figure 33B:
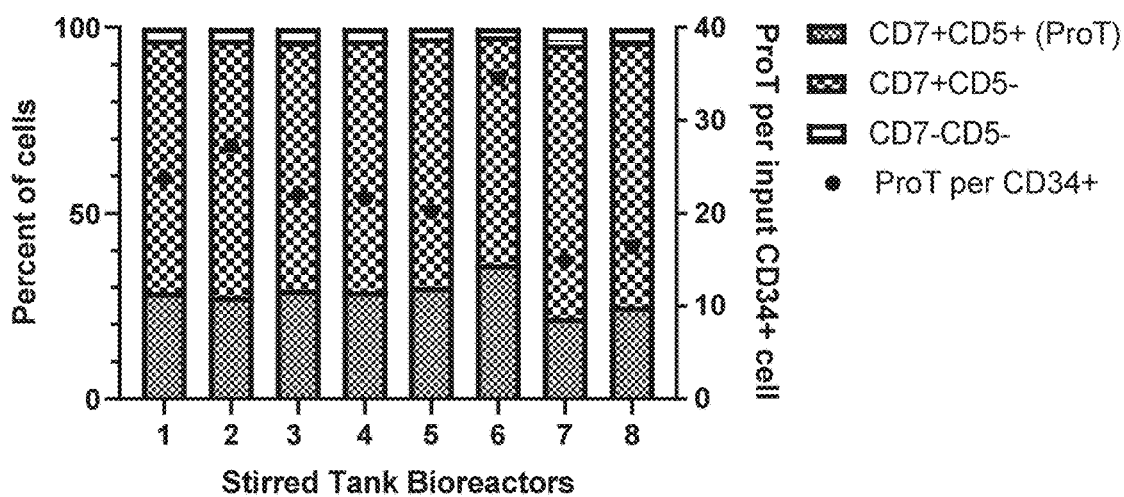

FIG. 33B is a graph depicting quantification of flow cytometry data showing CD7 and CD5 expression and percentage of total ProT cell population following 10 days of culture of CD34+ cells with the 3D ETN. One CD34+ cell bank was seeded in eight (8) bioreactors at 5×10$^4$ cells/mL.

Figure 34A:
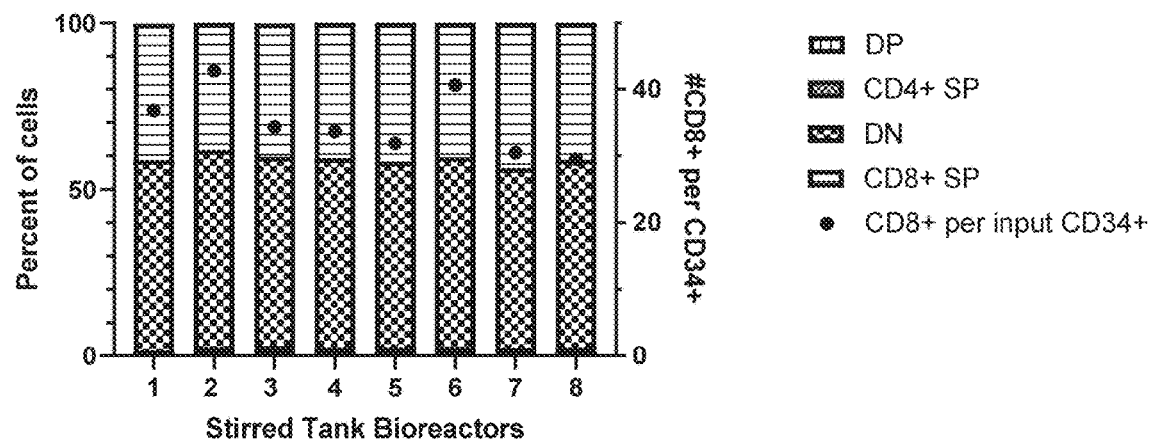

FIG. 34A is a graph depicting quantification of flow cytometry data showing percentage of CD4−CD8− (double-negative, DN), CD4+CD8− (CD4 ISP), CD4+CD8+ (double-positive, DP), and CD4−CD8+(CD8 single-positive, CD8SP) cells and yield of CD8+ cells following culture of ProT cells for 11 days with ETN at a 2.5× bead dose (1.35×10$^8$ beads/mL) in eight (8) bioreactors.

Figure 34B:
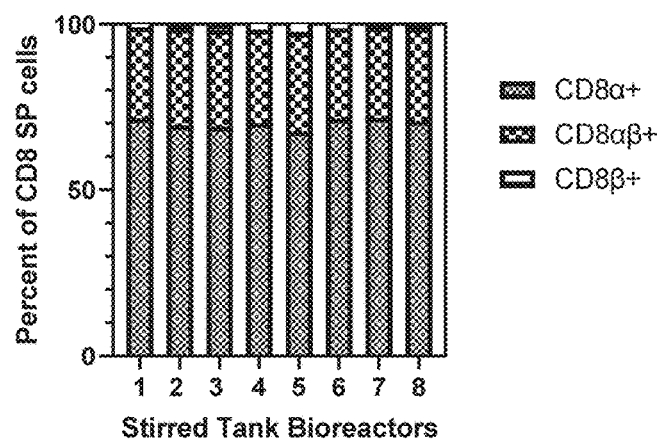

FIG. 34B is a graph depicting quantification of flow cytometry data showing percentage of CD8α+, CD8αβ+, and CD8β+ cells at day 8 of maturation with ETN at a 2.5× bead dose (1.35×10$^8$ beads/mL) in eight (8) bioreactors.

Figure 35A:
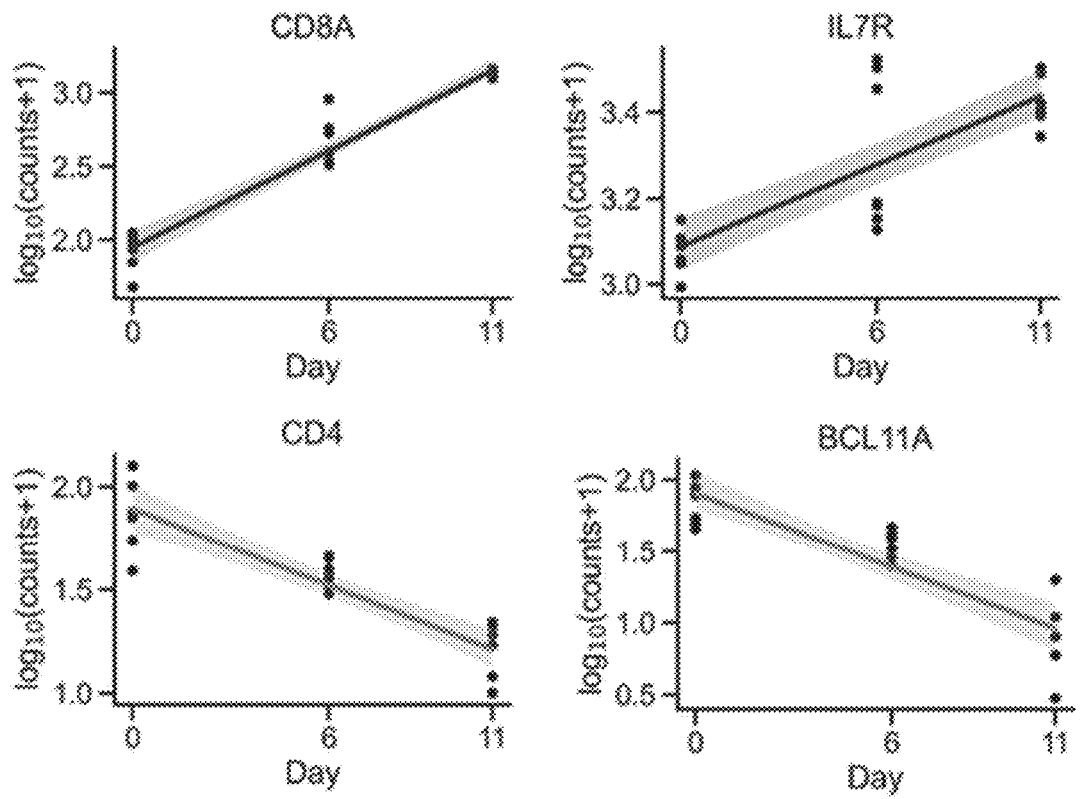

FIG. 35A is a graph depicting the expression of CD8A, IL7R, CD4, and BCL11A genes over 7 days in culture with ETN at a 2.5× bead dose (1.35×10$^8$ beads/mL) in the STR system.

Figure 35B:
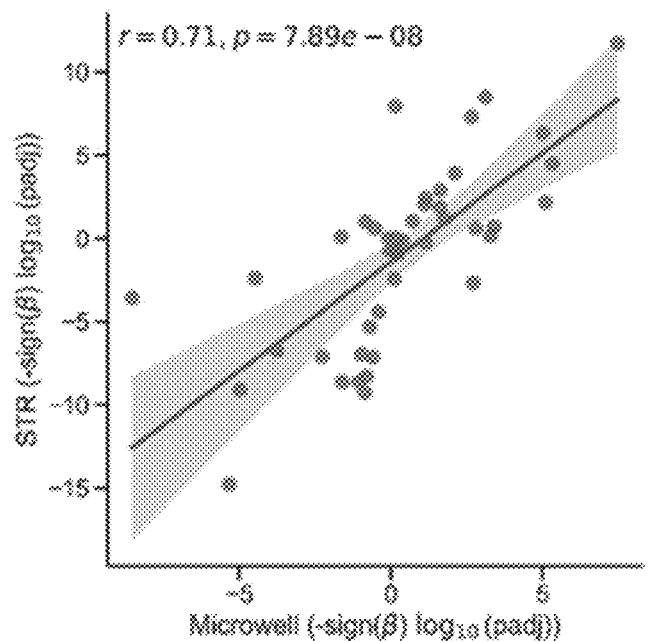

FIG. 35B is a graph depicting the correlation (Pearson's r=0.71, p<0.001) between gene expression following culture in microplates ("Microwell") or stirred tank bioreactor ("STR") systems with the 3D ETN for a panel of 24 genes related to leukocyte development.

Figure 36A:
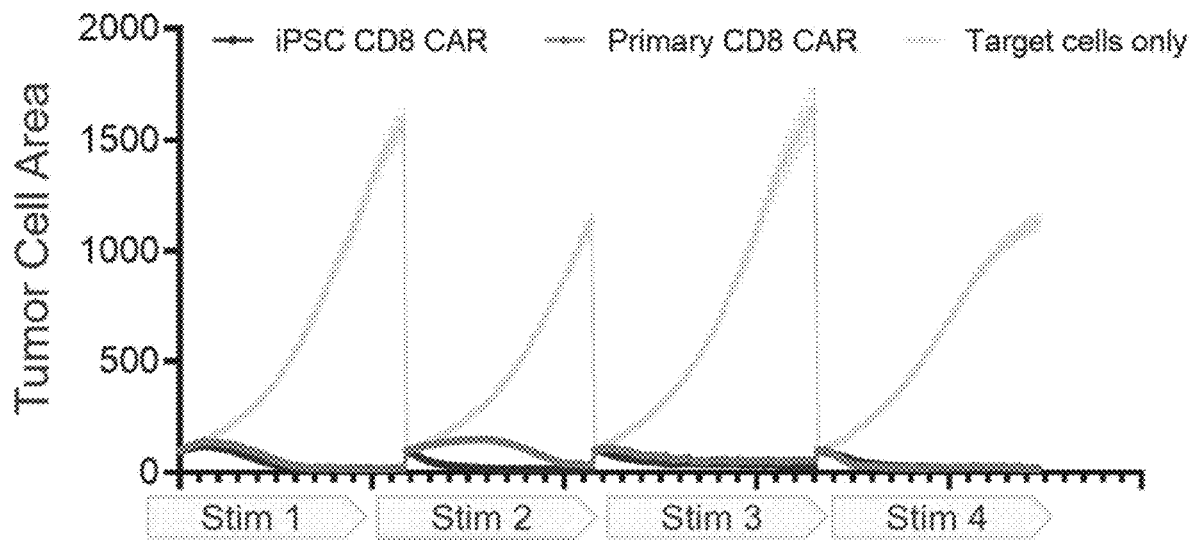

FIG. 36A is a graph depicting a serial restimulation assay to measure cytotoxic activity of iPSC-derived CD8+ CAR-T cells ("iPSC CD8 CAR") or primary CD8+ CAR-T cells ("Primary CD8 CAR"), with GFP-expressing CD19+ cells as target cells (n=3 technical replicates).

Figure 36B:
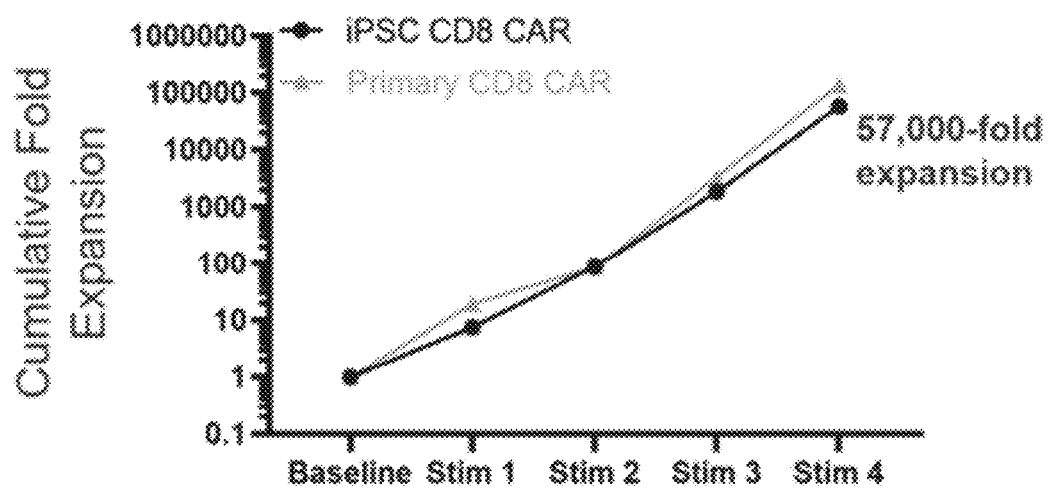

FIG. 36B is a graph depicting fold-expansion of iPSC-derived CD8+ CAR-T cells ("iPSC CD8 CAR") or primary CD8+ CAR-T cells ("Primary CD8 CAR") at the end of each round of target exposure. Cumulative fold expansion for iPSC-derived CD8+ CAR-T cells is noted in bold letters.

Figure 36C:
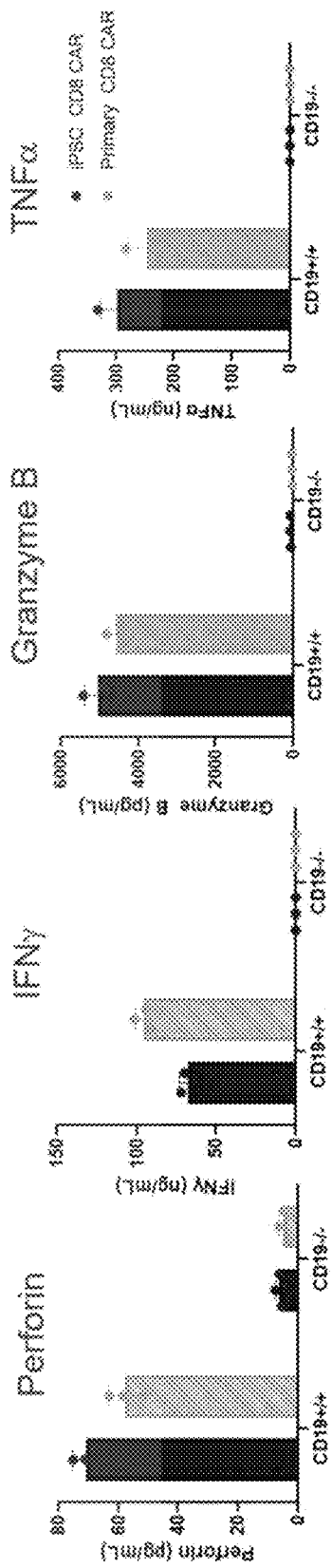

FIG. 36C is graphs depicting target cell-specific secretion of the effector molecules perforin (far left), interferon-γ (IFNγ, centre left), granzyme B (centre right), and tumour necrosis factor α (TNFα, far right) by iPSC-derived CD8+ CAR-T cells ("iPSC CD8 CAR") or primary CD8+ CAR-T cells ("Primary CD8 CAR").

Figure 36E:
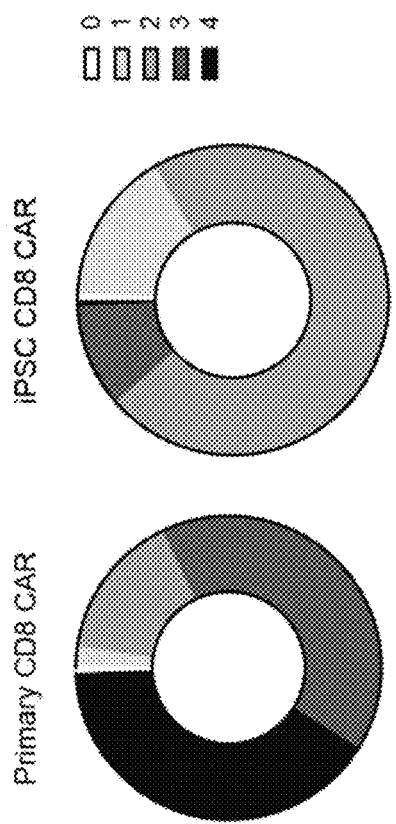
Figure 36D:
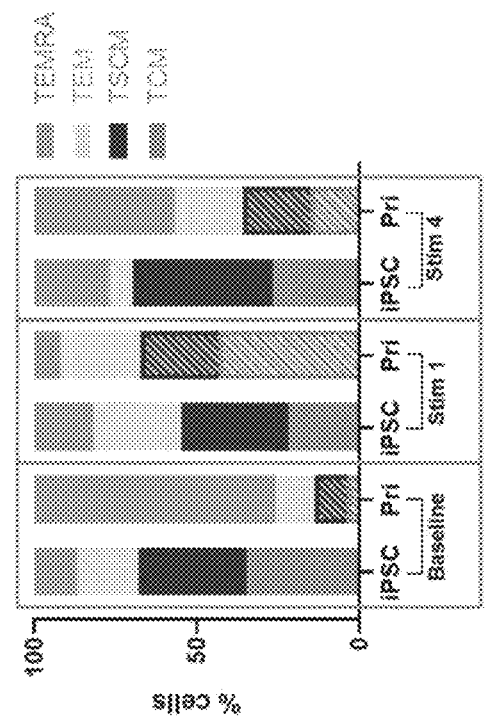

FIG. 36D is a graph depicting the percentage of T-cell subsets for iPSC-derived CD8+ CAR-T cells ("iPSC CD8 CAR") or primary CD8+ CAR-T cells ("Primary CD8 CAR") before (Baseline) and after one ("Stim 1") or four ("Stim 4") rounds of the serial restimulation assay. T-cell subsets were classified based on the expression of CD45RA, CD62L and CD95, as measured by flow cytometry.

FIG. 36E is graphs depicting the expression of T-cell exhaustion markers PD1, TIM3, LAG3, TIGIT and CD39 in primary CD8+ CAR-T cells ("Primary CD8 CAR") or iPSC-derived CD8+ CAR-T cells ("iPSC CD8 CAR"). Sections indicate the percentage of cells expressing none ("0"), one ("1"), two ("2"), three ("3"), or four ("4") of these markers.

Figure 37A:
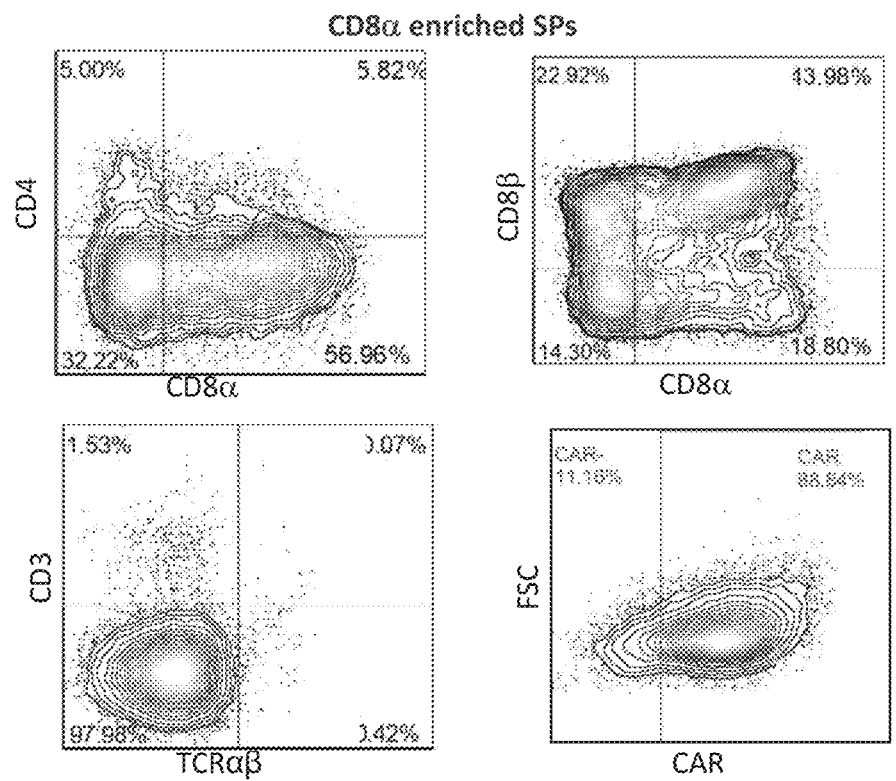

FIG. 37A is flow cytometry plots of iPSC-derived CAR+ CD8+ cells after CD8α enrichment.

Figure 37B:
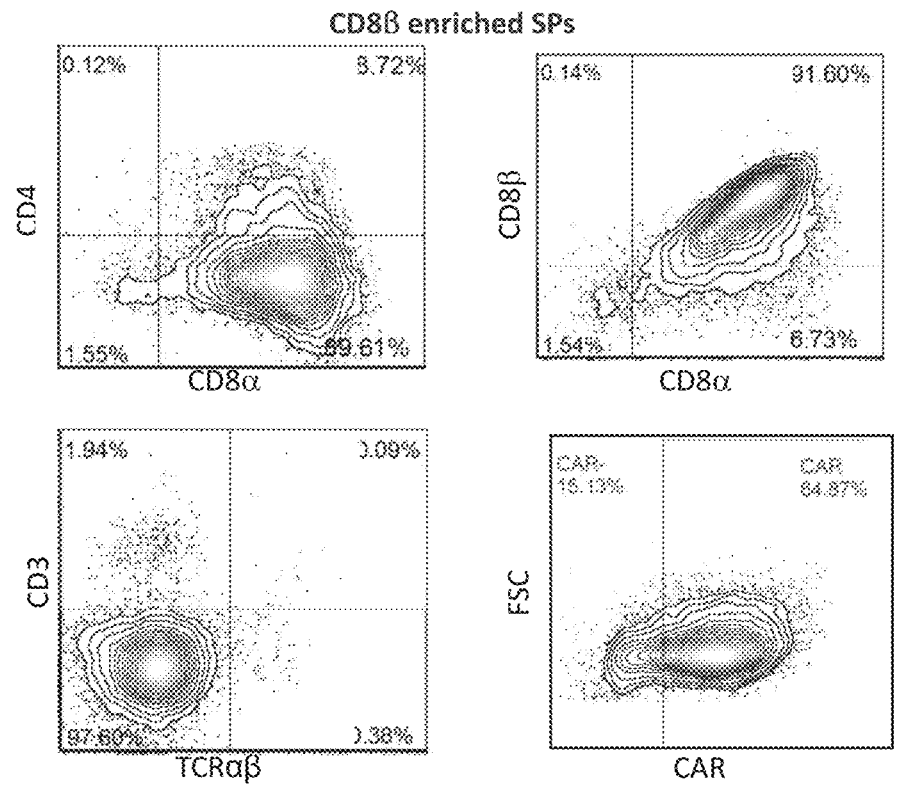

FIG. 37B is flow cytometry plots of iPSC-derived CAR+ CD8+ cells after CD8β enrichment.

Figure 38A:
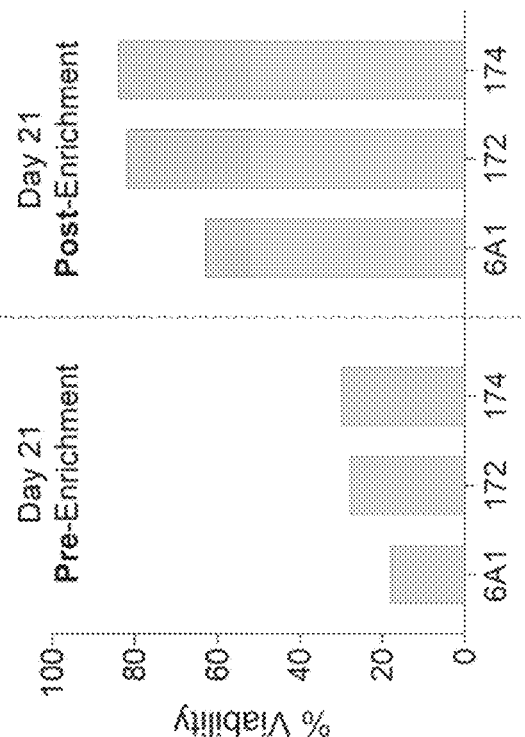

FIG. 38A is a graph depicting viability of unmodified ("6A1") and TCR-modified ("172", "174") iPSC-derived cells during differentiation.

Figure 38B:
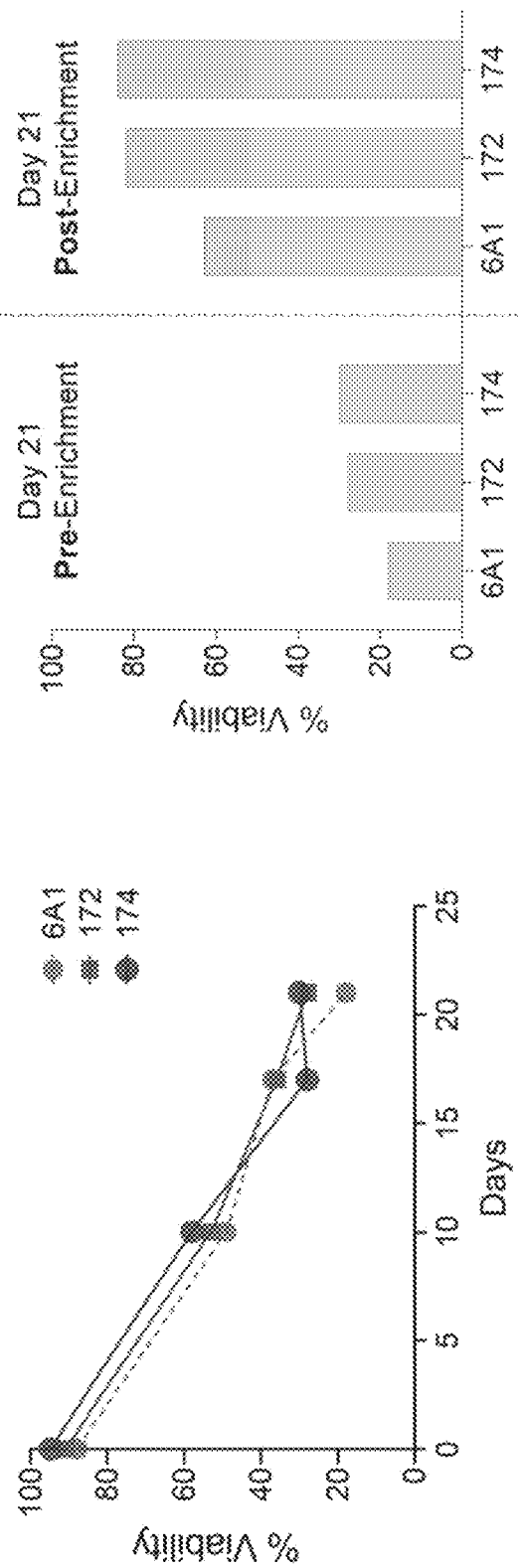

FIG. 38B is a graph depicting pre- and post-enrichment viability for unmodified ("6A1") and TCR-modified ("172", "174") iPSC-derived cells following differentiation.

Figure 38C:
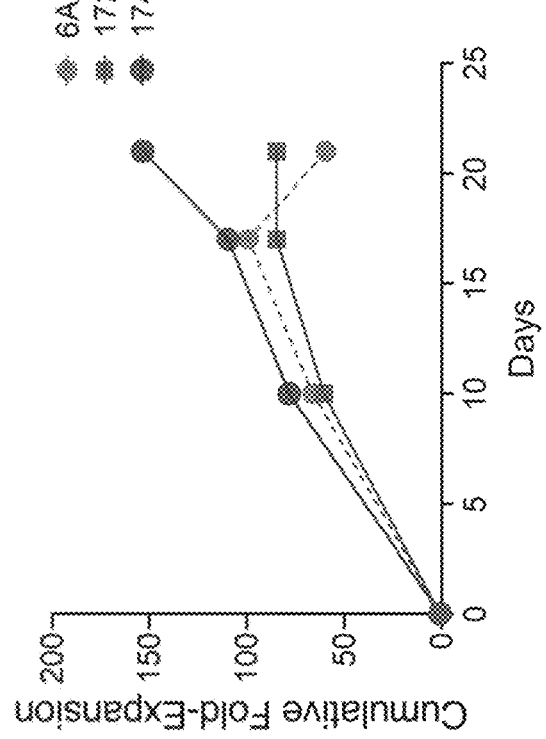

FIG. 38C is a graph depicting cumulative fold expansion for unmodified ("6A1") and TCR-modified ("172", "174") iPSC-derived cells during differentiation.

Figure 39A:
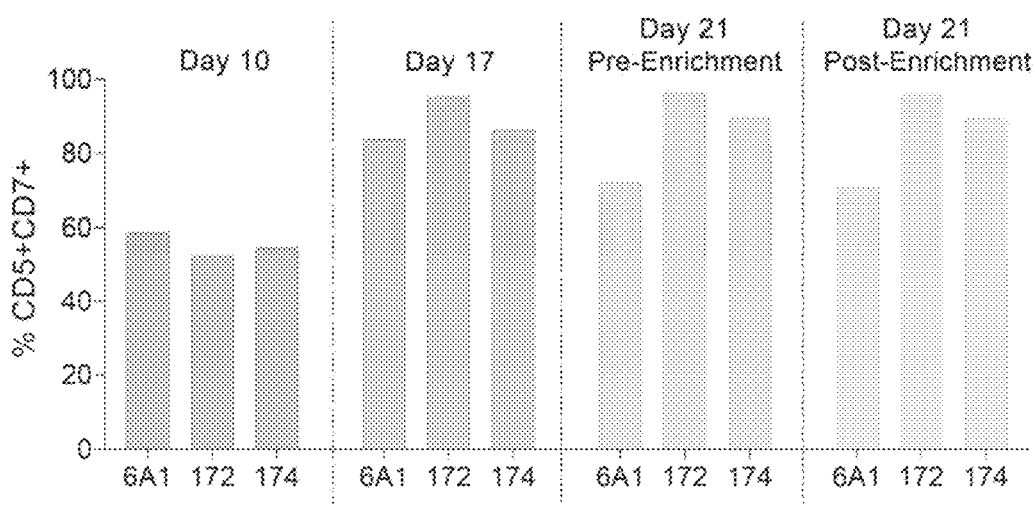

FIG. 39A is a graph depicting CD5 and CD7 co-expression for unmodified ("6A1") and TCR-modified ("172", "174") iPSC-derived cells at indicated time points.

Figure 39B:
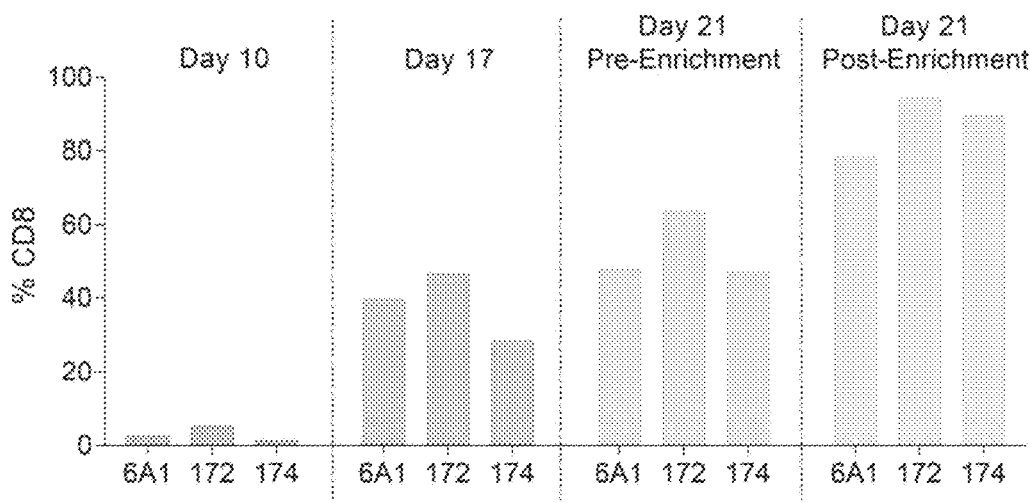

FIG. 39B is a graph depicting CD8 expression for unmodified ("6A1") and TCR-modified ("172", "174") iPSC-derived cells at indicated time points.

Figure 39C:
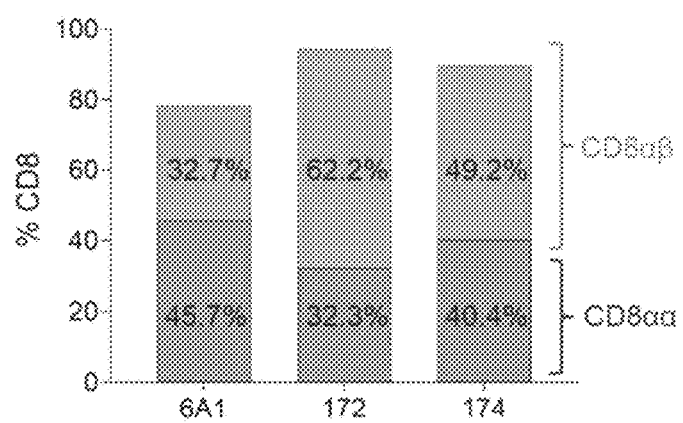

FIG. 39C is a graph depicting CD8α and CD8β expression for unmodified ("6A1") and TCR-modified ("172", "174") iPSC-derived cells following differentiation and enrichment.

Figure 40:
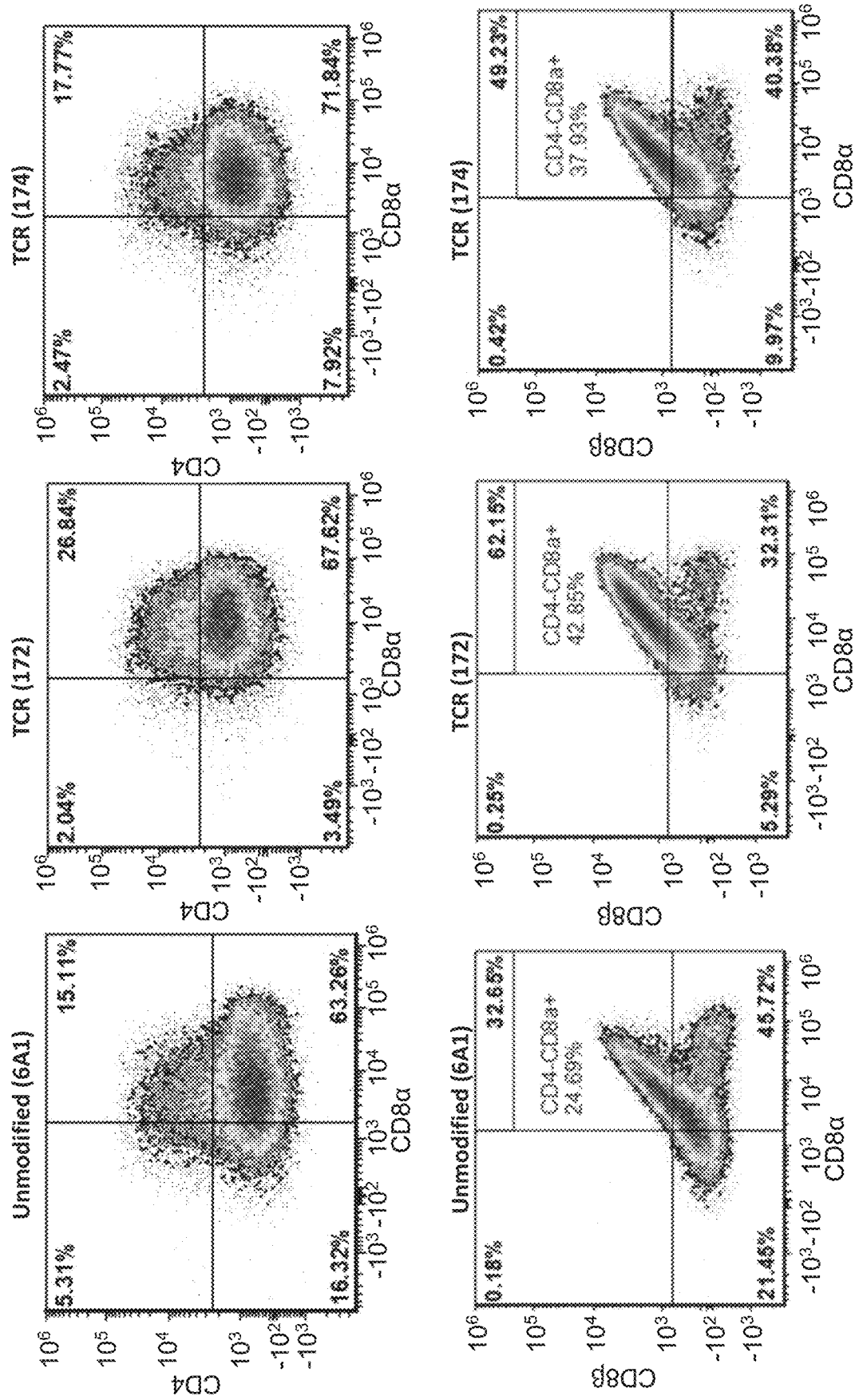

FIG. 40 is flow cytometry plots of cells differentiated from unmodified or TCR-modified iPSCs ("Unmodified (6A1)", "TCR (172)", or "TCR (174)").

Figure 41A:
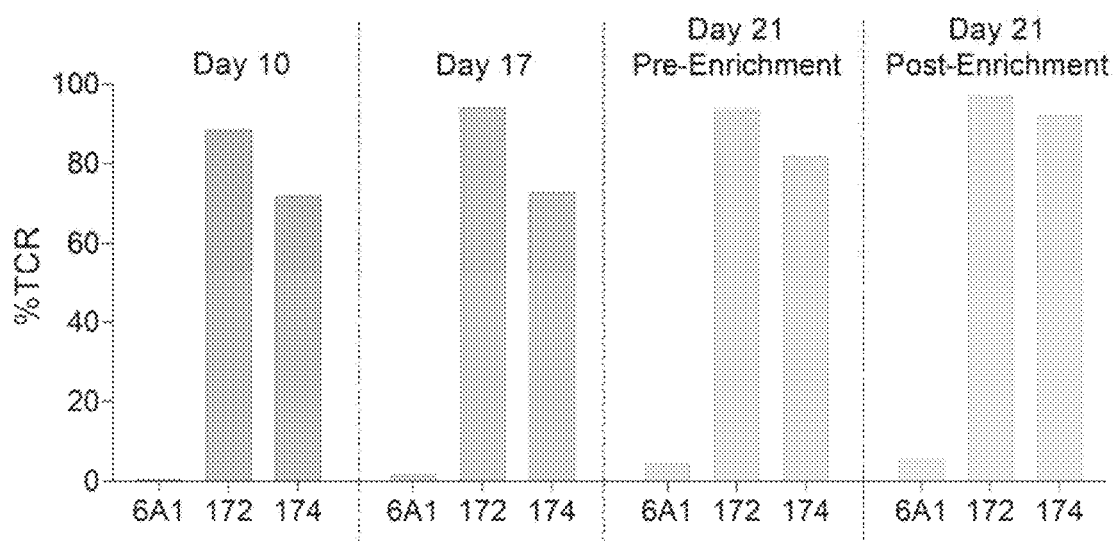

FIG. 41A is a graph depicting TCR expression for unmodified ("6A1") and TCR-modified ("172", "174") iPSC-derived cells at indicated time points.

Figure 41B:
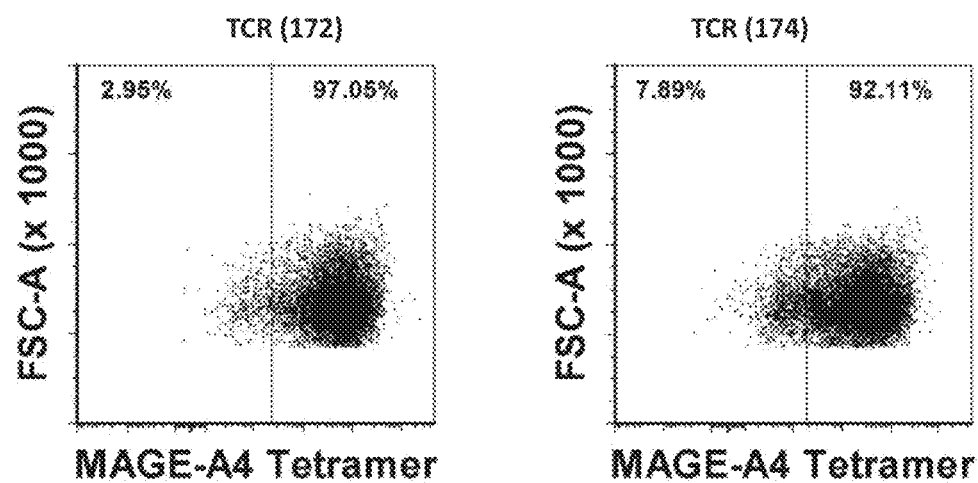

FIG. 41B is flow cytometry plots of TCR (MAGE-A4) expression for TCR-modified ("172", "174") iPSC-derived cells following differentiation and enrichment, as determined by tetramer staining.

Figure 42A:
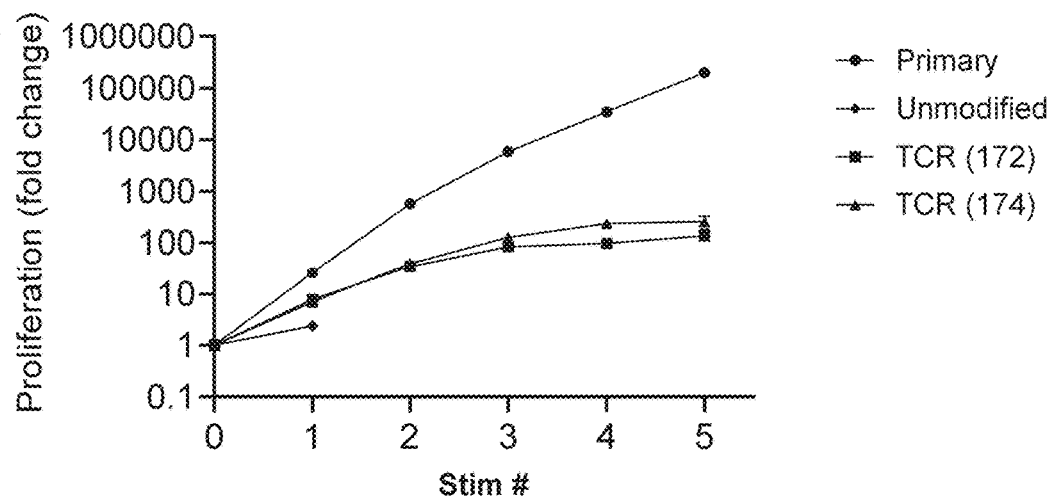

FIG. 42A is a graph depicting fold change in proliferation for primary T cells and unmodified ("6A1") and TCR-modified ("172", "174") iPSC-derived CD8+ cells during an in vitro serial restimulation assay.

Figure 42B:
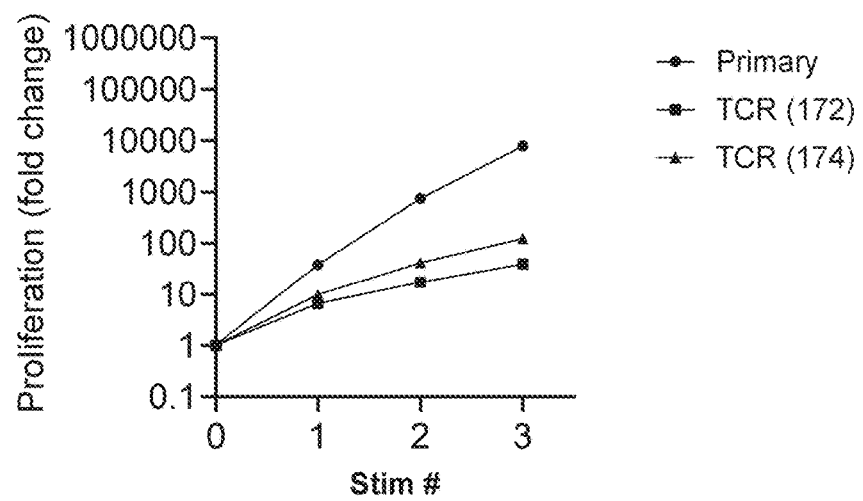

FIG. 42B is a graph depicting fold change in proliferation for primary T cells and TCR-modified ("172", "174") iPSC-derived CD8+ cells during an in vitro serial restimulation assay.

Figure 43:
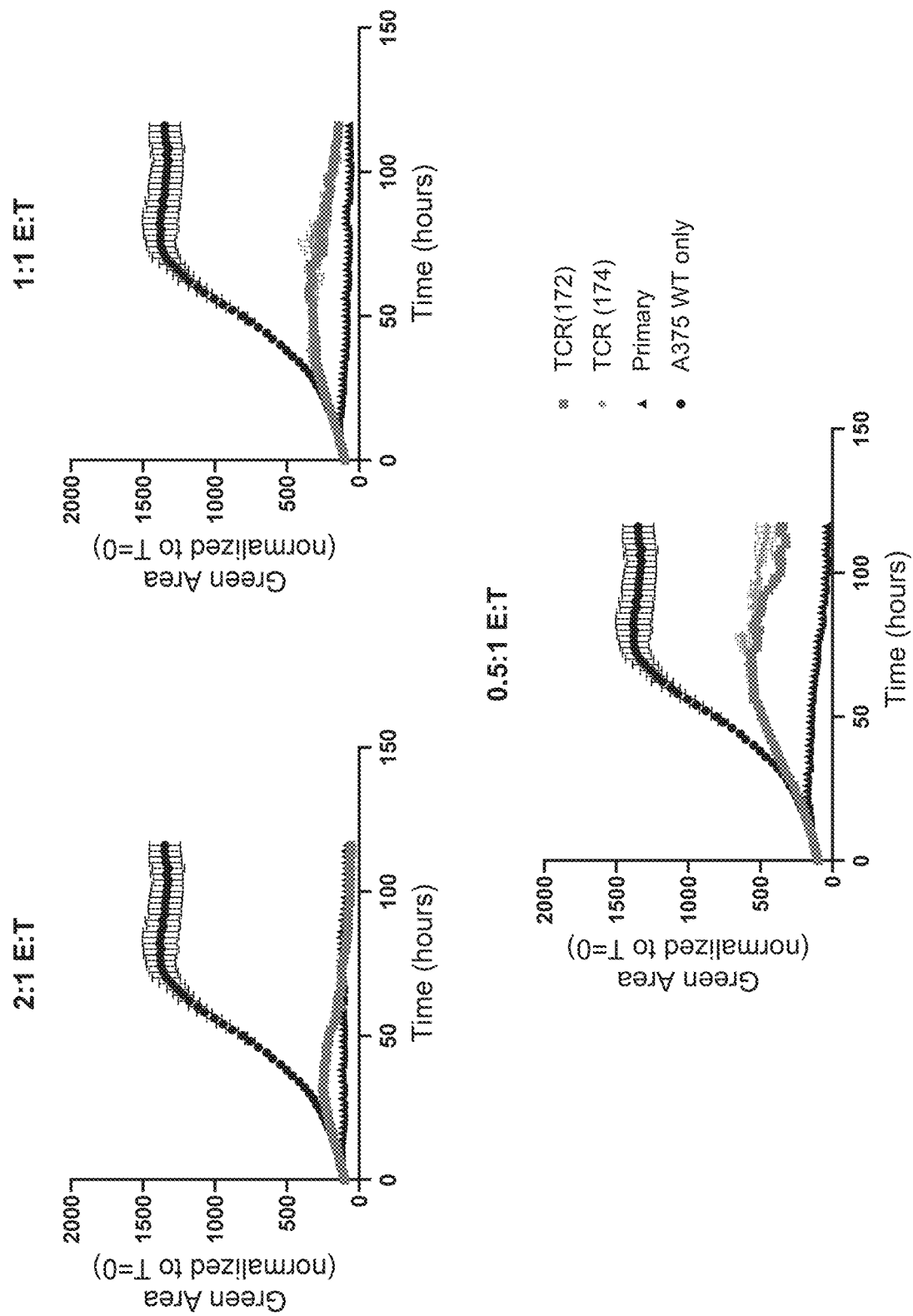

FIG. 43 is graphs depicting cytotoxicity of primary T cells and TCR-modified ("172", "174") iPSC-derived CD8+ cells in vitro against A375 target cells at varying effector to target (E:T) ratios, as indicated.

FIG. 44A is a graph depicting cytotoxicity of primary T cells and TCR-modified ("174") iPSC-derived CD8+ cells during an in vitro serial restimulation assay with A375 target cells, compared to target cell and unmodified iPSC-derived cell controls.

FIG. 44B is a graph depicting cytotoxicity of primary T cells and TCR-modified ("174") iPSC-derived CD8+ cells, enlarged from FIG. 44A.

FIG. 44C is a graph depicting cytotoxicity of primary T cells and TCR-modified ("174") iPSC-derived CD8+ cells during an in vitro serial restimulation assay with A375 target cells, compared to target cell and unmodified iPSC-derived cell controls.

FIG. 44D is a graph depicting cytotoxicity of primary T cells and TCR-modified ("174") iPSC-derived CD8+ cells, enlarged from FIG. 44C.

Figure 45:
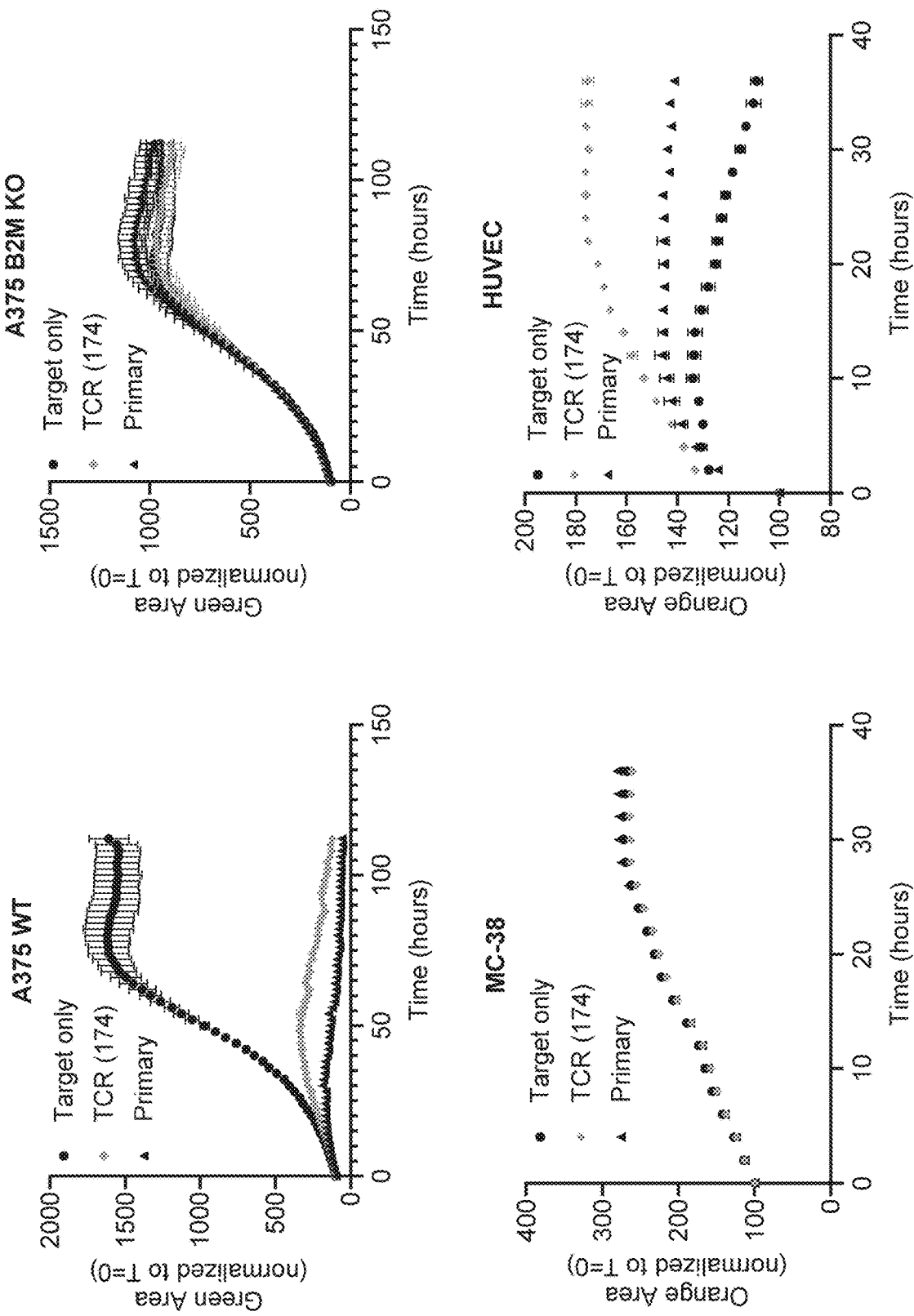

FIG. 45 is graphs depicting in vitro cytotoxicity of primary T cells and TCR-modified ("174") iPSC-derived CD8+ cells against varying target cells, as indicated.

Figure 46A:
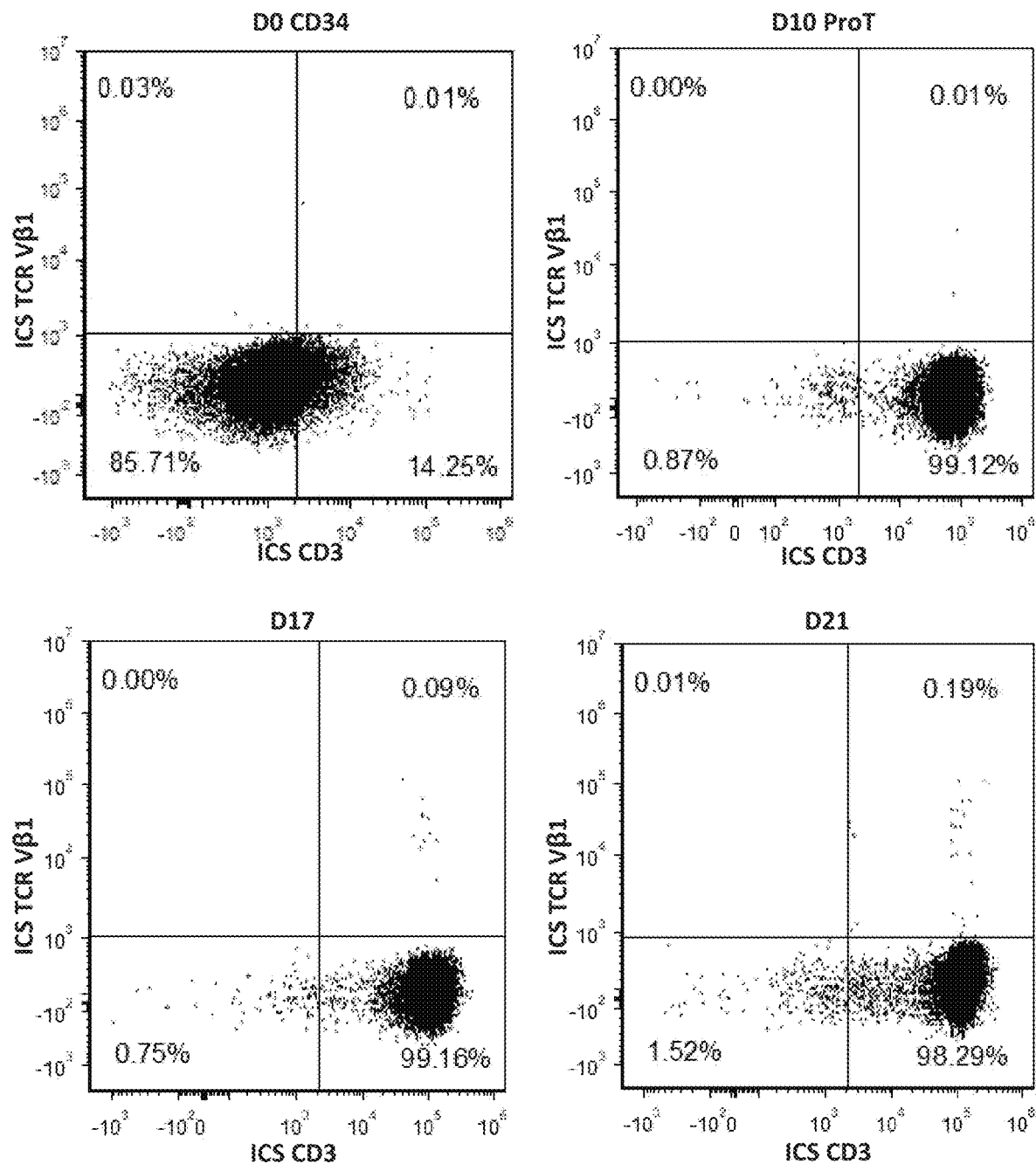

FIG. 46A is flow cytometry plots of iPSC-derived cells during differentiation, at indicated timepoints. Cells were analyzed for intracellular ("ICS") TCRβ and CD3.

FIG. 46B is a flow cytometry plot of iPSC-derived cells at day 24 of differentiation. Cells were analyzed for intracellular ("ICS") TCRβ and CD3.

FIG. 46C is a graph depicting viability and expression of CD4 and/or CD8α for iPSC-derived cells during differentiation.

Figure 47:
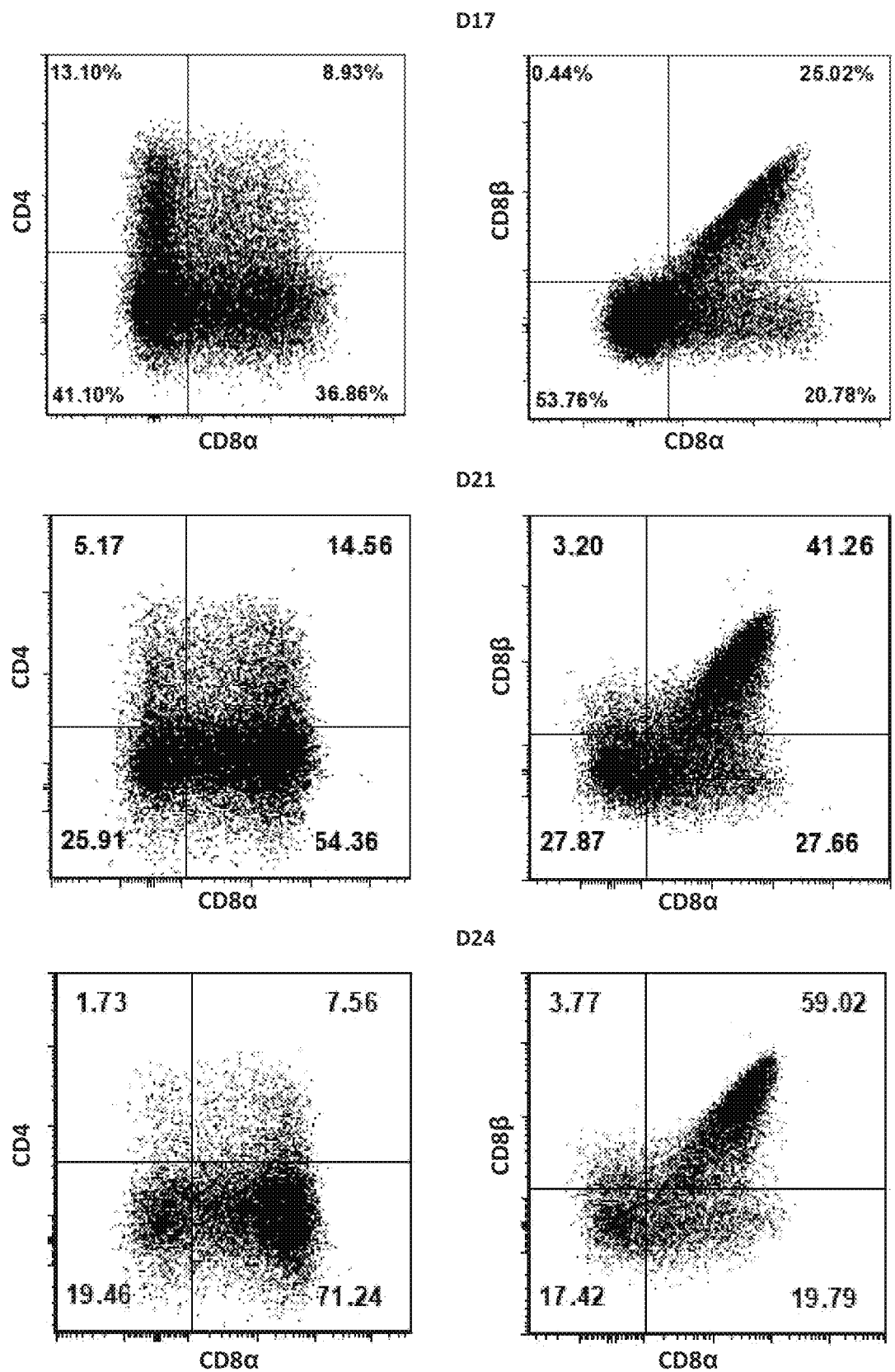

FIG. 47 is flow cytometry plots of iPSC-derived cells during differentiation, at indicated timepoints.

Figure 48:
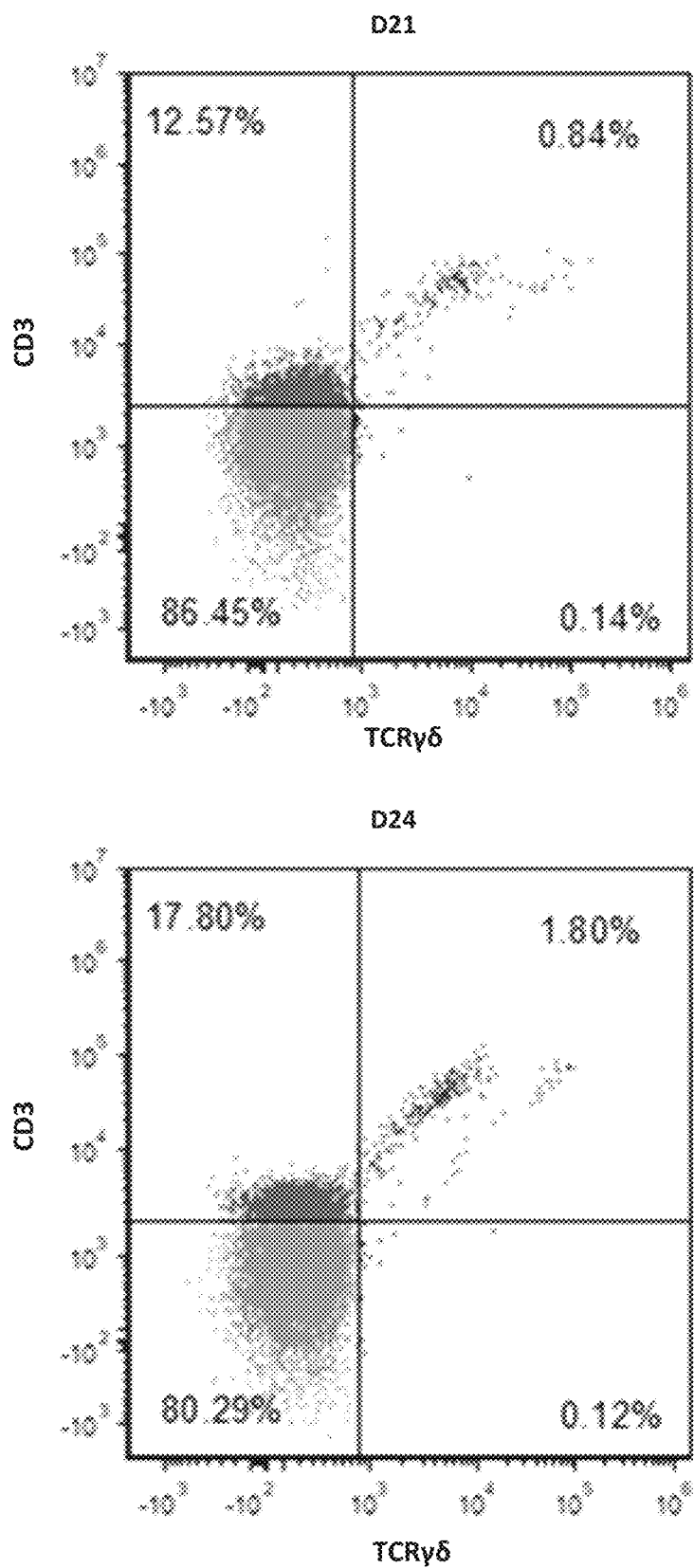

FIG. 48 is flow cytometry plots of iPSC-derived cells during differentiation, at indicated timepoints.

Figure 49A:
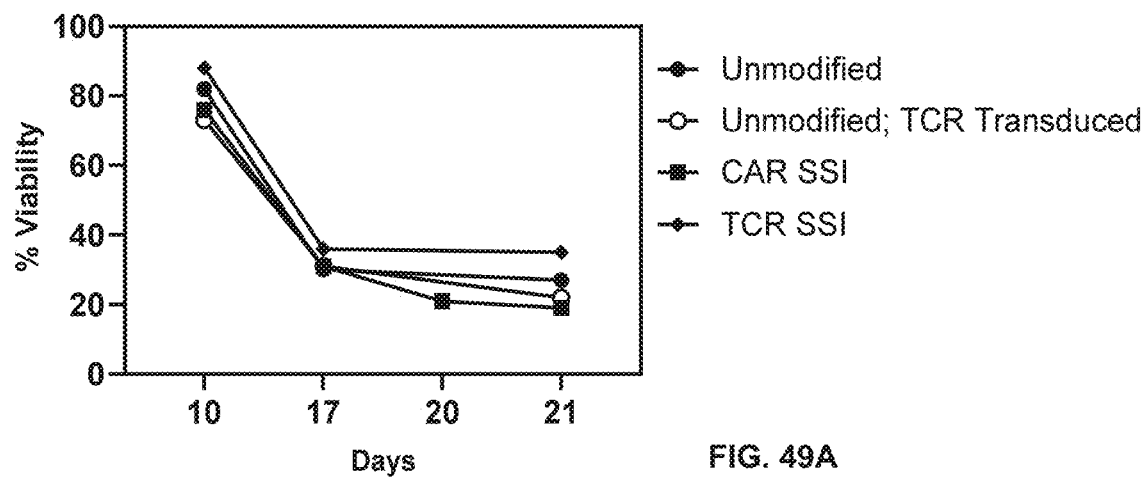

FIG. 49A is a graph depicting viability (FIG. 50A) during differentiation for the following cell lines: unmodified iPSC-derived cells ("Unmodified"), iPSC-derived cells with TCR transduction at day 7 ("Unmodified; TCR Transduced"), CAR-iPSC-derived cells ("CAR SSI") and TCR-iPSC-derived cells ("TCR SSI").

Figure 49B:
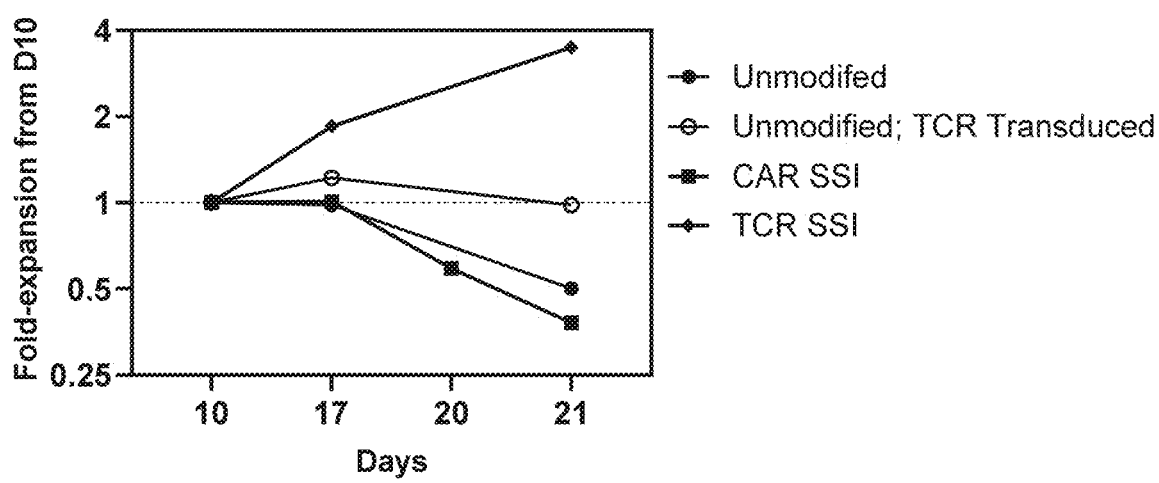

FIG. 49B is a graph depicting fold expansion (FIG. 50B) during differentiation for the following cell lines: unmodified iPSC-derived cells ("Unmodified"), iPSC-derived cells with TCR transduction at day 7 ("Unmodified; TCR Transduced"), CAR-iPSC-derived cells ("CAR SSI") and TCR-iPSC-derived cells ("TCR SSI").

Figure 49C:
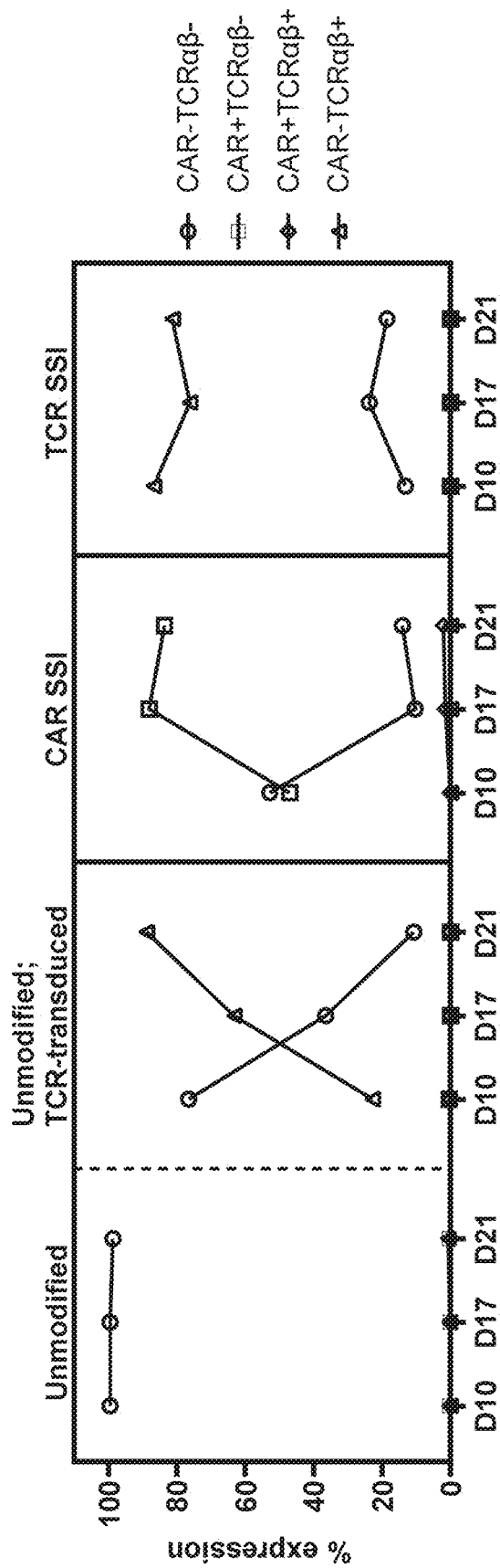

FIG. 49C is a graph depicting expression of CAR and/or TCR for the cell lines of FIG. 49A and FIG. 49B, as described above.

Figure 50A:
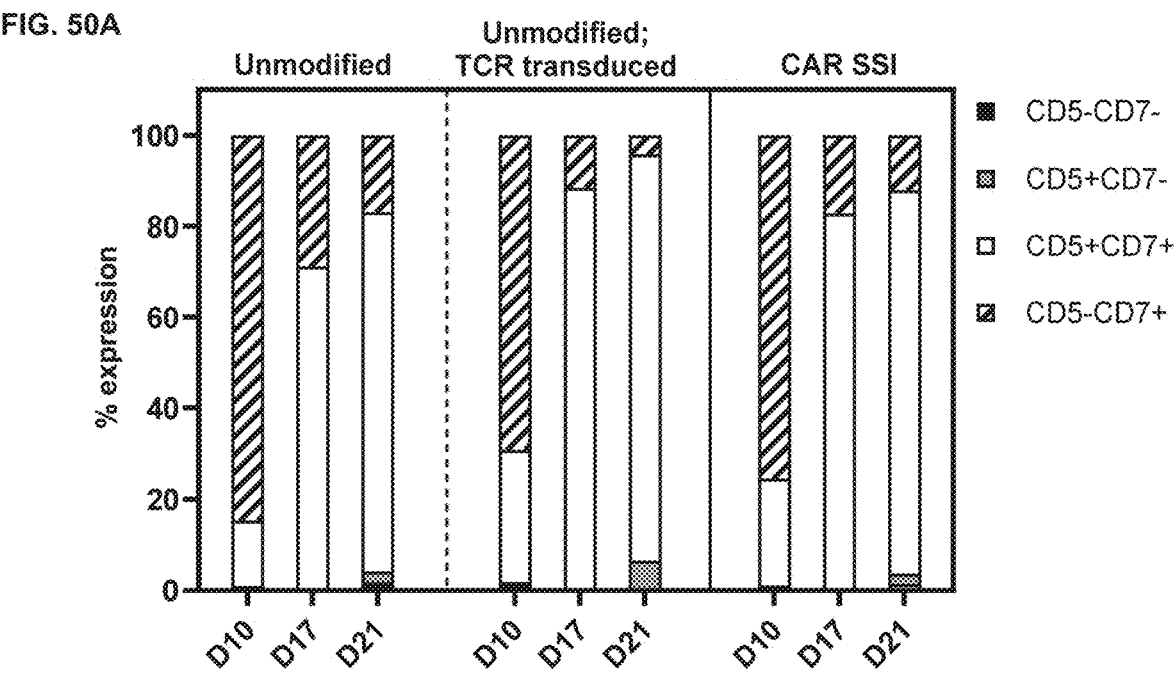

FIG. 50A is a graphs depicting expression of CD5 and/or CD7 (FIG. 50A) for the cell lines of FIG. 49A and FIG. 49B, as described above.

Figure 50B:
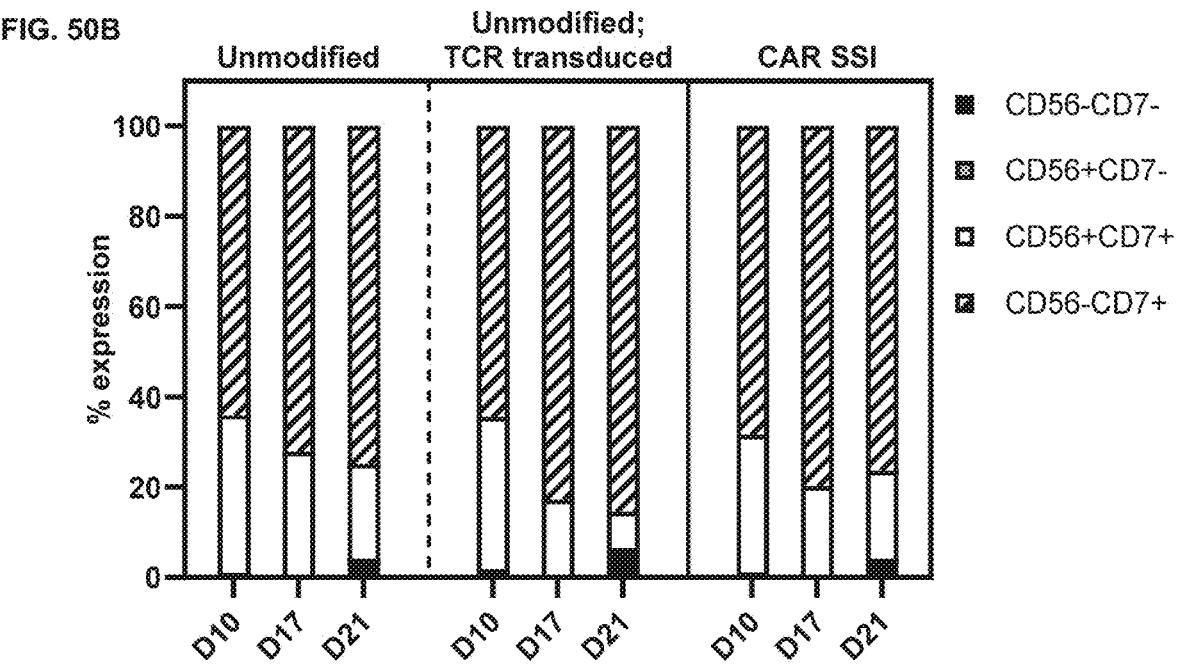

FIG. 50B is a graph depicting expression of CD56 and/or CD7 (FIG. 50B) for the cell lines of FIG. 49A and FIG. 49B, as described above.

Figure 51A:
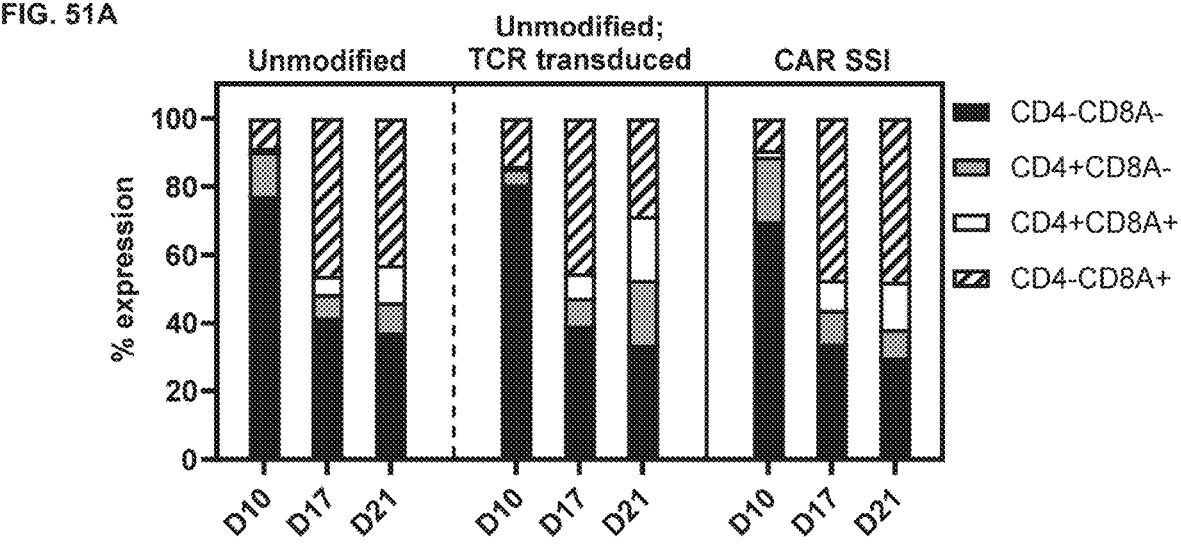

FIG. 51A is a graph depicting expression of CD4 and/or CD8α for the cell lines of FIG. 49A and FIG. 49B, as described above.

Figure 51B:
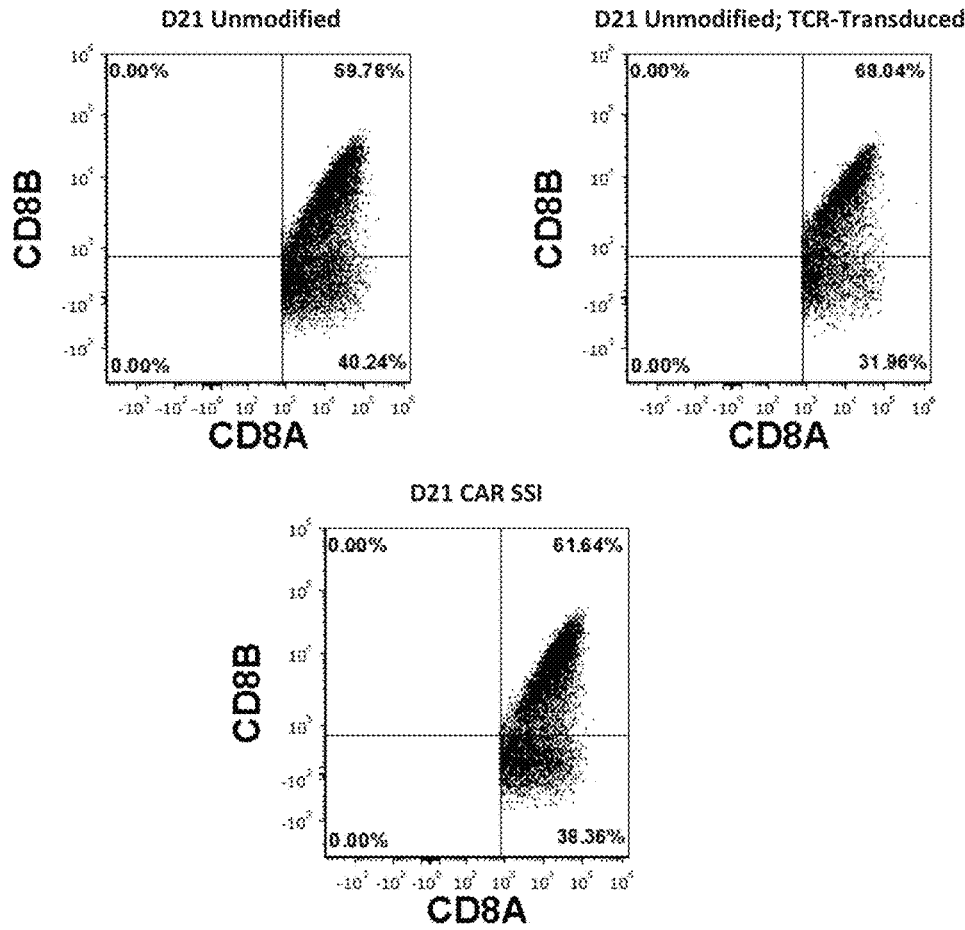

FIG. 51B is flow cytometry plots of CD8α and CD8β expression at day 21 of differentiation. Cells were sub-gated on CD4−CD8α+.

Figure 52A:
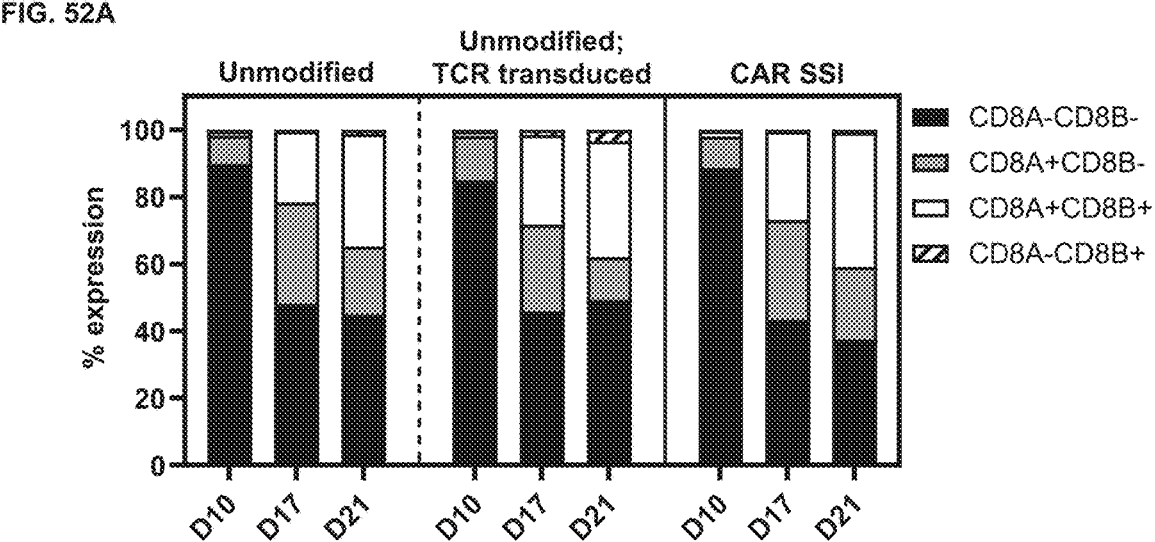

FIG. 52A is a graph depicting expression of CD8α and/or CD8β for the cell lines of FIG. 49A and FIG. 49B, as described above.

Figure 52B:
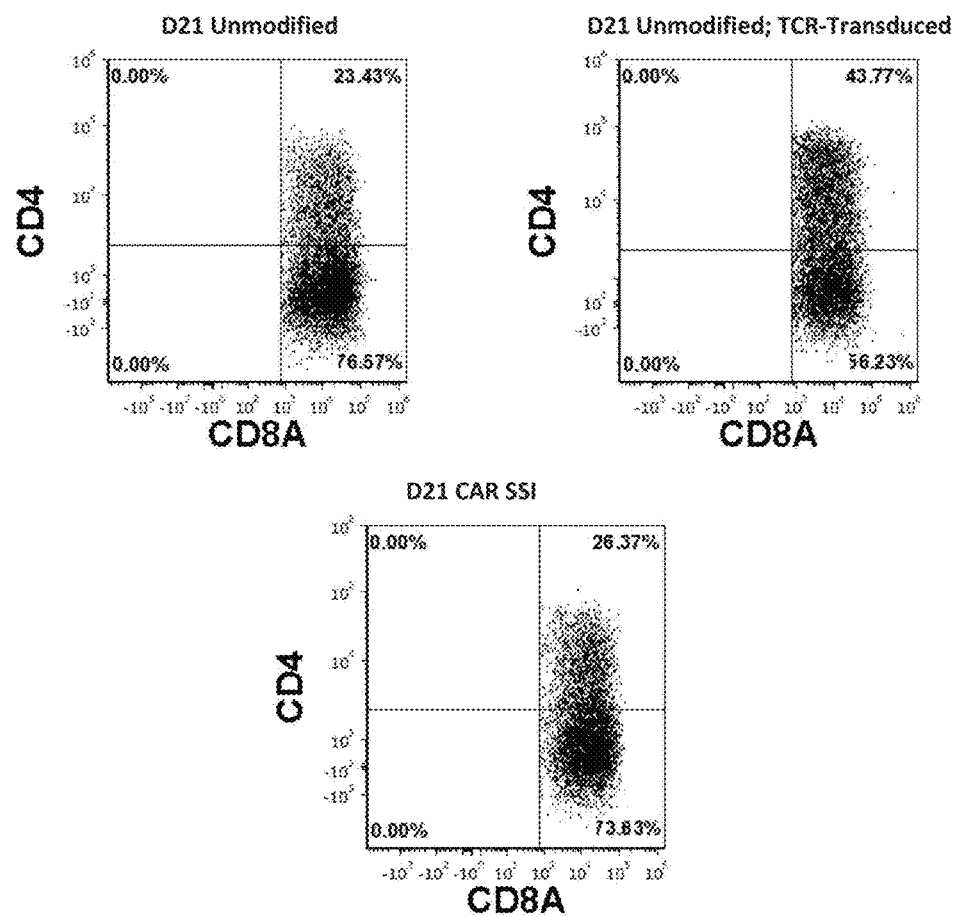

FIG. 52B is flow cytometry plots of CD4 and CD8β expression at day 21 of differentiation. Cells were sub-gated on CD8α+CD8β+.

Figure 53:
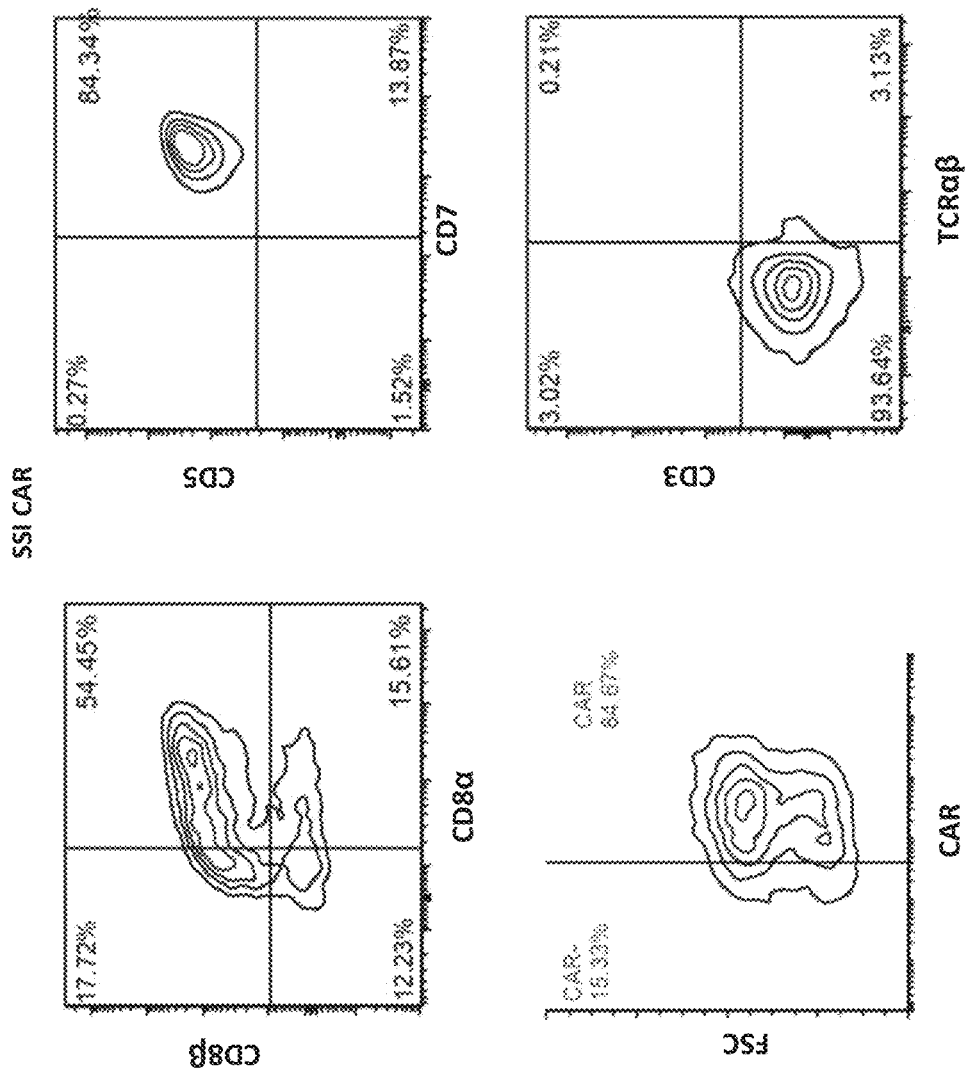

FIG. 53 is flow cytometry plots of CAR-modified cells ("SSI CAR") following differentiation, CD8α-enrichment, cryopreservation, and thaw.

Figure 54B:
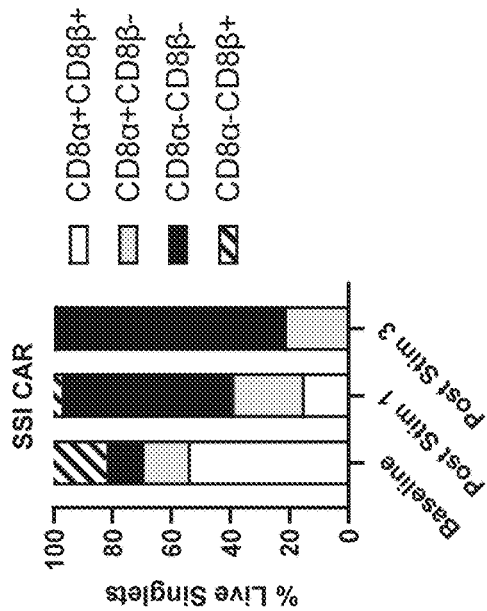
Figure 54A:
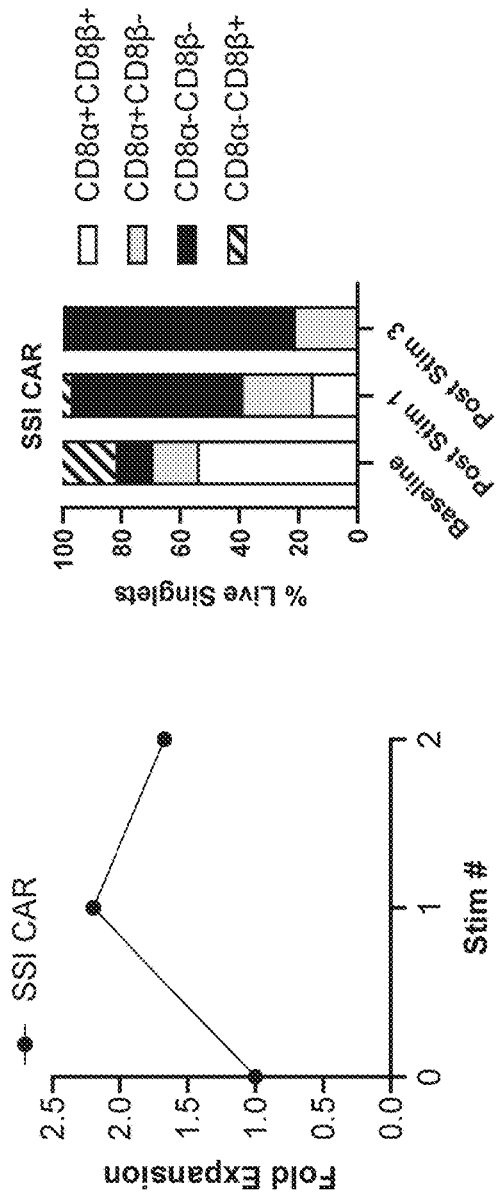

FIG. 54A is a graph depicting fold expansion for CAR-modified cells ("SSI CAR") during an in vitro serial restimulation assay with Raji CD19+ target cells.

FIG. 54B is a graph depicting the percentage of CD8α+ CD8β+, CD8α+CD8β−, CD8α−CD8β−, and CD8α− CD8β+ cells for CAR-modified cells ("SSI CAR") during an in vitro serial restimulation assay with Raji CD19+ target cells.

Figure 54C:
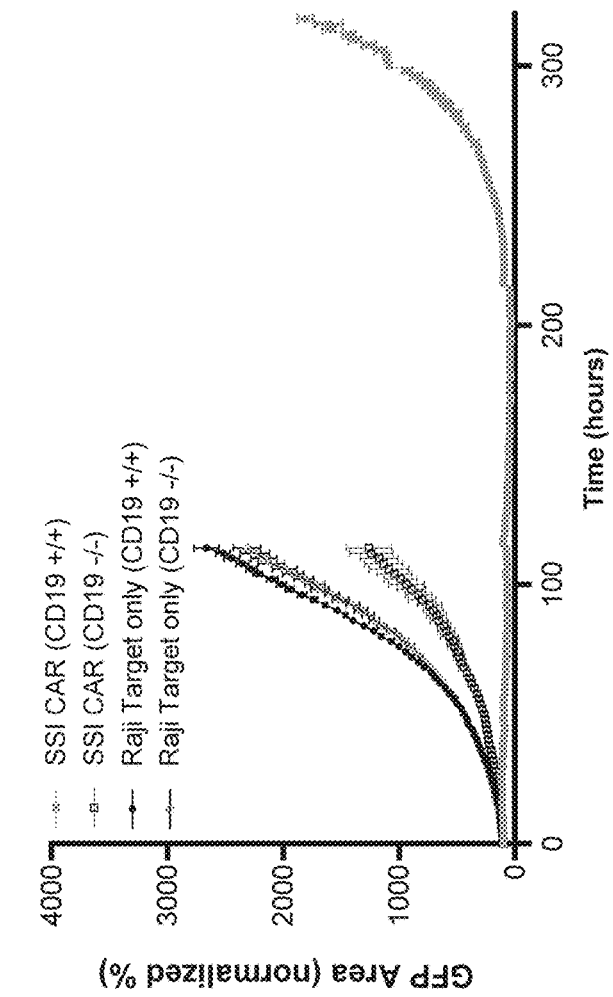

FIG. 54C is a graph depicting cytotoxicity of CAR-modified cells ("SSI CAR") during an in vitro serial restimulation assay with Raji CD19+ target cells.

Figure 55A:
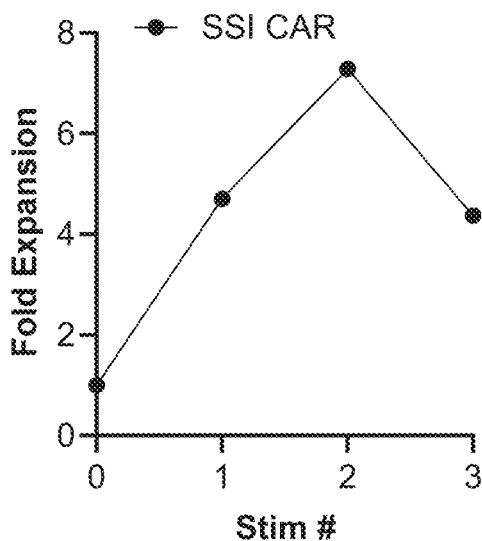

FIG. 55A is a graph depicting fold expansion for CAR-modified cells ("SSI CAR") during an in vitro serial restimulation assay with A549 CD19+ target cells.

Figure 55B:
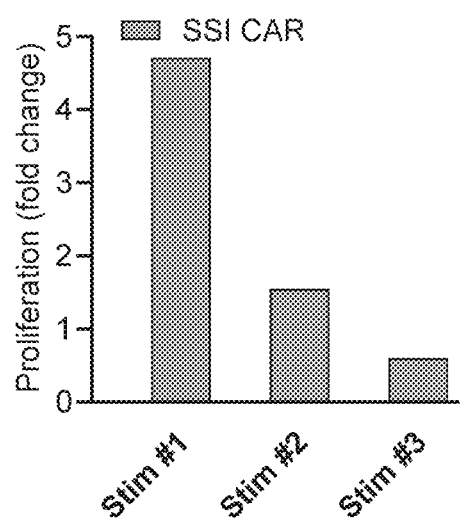

FIG. 55B is a graph depicting fold change in proliferation for CAR-modified cells ("SSI CAR") during an in vitro serial restimulation assay with A549 CD19+ target cells.

Figure 55C:
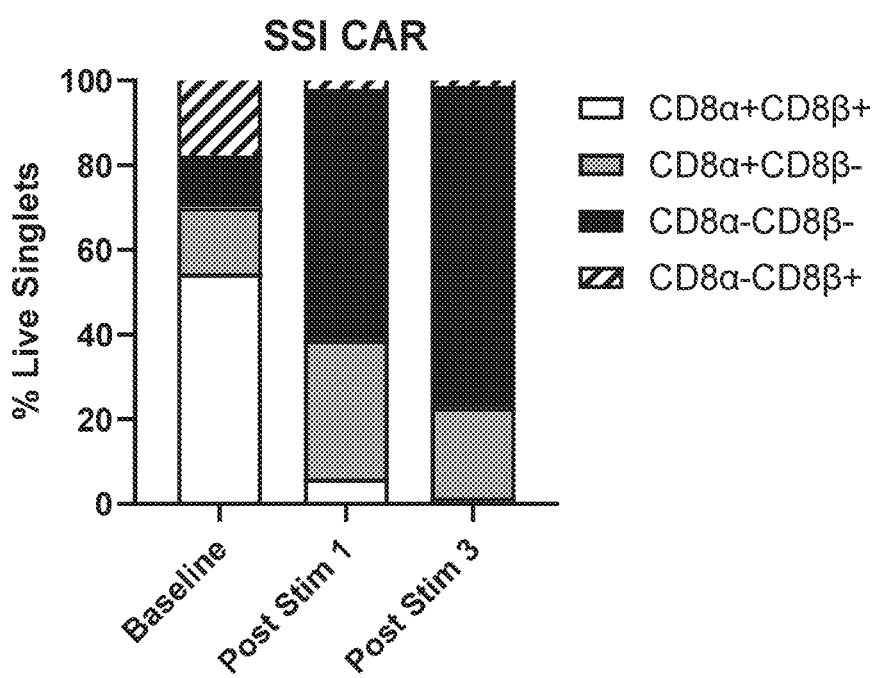

FIG. 55C is graphs depicting the percentage of CD8α+ CD8β+, CD8α+CD8β−, CD8α−CD8β−, and CD8α− CD8β+ cells for CAR-modified cells ("SSI CAR") during an in vitro serial restimulation assay with A549 CD19+ target cells.

Figure 56:
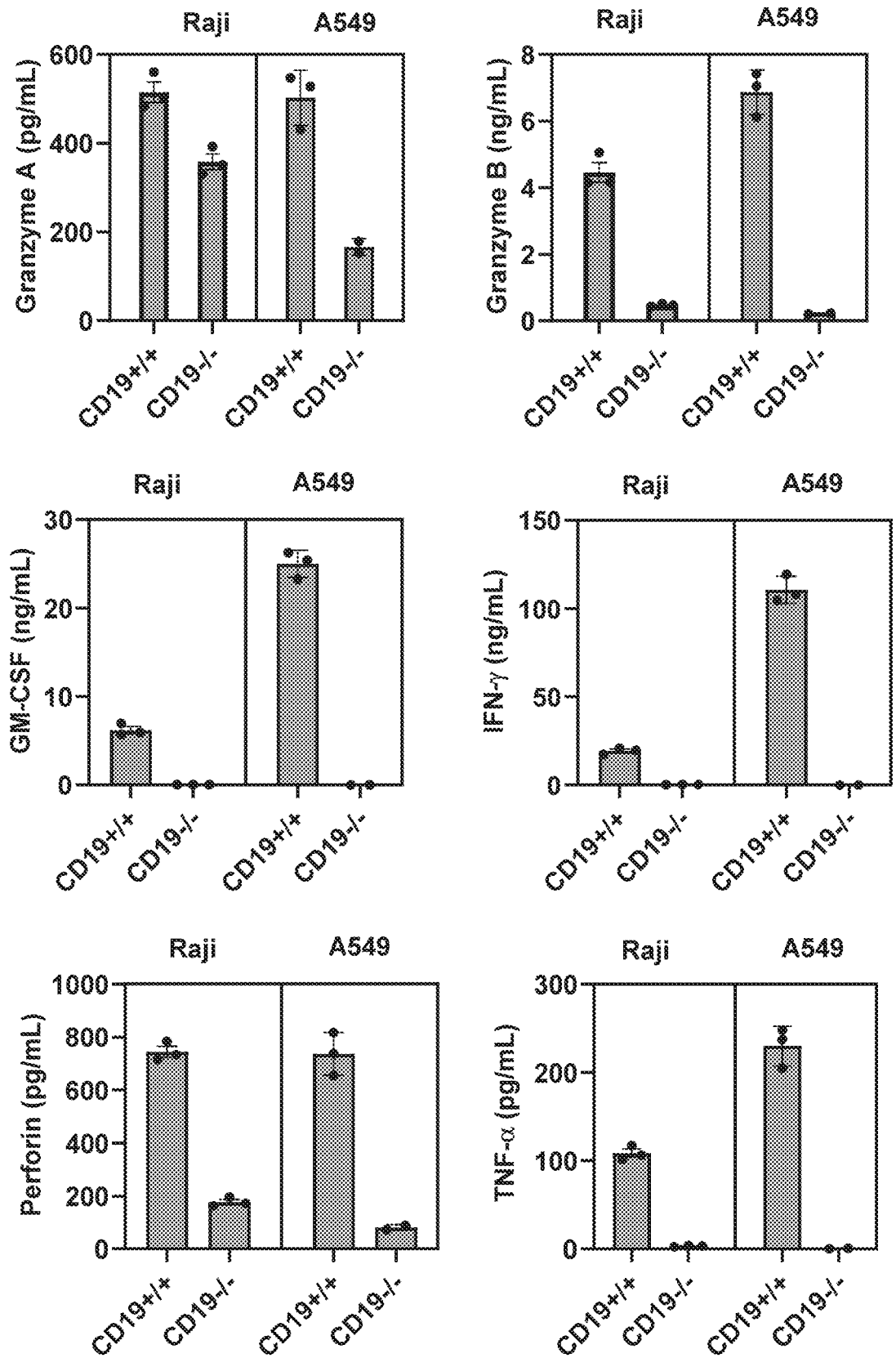

FIG. 56 is graphs depicting cytokine secretion of CAR-modified cells ("SSI CAR") following an in vitro serial restimulation assay with A549 or Raji CD19+/+ target cells or CD19−/− controls.

Figure 57A:
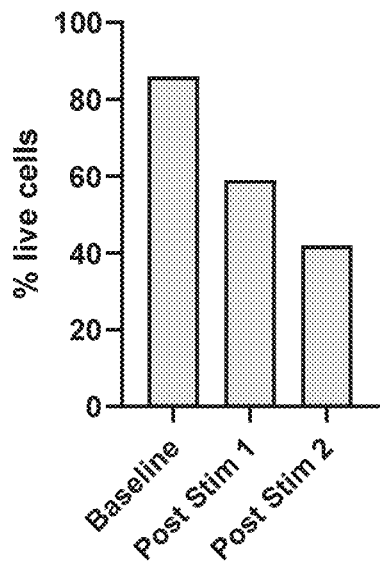

FIG. 57A is a graph depicting viability of CAR-modified cells ("SSI CAR") following an in vitro serial restimulation assay with Raji (FIG. 58) CD19+ target cells.

Figure 57B:
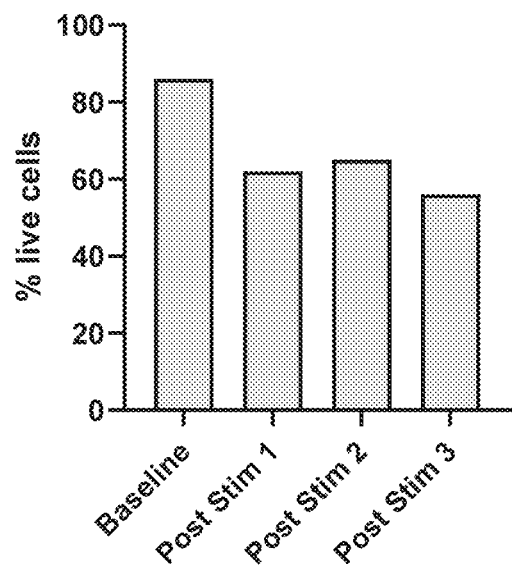

FIG. 57B is a graph depicting viability of CAR-modified cells ("SSI CAR") following an in vitro serial restimulation assay with A549 (FIG. 58) CD19+ target cells.

Figure 58:
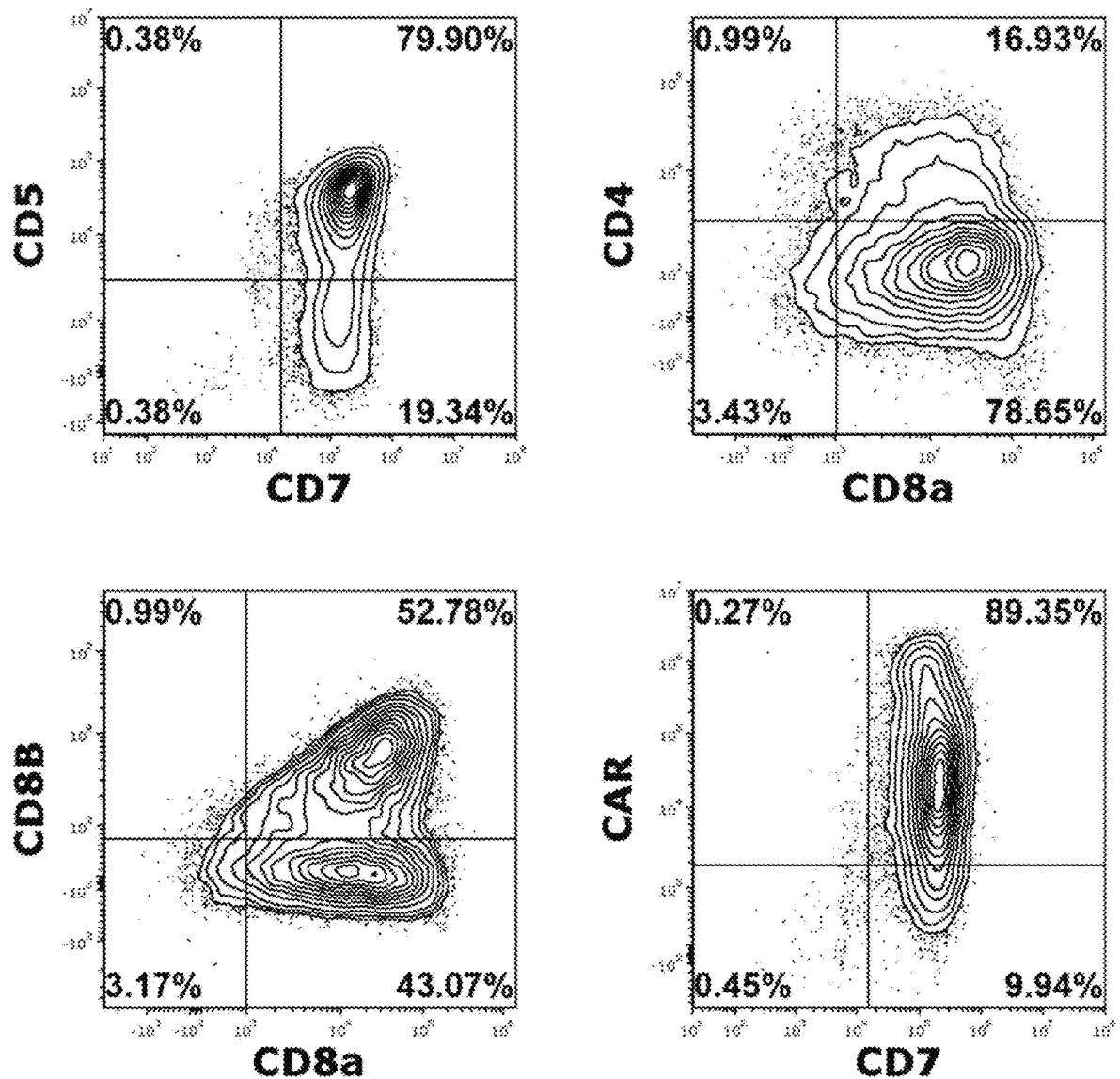

FIG. 58 is flow cytometry plots of CAR-iPSC-derived cells following differentiation and CD8 enrichment.

Figure 59A:
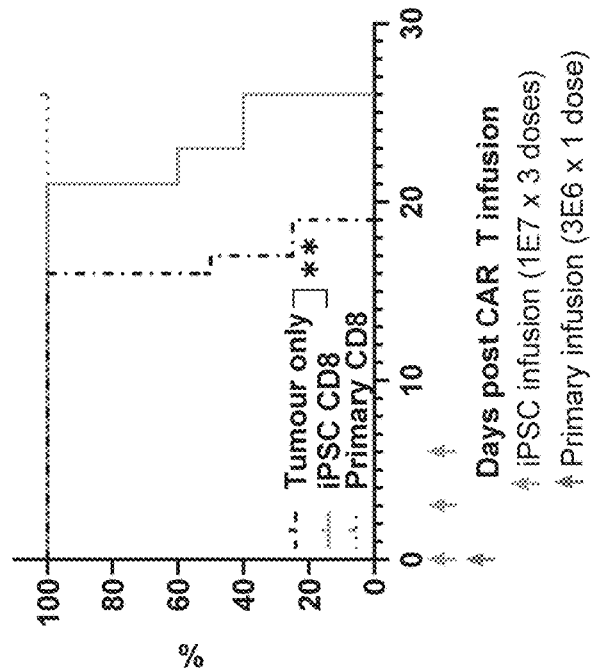

FIG. 59A is a graph depicting in vivo Raji tumor growth inhibition of CAR-iPSC-derived ("iPSC CD8") and primary CAR+ T cells ("primary CD8") in a mouse model. Statistical differences between tumor only and CAR-iPSC-derived groups were assessed by Welch's two samples t-test (two-tailed, *P<0.05; **P<0.01).

Figure 59B:
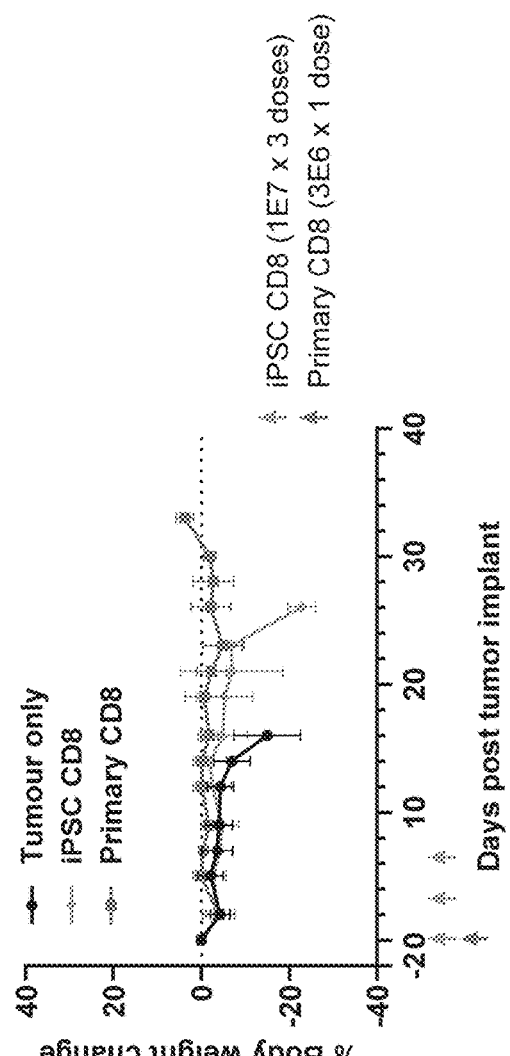

FIG. 59B is a graph depicting survival for untreated (tumor only), CAR-iPSC-derived CD8+ cell-treated, and primary CAR+ T cell-treated groups. Statistical difference between tumor only and CAR-iPSC-derived groups was assessed by Log-rank (Mantel-Cox) test (*P<0.05; **P<0.01).

Figure 59C:
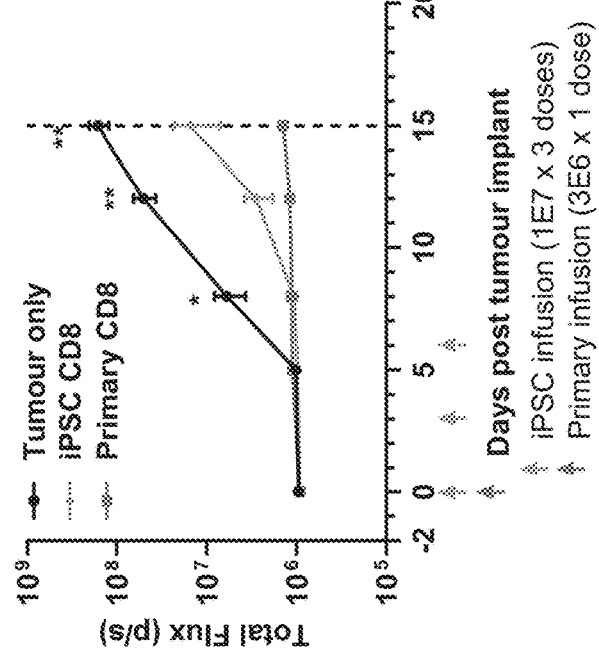

FIG. 59C is a graph depicting in vivo toxicity, as indicated by % body weight change, of CAR-iPSC-derived and primary CAR+ T cells.

Figure 60A:
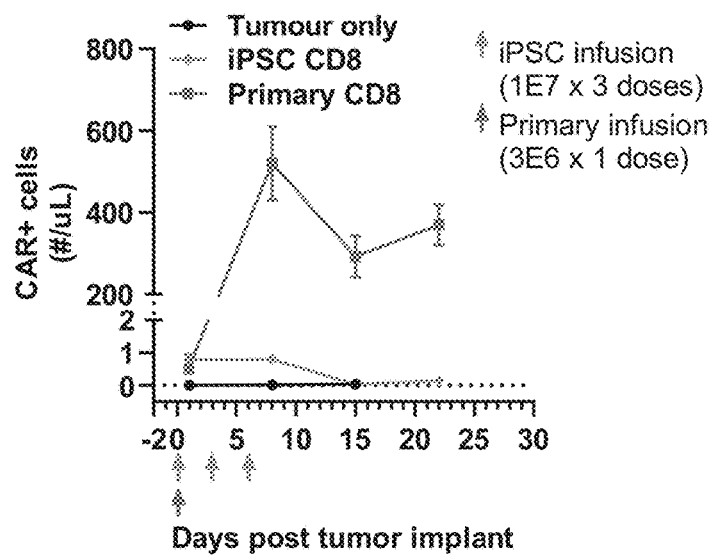

FIG. 60A is a graph depicting in vivo cellular kinetics of CAR-iPSC-derived and primary CAR+ T cells, as detected in peripheral blood.

Figure 60B:
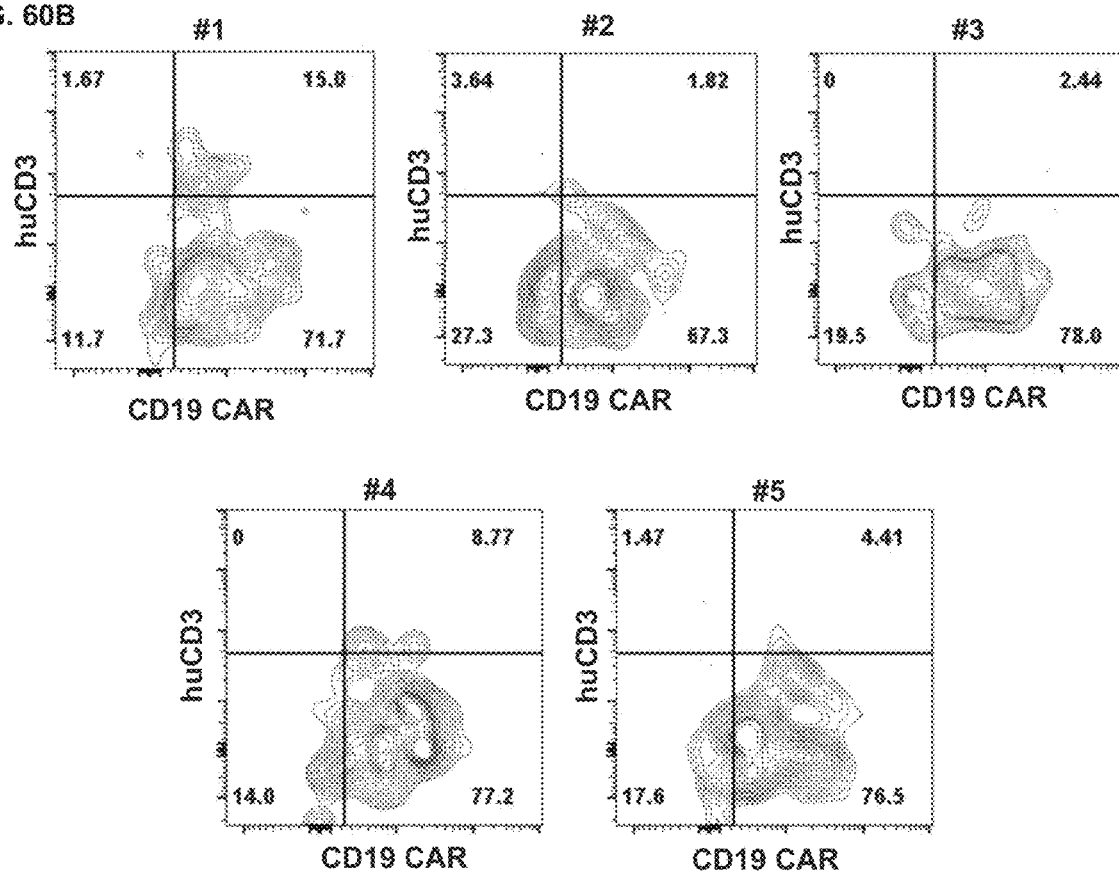

FIG. 60B is flow cytometry plots of CAR-iPSC-derived CD8+ cells at 8 days post-infusion, as detected in peripheral blood.

Figure 61A:
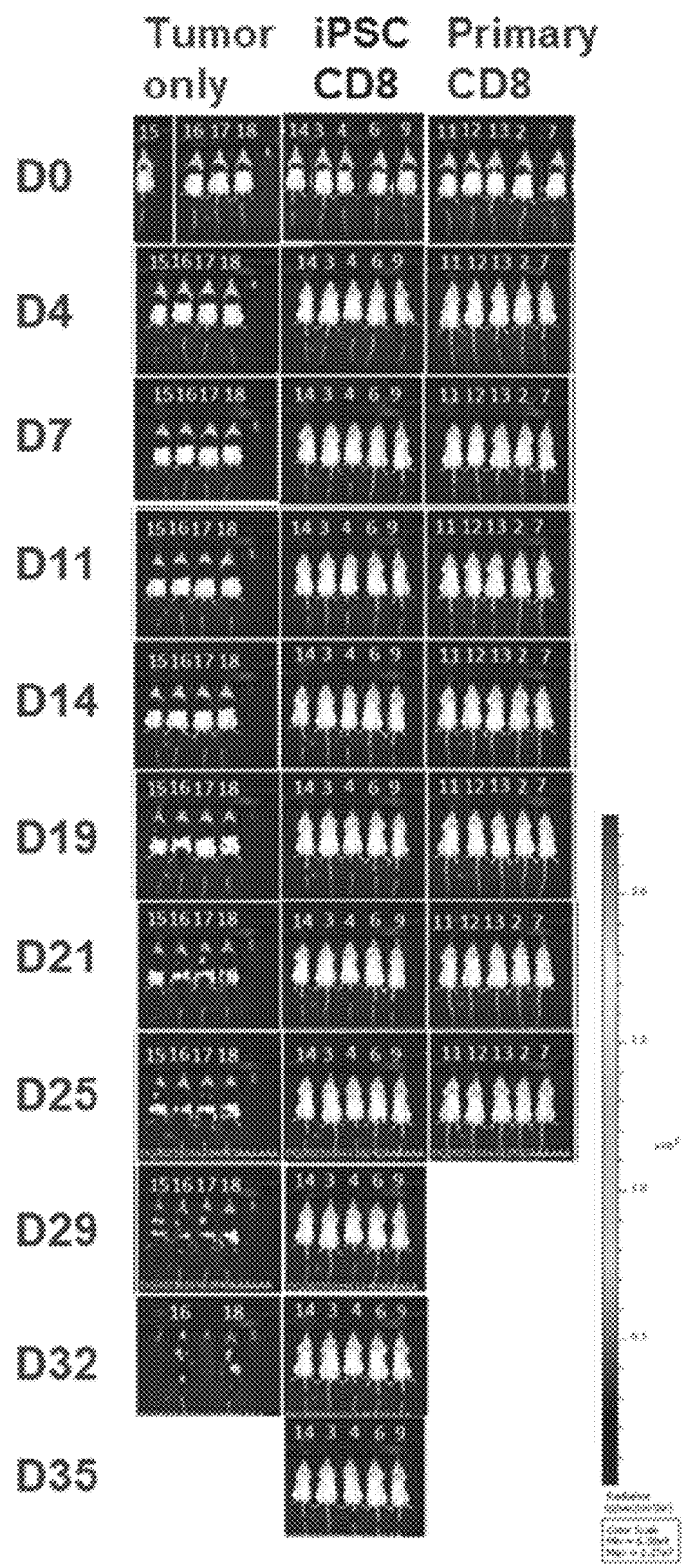

FIG. 61A is bioluminescence images of untreated (tumor only), CAR-iPSC-derived CD8+ cell-treated, and primary CAR+ CD8+ T cell-treated mice over time in an A549 CD19 tumor model.

FIG. 61B is a graph depicting in vivo A549–CD19 tumor growth inhibition of CAR-iPSC-derived and primary CAR+ CD8+ T cells.

FIG. 61C is a graph depicting survival for untreated (tumor only), CAR-iPSC-derived CD8+ cell-treated, and primary CAR+ CD8+ T cell-treated groups. Statistical difference between tumor only and CAR-iPSC-derived groups was assessed by Log-rank (Mantel-Cox) test (*P<0.05; **P<0.01).

FIG. 61D is a graph depicting in vivo toxicity, as indicated by % body weight change, of CAR-iPSC-derived and primary CAR+ CD8+ T cells.

FIG. 61E is a graph depicting in vivo cellular kinetics of CAR-iPSC-derived and primary CAR+ T cells, as detected in peripheral blood.

Figure 62A:
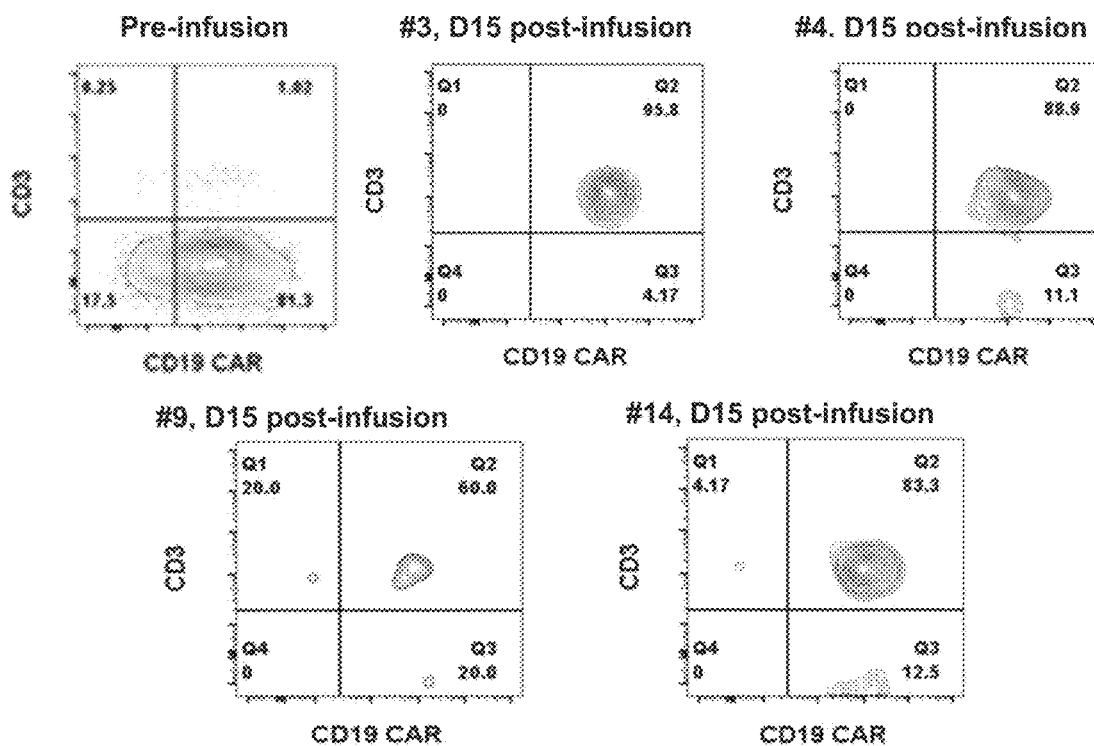

FIG. 62A is flow cytometry plots of CAR-iPSC-derived CD8+ cells at 15 days post-infusion, as detected in peripheral blood.

Figure 62B:
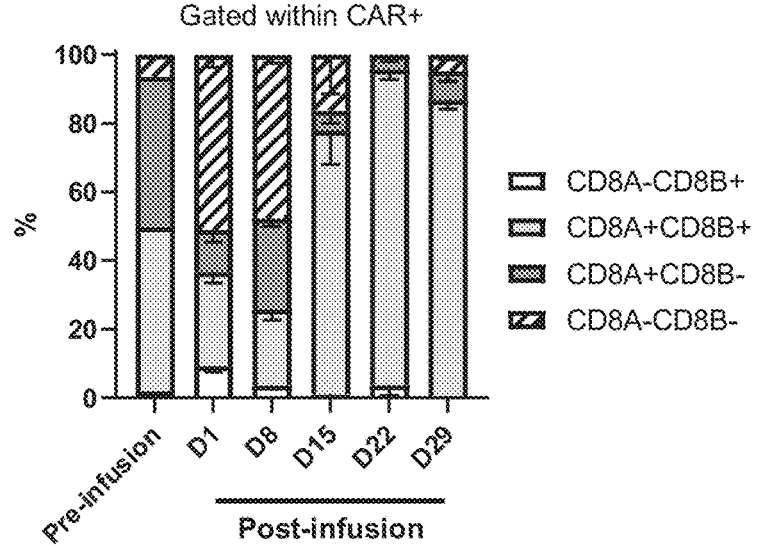

FIG. 62B is a graph depicting expression of CD8α and/or CD8β in CAR-iPSC-derived CD8+ cells pre- and post-infusion.

Figure 63:
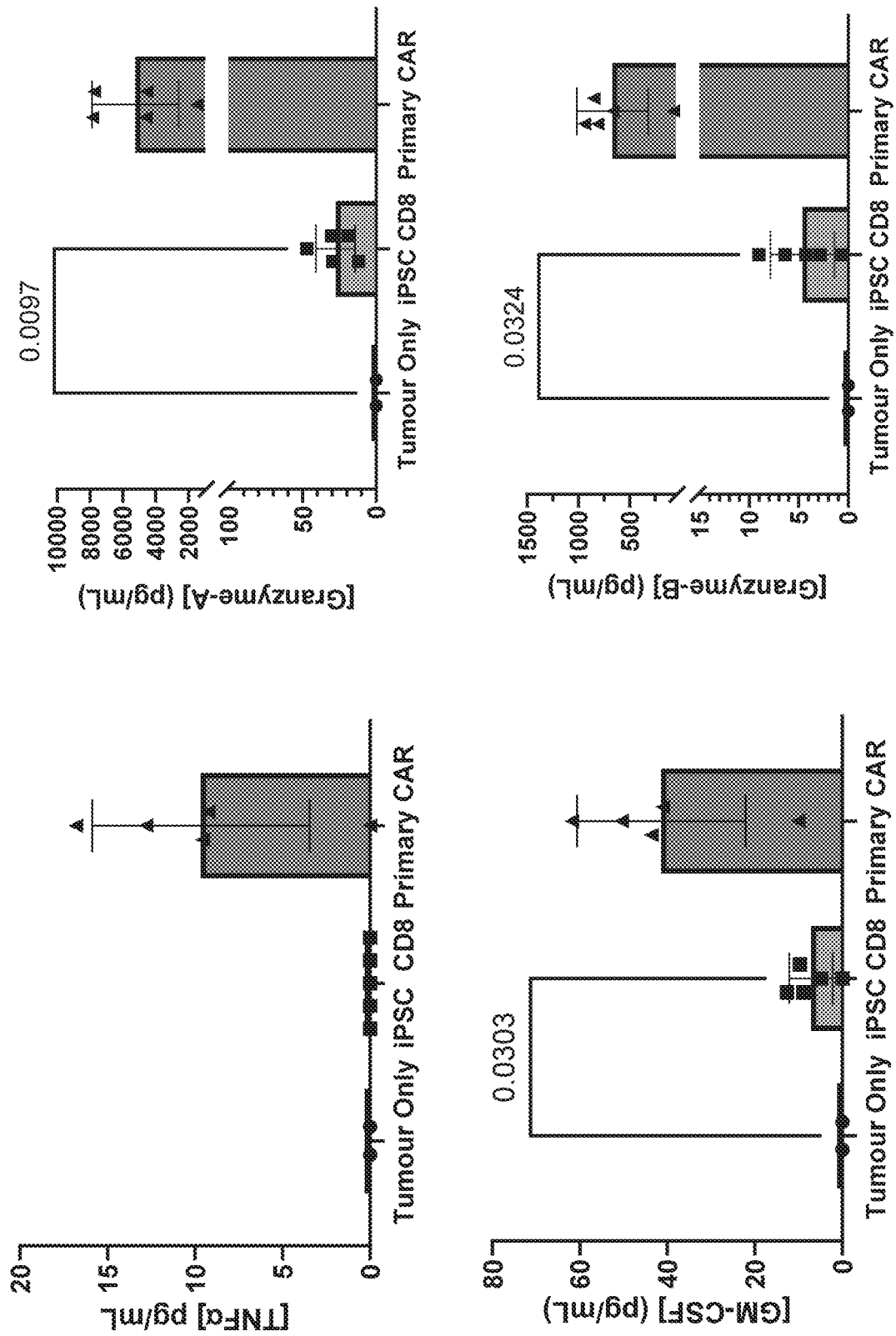

FIG. 63 is graphs depicting cytokine and cytolytic molecule secretions of CAR-iPSC-derived CD8+ cells and CAR+ primary CD8+ T cells detected in whole blood retrieved at 15 days post-infusion. Statistical differences between tumor only and CAR-iPSC-derived groups were assessed by unpaired, non-parametric t test with Welch's correction (p-value as noted).

Figure 64A:
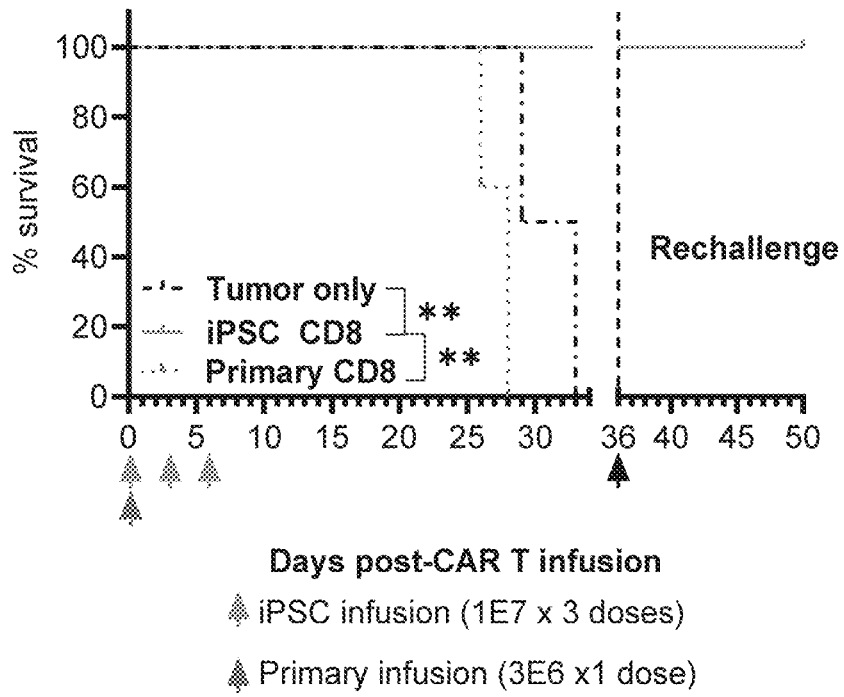

FIG. 64A is a graph depicting survival following initial infusion for untreated (tumor only), CAR-iPSC-derived CD8+ cell-treated, primary CAR+ CD8+ T cell-treated groups and rechallenge in the CAR-iPSC-derived CD8+ cell-treated group.

Figure 64B:
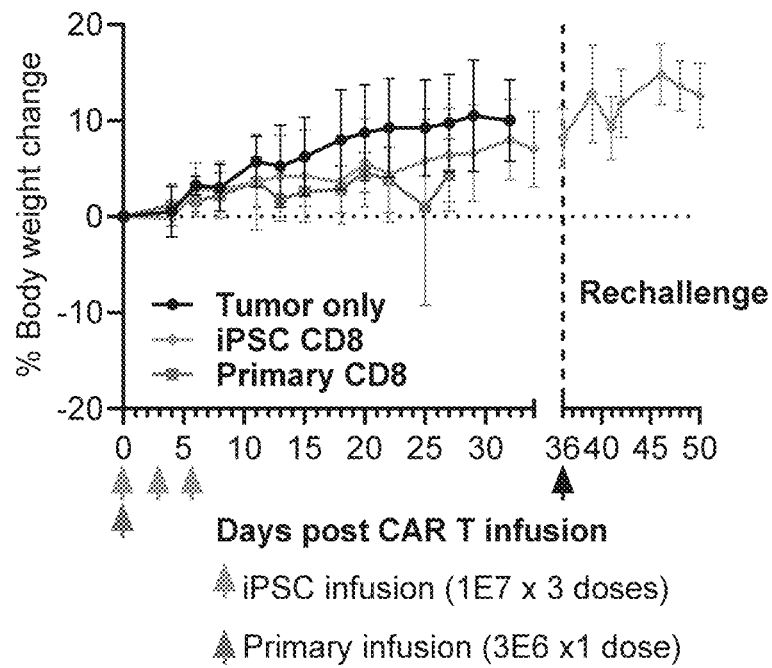

FIG. 64B is a graph depicting in vivo toxicity, as indicated by percent body weight change, following initial infusion for untreated (tumor only), CAR-iPSC-derived CD8+ cell-treated, primary CAR+ CD8+ T cell-treated groups and rechallenge in the CAR-iPSC-derived CD8+ cell-treated group.

Figure 65A:
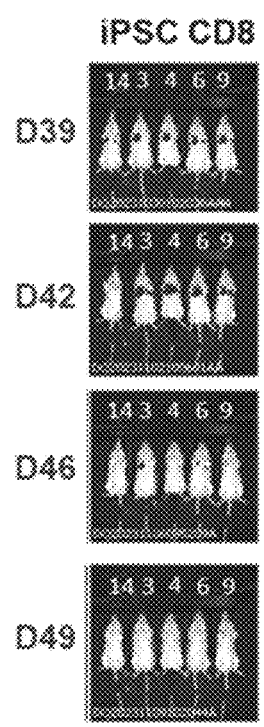

FIG. 65A is bioluminescence images of CAR-iPSC-derived CD8+ cell-treated mice following rechallenge.

Figure 65B:
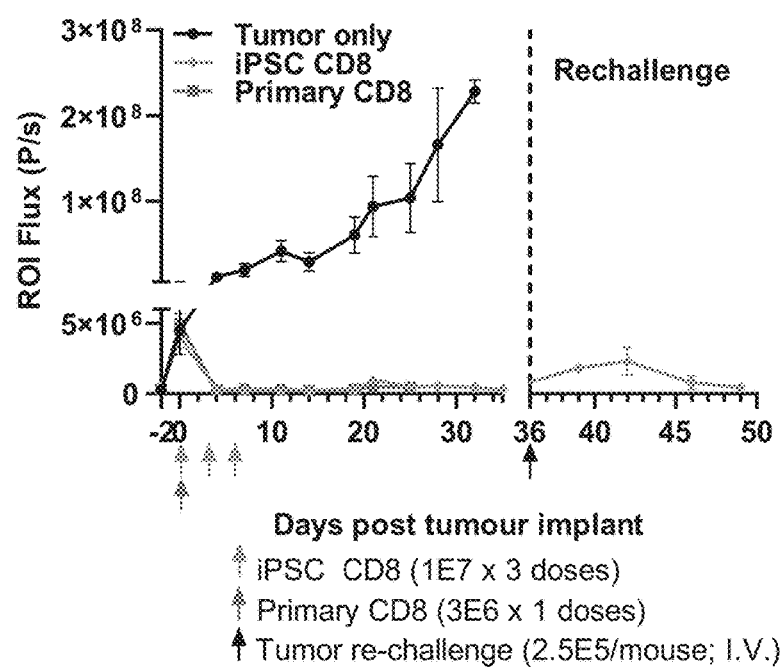

FIG. 65B is a graph depicting in vivo tumor growth inhibition, following initial infusion for CAR-iPSC-derived CD8+ cell-treated, primary CAR+ T cell-treated groups and rechallenge in the CAR-iPSC-derived CD8+ cell-treated group.

Figure 65C:
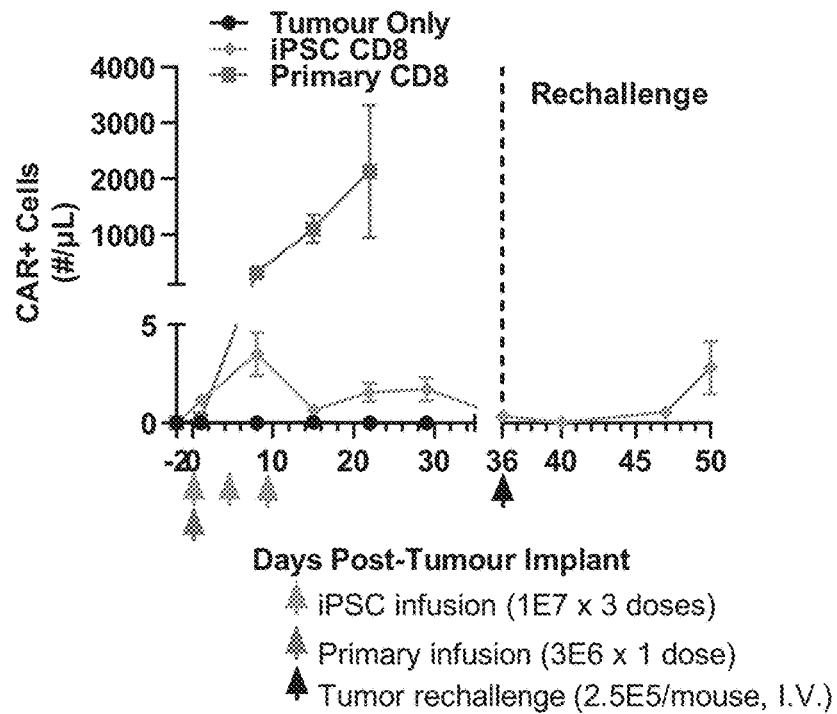

FIG. 65C is a graph depicting in vivo cellular kinetics of CAR-iPSC-derived and primary CAR+ T cells, as detected in peripheral blood following initial infusion (iPSC-derived and primary cells) and rechallenge (iPSC-derived cells only).

Figure 66A:
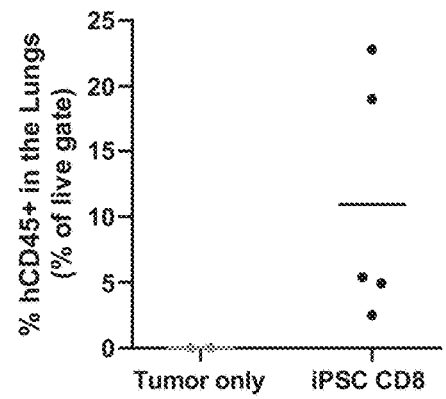

FIG. 66A is a graph depicting detection of iPSC-derived CD8+ cells in the lungs at endpoint, in comparison to tumor-only control.

Figure 66B:
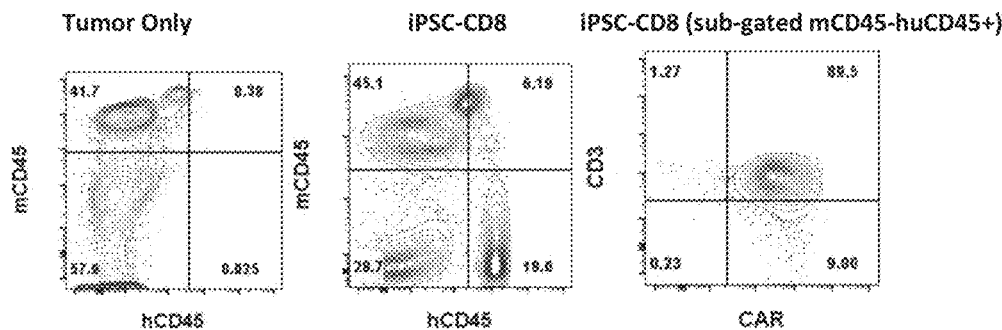

FIG. 66B is flow cytometry plots of tumor-only control (left) and iPSC-derived CD8+ cells (centre, right) of FIG. 66A.

Figure 66C:
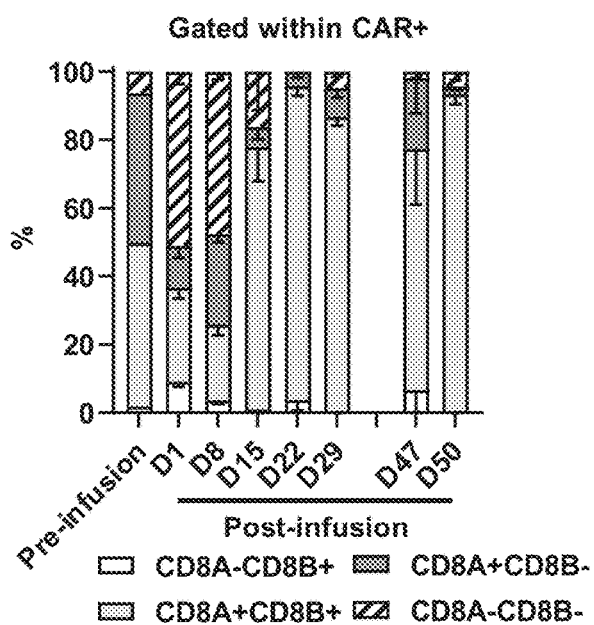

FIG. 66C is a graph depicting expression of CD8α and/or CD8β in CAR-iPSC-derived CD8+ cells pre- and post-infusion, extended to include tumor rechallenge.

Figure 67A:
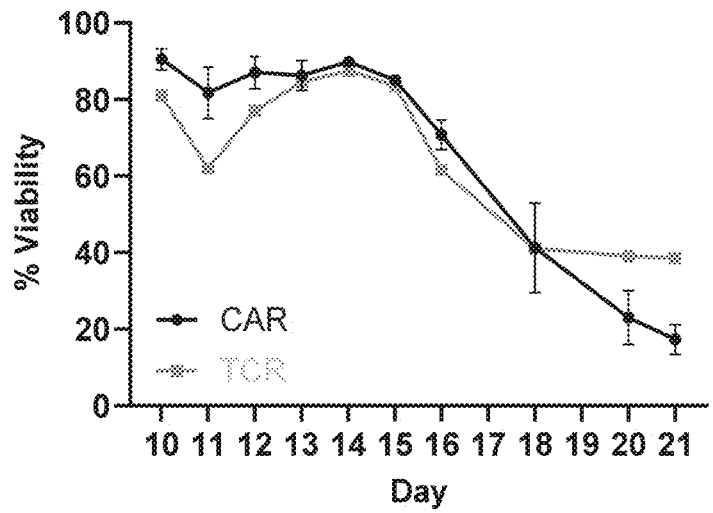

FIG. 67A is a graph depicting viability for CAR-iPSC-derived ("CAR"), TCR-iPSC-derived ("TCR"), and CAR-iPSC-derived, TCR-transduced ("TCR-CAR") cells during differentiation in stirred-tank bioreactors.

Figure 67B:
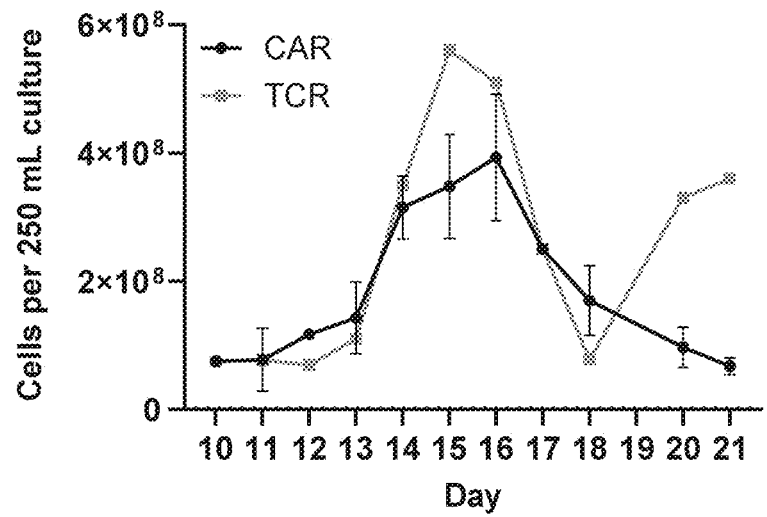

FIG. 67B is a graph depicting cell number for CAR-iPSC-derived ("CAR"), TCR-iPSC-derived ("TCR"), and CAR-iPSC-derived, TCR-transduced ("TCR-CAR") cells during differentiation in stirred-tank bioreactors.

Figure 68A:
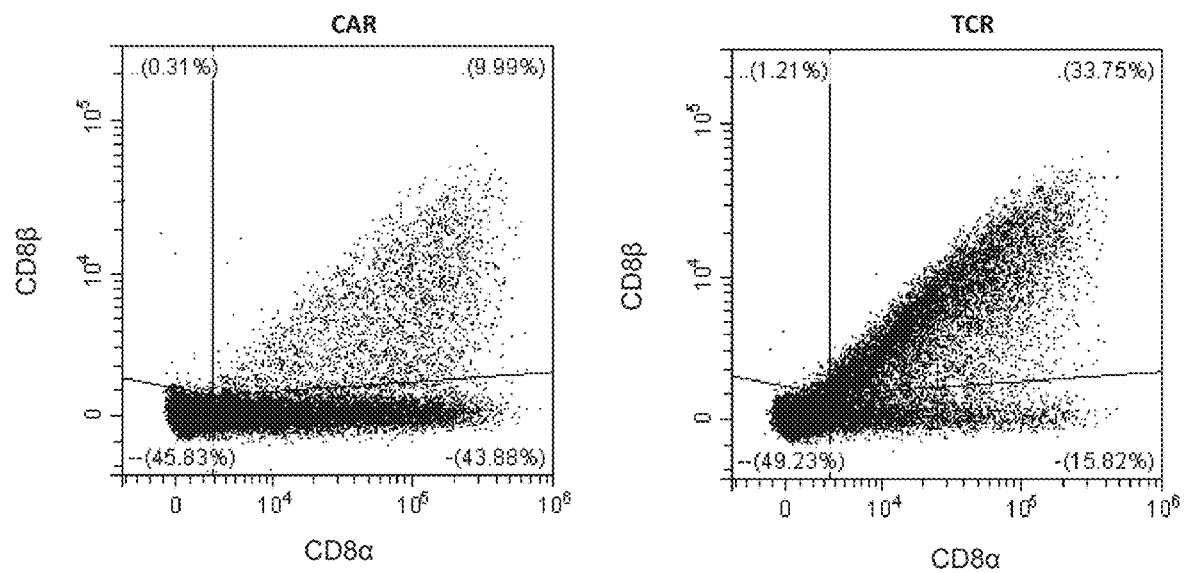

FIG. 68A is flow cytometry plots of CAR-iPSC-derived ("CAR"), TCR-iPSC-derived ("TCR"), and CAR-iPSC-derived, TCR-transduced ("TCR-CAR") cells following differentiation in stirred-tank bioreactors.

Figure 68B:
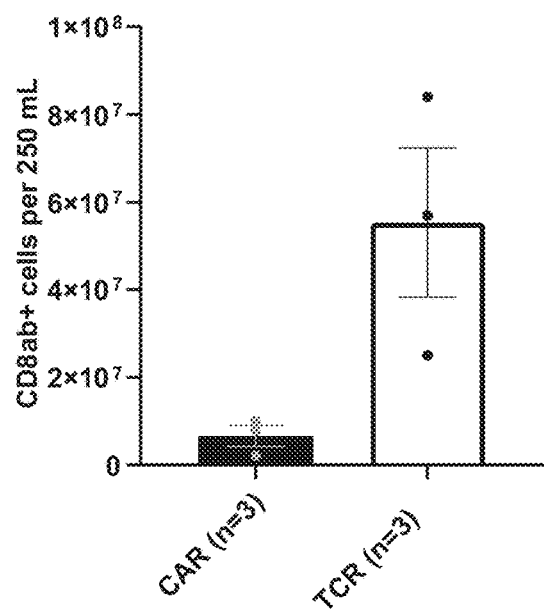

FIG. 68B is a graph depicting yield of CD8αβ+ cells for CAR-iPSC-derived ("CAR"), TCR-iPSC-derived ("TCR"), and CAR-iPSC-derived, TCR-transduced ("TCR-CAR") cells following differentiation in stirred-tank bioreactors.

FIG. 69A is a graph depicting in vitro cytotoxicity of TCR-iPSC-derived cells differentiated in stirred-tank bioreactors ("STR TCR+ CD8+") or in well-plates ("WP TCR+ CD8+"), in comparison to primary TCR+ CD8+ cells ("Primary TCR+ CD8+") in a serial restimulation assay at a 2:1 E:T ratio.

FIG. 69B is a graph depicting fold expansion of TCR-iPSC-derived cells differentiated in stirred-tank bioreactors ("STR TCR+ CD8+") or in well-plates ("WP TCR+ CD8+"), in comparison to primary TCR+ CD8+ cells ("Primary TCR+ CD8+") in a serial restimulation assay.

FIG. 69C is a graph depicting in vitro cytotoxicity at varying E:T ratios of TCR-iPSC-derived cells differentiated in stirred-tank bioreactors ("STR TCR+ CD8+") or in well-plates ("WP TCR+ CD8+"), in comparison to primary TCR+ CD8+ cells ("Primary TCR+ CD8+").

FIG. 69D is a graph depicting antigen-independent ("Antigen Negative") and antigen-dependent ("Antigen Positive") cytotoxicity of TCR-iPSC-derived cells differentiated in stirred-tank bioreactors ("STR TCR+ CD8+") or in well-plates ("WP TCR+ CD8+"), in comparison to primary TCR+ CD8+ cells ("Primary TCR+ CD8+") in a serial restimulation assay.

DETAILED DESCRIPTION OF THE DISCLOSURE

Unless defined otherwise, all technical and scientific terms used herein have the same meaning as commonly understood by one of ordinary skill in the art to which this disclosure belongs.

Generally, the present disclosure provides methods of generating T cell lineage populations from progenitor cells, a T cell lineage population generated by the methods disclosed herein; a pharmaceutical composition comprising T cell lineage population generated by the methods disclosed herein; use of a T cell lineage population in the manufacture of a medicament for the treatment of a disease or condition, wherein the T cell lineage population is generated by the methods disclosed herein; and a method of differentiating a progenitor T cell population by the methods disclosed herein.

Definitions

As used herein, the term "stem cell" refers to a cell that can differentiate into more specialized cells and has the capacity for self-renewal. Stem cells include pluripotent stem cells (PSCs), such as embryonic stem cells (ESCs) and induced pluripotent stem cells (iPSCs), and multipotent stem cells, such as mobilized peripheral blood-derived CD34+ stem cells, umbilical cord blood stem cells, and adult stem cells, which are found in various tissues. Methods for obtaining, deriving or producing stem cells are known in the art.

As used herein, the term "progenitor cell" refers to a cell that can differentiate into one or more types of cells, but typically has a limited capacity for self-renewal. Progenitor cells are derivatives of stem cells and have more limited potency relative to their corresponding source stem cells. For example, hematopoietic stem cells (HSCs), found in adult bone marrow, peripheral blood (in smaller numbers) and in umbilical cord blood, have the capacity to give rise to all other blood cells. Hematopoietic progenitor cells are multipotent or lineage-committed cells derived from HSCs that have the capacity to give rise to a more limited or specific type of blood cell. Hematopoietic stem and progenitor cells (HSPCs) typically exist as a heterogeneous population in vivo and have use as a heterogeneous population as described herein. Hematopoietic stem and progenitor cells may be characterized, for example, by surface CD34 (CD34+).

As used herein, the terms "progenitor T cell" and "proT cell" refer to a cell that is derived from a pluripotent stem cell or a CD34+ hematopoietic stem and/or progenitor cell and expresses at least CD7+, and has the capacity to differentiate into one or more types of immature and mature T cells. Examples of progenitor T cells include, but are not limited to, CD7+ cells, CD7+CD5+ cells, CD7+CD5+ CD34+ cells, CD7+CD5+CD45RA+ cells, and/or CD7+ CD5+CD1a+ cells.

As used herein, an "immature T cell" or mature T cell is a T lineage cell derived from a progenitor T cell. T cell development may be characterized by the progressive expression of cell surface receptors, particularly CD4 and CD8. In vivo, T lineage cells progress from progenitor T cells through CD4−CD8− (double-negative, DN), CD4+ CD8− (CD4 immature single-positive, CD4ISP), CD4+ CD8+ (double-positive, DP), and CD4−CD8+ (CD8 single-positive, CD8SP) and CD4 single-positive (CD4SP) stages. CD8 may be expressed as a heterodimer of CD8α and CD8β, resulting in CD8αβ+ cells, or as CD8αα homodimer, resulting in CD8αα+ cells. CD4−CD8+ cells may also be characterized by cell-surface expression of CD3 and one of TCRγδ (γδ T cells) or TCRαβ(αβ T cells).

As used herein, "serum-free medium" refers to a cell culture medium that lacks animal serum. Serum-free medium may include specific, known serum components isolated from an animal (including human animals), such as, for example, bovine serum albumin (BSA).

As used herein, a "Notch signalling ligand" refers to any ligand capable of interacting with a Notch protein receptor for regulation of T cell lineage commitment and differentiation. Examples of Notch signalling ligand include, Delta-like 4 (DL4), Delta-like-1 (DL1), Delta-like 3 (DL3), Jagged1 and Jagged2.

As used herein, Notch signalling ligand, for example, "Delta-like-4" and "DL4" refer to a protein that in humans is encoded by the DLL4 gene. DL4 is a member of the Notch signalling pathway and is also referred to in the art as "Delta like ligand 4" and "DLL4". Herein, reference to DL4 is not limited to the entire DL4 protein, but includes at least the signalling peptide portion of DL4. For example, a commercially available product (Sino Biologicals) comprising the extracellular domain (Met 1-Pro 524) of human DL4 (full-length DL4 accession number NP 061947.1; SEQ ID NO: 1) fused to the Fc region of human IgG1 at the C-terminus is a DL4 protein suitable for use in the methods provided herein.

As used herein, Notch signalling ligand also includes a variant of a known Notch signalling ligand, for example, DL4. A variant Notch signalling ligand refers to a protein molecule which differs in amino acid sequence from the wild type amino acid sequence by one or more additions, deletions, and/or substitutions and retains the desired Notch signalling activity of the wild type DL4. Also included within the definition are variants such as polypeptides, oligopeptides, peptides and proteins having amino acid sequence identity to a given polypeptide, oligopeptide, peptide or protein. The percent identity can be, for example, at least about 50%, 55%, 60%, 65%, 70%, 75%, 80%, 85%, 90% 91%, 92%, 93%, 94%, 95%, 96%, 97%, 98%, 99%, or 100% amino acid identity to the given polypeptide, oligopeptide, peptide or protein over a specified length, for example, over the full length of the polypeptide.

As used herein, "Vascular cell adhesion molecule 1" and "VCAM-1" refer to a protein that in humans is encoded by the VCAM1 gene. VCAM-1 is a cell surface sialoglycoprotein, a type I membrane protein that is a member of the Ig superfamily. VCAM-1 is also referred to in the art as "vascular cell adhesion protein 1 and cluster of differentiation 106" (CD106). Herein, reference to VCAM-1 is not limited to the entire VCAM-1 protein, but includes at least the signalling peptide portion of VCAM-1 (QIDSPL (SEQ ID NO: 2) or TQIDSPLN (SEQ ID NO: 3)). For example, a commercially available mouse VCAM-1-Fc chimeric protein (R&D) that comprises (Phe25-Glu698) region of mouse VCAM-1 (full-length murine VCAM-1 accession number CAA47989; SEQ ID NO: 4) fused with the Fc region of human IgG1 is a VCAM-1 protein suitable for use herein.

Use of at least a portion of human VCAM-1 (full-length human VCAM-1 accession number P19320, NP001069, EAW72950; SEQ ID NO: 5) may also be suitable for use in the methods provided herein. Herein, reference to VCAM-1 also includes a variant, which differs in amino acid sequence from the wild type amino acid sequence of VCAM-1 by one or more additions, deletions, and/or substitutions and retains the desired activity of the wild type VCAM-1. Also included within the definition are variants such as polypeptides, oligopeptides, peptides and proteins having amino acid sequence identity to a given polypeptide, oligopeptide, peptide or protein. The percent identity can be, for example, at least about 50%, 55%, 60%, 65%, 70%, 75%, 80%, 85%, 90% 91%, 92%, 93%, 94%, 95%, 96%, 97%, 98%, 99%, or 100% amino acid identity to the given polypeptide, oligopeptide, peptide or protein over a specified length, for example, over the full length of the polypeptide. VCAM-1 has been shown to synergistically increase Notch signalling in combination with DL4 (e.g., Shukla et al., 2017).

As used herein, "two-dimensional engineered thymic niche (2D ETN)" refers to a two-dimensional substrate immobilized with a Notch signalling ligand, for example, DL4, and optionally VCAM-1. A two-dimensional (2D) substrate can include, for example, a tissue culture plate. Methods of immobilizing Notch signalling ligands on a 2D substrate are known in the art and are described, for example in Shukla et al., 2017.

As used herein, "three-dimensional engineered thymic niche (3D ETN)" refers to a three-dimensional substrate immobilized with a Notch signalling ligand, for example, DL4 and optionally VCAM-1. A three-dimensional (3D) substrate can include, for example, micron-size particles (or beads), with or without a magnetic core, coated with one or more full proteins, protein domains (e.g., extracellular, intracellular, or other domain), peptides or protein fragments to activate Notch signalling. Several approaches can be used individually or in combination to produce protein coated particles, e.g.: physisorption driven by protein affinity to the particle material, chemical conjugation by reaction with, among others, amine, carboxyl, thiol, epoxy, azide reactive groups, or by coating an appropriate ligand to capture the protein of interest by affinity. Examples of affinity tags include but are not limited to: Fc, biotin, Halo, aldehyde, Snap, Spy-Catcher, VIPER. Particles or beads may be composed of, for example, polystyrene, iron oxide, gold, or other suitable materials known in the art. 3D ETN may be used for culturing cells on a tissue culture plate, flasks, or other vessels utilized for culturing cells.

As used herein, "surface-bound" refers to a Notch signalling ligand immobilized on 2D ETN or 3D ETN through covalent or non-covalent interactions, affinity-based interactions, or other suitable forms of interactions.

As used herein, "enriched" cell population refers to when the cell population comprising one or more cell phenotypes (for example, CD4−CD8+ (CD8SP), CD4+CD8+ (DP), CD4+CD8− (CD4 ISP), CD4−CD8− (DN)) exhibits a higher absolute number or the ratio of one of the cell phenotypes (for example, CD4−CD8+ (CD8SP)) compared to other cell phenotypes, where at least 25% of the cell population is comprised of a single cell phenotype. For example, when progenitor T cells are cultured with 3D ETN bead concentration of $10 \times 10^7$ beads/mL (1.852× bead dose), the cell population is enriched with CD4−CD8+ (CD8SP) comprising approximately 50% of the cell population, when compared to progenitor T cells cultured with SCT (Commercial Coating), where CD4−CD8+ (CD8SP) comprises less than approximately 10% of the cell population.

As used herein, "enriched" cell population also refers to a cell population generated from culturing progenitor T cells with DL4 and optionally, VCAM-1, when the cell population comprises one or more cell phenotypes (for example, CD4−CD8+ (CD8SP), CD4+CD8+ (DP), CD4+CD8− (CD4 ISP), CD4−CD8− (DN)) and exhibits a higher absolute number or the ratio of one of the cell phenotypes (for example, CD4−CD8+ (CD8SP)) compared to other cell phenotypes, where at least 25% of the cell population is comprised of a single cell phenotype, when compared to progenitor T cells not cultured with DL4, and optionally, VCAM-1. For example, when progenitor T cells are cultured with 3D ETN bead concentration of $10 \times 10^7$ beads/mL (1.85× bead dose), the cell population is enriched with CD4−CD8+ (CD8SP) comprising approximately 50% of the cell population, when compared to progenitor T cells cultured with 3D ETN bead concentration of $0.1 \times 10^7$ beads/mL (0.018× bead dose), where CD4−CD8+ (CD8SP) only comprises less than approximately 10% of the cell population.

As used herein, the term "subject" refers to a vertebrate, preferably a mammal (e.g., a non-human mammal), more preferably a primate and still more preferably a human. Mammals include, but are not limited to, primates, humans, farm animals, sport animals, and pets.

As used herein, the term "treatment", "treat" or "treating" is an approach for obtaining beneficial or desired clinical results. For purposes of this disclosure, beneficial or desired clinical results include, but are not limited to, one or more of the following: increased immune response, increased T cell response, decreased extent of damage from a disease, condition, or disorder, decreased duration of a disease, condition, or disorder, and/or reduction in the number, extent, or duration of symptoms related to a disease, condition, or disorder. The term includes the administration of the compounds, agents, drugs or pharmaceutical compositions of the present disclosure to prevent or delay the onset of one or more symptoms, complications, or biochemical indicia of a disease or condition; lessening or improving one or more symptoms; shortening or reduction in duration of a symptom; or arresting or inhibiting further development of a disease, condition, or disorder. Treatment may be prophylactic (to prevent or delay the onset of a disease, condition, or disorder, or to prevent the manifestation of clinical or subclinical symptoms thereof) or therapeutic suppression or alleviation of symptoms after the manifestation of the disease, condition, or disorder. The beneficial or desired clinical result may be an increase or decrease (as appropriate) of 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% relative to an appropriate control, for example, a subject that did not receive the therapy.

The term "administering" or "administration" as used herein refers to the placement of an agent, a drug, a compound, or a pharmaceutical composition as disclosed herein into a subject by a method or route which results in at least partial delivery of the composition to a desired site. The compounds and pharmaceutical compositions disclosed herein can be administered by any appropriate route which results in an effective treatment in the subject. Routes of administration of the compounds and pharmaceutical compositions disclosed herein include, but are not limited to, intravenous, or intraperitoneal routes of administration, or a combination thereof.

The term "effective amount" or "therapeutically effective amount", for example an effective amount or therapeutically effective amount of a T cell lineage population as used herein is an amount sufficient to bring about any one or more beneficial or desired results. In more specific aspects, an effective amount may alleviate or ameliorate one or more symptoms of a disease; decrease the duration of time that one or more symptoms of a disease, are present in a subject; increase the survival rate of a subject having a disease. For prophylactic use, beneficial or desired results may include eliminating or reducing the risk, lessening the severity, or delaying the onset of a disease, including biochemical and/or histological symptoms of the infection, its complications and intermediate pathological phenotypes presenting during development of the disease. For therapeutic use, beneficial or desired results may include clinical results such as reducing one or more symptoms of a disease; decreasing the dose or length of administration of other medications required to treat the disease; enhancing the effect and/or reducing the toxicity of another medication; delaying the progression of the disease in a subject, decreasing the duration of time that one or more symptoms of a disease, are present in a subject, and/or increasing the overall survival rate of a subject having a disease. An effective amount can be administered in one or more than one dose, round of administration, or course of treatment.

For purposes of this disclosure, an effective dosage of a cell population or a pharmaceutical composition is an amount sufficient to accomplish prophylactic or therapeutic treatment either directly or indirectly. As is understood in the clinical context, an effective dosage of a compound, or a pharmaceutical composition may or may not be achieved in conjunction with another agent, drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved. The amount may vary from one subject to another and may depend upon one or more factors, such as, for example, subject gender, age, body weight, subject's health history, and/or the underlying cause of the disease, condition, or disorder to be prevented, inhibited and/or treated.

The term "pharmaceutically acceptable carrier, diluent, or excipient" as used herein includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. In some embodiments, diluents for aerosol or parenteral administration are phosphate buffered saline (PBS) or normal (0.9%) saline. Compositions comprising such carriers are formulated by well-known conventional methods (see, for example, Remington's Pharmaceutical Sciences, 18th edition, A. Gennaro, ed., Mack Publishing Co., Easton, PA, 1990; and Remington, The Science and Practice of Pharmacy 20th Ed. Mack Publishing, 2000).

As used herein, the singular forms "a," "an," and "the," are intended to include the plural forms as well, unless the context clearly indicates otherwise.

The phrase "and/or" should be understood to mean "either or both" of the elements so conjoined, i.e., elements that are conjunctively present in some cases and disjunctively present in other cases. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein, the phrase "one or more," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "one or more" refers, whether related or unrelated to those elements specifically identified. Thus, as a non-limiting example, "one or more of A and B" (or, equivalently, "one or more of A or B," or, equivalently "one or more of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the term "about" is used in conjunction with a numerical range, it modifies that range by extending the boundaries above and below those numerical values. In general, the term "about" is used herein to modify a numerical value above and below the stated value by a variance of 20%, 10%, 5%, or 1%. In certain embodiments, the term "about" is used to modify a numerical value above and below the stated value by a variance of 10%. In certain embodiments, the term "about" is used to modify a numerical value above and below the stated value by a variance of 5%. In certain embodiments, the term "about" is used to modify a numerical value above and below the stated value by a variance of 1%.

When a range of values is listed herein, it is intended to encompass each value and sub-range within that range. For example, "1-5 mL" is intended to encompass 1 mL, 2 mL, 3 mL, 4 mL, 5 mL, 1-2 mL, 1-3 mL, 1-4 mL, 1-5 mL, 2-3 mL, 2-4 mL, 2-5 mL, 3-4 mL, 3-5 mL, and 4-5 mL.

It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

The term "consisting of" and its derivatives, as used herein, are intended to be closed terms that specify the presence of stated features, integers, steps, operations, elements, and/or components, and exclude the presence or addition of one or more other features, integers, steps, operations, elements and/or components.

General Techniques

Unless otherwise defined herein, scientific and technical terms used in connection with the present disclosure shall have the meanings that are commonly understood by those of ordinary skill in the art. Generally, nomenclatures used in connection with, and techniques of, cell and tissue culture, molecular biology, immunology, microbiology, genetics and protein and nucleic acid chemistry and hybridization described herein are those well-known and commonly used in the art.

The practice of the present disclosure will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Cales, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Sambrook and Russell, Molecular Cloning: A Laboratory Manual, $3^{rd}$. ed., Cold Spring Harbor Laboratory Press, Cold Spring Harbor, N Y (2001); Ausubel et al., Current Protocols in Molecular Biology, John Wiley & Sons, N Y (2002); Harlow and Lane Using Antibodies: A Laboratory Manual, Cold Spring Harbor Laboratory Press, Cold Spring Harbor, N Y (1998); Coligan et al., Short Protocols in Protein Science, John Wiley & Sons, N Y (2003); Short Protocols in Molecular Biology (Wiley and Sons, 1999); and Immunobiology (C. A. Janeway and P. Travers, 1997).

Method of Generating T Cell Lineage Populations In Vitro

Generally, the in vitro methods of generating T cell lineage populations provided herein involve culturing progenitor T cells (proT cells) in the presence of Notch signalling ligands under conditions and for a time suitable for differentiation into T cell lineage populations.

Methods of generating proT cells from stem/progenitor cells such as hematopoietic progenitor cells (HPCs), hematopoietic stem/progenitor cells (HSPCs), or CD34+ cells are known in the art, for example, differentiation on immobilized VCAM-1 and Notch signalling ligands, for example DL4, under suitable media conditions (e.g., Shukla et al., 2017) or using DL4-coated microbeads (e.g., Trotman-Grant et al., 2021).

To confirm generation of proT cells, the cells may be analyzed for one or more features indicative of proT cells, such as, for example, one or more cell surface markers such as CD5 and CD7. Suitable techniques for analyzing cell surface markers are known to those of ordinary skill in the art, and may include, for example, flow cytometry as used herein, or immunocytochemistry. The number of cells and viability of the cells may be analyzed by techniques well known to those of ordinary skill in the art, and may include, for example use of an automated cell counter as disclosed herein.

In an embodiment, the CD34+ cells may be obtained from cord blood, peripheral blood or bone marrow or they may be derived in vitro from pluripotent stem cells such as embryonic stem cells (ESCs) or induced pluripotent stem cells (iPSCs) or other intermediate stem cells. In a preferred embodiment, the stem and/or progenitor cells are human cells. In an embodiment, the stem cells are mobilized peripheral blood-derived CD34+ cells. In a preferred embodiment, the CD34+ cells are derived in vitro from iPSCs. Methods of generating CD34+ cells from iPSCs are known in the art, for example, differentiation with appropriate medium conditions (e.g., Trotman-Grant et al., 2021).

Cells may be cultured in types of cell culture systems known in the art, for example, cell culture plates, culture dishes, and bioreactors including stirred-tank reactors (STRs), rocking bag bioreactors, and other suitable cell culture formats. Cell culture may be carried out under static conditions, dynamic or agitated conditions, or a combination of static and dynamic conditions. Bioreactors can be any type of bioreactor known in the art and can use any type of processing/culturing conditions and methods, including, for example, batch processes, fed-batch processes, and perfusion culturing methods and conditions.

The present invention of generating a T cell lineage population can be carried out using a population of HPCs, HSPCs, and/or progenitor T cells in the presence of a Notch signaling ligand and in the absence of a T cell receptor stimulator. The T cell receptor stimulator can be a molecule that engages and/or activates CD3 signaling, such as an anti-CD3 antibody, an antigen-presenting cell, or an artificial antigen-presenting cell. The present invention can be carried out in the absence of exogenous CD3 engagement and activation.

The present invention can also be used to generate cells that are surface CD3 negative (sCD3−) (e.g., cells on which CD3 is not detectable as a cell surface marker). The present invention can also be used to generate cells that are TCR− (such as cells that do not express an endogenous (i.e., native) TCR, or cells in which a TCR cell surface expression is not detectable). The present invention can also be used to generate cells that are both sCD3− and cell surface TCR− (i.e., cells in which both CD3 and a TCR are not expressed on the cell surface).

The present invention of generating a T cell lineage population can also be carried out using a population of HPCs, HSPCs, and/or progenitor T cells in the presence of a Notch signaling ligand and without engagement and/or stimulation of a chimeric antigen receptor (CAR) in cells that are CAR+.

The present invention can also be carried out using serum-free culture conditions and/or feeder-free (e.g., no stromal cells) culture conditions.

Substrates

In an embodiment, proT cells are cultured in a two-dimensional culture system utilizing a suitable 2D substrate, which can include, for example, a standard culture plate coated with Notch signalling ligands, for example, DL4. The culture plate may also be coated with VCAM-1.

In an embodiment, proT cells are cultured in a three-dimensional culture system utilizing a suitable 3D substrate, which can include, for example, micron-size particles (or beads), with or without a magnetic core, coated with one or more full proteins, protein domains (e.g. extracellular, intracellular, or other domain), peptides or protein fragments to activate Notch signalling. Several approaches can be used individually or in combination to produce protein coated particles, e.g.: physisorption driven by protein affinity to the particle material, chemical conjugation by reaction with, among others, amine, carboxyl, thiol, epoxy, azide reactive groups, or by coating an appropriate ligand to capture the protein of interest by affinity. Examples of affinity tags include but are not limited to: Fc, biotin, Halo, aldehyde, Snap, Spy-Catcher, VIPER.

Particles or beads may be composed of, for example, polystyrene, including carboxylated polystyrene, iron oxide, gold, or other suitable materials known in the art.

In one example, the Notch signalling ligand, for example, DL4, alone or in combination with VCAM-1, may be conjugated to polystyrene microbeads as described in Trotman-Grant et al., 2021, and WO2019157597.

In another example, 3D ETN beads can be manufactured by affinity capturing DL4 and VCAM-1 carrying the appropriate affinity tag on streptavidin or protein G coated beads, where beads are diluted to 0.1% solids in Dulbecco's phosphate-buffered saline (DPBS) without $Ca^{2+}$ or $Mg^{2+}$, supplemented with 0.05% BSA, and incubated with the protein solution (0.1×-20× protein molar excess) for 60 min at room temperature with continuous stirring. At the end of the incubation period, excess free protein is removed by magnetic separation followed by a buffer exchange. The procedure is repeated an additional four times, after which 3D ETN beads are concentrated ten-fold for storage.

Quantification of protein immobilization may be carried out according to methods known in the art such as, for example, the colorimetric bicinchoninic acid (BCA) assay, an immunofluorescence assay, or other known detection methods.

T Cell Therapies

T cells have a broad range of therapeutic applications. T cells may be modified by, for example, conventional gene editing approaches such as nuclease editing or viral vector transduction, to express a chimeric antigen receptor (CAR), and/or an exogenous T Cell Receptor (TCR), to generate engineered T cell therapies (Weber et al., 2020). T cells derived from progenitor cells, including pluripotent stem cells, may be genetically engineered at the pluripotent or progenitor cell stage to comprise a nucleic acid encoding a CAR or TCR that may be expressed at the pluripotent cell, progenitor cell, or derivative cell stage. Engineered T cell therapies have applicability in, for example, oncology and autoimmune disorders. In oncology, engineered T cell therapies have applicability in, for example, hematologic cancers, such as B cell lymphoma, B cell acute lymphoblastic leukemia and other B cell malignancies, multiple myeloma, and other hematologic cancers, as well as in solid tumours such as, for example, mesothelioma, adenocarcinomas, gliomas, and sarcomas (Weber et al., 2020). In autoimmune disorders, engineered T cell therapies have applicability in, for example, Type I diabetes, rheumatoid arthritis, multiple sclerosis, and other autoimmune disorders or conditions (Weber et al., 2020).

Engineered T cell therapies may target antigens known to be expressed on target cell types, including tumour cells or within tumour tissues. Chimeric antigen receptors (CARs) may be designed to target surface antigens or multivalent soluble antigens. The targeting ectodomain of the CAR may be a single-chain variable fragment (scFv), single-domain antibodies (single variable domain on a heavy chain, VHH), nanoantibodies, or other antigen-binding domain (Qu et al., 2022). CAR-T cell therapies may be directed towards multiple antigens using varying CAR designs or multiple CARs (Qu et al. 2022). Exemplary oncology antigens and corresponding cancer types for CAR-T cell therapies are listed in Table 1 below (Qu et al., 2022; Guha et al., 2022; Drougkas et al., 2023; Want et al., 2023).

TABLE 1

| Antigen/Antigen Type | Cancer Type |
|---|---|
| 5 T4 (TPBG) | ovarian cancer |
| AE1/2 | gastric cancer |
| AFP | hepatocellular carcinoma (HCC) |
| Alpha folate receptor | serous ovarian, Fallopian tube, or primary peritoneal cancer (epithelial cancer) |
| ALPPL2 (PLAP-like) | ovarian cancer |
| ANXA2 (ANX2L4, CAL1H, LIP2, LPC2, LPC2D, P36) | ovarian cancer |
| ARP2/3 (p41-ARC) | gastric cancer |
| AXL (UFO, ARK) | breast cancer, glioma, lung cancer |
| B7H3 (CD276) | colorectal cancer, esophageal cancer, Ewing's sarcoma, gastric cancer, glioma, hepatocellular carcinoma (HCC), lung cancer, melanoma, pancreatic cancer, prostate cancer, osteosarcoma, ovarian cancer |
| B7H6 | gastric cancer |
| BAFF-R (TNFRSF13C, CD268) | B-acute lymphoblastic leukemia (B-ALL) |
| BCMA (TNFRSF17, CD269) | chronic lymphocytic leukemia (CLL), multiple myeloma (MM) |
| BRCA | serous ovarian, Fallopian tube, or primary peritoneal cancer (epithelial cancer) |
| BT-001 | solid tumor |
| CA19-9 (sialyl-Lewis) | gastric cancer |
| CAIX | renal cell carcinoma (RCC) |
| CD117 (c-kit, KIT) | acute myeloid leukemia (AML), Ewing's sarcoma, osteosarcoma |
| CD123 (IL3RA) | acute myeloid leukemia (AML), B-acute lymphoblastic leukemia (B-ALL) |
| CD126 (IL6R, gp80) | melanoma, multiple myeloma (MM), prostate cancer |
| CD133 (Prominin-1, PROM1, AC133) | breast cancer, colorectal cancer, Ewing's sarcoma, gastric cancer, glioma, hepatocellular carcinoma (HCC), lung cancer, osteosarcoma, ovarian cancer, pancreatic cancer |
| CD138 (Syndecan, SDC) | multiple myeloma (MM) |
| CD147 (BSG) | glioma, hepatocellular carcinoma (HCC), lung cancer |
| CD16 (FCG3, FCGR3, IGFR3, IMD20) | melanoma |
| CD166 (ALCAM) | Ewing's sarcoma, osteosarcoma |
| CD171 | neuroblastoma |
| CD177 (NB1 GP, PRV-1) | Ewing's sarcoma, osteosarcoma |
| CD19 (B lymphocyte surface antigen B4, T cell surface antigen LEU-12) | B-acute lymphoblastic leukemia (B-ALL), B-cell non-Hodgkin's lymphoma (B-NHL), Hodgkin's lymphoma (HL), chronic lymphocytic leukemia (CLL), multiple myeloma (MM) |
| CD20 (B Lymphocyte surface antigens B1, Bp35, leU-16, MS4A1) | B-acute lymphoblastic leukemia (B-ALL), B-cell non-Hodgkin's lymphoma (B-NHL), chronic lymphocytic leukemia (CLL), Mantle cell lymphoma (MCL), melanoma |
| CD20/CD22 | Relapsed or refractory lymphoid cancers |
| CD22 (Siglec-2, BL-CAM, T cell surface antigen LEU-14) | B-acute lymphoblastic leukemia (B-ALL), B-cell non-Hodgkin's lymphoma (B-NHL), T-cell non-Hodgkin's lymphoma (T-NHL) |
| CD23 (Low affinity immunoglobulin, εFc receptor, BLAST-2, FcεRII, FCER2, CLEC4J) | chronic lymphocytic leukemia (CLL) |
| CD30 (TNF receptor superfamily member 8, TNFRSF8, Ki-1 antigen) | Hodgkin's lymphoma (HL), T-cell non-Hodgkin's lymphoma (T-NHL) |
| CD318 (CDCP 1) | pancreatic cancer |
| CD32b (FcγRII, FCGR2A, FCGR2B) | chronic lymphocytic leukemia (CLL) |
| CD33 (Siglec-3) | acute myeloid leukemia (AML), myeloid malignancies |
| CD38 (ADP ribocyclase 1) | acute myeloid leukemia (AML), B-acute lymphoblastic leukemia (B-ALL), multiple myeloma (MM) |
| CD4 (OKT4) | T-cell non-Hodgkin's lymphoma (T-NHL) |
| CD44 (Hermes, Pgp1, H-CAM, Hutch) | hepatocellular carcinoma (HCC), ovarian cancer |
| CD44v6 (Epican, HUTCH-I, LHR, ECMR-III) | acute myeloid leukemia (AML), breast cancer, gastric cancer, head and neck squamous cell carcinoma (HNSCC), lung cancer, multiple myeloma (MM) |
| CD47 (MER6, IAP) | lung cancer, ovarian cancer |
| CD5 (LEU1) | T-acute lymphoblastic leukemia (T-ALL), T-cell non-Hodgkin's lymphoma (T-NHL) |
| CD56 (NCAM1) | multiple myeloma (MM) |
| CD7 (LEU 9, GP40, TP41) | acute myeloid leukemia (AML), T-acute lymphoblastic leukemia (T-ALL), T-cell non-Hodgkin's lymphoma (T-NHL) |
| CD70 (CD27L) | acute myeloid leukemia (AML), breast cancer, esophageal cancer, head and neck squamous cell carcinoma (HNSCC), melanoma, ovarian cancer, pancreatic cancer, renal cell carcinoma (RCC) |
| CD72 | B-acute lymphoblastic leukemia (B-ALL) |
| CDH17 | colorectal cancer, gastric cancer |
| CDH6 | ovarian cancer |
| CEA (CEACAM5) | breast cancer, colorectal cancer, metastatic colorectal cancer, gastric cancer, hepatocellular carcinoma (HCC), lung cancer, pancreatic cancer/pancreatic-biliary tract cancer, peritoneal cancer, prostate cancer |

TABLE 1-continued

| Antigen/Antigen Type | Cancer Type |
|---|---|
| CLDN18.2 (CLDN18, Claudin 18, SFTA5) | esophageal cancer, gastric cancer, lung cancer, pancreatic/pancreatic-biliary tract cancer |
| CLDN6 (Skullin) | ovarian cancer, testicular cancer |
| CLEC14A (EGFR5) | lung cancer |
| CLL1 (CLEC12A) | acute myeloid leukemia (AML) |
| CLTX | glioma |
| c-MET (HGFR) | breast cancer, colorectal cancer, gastric cancer, glioma, hepatocellular carcinoma (HCC), lung cancer |
| CSPG4 (NG2, MCSP, MCSPG, MSK16, HMW-MAA, MEL-CSPG) | breast cancer, glioma, head and neck squamous cell carcinoma (HNSCC), melanoma |
| CXCR1 | ovarian cancer |
| CXCR4 (CD184, Fusin, NPYR, HSY3RR, LAP3, LCR1) | lung cancer |
| CXCR5 (CD185) | B-cell non-Hodgkin's lymphoma (B-NHL) |
| DLL3 (SCDO1) | lung cancer |
| DR5 | hepatocellular carcinoma (HCC) |
| DSC2 | gastric cancer |
| EGFR and CD133 | pancreatic cancer/pancreatic-biliary tract cancer |
| EGFR(ERBB1) | breast cancer, colorectal cancer, Ewing's sarcoma, gastric cancer, head and neck squamous cell carcinoma (HNSCC), lung cancer (malignant pleural mesothelioma), osteosarcoma, pancreatic cancer/pancreatic-biliary tract cancer |
| EGFR806 | central nervous system tumor, pediatric glioma |
| EGFRIII | glioblastoma, gliosarcoma and brain tumor |
| EGFRvIII | glioblastoma, glioma, hepatocellular carcinoma (HCC), pancreatic cancer |
| EpCAM (CD326, TACSTD1) | breast cancer, colorectal cancer, gastric cancer, hepatocellular carcinoma (HCC), pancreatic cancer, prostate cancer |
| EphA10 | breast cancer |
| EphA2 (ECK, CTPA, ARCC2, CTPP1, CTRCT6) | Ewing's sarcoma, glioma, lung cancer, osteosarcoma |
| FAP (SIMP, DPPIV, FAPA) | glioma, lung cancer (malignant pleural mesothelioma), pancreatic cancer |
| FcµR | chronic lymphocytic leukemia (CLL) |
| FLT3 (CD135, FLK2) | acute myeloid leukemia (AML) |
| Fn14 | glioma |
| FR-a | ovarian cancer |
| FRα (FOLR1) | breast cancer, gastric cancer, lung cancer, ovarian cancer |
| FRβ | acute myeloid leukemia (AML), lung cancer |
| GD2 | breast cancer, Ewing's sarcoma, glioma, lung cancer, melanoma, osteosarcoma |
| GD3 | melanoma |
| GFRα4 (GDNF family receptor alpha-4) | thyroid cancer |
| Glypican-3 | liver cancer |
| gp100 | breast cancer, hepatocellular carcinoma (HCC), melanoma |
| GPC3 (DGSX, OCI5, SDYS, SGB, SGBS1, MXR7) | hepatocellular carcinoma (HCC), lung cancer, renal cell carcinoma (RCC) |
| GPRC5D | multiple myeloma (MM) |
| GUCY2C (GUC2C, STAR) | colorectal cancer, pancreatic cancer |
| HER2 (ERBB2) | breast cancer, colorectal cancer, esophageal cancer, Ewing's sarcoma, gastric cancer, glioblastoma, glioma/pediatric glioma, head and neck squamous cell carcinoma (HNSCC), hepatocellular carcinoma (HCC), melanoma, lung cancer, osteosarcoma, ovarian cancer, pancreatic cancer/pancreatic-biliary tract cancer |
| HLA-A2 | ependymoma |
| ICAM-1 (CD54) | breast cancer, , gastric cancer, thyroid cancer |
| IGF1R (CD221, JTK13, MGC18216) | Ewing's sarcoma osteosarcoma |
| IL13Rα2 (CD213A2, IL13BP, CT19) | glioblastoma, glioma, melanoma |
| IM83 | liver cancer |
| KK-LC-1 | serous ovarian, Fallopian tube, or primary peritoneal cancer (epithelial cancer) |
| L1-CAM (CD171, HSAS, MASA) | ovarian cancer |
| LewisY | acute myeloid leukemia (AML), lung cancer, multiple myeloma (MM) |
| LILRB4 (CD85, LILRB3, ILT5, LIR3) | acute myeloid leukemia (AML) |
| LMP1 | hematological malignancies |
| Mesothelin (MSLN) | acute myeloid leukemia (AML), breast cancer, cervical cancer, colorectal cancer, gastric cancer, lung cancer (malignant pleural mesothelioma), ovarian cancer, pancreatic cancer |
| MG7 | hepatocellular carcinoma (HCC) |
| MPL (MPF, SMRP) | acute myeloid leukemia (AML) |
| MUC1 (PEM, PUM, DF3, MAM-6) | breast cancer, cervical cancer, colorectal cancer, esophageal cancer, Ewing's sarcoma, gastric cancer, glioma, head and neck squamous cell carcinoma (HNSCC), hepatocellular carcinoma (HCC), lung cancer, osteosarcoma, ovarian cancer, pancreatic cancer, renal cell carcinoma (RCC) |

TABLE 1-continued

| Antigen/Antigen Type | Cancer Type |
|---|---|
| MUC16 (CA125) | ovarian cancer |
| NKG2DL | acute myeloid leukemia (AML), breast cancer, colorectal cancer, Ewing's sarcoma, gastric cancer, glioma, hepatocellular carcinoma (HCC), multiple myeloma (MM), osteosarcoma, prostate cancer, T-acute lymphoblastic leukemia (T-ALL) |
| NRP-1 (VEGF165R, NRP) | gastric cancer |
| NY-ESO-1 (CTAG1B, ESO1, LAGE2) | esophageal cancer, lung cancer, melanoma, multiple myeloma (MM) |
| OR2H1 | lung cancer, ovarian cancer |
| P32 | glioma |
| PAK4 | glioma |
| PD-L1 (CD274, B7-H1) | breast cancer, gastric cancer, head and neck squamous cell carcinoma (HNSCC), hepatocellular carcinoma (HCC), lung cancer, melanoma |
| PDPN (GP36) | glioma |
| PODXL (PCLP, PCLP1, Gp200) | pancreatic cancer |
| PR1 | acute myeloid leukemia (AML) |
| PSCA | colorectal cancer, gastric cancer, lung cancer, pancreatic cancer/pancreatic-biliary tract cancer, metastatic pancreatic cancer, prostate cancer, metastatic castration-resistant prostate cancer |
| PSMA, prostate-specific membrane antigen (GIG27, FOLH, NAALAD1, PSM) | prostate cancer, metastatic castration-resistant prostate cancer, salivary gland cancers |
| PTK7 (CCK4) | breast cancer, lung cancer, ovarian cancer |
| ROBO1 (DUTT1) | pancreatic cancer |
| ROR1 (NTRKR1) | breast cancer, chronic lymphocytic leukemia (CLL), Ewing's sarcoma, lung cancer, osteosarcoma |
| ROR2 | gastric cancer, pancreatic cancer, renal cell carcinoma (RCC) |
| Siglec-6 (CD327, OB-BP1) | acute myeloid leukemia (AML), chronic lymphocytic leukemia (CLL) |
| SLAMF3 (CD229, Ly9) | multiple myeloma (MM) |
| SLAMF7 (CS1, CD319, CRACC) | multiple myeloma (MM) |
| TAA-T | acute myeloid leukemia (AML), Hodgkin's lymphoma (HL), myelodysplastic syndrome (MDS), |
| TAG 72 (CA72-4) | colorectal cancer, metastatic colorectal cancer, gastric cancer, ovarian cancer |
| TEM8 (ATR, GAPO) | breast cancer |
| TGFβ (IBDIMDE) | hepatocellular carcinoma (HCC), lung cancer |
| Tim3 (CD366, HAVCR2) | acute myeloid leukemia (AML) |
| TRBC | T-cell non-Hodgkin's lymphoma (T-NHL) |
| TROP2 (TACSTD2, GA733-1, M1S1) | breast cancer, gastric cancer, pancreatic cancer |
| TRP1/2 | melanoma |
| TSHR (LGR3, CHNG1) | thyroid cancer |
| TSLPR (CRL2, CRLF2) | B-acute lymphoblastic leukemia (B-ALL) |
| TSPAN8 | pancreatic cancer |
| U87 | pancreatic cancer |
| uPAR (CD87) | gastric cancer, ovarian cancer |
| VEGFR-2 (FLK-1) | melanoma, renal cell carcinoma (RCC) |
| WT1 (WIT-1) | acute myeloid leukemia (AML) |
| αvβ3 (CD51, CD61, GP3A) | melanoma |
| κ light chain | B-cell non-Hodgkin's lymphoma (B-NHL), chronic lymphocytic leukemia (CLL), multiple myeloma (MM) |
| λ light chain | B-cell non-Hodgkin's lymphoma (B-NHL), chronic lymphocytic leukemia (CLL) |

TCR-T cell therapies target antigens expressed as peptide-human leukocyte antigen (HLA) complexes on the surface of a target cell. These targets may include tumour-associated antigens (TAAs) and tumour-specific antigens (TSAs) (Baulu et al., 2023). Exemplary oncology antigens and corresponding cancer types for TCR-T cell therapies are listed in Table 2 below (Baulu et al., 2023; Sun et al., 2021; Want et al., 2023).

TABLE 2

| Antigen/Antigen Type | Cancer Type |
|---|---|
| AFP | hepatocellular carcinoma (HCC) |
| CEA | colorectal cancer |
| CTAG1A (NY-ESO-1) | bladder carcinoma, breast cancer, esophageal cancer, gastric cancer, hepatocellular carcinoma (HCC), lung cancer, myeloma, melanoma, neoplasms, serous ovarian, Fallopian tube, or primary peritoneal cancer (epithelial cancer), synovial sarcoma |
| EBV | acute myeloid leukemia (AML), head and neck squamous cell carcinoma (HNSCC), nasopharyngeal carcinoma, neuroblastoma |
| gp100 | melanoma |
| HA-1H | juvenile myelomonocytic leukemia (JMML), recurrent acute biphenotypic leukemia, recurrent acute undifferentiated leukemia |

TABLE 2-continued

| Antigen/Antigen Type | Cancer Type |
|---|---|
| HBV | HBV-hepatocellular carcinoma (HCC) |
| HERV-E | kidney cancer |
| HPV16-E6 | human papillomavirus (HPV)-16+ cancers (cervical, vulvar, vaginal, penile, anal, and oropharyngeal cancers) |
| HPV16-E7 | human papillomavirus (HPV)-16+ cancers (cervical, vulvar, vaginal, penile, anal, and oropharyngeal cancers), neoplasia |
| Kita-kyushu Lung Cancer Antigen 1/cancer testis antigen (KK-LC-1) | breast cancer, cervical cancer, gastric cancer, lung cancer |
| KRAS mutations e.g. KRAS G12D | gastric cancer, gastrointestinal cancer, pancreatic cancer, pancreatic ductal adenocarcinoma, |
| LMP2 | nasopharyngeal carcinoma, recurrent and metastatic nasopharyngeal carcinoma |
| MAGE family | bladder cancer, breast cancer, cervical cancer, head and neck squamous cell carcinoma (HNSCC), melanoma, metastatic non-small cell lung carcinoma (NSCLC), metastatic malignant solid neoplasm, renal cell carcinoma (RCC), uveal melanoma |
| MAGEA10 | non-small cell lung carcinoma (NSCLC) |
| MAGEA3 | esophageal cancer, melanoma, metastatic solid tumors, myeloma, synovial sarcoma |
| MAGEA4 | esophageal cancer, solid tumors |
| MAGEC2 | head and neck squamous cell carcinoma (HNSCC), melanoma, uveal melanoma |
| MART-1 (MLANA) | melanoma |
| MCPyV | Merkel cell carcinoma |
| Mesothelin (MSLN) | Metastatic pancreatic ductal adenocarcinoma, ovarian cancer |
| NY-ESO-1 | liposarcoma, melanoma, myeloma, malignant Peripheral Nerve Sheath Tumor (MPNST), osteosarcoma, serous ovarian, Fallopian tube, or primary peritoneal cancer (epithelial cancer), soft tissue sarcoma, synovial sarcoma |
| PMEL (gp100) | skin cancer, melanoma |
| PRAME | acute myeloid leukemia (AML), myelodysplastic syndrome (MDS), uveal melanoma |
| TAC-1 | HER2-positive solid tumors |
| TP53 | breast cancer, metastatic breast cancer, kidney cancer, melanoma |
| TSA | malignant epithelial neoplasms |
| WT1 | acute myeloid leukemia (AML), chronic myeloid leukemia (CML), myelodysplastic syndromes (MDS), pleural malignant, recurrent non-small cell lung carcinoma (NSCLC) |

The pharmaceutical composition provided herein may be administered to a subject in order to alleviate or ameliorate one or more symptoms of a disease; decrease the duration of time that one or more symptoms of a disease, are present in a subject; and increase the survival rate of a subject having a disease.

The pharmaceutical composition provided herein may be administered to a subject to treat cancer or autoimmune disorders in the subject.

The pharmaceutical composition provided herein may be administered to a subject in an effective amount or a therapeutically effective amount. A person of ordinary skill in the art would be able to determine such amounts based on such factors as the subject's size (e.g., weight), age and/or sex; the severity of the subject's symptoms; and the particular composition or route of administration selected. A person skilled the art would also know how to select the proper route of administration and to administer the compounds and compositions provided herein.

The dosage of the pharmaceutical composition of the disclosure varies depending on many factors, such as the pharmacodynamic properties of the composition, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors. In some embodiments, the pharmaceutical composition is administered initially in a suitable dosage that is adjusted as required, depending on the clinical response.

Kits

The invention also provides kits comprising the pharmaceutical composition described herein. Kits of the invention include one or more containers comprising the pharmaceutical composition described herein and instructions for use in accordance with any of the methods of the invention described herein. Generally, these instructions comprise a description of administration of the pharmaceutical composition for the above-described therapeutic treatments. In some embodiments, kits are provided for producing a single-dose administration unit.

The instructions relating to the use of the pharmaceutical composition generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The disclosure is further described in detail by reference to the following experimental examples. These examples are provided for purposes of illustration only, and are not intended to be limiting unless otherwise specified. Thus, the disclosure should in no way be construed as being limited to the following examples, but rather, should be construed to encompass any and all variations which become evident as a result of the teaching provided herein.

Example 1: Preparation of an Engineered Thymic Niche (ETN)

DL4 and VCAM-1 Production

Recombinant DL4-Fc fusion protein was purchased from Sino Biological or manufactured in-house using HEK-293T cells and purified with HiTrap Protein G affinity columns (GE Healthcare) as previously described (e.g., Trotman-Grant et al., 2017). Recombinant VCAM-1-FC fusion protein was purchased from R&D Systems. DL4 and VCAM-1 that are suitable for preparation of 2D ETN and 3D ETN as further described below, are shown in Table 3.

TABLE 3

| Protein | Species | Sequence |
|---|---|---|
| DL4 | Human | MAAASRSASGWALLLLLVALWQQRAAGSGVFQLQLQEFINERGVLASGRPCEPG CRTFFRVCLKHFQAVVSPGPCTFGTVSTPVLGTNSFAVRDDSSGGGRNPLQLP FNFTWPGTFSLIIEAWHAPGDDLRPEALPPDALISKIAIQGSLAVGONWLLDE QTSTLTRLRYSYRVICSDNYYGDNCSRLCKKRNDHFGHYVCQPDGNLSCLPGW TGEYCQQPICLSGCHEQNGYCSKPAECLCRPGWQGRLCNECIPHNGCRHGTCS TPWQCTCDEGWGGLFCDQDLNYCTHHSPCKNGATCSNSGQRSYTCTCRPGYTG VDCELELSECDSNPCRNGGSCKDQEDGYHCLCPPGYYGLHCEHSTLSCADSPC FNGGSCRERNQGANYACECPPNFTGSNCEKKVDRCTSNPCANGGQCLNRGPSR MCRCRPGFTGTYCELHVSDCARNPCAHGGTCHDLENGLMCTCPAGFSGRRCEV RTSIDACASSPCFNRATCYTDLSTDTFVCNCPYGFVGSRCEFPVGLPPSFPWV AVSLGVGLAVLLVLLGMVAVAVRQLRLRRPDDGSREAMNNLSDFQKDNLIPAA QLKNTNQKKELEVDCGLDKSNCGKQQNHTLDYNLAPGPLGRGTMPGKFPHSDK SLGEKAPLRLHSEKPECRISAICSPRDSMYQSVCLISEERNECVIATEV (SEQ ID NO: 1) |
| VCAM-1 | Human | QIDSPL (SEQ ID NO: 2) |
| VCAM-1 | Human | TQIDSPLN (SEQ ID NO: 3) |
| VCAM-1 | Mouse | MPVKMVAVLGASTVLWILFAVSQAFKIEISPEYKTIAQIGDSMALTCSTTGCE SPLFSWRTQIDSPLNAKVRTEGSKSVLTMEPVSFENEHSYLCTATCGSGKLER SIHVDIYSFPKDPEIQFSGPLEVGKPVTVKCLAPDIYPVYRLEIDLFKGDQLM NRQEFSSEEMTKSLETKSLEVTFTPVIEDIGKALVCRAKLHIDQIDSTLKERE TVKELQVYISPRNTTISVHPSTRLQEGGAVTMTCSSEGLPAPEIFWGRKLDN EVLOLLSGNATLTLIAMRMEDSGVYVCEGVNLIGRDKAEVELVVQEKPFIVDI SPGSQVAAQVGDSVVLTCAAIGCDSPSFSWRTQTDSPLNGVVRNEGAKSTLVL SSVGFEDEHSYLCAVTCLQRTLEKRTQVEVYSFPEDPVIKMSGPLVHGRPVTV NCTVPNVYPFDHLEIELLKGETTLMKKYFLEEMGIKSLETKILETTFIPTIED TGKSLVCLARLHSGEMESEPKQRQSVQPLYVNVAPKETTIWVSPSPILEEGSP VNLTCSSDGIPAPKILWSRQLNNGELQPLSENTTLTFMSTKRDDSGIYVCEGI NEAGISRKSVELIIQVSPKDIQLTVFPSKSVKEGDTVIISCTCGNVPETWIIL KKKAKTGDMVLKSVDGSYTIRQAQLQDAGIYECESKTEVGSQLRSLTLDVKGK EHNKDYFSPELLALYCASSLVIPAIGMIVYFARKANMKGSYSLVEAQKSKV (SEQ ID NO: 4) |
| VCAM-1 | Human | MPGKMVVILGASNILWIMFAASQAFKIETTPESRYLAQIGDSVSLTCSTTGCE SPFFSWRTQIDSPLNGKVTNEGTTSTLTMNPVSFGNEHSYLCTATCESRKLEK GIQVEIYSFPKDPEIHLSGPLEAGKPITVKCSVADVYPFDRLEIDLLKGDHLM KSQEFLEDADRKSLETKSLEVTFTPVIEDIGKVLVCRAKLHIDEMDSVPTVRQ AVKELQVYISPKNTVISVNPSTKLQEGGSVTMTCSSEGLPAPEIFWSKKLDNG NLQHLSGNATLTLIAMRMEDSGIYVCEGVNLIGKNRKEVELIVQEKPFTVEIS PGPRIAAQIGDSVMLTCSVMGCESPSFSWRTQIDSPLSGKVRSEGTNSTLTLS PVSFENEHSYLCTVTCGHKKLEKGIQVELYSFPRDPEIEMSGGLVNGSSVTVS CKVPSVYPLDRLEIELLKGETILENIEFLEDTDMKSLENKSLEMTFIPTIEDT GKALVCQAKLHIDDMEFEPKQRQSTQTLYVNVAPRDTTVLVSPSSILEEGSSV NMTCLSQGFPAPKILWSRQLPNGELQPLSENATLTLISTKMEDSGVYLCEGIN QAGRSRKEVELIIQVTPKDIKLTAFPSESVKEGDTVIISCTCGNVPETWIILK KKAETGDTVLKSIDGAYTIRKAQLKDAGVYECESKNKVGSQLRSLTLDVQGRE NNKDYFSPELLVLYFASSLIIPAIGMIIYFARKANMKGSYSLVEAQKSKV (SEQ ID NO: 5) |

Preparation of 2D ETN

Tissue culture plates with 6-well, 12-well, 24-well, 48-well and 96-well were coated with the Notch signalling ligand, DL4, and VCAM-1 overnight at 4° C. or for 3 hours at 37° C. Tissue culture plates may be stored at 4° C. for up to 2 weeks after coating. To coat, a solution of 20 μg/mL DL4 and 10 μg/mL VCAM-1 was prepared in Dulbecco's phosphate-buffered saline (DPBS) (−/−). The appropriate coating volume per well of DL4 and VCAM-1 diluted in DPBS were added to the tissue culture plates as shown in Table 4.

TABLE 4

| Plate format | Surface area (cm2/well) | Coating volume (μL/well) |
|---|---|---|
| 96-well | 0.32 | 50 |
| 48-well | 0.95 | 150 |
| 24-well | 1.9 | 300 |

TABLE 4-continued

| Plate format | Surface area (cm2/well) | Coating volume (μL/well) |
|---|---|---|
| 12-well | 4 | 650 |
| 6-well | 9.5 | 1500 |

The tissue culture plate(s) were tapped gently to ensure that the coating solution comprising the Notch signalling ligand, DL4, and VCAM-1 is evenly spread out throughout the well surface. The tissue culture plates were sealed with Parafilm® prior to being stored at 4° C. overnight or at 37° C. for 3 hours. Tissue culture plates coated with Notch signalling ligand DL4, and VCAM-1 overnight at 4° C. were placed in a 37° C. incubator for equilibration for three hours before plating cells. Following equilibration, or coating the tissue culture plates with the Notch signalling ligand DL4, and VCAM-1 for 3 hours at 37° C., the coating solution was aspirated from the wells. The wells were rinsed with DPBS (−/−) using the volumes shown in Table 5, immediately followed by addition of the cell suspension into the tissue culture plates.

TABLE 5

| Plate format | DPBS (—/—) wash volume (μL/well) |
|---|---|
| 96-well | 200 |
| 48-well | 800 |
| 24-well | 1600 |
| 12-well | 3200 |
| 6-well | 7500 |

Preparation of 3D ETN

The dose of 3D ETN may be calculated to scale with the bead diameter, and may be expressed as: a dose proportional to the surface area of the culturing surface of the culture plate or flask (e.g., as in Table 4), the number of beads per unit volume of culture, or the bead surface area per unit volume of culture. As calculated on a per unit volume basis, the bead per mL concentration does not change for different vessels. A "1×" bead dose denotes complete coverage of the plate surface by one layer of beads; as the beads are approximately spherical, the total surface area of the beads is 4 times the surface area of the surface of the plate or culture vessel. Table 6 provides a range of bead concentrations for a 3.05 μm diameter polystyrene bead.

TABLE 6

| Bead dose | Bead concentration (beads/mL) | Bead surface area per unit volume (cm²/mL) | Ratio of bead surface area to culture vessel area |
|---|---|---|---|
| 0.02 | 1.00E+06 | 0.29210 | 0.08:1 |
| 0.05 | 2.70E+06 | 0.78867 | 0.2:1 |
| 0.1 | 5.40E+06 | 1.57733 | 0.4:1 |
| 0.2 | 1.80E+07 | 3.15466 | 0.8:1 |
| 0.25 | 1.35E+07 | 3.94333 | 1:1 |
| 0.5 | 2.70E+07 | 7.88666 | 2:1 |
| 1 | 5.40E+07 | 15.77332 | 4:1 |
| 1.5 | 8.10E+07 | 23.65998 | 6:1 |
| 2 | 1.08E+08 | 31.54664 | 8:1 |
| 2.5 | 1.35E+08 | 39.4333 | 10:1 |
| 3 | 1.62E+08 | 47.31996 | 12:1 |
| 3.5 | 1.89E+08 | 55.20662 | 14:1 |

The Notch signalling ligand density (such as, for example, the density of surface-bound DL4) on the bead may vary from, for example, 100 molecules per square micrometer (100 molecules/m²) to 3000 molecules per square micrometer (3000 molecules/μm²). Table 7 provides a calculation of the Notch signalling ligand concentration for a range of bead doses and Notch signalling ligand densities for 3.05 am polystyrene beads. The concentration of Notch signaling ligand, e.g. DL4, was calculated based on the amount of DL4 capable of binding to soluble Notch1. The total concentration of Notch signaling ligand on beads may therefore be slightly higher.

TABLE 7

| Bead dose | Bead concentration (beads/mL) | Bead surface area per unit volume (cm²/mL) | Notch ligand concentration (molecules/mL media) for bead with surface density of 100 molecules/μm² | Notch ligand concentration (molecules/mL media) for bead with surface density of 800 molecules/μm² | Notch ligand concentration (molecules/mL media) for bead with surface density of 3000 molecules/μm² |
|---|---|---|---|---|---|
| 0.05 | 2.70E+06 | 0.78867 | 7.89E9 | 6.31E10 | 2.37E11 |
| 0.1 | 5.40E+06 | 1.57733 | 1.58E10 | 1.26E11 | 4.73E11 |
| 0.25 | 1.35E+07 | 3.94333 | 3.94E10 | 3.15E11 | 1.18E12 |
| 0.5 | 2.70E+07 | 7.88666 | 7.89E10 | 6.31E11 | 2.37E12 |
| 1 | 5.40E+07 | 15.77332 | 1.58E11 | 1.26E12 | 4.73E12 |
| 1.5 | 8.10E+07 | 23.65998 | 2.37E11 | 1.89E12 | 7.10E12 |
| 2 | 1.08E+08 | 31.54664 | 3.15E11 | 2.52E12 | 9.46E12 |
| 3 | 1.62E+08 | 47.31996 | 4.74E11 | 3.78E12 | 1.42E13 |
| 3.5 | 1.89E+08 | 55.20662 | 5.53E11 | 4.41E12 | 1.66E13 |

Table 8 provides the Notch signalling ligand (such as, for example, DL4) surface area per unit volume for a range of bead doses and Notch signalling ligand densities for both 3.05 μm and 3.29 μm diameter polystyrene beads.

TABLE 8

| Bead dose | Bead concentration (beads/mL) | Bead surface area per unit volume (cm²/mL) | Notch ligand concentration (molecules/mL) for beads with surface density of 100 molecules/μm² | Notch ligand concentration (molecules/mL) for beads with surface density of 800 molecules/μm² | Notch ligand concentration (molecules/mL) for beads with surface density of 3000 molecules/μm² | Bead diameter (μm) |
|---|---|---|---|---|---|---|
| 0.5 | 2.70E+07 | 7.88666 | 7.89E10 | 6.31E11 | 2.37E12 | 3.05 |
| 2 | 1.08E+08 | 31.54664 | 3.15E11 | 2.52E12 | 9.46E12 | |

TABLE 8-continued

| Bead dose | Bead concentration (beads/mL) | Bead surface area per unit volume (cm²/mL) | Notch ligand concentration (molecules/mL) for beads with surface density of 100 molecules/μm² | Notch ligand concentration (molecules/mL) for beads with surface density of 800 molecules/μm² | Notch ligand concentration (molecules/mL) for beads with surface density of 3000 molecules/μm² | Bead diameter (μm) |
|---|---|---|---|---|---|---|
| 3 | 1.62E+08 | 47.31996 | 4.74E11 | 3.78E12 | 1.42E13 | |
| 3.5 | 1.89E+08 | 55.20662 | 5.53E11 | 4.41E12 | 1.66E13 | |
| 0.5 | 2.25E+07 | 7.64723 | 7.65E10 | 6.12E11 | 2.29E12 | 3.29 |
| 2 | 9.00E+07 | 30.58891 | 3.06E11 | 2.45E12 | 9.18E12 | |
| 3 | 1.35E+08 | 45.88338 | 4.59E11 | 3.67E12 | 1.37E13 | |
| 3.5 | 1.58E+08 | 53.53059 | 5.36E11 | 4.28E12 | 1.60E13 | |

The 3D ETN may also comprise surface-bound VCAM-1. VCAM-1 may be immobilized to 3D ETN at an input molar ratio ranging from 1:6 to 10:1 DL4:VCAM-1. In an embodiment, the 3D ETN is prepared with an input molar ratio of 2.5:1 DL4:VCAM-1. In an embodiment, the final density of the surface-bound VCAM-1 on the bead is equivalent to the density of the Notch ligand. For example, the VCAM-1 surface area per unit volume may be equivalent to the Notch ligand surface area per unit volume shown in Table 8 above.

Cells may be cultured at densities appropriate for culture scale and format. In microplate culture cells may be cultured at, for example, $2.5 \times 10^5$-$2 \times 10^6$ cells/mL. In STR culture cells may be cultured at, for example, $5 \times 10^4$-$6 \times 10^6$ cells/mL.

Example 2: Generation of CD4−CD8+ T Cells

Figure 1A:
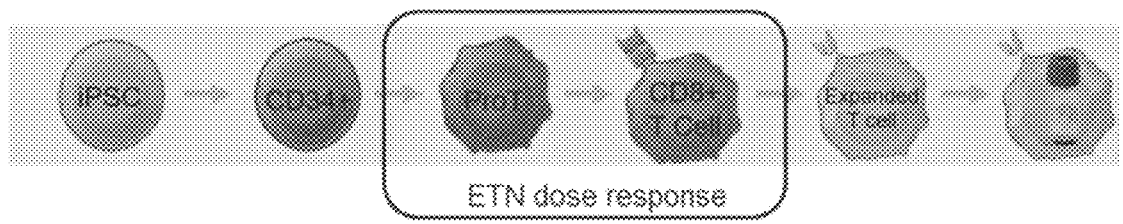
FIG. 1A is a schematic representation of the induced pluripotent stem cells (iPSC) to T cell maturation process, highlighting the progenitor T (proT) cell to CD4−CD8+ (CD8 single-positive, CD8SP) cell progression resulting from exposure of iPSC to three-dimensional engineered thymic niche (3D ETN) in a concentration-responsive manner.
Figure 1B:
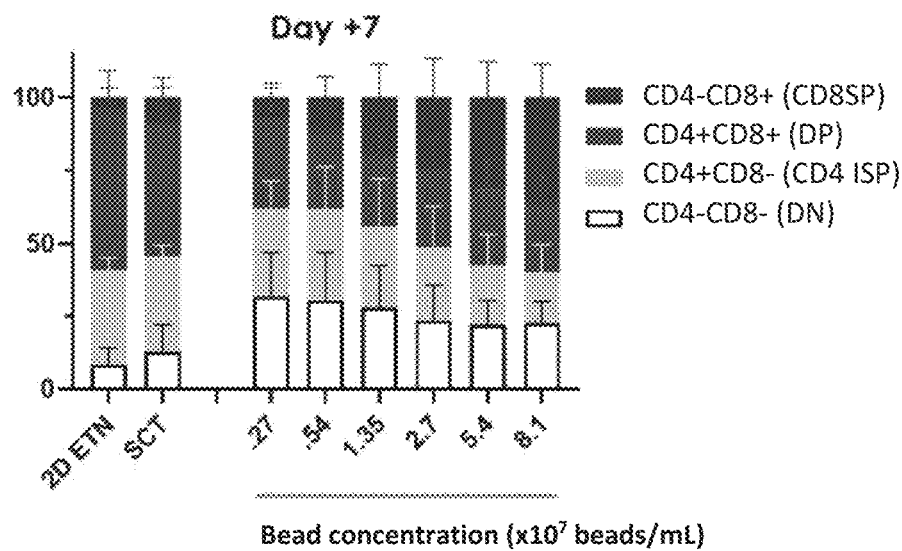
FIG. 1B is a graph depicting the proportion of cells comprising 4 cell populations: CD4−CD8+(CD8SP), CD4+CD8+ (double-positive, DP), CD4+CD8− (CD4 immature single-positive, CD4 ISP), and CD4−CD8− (double-negative, DN), after progenitor T cells were cultured for 7 days with two-dimensional engineered thymic niche (2D ETN), StemSpan™ Lymphoid Differentiation Coating Material (termed SCT or Commercial Coating; STEMCELL Technologies), and 3D ETN with increasing bead concentrations (0.27×10$^7$ beads/mL-8.1×10$^7$ beads/mL (0.5×-1.5× bead dose)).
Figure 1C:
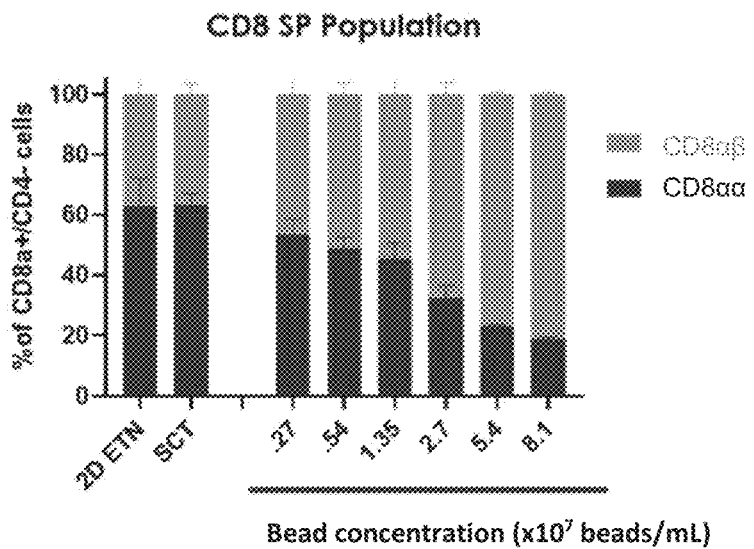
FIG. 1C is a graph depicting the percentage of CD4−CD8+ cells that are either CD8αα+ or CD8αβ+ after culturing progenitor T cells for 7 days with 2D ETN, SCT, and 3D ETN with increasing bead concentrations (0.27×10$^7$ beads/mL-8.1×10$^7$ beads/mL (0.5×-1.5× bead dose)).

To assess the effect of 3D ETN bead concentration in T cell differentiation (FIG. 1A), two independently-derived populations of progenitor T cells, both cryopreserved ("proT Bank A", "proT Bank C") after 18 days of differentiation with 2D ETN (DL4 and VCAM-1) from iPSC-derived CD34+ cells, were thawed and plated in Lymphoid Maturation Media (LMM; STEMCELLTechnologies) in 24 well cell culture plate at $1 \times 10^6$ cells/mL. 3D ETN beads modified with Notch signalling ligand, DL4, and VCAM-1 were added to the cells at 6 different concentrations: 0.27, 0.54, 1.35, 2.7, 5.4 and $8.1 \times 10^7$ beads/mL (0.05×, 0.1×, 0.25×, 0.5×, 1× and 1.5× bead dose). Cells were also plated onto 2D ETN (as described in Example 1) and StemSpan™ Lymphoid Differentiation Coating Material (termed SCT or Commercial Coating; STEMCELL Technologies) in 24 well cell culture plates. Cells were cultured with 2D ETN and 3D ETN or SCT for 3 days and 7 days, and cells were dislodged from plates by pipetting and collected for analysis by flow cytometry, and for assessment of cell number and viability by an automated cell counter (Cellaca® MX). After cells were cultured for 3 days, more CD4+CD8− (CD4 immature single positive, CD4 ISP) cells were generated when cultured with lower 3D ETN bead concentrations (0.27, 0.54× $10^7$ beads/mL (0.05, 0.1× bead dose)) and 2D ETN, while more CD4−CD8+ (CD8 single-positive, CD8SP) cells were generated at higher 3D ETN bead concentrations (2.7, 5.4, $8.1 \times 10^7$ beads/mL (0.5, 1, 1.5× bead dose)). This 3D ETN dose dependent generation of CD4−CD8+ cells was also observed in cells cultured with 3D ETN for 7 days, at which point the effect was more pronounced (FIG. 1B), with the most CD4−CD8+ cells produced at the highest 3D ETN bead concentration ($8.1 \times 10^7$ beads/mL (1.5× bead dose)). Among the CD4−CD8+ cells, the proportion of CD8αβ cells was also observed to be responsive to 3D ETN bead dose, where approximately 80% of the CD4−CD8+ cells were CD8αβ cells at the highest bead concentration ($8.1 \times 10^7$ beads/mL (1.5× bead dose)), whereas only 46% of CD4−CD8+ cells were CD8αβ cells at the lowest bead concentration ($0.27 \times 10^7$ beads/mL (0.05× bead dose)). Among the CD4−CD8+ cells cultured with 2D ETN and SCT, less than 40% of CD4−CD8+ cells were CD8αβ cells (FIG. 1C).

Figure 2A:
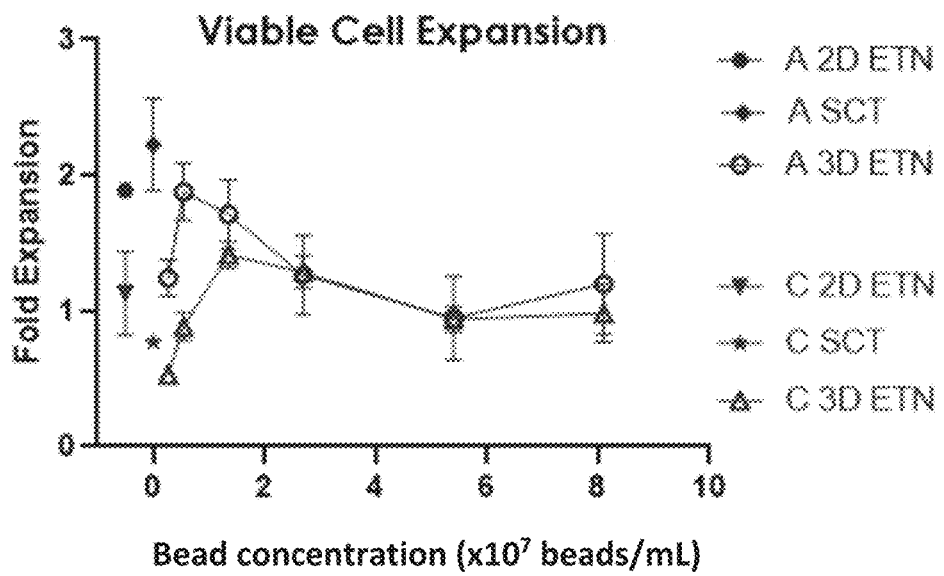
FIG. 2A is a graph depicting the expansion of cells as a function of 3D ETN bead concentration after 7 days of culture. Two input populations (A and C) are plotted separately. Cell number was determined using the Cellaca® automated cell counter.
Figure 2B:
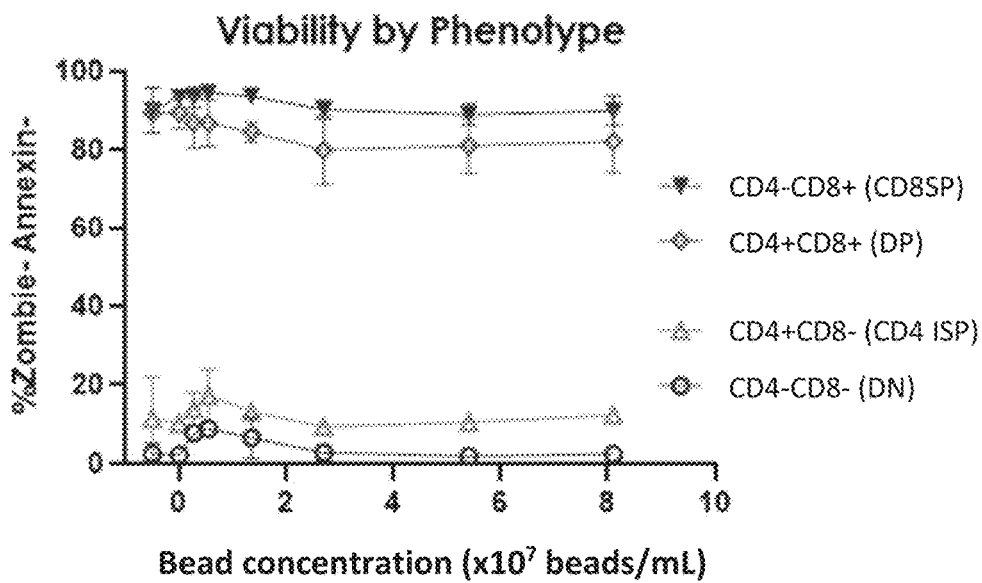
FIG. 2B is a graph depicting the viability of 4 cell populations illustrated in FIG. 1B: CD4−CD8+(CD8SP), CD4+CD8+ (DP), CD4+CD8− (CD4 ISP), and CD4−CD8− (DN), after culturing progenitor T cells for 7 days with increasing 3D ETN bead concentrations (0.27×10$^7$ beads/mL-8.1×10$^7$ beads/mL (0.5×-1.5× bead dose)). Cell viability was determined by Acridine Orange+/Propidium Iodide using the Cellaca® automated cell counter.

Viable cell expansion varied with 3D ETN bead dose—after 7 days, cells cultured with $0.54 \times 10^7$ and $1.35 \times 10^7$ beads/mL (0.1× and 0.25× bead dose) had the highest expansion, with most doses having expansion between 1 to 1.5-fold (FIG. 2A). When viability was assessed as a function of phenotype, 3D ETN bead dose was not observed to have an effect. Instead, CD4+CD8+ (double positive, CD4+CD8−) and CD4−CD8+ cells were observed to have high viability (>80%) whereas CD4−CD8− (double negative, DN) and CD4+CD8− cells CD4+CD8-were observed to have low viability (<20%), irrespective of bead dose (FIG. 2B).

Figure 3A:
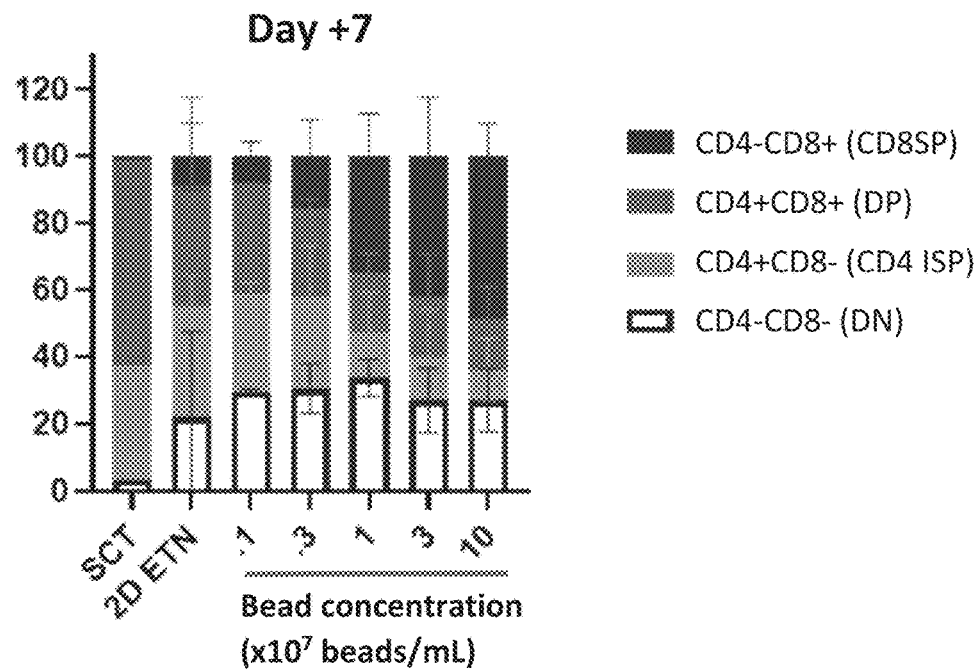
FIG. 3A is a graph depicting the proportion of cells comprising 4 cell populations described in FIG. 1B: CD4−CD8+ (CD8SP), CD4+CD8+ (DP), CD4+CD8− (CD4 ISP), and CD4−CD8− (DN), after culturing progenitor T cells for 7 days with 2D ETN, SCT, and 3D ETN with increasing bead concentrations (0.02×-2× bead dose, or 1.08×10$^6$ beads/mL-10.8×10$^7$ beads/mL (shown as 0.1-10×10$^7$ beads/mL)), as determined by flow cytometry.
Figure 3B:
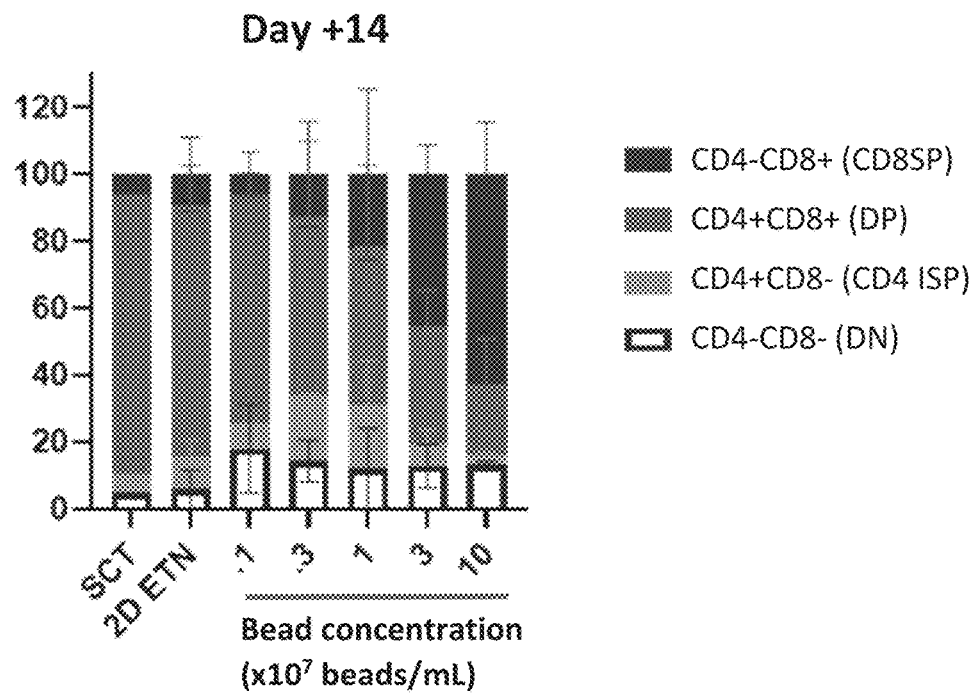
FIG. 3B is a graph depicting the proportion of cells comprising 4 cell populations described in FIG. 3A: CD4−CD8+ (CD8SP), CD4+CD8+ (DP), CD4+CD8− (CD4 ISP), and CD4−CD8− (DN), after culturing progenitor T cells for 14 days with 2D ETN, SCT, and 3D ETN with increasing bead concentrations (0.02×-2× bead dose, or 1.08×10$^6$ beads/mL-10.8×10$^7$ beads/mL (shown as 0.1-10×10$^7$ beads/mL)), as determined by flow cytometry.

Assessment of the effect of 3D ETN bead concentration in T cell differentiation as described above was repeated with a broader range of 3D ETN bead concentrations (0.02×-2× bead dose, or $1.08 \times 10^6$ beads/mL-$10.8 \times 10^7$ beads/mL (shown as 0.1-10×$10^7$ beads/mL)), along with culturing the progenitor T cells with 2D ETN and SCT. Additionally, the duration of cell culture with 2D ETN, SCT and 3D ETN was extended to 7 and 14 days. Consistent with the first experiment as described above, the generation of CD4+CD8−CD4+CD8− and CD4−CD8+ cell populations were 3D ETN bead concentration-responsive after 7 days of culture, with more CD4+CD8CD4+CD8-cells observed at lower bead concentrations ($0.1 \times 10^7$ beads/mL and $0.3 \times 10^7$ beads/mL (0.2× and 0.05× bead dose)), and more CD4−CD8+ cells observed with higher bead concentrations ($3 \times 10^7$ beads/mL and $10 \times 10^7$ beads/mL (0.5× and 2× bead dose)) (FIG. 3A). After an additional 7 days of culture, these effects were even more pronounced, with approximately 60% CD4−CD8+ cells observed at the highest bead concentration ($10 \times 10^7$ beads/mL (2× bead dose)) (FIG. 3B). Interestingly, progenitor T cells cultured with the lowest bead concentration ($0.1 \times 10^7$ beads/mL (0.02× bead dose)) resulted in similar cell populations as progenitor T cells cultured with 2D ETN, with a high percentage of CD4+CD8+ cells and a very small percentage of CD4−CD8+ cells.

Figure 4A:
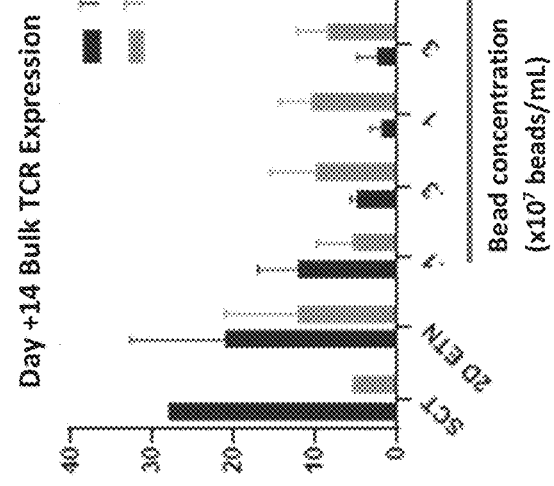
FIG. 4A is a graph depicting the percentage of cells that are CD3−TCRαβ−, CD3+TCRαβ− or CD3+TCRαβ+ after culturing progenitor T cells for 14 days with 2D ETN, SCT, and 3D ETN with increasing bead concentrations (0.02×-2× bead dose, or 1.08×10$^6$ beads/mL-10.8×10$^7$ beads/mL (shown as 0.1-10×10$^7$ beads/mL)), as determined by flow cytometry.
Figure 4C:
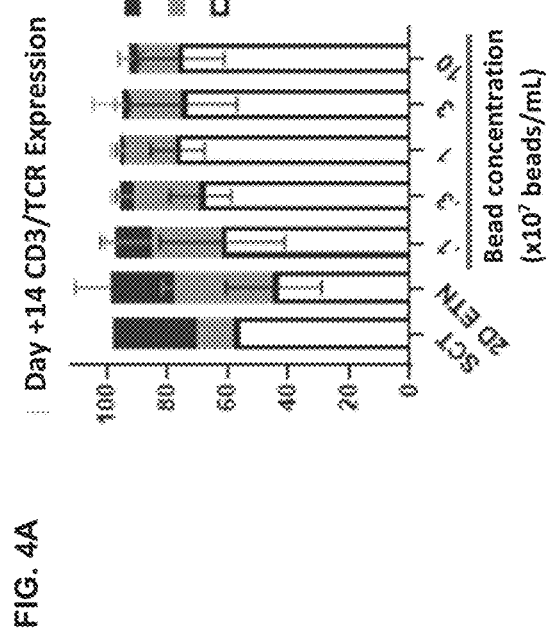
FIG. 4C is a graph depicting the expression of TCRαβ and TCRγδ in CD8+CD4+ (DP) cells after culturing the progenitor T cells for 14 days with 2D ETN, SCT and 3D ETN with increasing bead concentrations (0.02×-2× bead dose, or $1.08 \times 10^6$ beads/mL-$10.8 \times 10^7$ beads/mL (shown as $0.1$-$10 \times 10^7$ beads/mL)), as determined by flow cytometry.
Figure 4B:
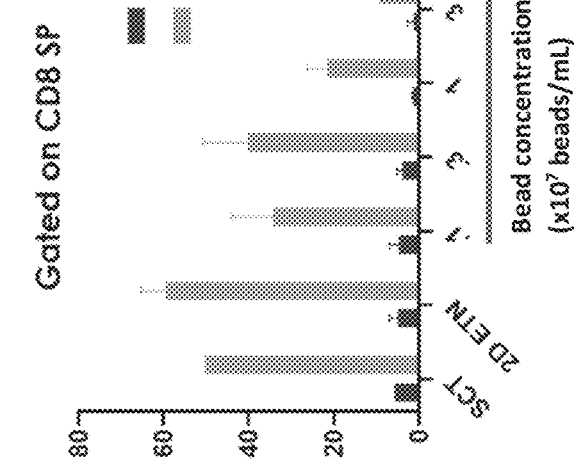
FIG. 4B is a graph depicting the expression of TCRαβ and TCRγδ in the cell population after culturing the progenitor T cells for 14 days with 2D ETN, SCT, and 3D ETN with increasing bead concentrations (0.02×-2× bead dose, or 1.08×10$^6$ beads/mL-10.8×10$^7$ beads/mL (shown as 0.1-10×10$^7$ beads/mL)), as determined by flow cytometry.
Figure 4D:
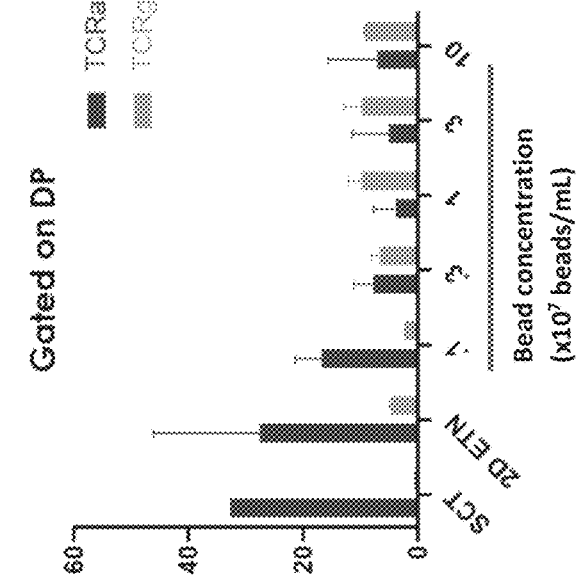
FIG. 4D is a graph depicting the expression of TCRαβ and TCRγδ in CD4−CD8+ (CD8SP) cells after culturing the progenitor T cells for 14 days with 2D ETN, SCT, and 3D ETN with increasing bead concentrations (0.02×-2× bead dose, or $1.08 \times 10^6$ beads/mL-$10.8 \times 10^7$ beads/mL (shown as $0.1$-$10 \times 10^7$ beads/mL)), as determined by flow cytometry.

Progenitor T cells cultured with 2D ETN, SCT and 3D ETN with a range of bead concentrations were evaluated for expression of CD3 and TCR. CD3 and TCR expression increased in cells cultured with 2D ETN and SCT by day 14, with approximately 60% of cells expressing CD3 with 2D ETN, and approximately 20% expressing TCRαβ (FIG. 4A). For progenitor T cells cultured with 3D ETN, CD3 expression was inversely concentration-responsive, with the lowest bead concentrations ($0.1\times10^7$ beads/mL and $0.3\times10^7$ beads/mL (0.02× and 0.05× bead dose)) resulting in the highest CD3 expression. At the highest bead concentration ($10\times10^7$ beads/mL (2× bead dose)), <30% of cells were CD3+, and almost no TCRαβ expression was observed (<5%) (FIGS. 4A and B). The expression of TCRγδ in the bulk population did not appear to be concentration-responsive, as cells cultured with 3D ETN concentrations ranging from $0.3\times10^7$ beads/mL to $10\times10^7$ beads/mL (0.05× to 2× bead dose) resulted in approximately 10% TCRγδ+ cells (FIG. 4B). Expression of TCRαβ and TCRγδ were examined in the CD4+CD8+ and CD4−CD8+ populations, which revealed that the TCRαβ+ cells were found predominantly in the CD4+CD8+ population. The CD4−CD8+ population contained a significant contingent of TCRγδ+ cells when cultured with 2D ETN, SCT, and 3D ETN with lower bead concentrations ($0.1\times10^7$ beads/mL and $0.3\times10^7$ beads/mL (0.02× and 0.05× bead dose)). However, for cells cultured with 3D ETN with higher bead concentrations ($3\times10^7$ and $10\times10^7$ beads/mL (0.5× and 2× bead dose)), only a small fraction of the cells were TCRγδ+ (approximately 10%) and almost no TCRαβ expression was observed (FIG. 4D).

Similar to the first experiment, cell viability had a modest concentration-response after culturing for 7 days with 3D ETN, with the highest cell viability observed with $0.3\times10^7$ beads/mL (0.02× bead dose) for proT Bank A and $3\times10^7$ beads/mL (0.05× bead dose) for proT Bank C (FIG. 5A). However, by day 14, cell viability was observed to increase with bead concentration, though proT Bank C displayed very low viability in all conditions (FIG. 5B). When viability was assessed as a function of phenotype, 3D ETN bead concentration appeared to be less significant than phenotype, as CD4−CD8+ and CD4+CD8+ had consistently high viability, whereas CD4−CD8− and CD4 ISPs had low viability, irrespective of bead dose (FIGS. 5C and D). Collectively, these data suggest that the use of 3D ETN beads at a concentration of ~$3\times10^7$ beads/mL (0.05× bead dose) or higher produces a population of CD4−CD8+ cells that express CD8αα and CD8αβ but not TCRαβ, and only a low percentage of CD3 (<30%) and CD3+TCRγδ (approximately 10%).

Figure 6A:
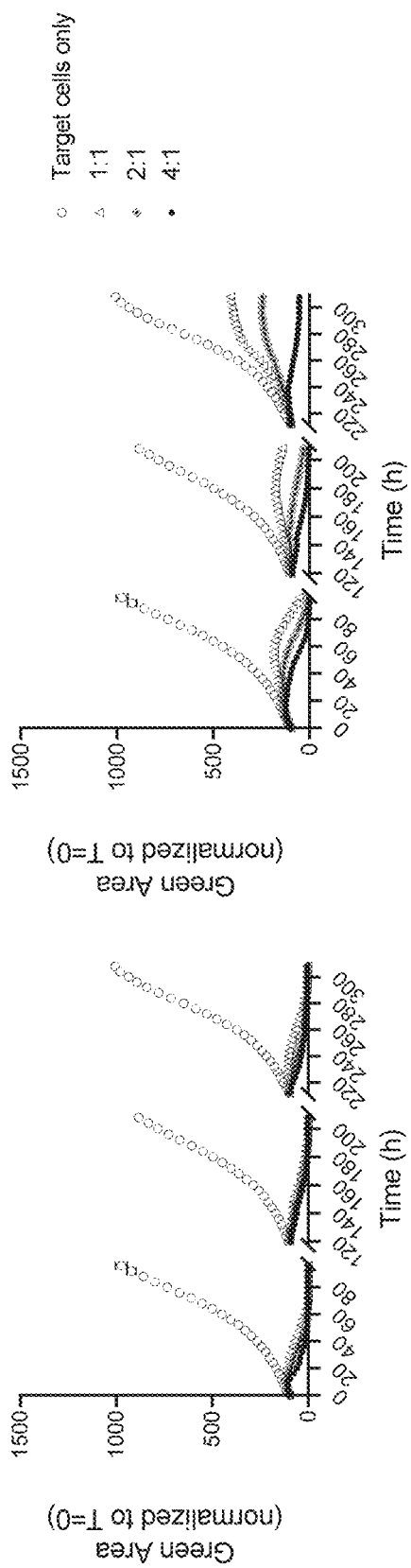
FIG. 6A is graphs depicting cell counts over time for CD19+A549 cells ("Target cells") co-cultured with primary CD8+ CAR-T cells (left) or iPSC-derived CAR+ CD4−CD8+ (CD8SP) cells (right), at varying effector:target (E:T) cell ratios.
Figure 6B:
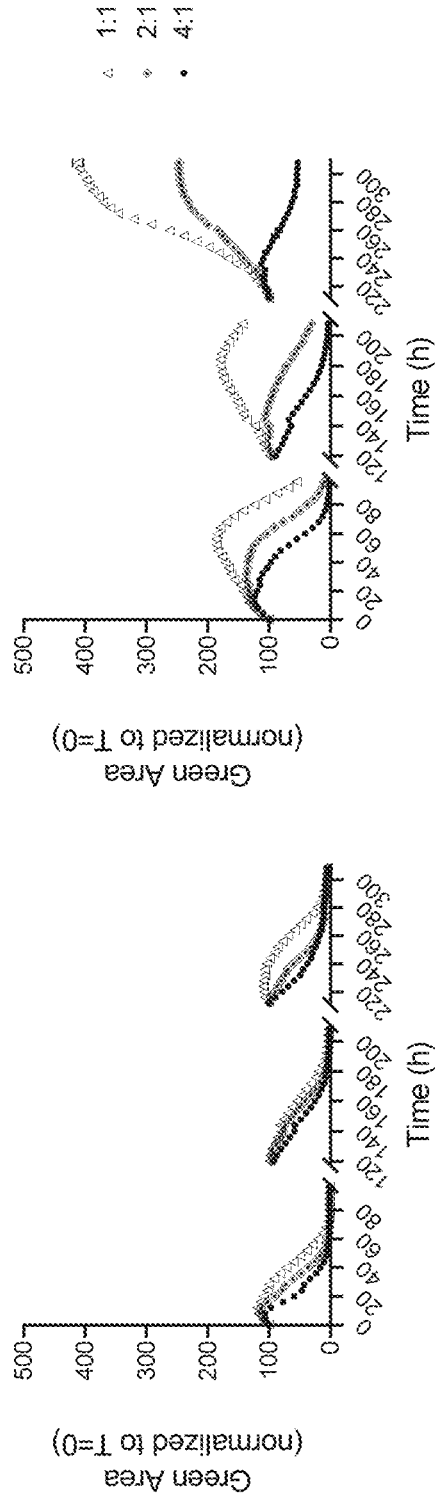
FIG. 6B is enlarged graphs of data in FIG. 6A, omitting target cell-only control.

To examine cytotoxic potential, progenitor T cells transduced with lentiviral vector to express a CD19 CAR were cultured with 3D ETN ($5.4\times10^7$ beads/mL (1× bead dose)), as described above, to generate CAR+ CD4−CD8+ cells. Cells were then co-cultured with target CD19 A549 cells (effector to target cell ratios of 4:1, 2:1, 1:1, or target cells only). Similarly to primary CAR-transduced CD8+ T cells (left), CAR+ CD4−CD8+ cells (right) generated using ETN beads demonstrated concentration-responsive cytotoxicity over multiple rounds of stimulation (FIGS. 6A and 6B).

Example 3: Generation of CD4−CD8+ Cells in a Stirred-Tank Reactor (STR)

Figure 7:
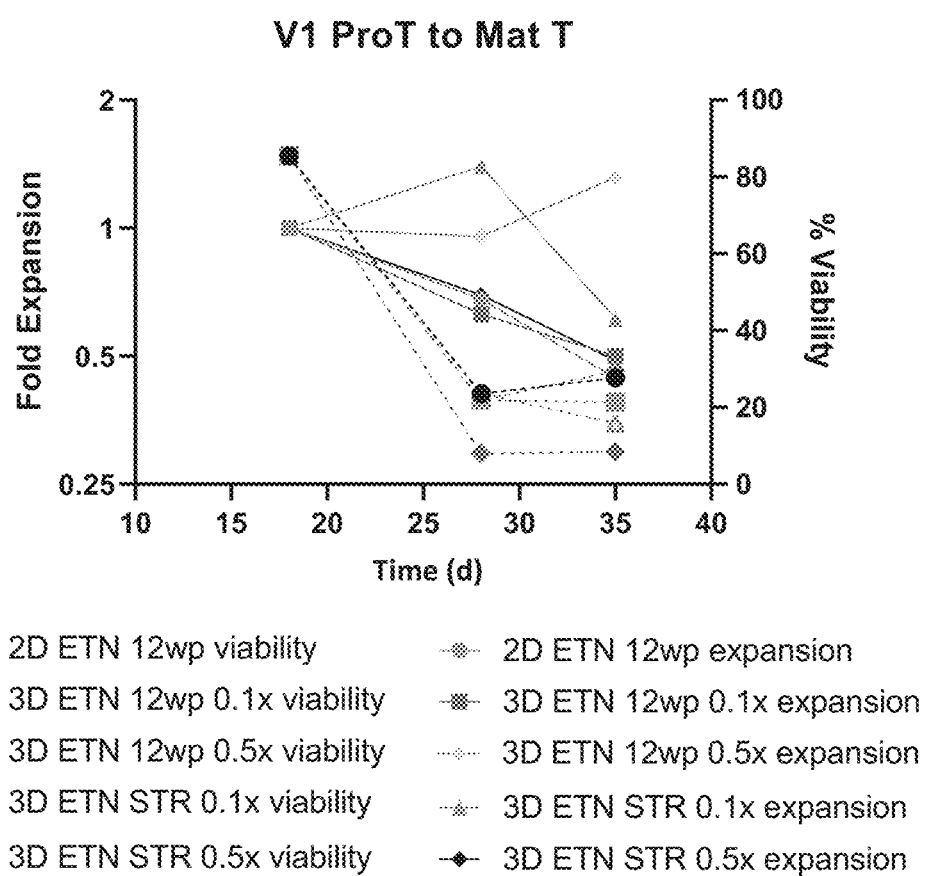
FIG. 7 is a graph depicting cell expansion (left axis) and viability (right axis) of cells cultured with 2D ETN and 3D ETN in a 12 well cell culture plate (wp), and 3D ETN in a stirred-tank reactor (STR). 3D ETN bead concentrations of $0.54 \times 10^7$ beads/mL (0.1× bead dose) and $2.7 \times 10^7$ beads/mL (0.5× bead dose) were utilized in both the 12 well cell culture plate and STR.
Figure 8A:
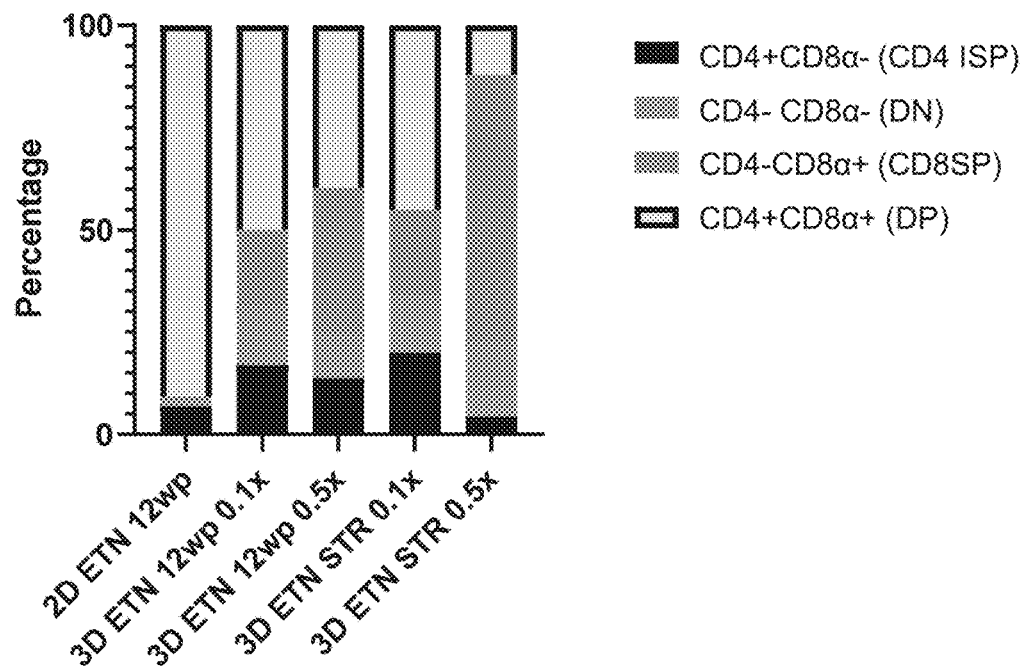
FIG. 8A is a graph depicting quantification of flow cytometry data showing percentage of CD4+CD8− (CD4 ISP), CD4−CD8− (DN), CD4−CD8+ (CD8SP) and CD4+CD8+ (DP) cells after cells were cultured with 2D ETN and 3D ETN in a 12 well cell culture plate (wp), and 3D ETN in a STR. 3D ETN bead concentrations of $0.54 \times 10^7$ beads/mL (0.1× bead dose) and $2.7 \times 10^7$ beads/mL (0.5× bead dose) were utilized in both the 12 well cell culture plate and STR.
Figure 8B:
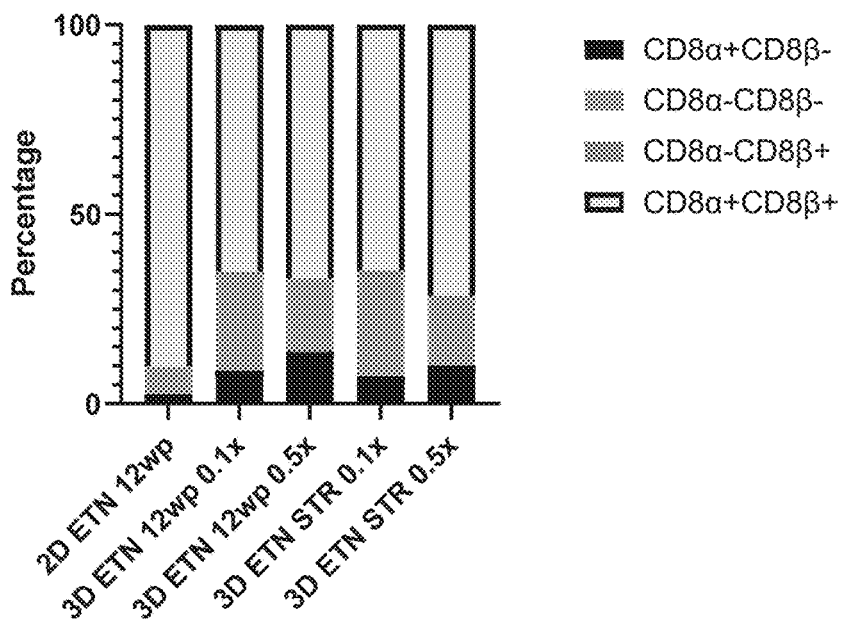
FIG. 8B is a graph depicting quantification of flow cytometry data showing percentage of cells expressing CD8αα and/or CD8αβ after cells were cultured with 2D ETN and 3D ETN in a 12 well cell culture plate (wp), and 3D ETN in a STR. 3D ETN bead concentrations of $0.54 \times 10^7$ beads/mL (0.1× bead dose) and $2.7 \times 10^7$ beads/mL (0.5× bead dose) were utilized in both the 12 well cell culture plate and STR.

Cell expansion and viability of progenitor T cells cultured in the presence of 3D ETN beads ($0.54\times10^7$ beads/mL and $2.7\times10^7$ beads/mL (0.1× and 0.5× bead dose) in a stirred-tank reactor (STR) culture system (140 ml DASbox®, Eppendorf) was assessed and compared to progenitor T cells cultured with 2D ETN and 3D ETN utilizing a 12 well cell culture plate. Progenitor T cells were cultured with Lymphoid Maturation Medium (LMM, STEMCELL Technologies) in all conditions for 17 days. Cell viability decreased over the culture period in all conditions (FIG. 7; days 18-35). As demonstrated in Example 2 (see FIG. 3B), a greater number of CD4+CD8+ cells were observed when progenitor T cells were cultured with 2D ETN or low concentration 3D ETN beads ($0.54\times10^7$ beads/mL (0.1× bead dose) in a 12 well cell culture plate (FIG. 8A). For progenitor T cells cultured with 3D ETN in both the 12 well cell culture plate and STR conditions, a greater percentage of CD4−CD8+ cells were observed at the higher bead concentration ($2.7\times10^7$ beads/mL (0.5× bead dose) (FIG. 8A) Among the CD4−CD8+ cells generated by culturing progenitor T cells with 3D ETN in both the 12 well cell culture plate and STR conditions, the CD4−CD8+ cells were primarily CD8αβ cells for both bead concentrations ($0.54\times10^7$ beads/mL and $2.7\times10^7$ beads/mL (0.1× and 0.5× bead dose) (FIG. 8B).

Example 4: Generation of TCR-Transduced T Cells with the 3D ETN

Hematopoietic stem/progenitor cells expressing CD34 were derived from iPSCs modified to lack endogenous TCR expression, based on methods known in the art (e.g., Blassberg, 2022). Cells were then differentiated with 2D ETN for 10 days, to generate a progenitor T cell population (e.g., Shukla et al, 2017), as demonstrated by CD7 expression (FIG. 9A) and limited CD4 and CD8 expression (FIG. 9B). At day 7, cells were modified for MAGE-A4 αβTCR expression by lentiviral transduction, based on methods known in the art (e.g., Iriguchi et al., 2021). Approximately 20% of transduced cells expressed TCRαβ and CD3 at day 10, with no TCR and minimal CD3 expression observed in untransduced cells (FIG. 9C).

Progenitor T cells were then cultured for a total of 11 days with Lymphoid Maturation Medium (LMM, STEMCELL Technologies) and 3D ETN ($1.08\times10^8$ beads/mL (2× bead dose)). During this period, the cells were harvested and analyzed by flow cytometry at day 7, with the 3D ETN removed from the cell population using conventional separation techniques (e.g., Trotman-Grant et al., 2021). Cells were then re-cultured with new 3D ETN ($1.08\times10^8$ beads/mL (2× bead dose)) for a further 4 days.

After 7 days in culture with 3D ETN, a subset of cells co-expressed CD5+ and CD7+ (FIG. 10A), and a population of CD8+ cells that were CD8αβ+ also were observed in both transduced and untransduced cells (FIGS. 10B and 10D). MAGE-A4 αβTCR expression and CD3 expression increased in transduced cells to approximately 50% at day 7 of culture with 3D ETN (FIG. 10C, bottom). Untransduced cells were primarily TCR−/CD3−(FIG. 10C, top).

After 11 days of culturing the cells with 3D ETN, a greater subset of transduced cells were observed to transition into CD4+CD8+ cells, compared to untransduced cells (FIG. 11B). Approximately 25% of cells in both groups retained a CD4−CD8+ phenotype (FIG. 11B), with greater CD8αβ+ expression observed in transduced cells (FIG. 11D). TCR and CD3 expression also increased in transduced cells from day 7 to day 11 (FIG. 11C, middle). Untransduced cells remained TCR−/CD3−(FIG. 11C, top).

TCR-transduced cells were then enriched for CD8β by positive selection (EasySep™ Human Pe Positive Selection Kit, STEMCELL Technologies; PE Mouse Anti-Human CD8β, BD Biosciences). Post-enrichment, the fraction of CD4−CD8+ cells increased, as well as greater expression of CD8αβ(FIG. 11B, bottom) and an increase in TCR expression (FIG. 11C, bottom).

Figure 12A:
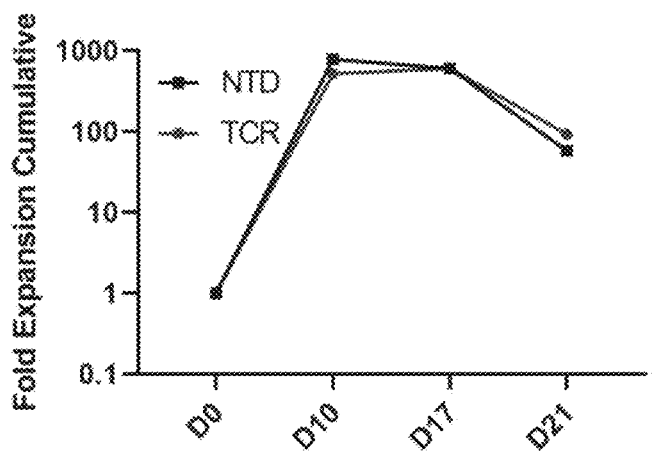
FIG. 12A is a graph depicting cumulative fold expansion over time for untransduced (NTD, squares) and TCR-transduced (TCR, circles) cells cultured with 3D ETN bead concentration of $1.08 \times 10^8$ beads/mL (2× bead dose). D17 and D21 correspond to 7 and 11 days of culturing with 3D ETN, respectively.
Figure 12B:
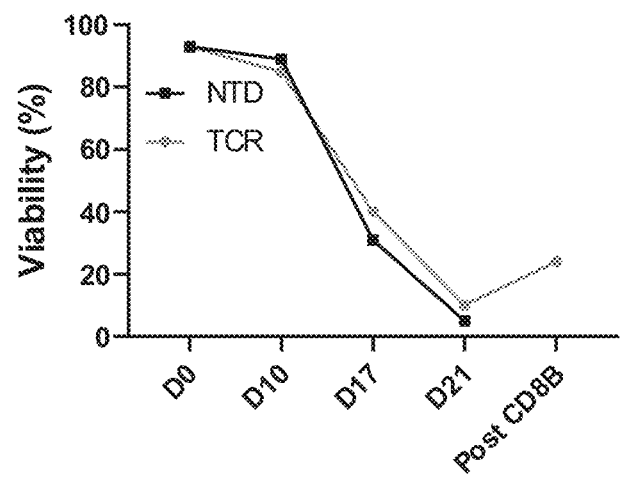
FIG. 12B is a graph depicting cell viability over time for untransduced (NTD, squares) and TCR-transduced (TCR, circles) cells cultured with 3D ETN bead concentration of $1.08 \times 10^8$ beads/mL (2× bead dose). D17 and D21 correspond to 7 and 11 days of culturing with 3D ETN, respectively. TCR-transduced cells were also analyzed following CD8β-selection (Post CD8B).
Figure 12C:
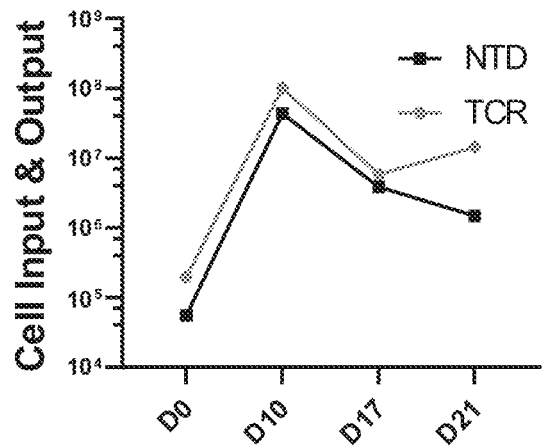
FIG. 12C is a graph depicting the ratio of cell input/output over time for untransduced (NTD, squares) and TCR-transduced (TCR, circles) cells cultured with 3D ETN bead concentration of $1.08 \times 10^8$ beads/mL (2× bead dose). D17 and D21 correspond to 7 and 11 days of culturing with 3D ETN, respectively.

TCR-transduced and untransduced cells behaved similarly in terms of optimal viability and expansion over the early 2D ETN culture period (FIG. 12A-C, "D0, D10"). However, these metrics decreased during the later CD8αβ differentiation phase ("D17, D21") despite improvements in cell outputs and viability observed in TCR transduced cultures after 11 days with the 3D ETN and post-CD8β selection, respectively (FIG. 12A-C). CD8αβT cell output of 100-fold per CD34+ HSPC cell input was observed following 11-day differentiation on the 3D ETN ($1.08 \times 10^8$ beads/mL (2× bead dose)).

Example 5: Gene Expression and Cell Phenotype of Generated Cells

As described in Example 2, iPSC-derived CD34+ cells were differentiated into proT cells for 18 days with 2D ETN. Subsequently, T cell maturation was induced by culturing the cells with 3D ETN beads, with a 30-fold range of bead concentrations (0.27 to $8.1 \times 10^7$ beads/mL (0.05× to 1.5× bead dose)) tested. Cells were also cultured with 2D ETN and SCT. After culturing the cells for 7 days, cell phenotype was assessed by flow cytometry (FIG. 13A). Higher bead concentrations ($5.4 \times 10^7$ beads/mL and $8.1 \times 10^7$ beads/mL (1× and 1.5× bead dose)) produced more CD4−CD8+ (CD8SP) cells than lower bead concentrations ($0.27 \times 10^7$ beads/mL and $0.54 \times 10^7$ beads/mL (0.05× and 0.1× bead dose)), while lower bead concentrations ($0.27 \times 10^7$ beads/mL and $0.54 \times 10^7$ beads/mL (0.05× and 0.1× bead dose)) produced more CD4+CD8− (CD4 ISPs) and CD4−CD8− (DN) (FIG. 13A, FIG. 1B). After culturing the cells for 3 days, expression of the Notch signalling-related genes DTX1, TCF7 and BCL11B was concentration-responsive, with saturation occurring around the bead concentration of $5.4 \times 10^7$ beads/mL (1× bead dose) (FIG. 13B). The Notch-responsive gene GATA3 displayed an inverse concentration-response, with expression highest at lower bead concentrations of $0.27 \times 10^7$ beads/mL (0.05× bead dose) and $0.54 \times 10^7$ beads/mL (0.1× bead dose) (FIG. 13B).

Figure 13C:
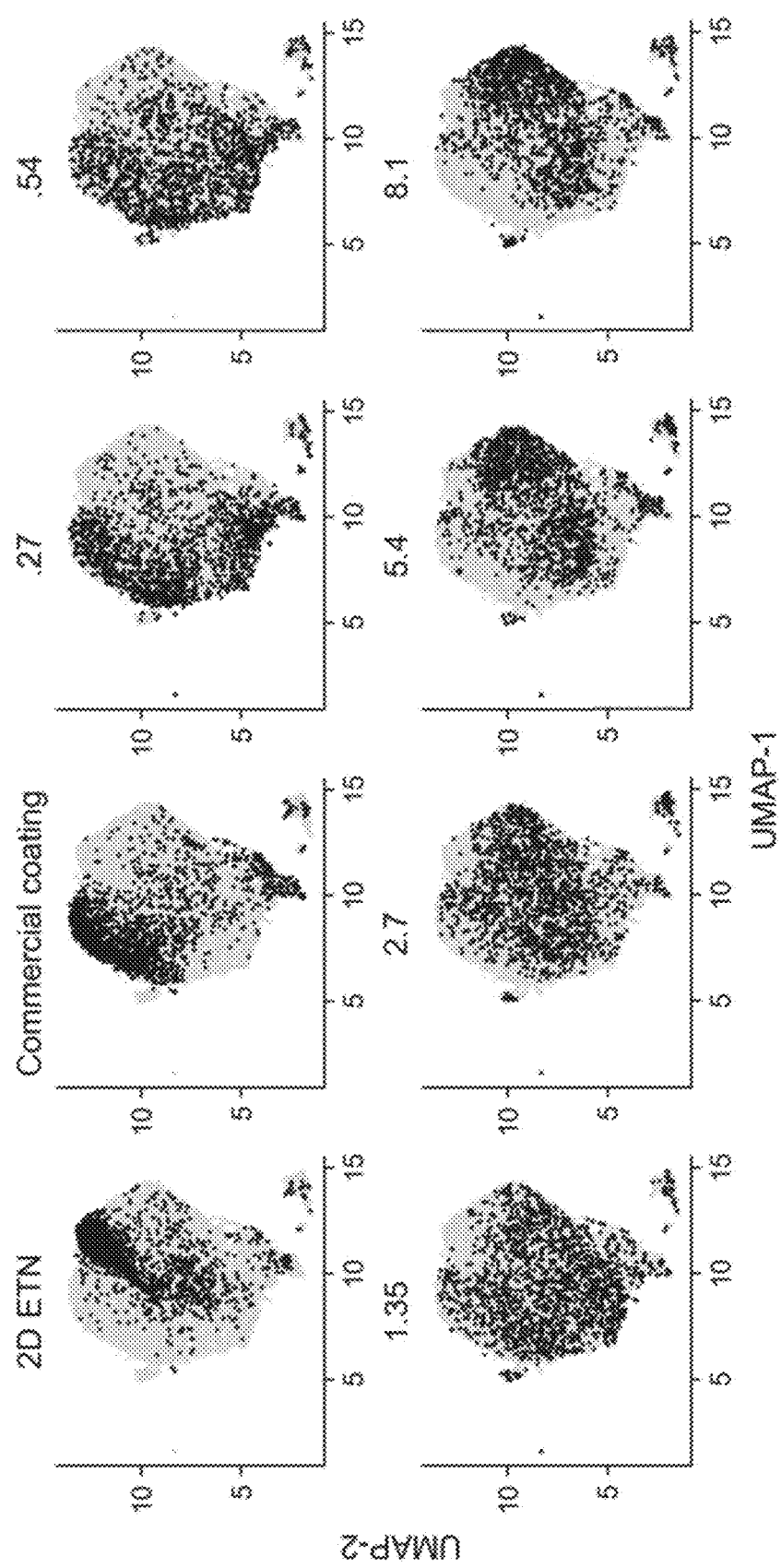
FIG. 13C is Uniform Manifold Approximation and Projection (UMAP) plots of a thirteen-color flow cytometry dataset of progenitor T cells cultured for 7 days with 2D ETN, SCT (Commercial Coating), and 3D ETN with increasing bead concentrations ($0.27 \times 10^7$ beads/mL-$8.1 \times 10^7$ beads/mL (0.5×-1.5× bead dose)).
Figure 13D:
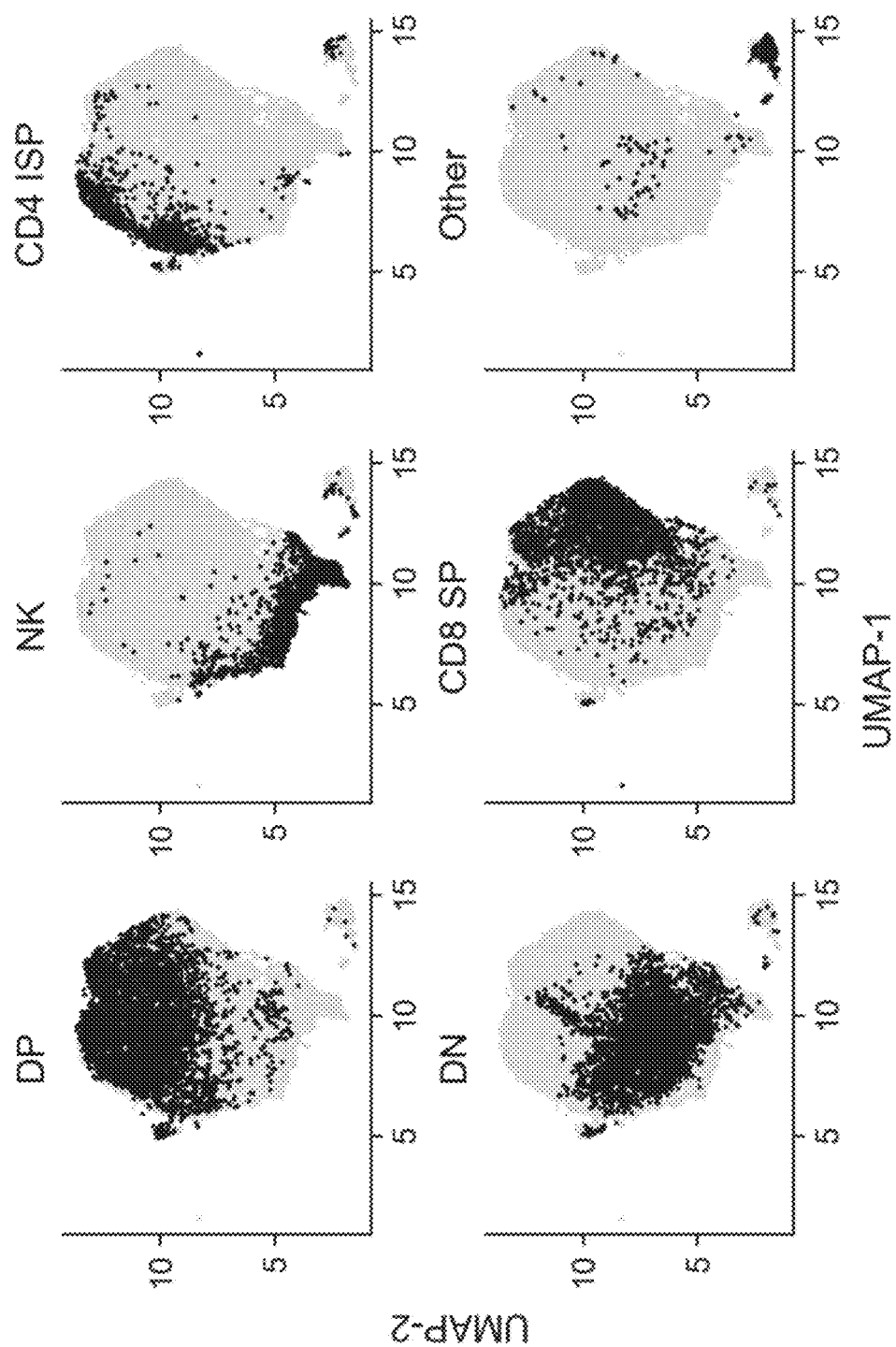
FIG. 13D is UMAP plots of the cells in each of 6 clusters identified by unsupervised machine learning using FlowSOM (Van Gassen et al., 2015). Each cluster is defined by different combinations of expressed surface proteins, as identified by flow cytometry.

After culturing the cells for 7 days, a 13-color flow cytometry panel was used to assess cell phenotype, and Uniform Manifold Approximation and Projection (UMAP) was used to perform dimensionality reduction of this multi-dimensional dataset (FIG. 13C). Cells were observed to cluster based on the concentration of 3D ETN (FIG. 13C). Unsupervised machine learning (FlowSOM, Van Gassen et al.) was used to identify expression patterns within the multi-color flow cytometry dataset. Six clusters were identified, with expression of CD8α, CD8β and CD4 used to describe the clusters as CD4+CD8+ (DP), CD4+CD8− (CD4 ISP), CD4−CD8+ (CD8SP), and CD4−CD8− (DN) (FIG. 13E). The CD4−CD8+ (CD8SP) cluster mapped with high 3D ETN bead concentrations, the CD4+CD8+ (DP) cluster with 2D ETN, and CD4+CD8− (CD4 ISP) with SCT (FIG. 13D). The proportion of cells in each cluster was dependent on the concentration of DL4, with higher ETN bead concentrations ($5.4 \times 10^7$ beads/mL and $8.1 \times 10^7$ beads/mL (1× and 1.5× bead dose)) containing more of the CD4−CD8+(CD8SP) cluster, while lower bead concentrations ($0.27 \times 10^7$ beads/mL and $0.54 \times 10^7$ beads/mL (0.05× and 0.1× bead dose)) contained a higher proportion of CD4+CD8− (CD4 ISP) cluster (FIG. 13F), similar to the data illustrated in FIG. 13A.

Figure 13G:
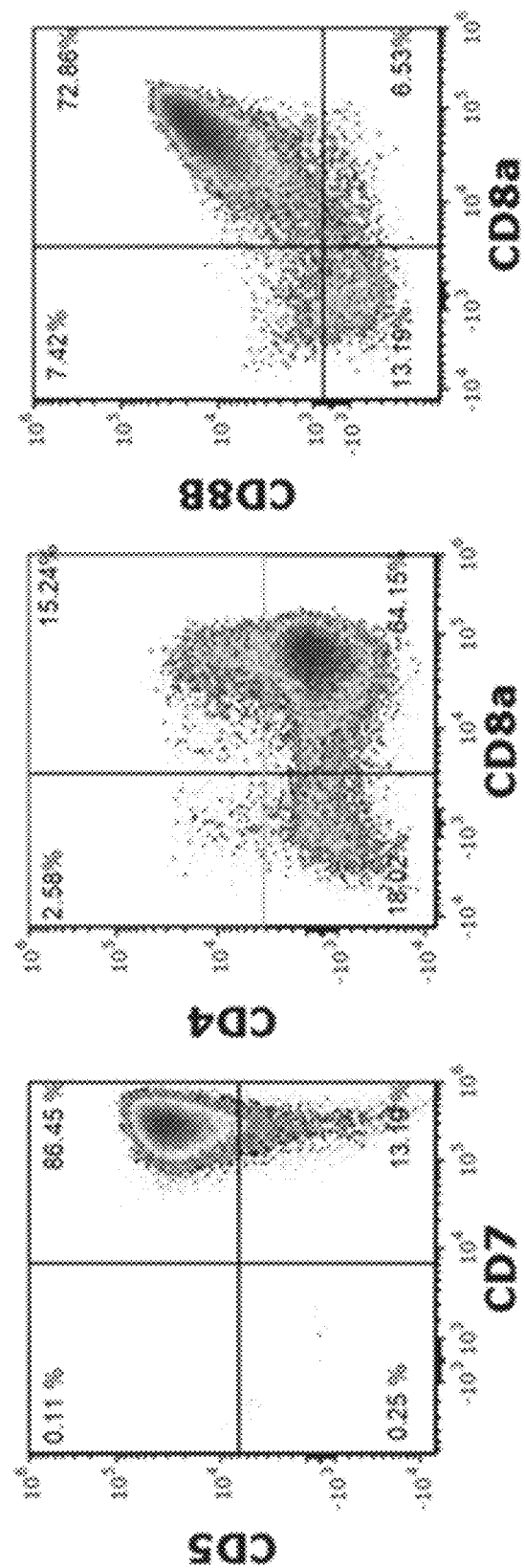
FIG. 13G is flow cytometry plots of CD5 and CD7 expression, CD4 and CD8α (CD8A) expression, and CD8β (CD8B) and CD8α (CD8A) expression for cells cultured with a 3D ETN bead concentration of $5.4 \times 10^7$ beads/mL (1× bead dose) for 14 days.

Differentiation with high ETN bead concentration ($5.4 \times 10^7$ beads/mL (1× bead dose)) was extended for an additional 7 days. After 14 days of differentiation using a high ETN bead concentration ($5.4 \times 10^7$ beads/mL (1× bead dose)), over 86% of cells were CD7+CD5+, over 64% were CD4−CD8α+, and 73% were CD8αβ+ (FIG. 13G).

Example 6: scRNA-Seq Analysis of Generated Cells

Figure 14A:
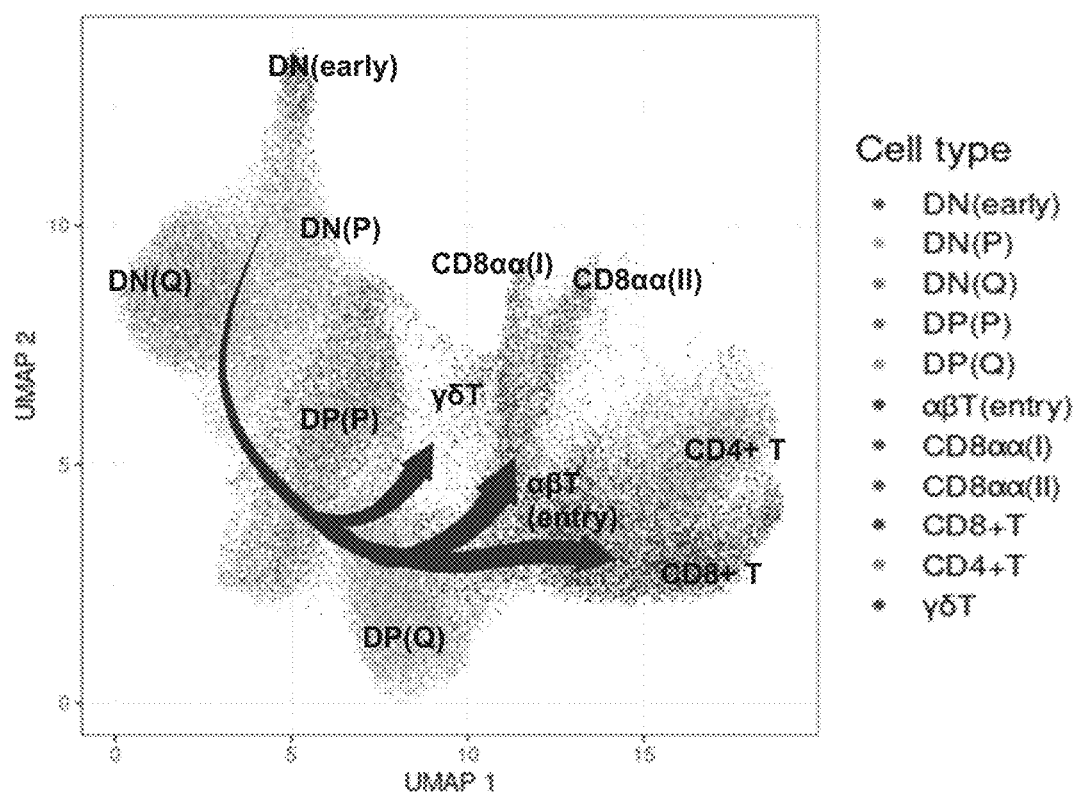
FIG. 14A is a UMAP plot of single-cell RNA sequencing (scRNAseq) data demonstrating developmental trajectories of T cell maturation stages in the human thymus. Data was sourced from Park et al., 2020.
Figure 14B:
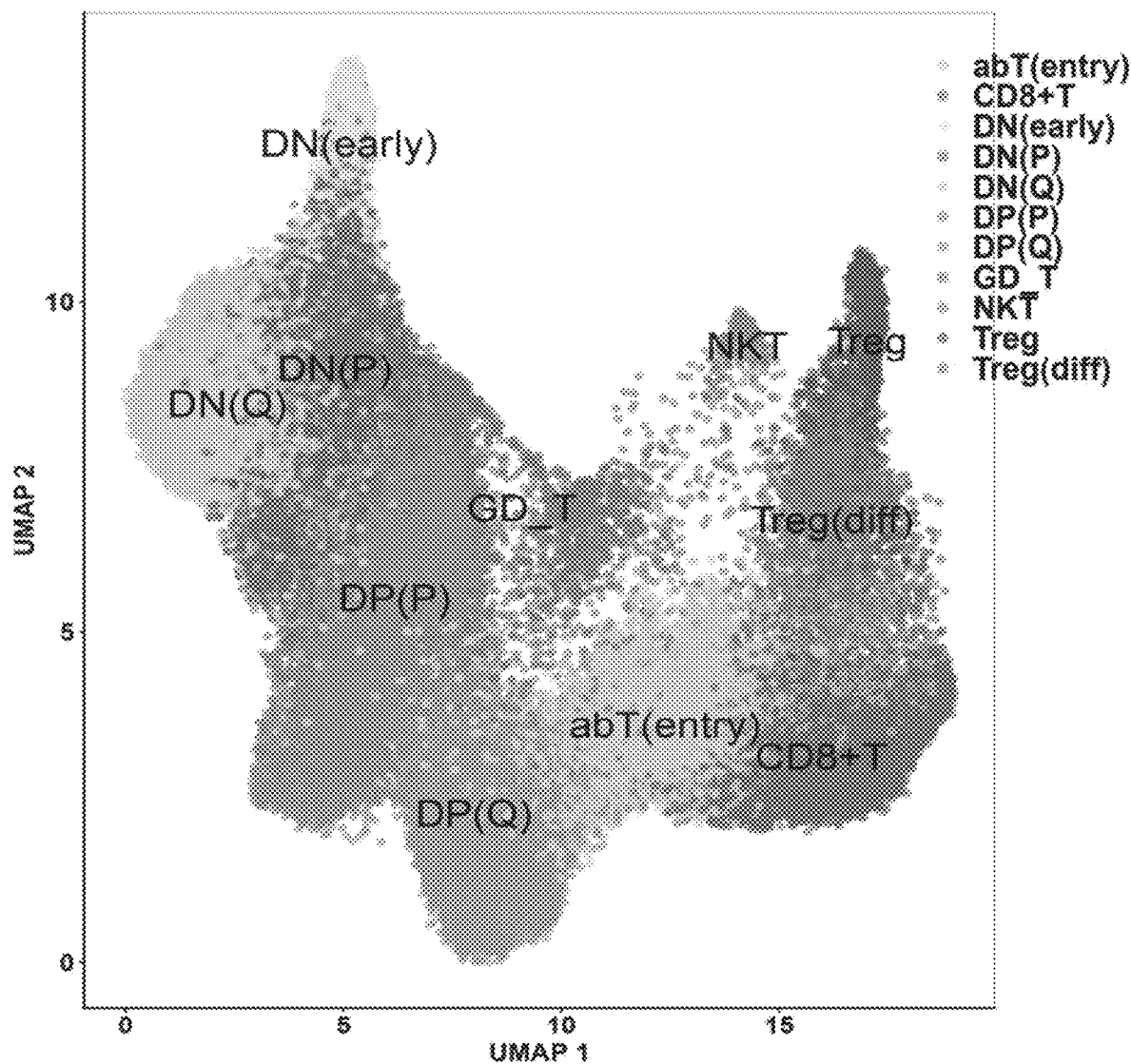
FIG. 14B is a UMAP plot of T cell maturation in the human thymus. Selected single cell RNAseq data from the Thymic Atlas (Park et al., 2020) was represented as a UMAP and annotated by cell type, including the NK-T cell ("NKT") cell type.

An analysis of in vivo T cell maturation stages was performed using single-cell RNA sequencing data (Park et al., 2020). Trimming, alignment, demultiplexing and gene counts were generated from FASTQ files using CellRanger and gene counts matrices normalized using Seurat (4.0.1, Satja et al., 2015). Doublets were identified and removed, and dead cells removed by filtering those with greater than 5% mitochondrial reads. Cell type labels were adapted from Park et al., 2020. As indicated by the arrows, the data demonstrates progression of T cell maturation from early CD4−CD8− cells (DN (early)) to CD8αα cells, γδT cells, CD8+ T cells, and CD4+ T cells (FIG. 14A). In a separate analysis, data from Park et al. was analyzed with the inclusion of the NK-T cell (NK-T) cell phenotype (FIG. 14B).

To examine Notch and TCR signalling during in vivo T cell development, single sample GSEA (ssGSEA) scores were calculated at the single cell level with Gene Set Variation Analysis (GSVA 1.40.1, Hanzelmann et al., 2013) using NOTCH (custom NanoString® panel) and TCR signalling (BioCarta) gene sets isolated from the dataset of Park et al. Notch signalling was enriched at early stages of in vivo T cell development, whereas TCR signalling was enriched at later stages of in vivo T cell development (FIGS. 15A-C).

Figure 15D:
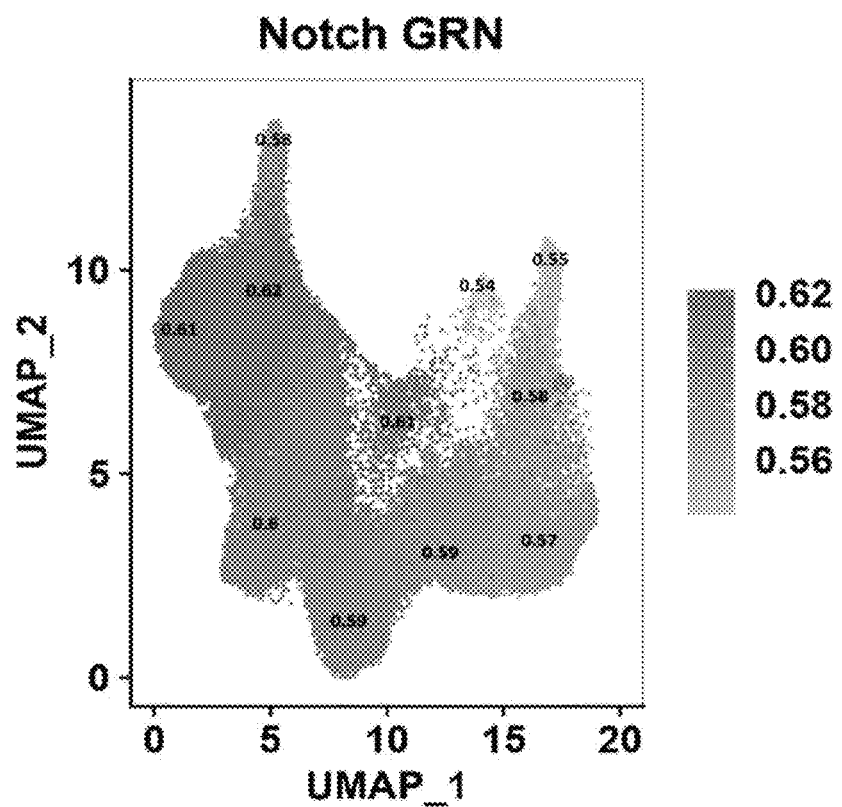
FIG. 15D is a UMAP plots of single cell RNAseq data (Park et al., 2020) annotated by median Notch gene regulatory network ("Notch GRN", FIG. 15D) and TCR signalling ("TCR Signaling", FIG. 15E) transcriptional signals (ssGEA score) by population.
Figure 15E:
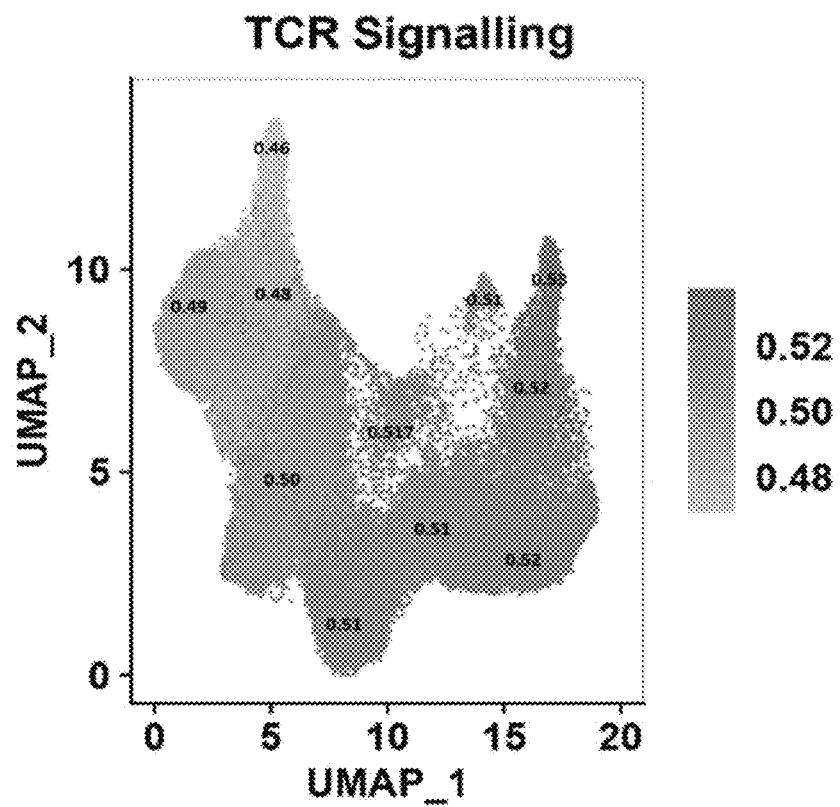
FIG. 15E is a UMAP plots of single cell RNAseq data (Park et al., 2020) annotated by median Notch gene regulatory network ("Notch GRN", FIG. 15D) and TCR signalling ("TCR Signaling", FIG. 15E) transcriptional signals (ssGEA score) by population.

In a further analysis, ssGEA scores were calculated using NOTCH (custom NanoString® panel) and TCR signalling (NanoString® panel) gene sets isolated from the dataset of Park et al., and also demonstrated enriched Notch signalling at early stages of in vivo T cell development and enriched TCR signalling at later stages of in vivo T cell development (FIGS. 15D,E).

Figure 16A:
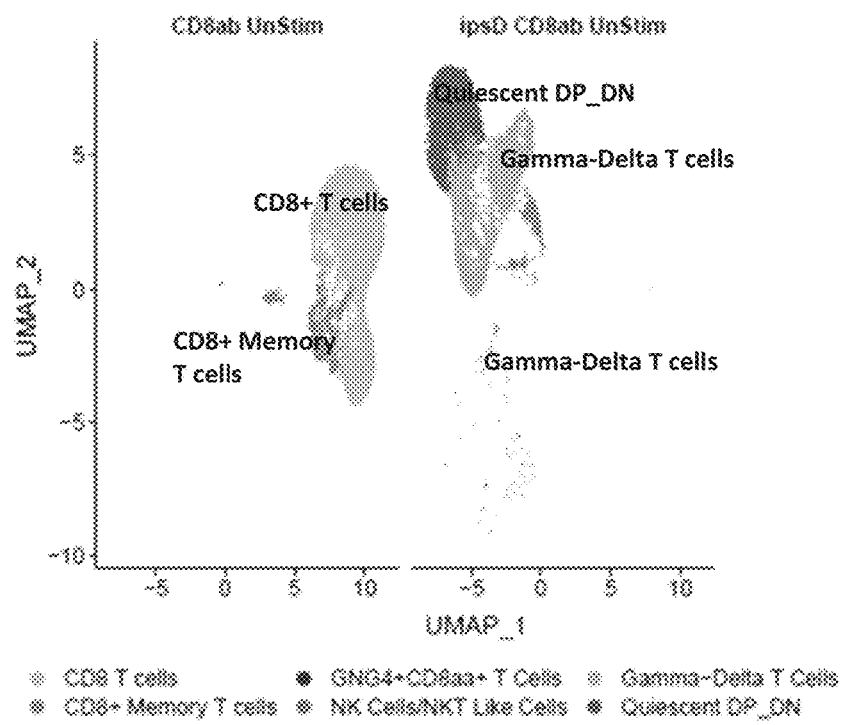
FIG. 16A is a UMAP plot for primary, unstimulated primary T cells CD8αβ(CD8ab UnStim) and iPSC-derived CD4−CD8+ cells cultured with 3D ETN bead concentration of $5.4 \times 10^7$ beads/mL (1× bead dose) (ipsD CD8ab UnStim). Cell annotation was performed with SingleR package in reference to the Thymic Cell Atlas (Park et al., 2020).
Figure 16B:
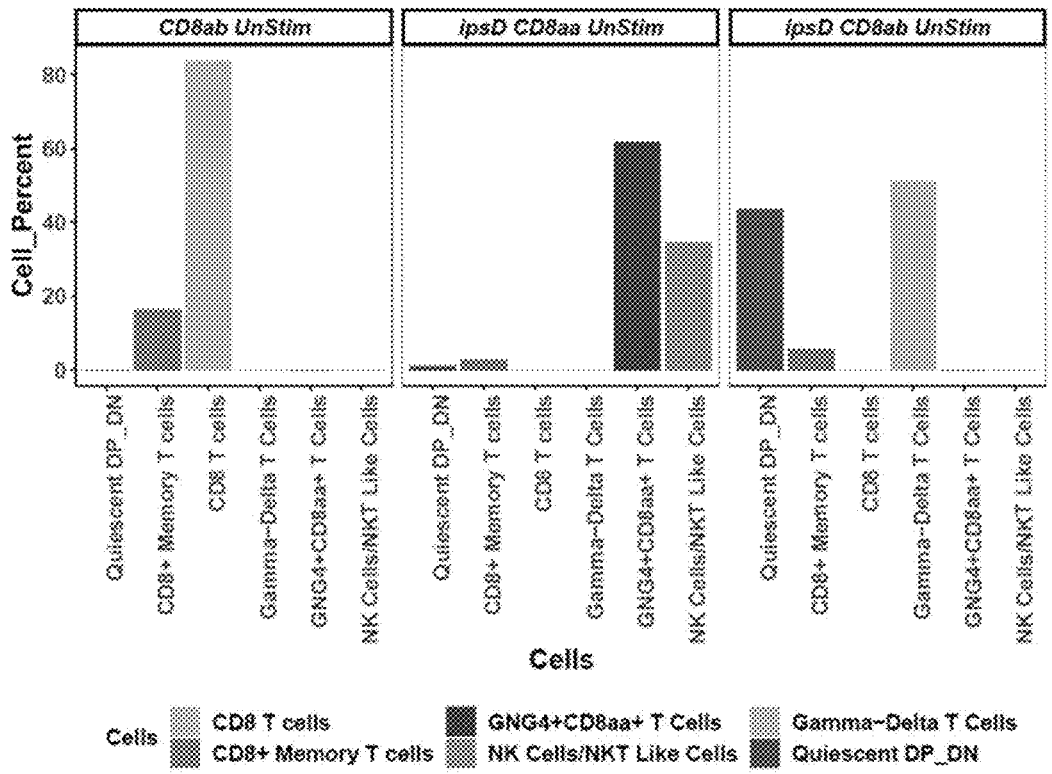
FIG. 16B is a graph quantifying the proportion of cells corresponding to T cell maturation stages in the thymus (Park et al., 2020) for primary, unstimulated primary T cells CD8αβ(CD8ab UnStim) and iPSC-derived CD4−CD8+ cells cultured with 3D ETN bead concentration of $5.4 \times 10^7$ beads/mL (1× bead dose) (ipsD CD8ab UnStim).
Figure 17A:
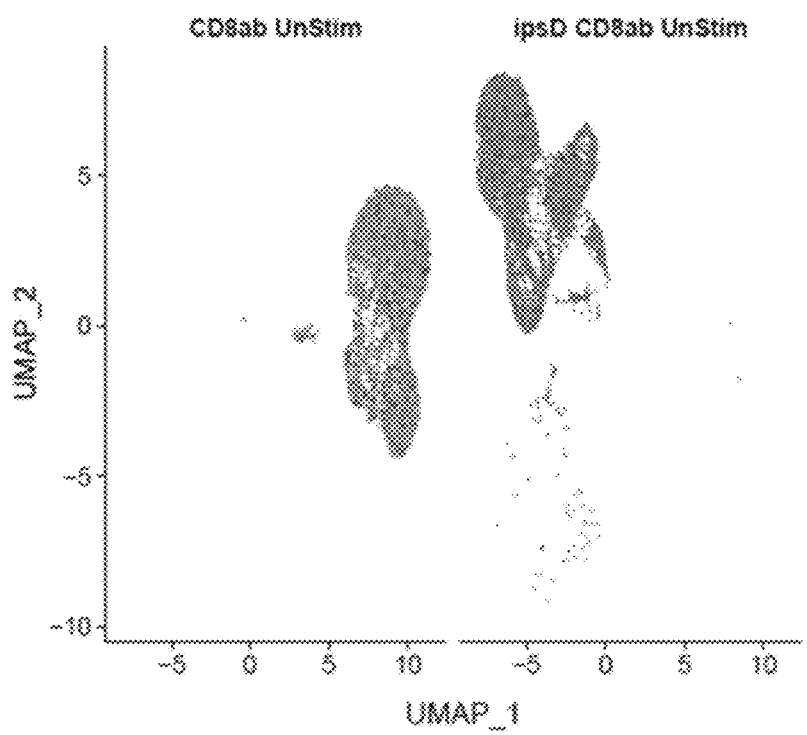
FIG. 17A is a UMAP plot depicting the T cell states derived from ProjecTILs (Andreatta et al., 2021) for primary, unstimulated CD8αβ+ T cells (CD8ab UnStim) and iPSC-derived CD4−CD8+ cells cultured with 3D ETN bead concentration of $5.4 \times 10^7$ beads/mL (1× bead dose) (ipsD CD8ab UnStim).
Figure 17B:
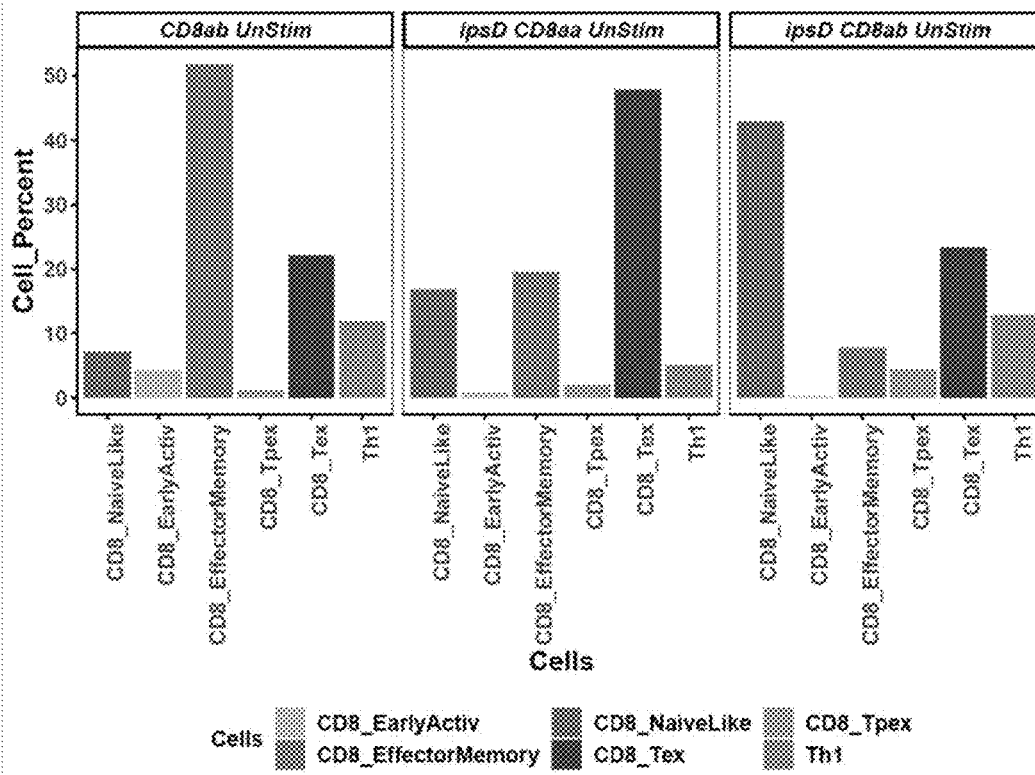
FIG. 17B is a graph quantifying the percentage of T cells in each state from FIG. 17A in primary, unstimulated CD8αβ+ T cells (CD8ab UnStim) and unstimulated iPSC-derived CD4−CD8+ T cells cultured with 3D ETN bead concentration of $5.4 \times 10^7$ beads/mL (1× bead dose) (ipsD CD8ab UnStim).

Single-cell RNAseq analysis was performed to compare iPSC-derived CD4−CD8+ cells generated with 3D ETN ($5.4 \times 10^7$ beads/mL (1× bead dose), as described in Example 2) to primary CD8αβT cells. Cells were annotated using two reference datasets: Human Thymic Cell Atlas (Park et al., 2020) and ProjecTILS (Andreatta et al., 2021). In reference to the Thymic Cell Atlas dataset, primary T cells were annotated as CD8+ memory T cells and CD8, and iPSC-derived CD4−CD8+ cells were annotated as quiescent double-positive (DP) and double-negative (DN) cells, CD8+ memory T cells, and γδT cells (Gamma-delta T cells) (FIGS. 16A and 16B). In reference to the ProjecTILS dataset, primary T cells were annotated as CD8 effector memory and exhausted CD8 (CD8_Tex) cells, with a low percentage of Th1 cells and CD8 naïve-like cells (FIGS. 17A and 17B). Compared to primary CD8 T cells, a higher percentage of iPSC-derived CD4−CD8+ cells were annotated as CD8 naïve-like cells, with a comparable percentage of CD8 (CD8_Tex) cells and Th1 cells (FIGS. 17A and 17B).

Figure 18A:
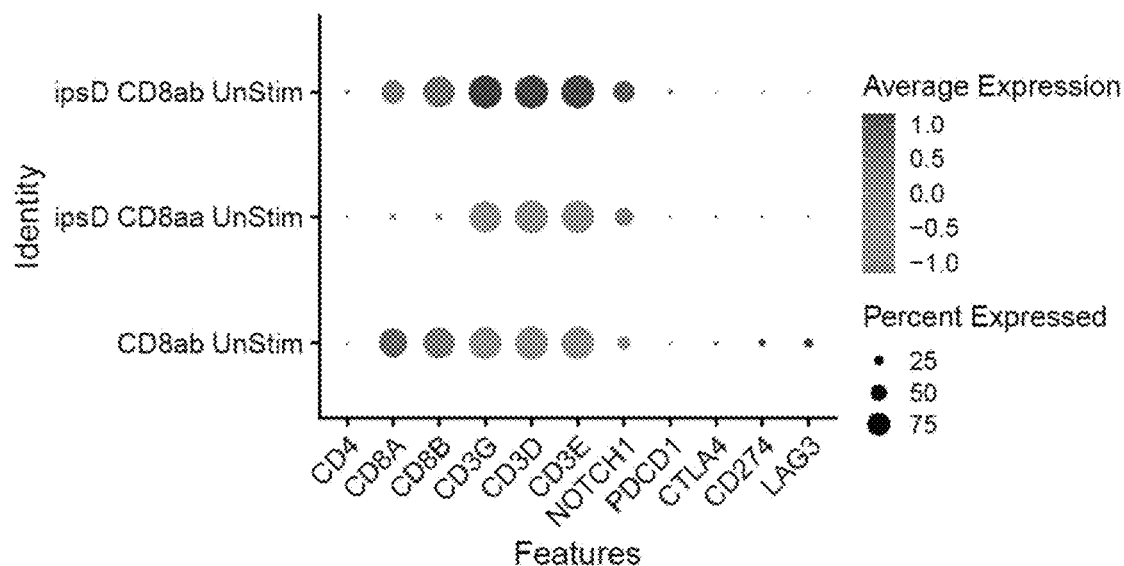
FIG. 18A is a graph depicting expression of selected genes in primary, unstimulated CD8αβT cells (CD8ab UnStim) and iPSC-derived CD4−CD8+ cells cultured with 3D ETN bead concentration of $5.4 \times 10^7$ beads/mL (1× bead dose) (ipsD CD8ab UnStim), as determined by scRNAseq.
Figure 18B:
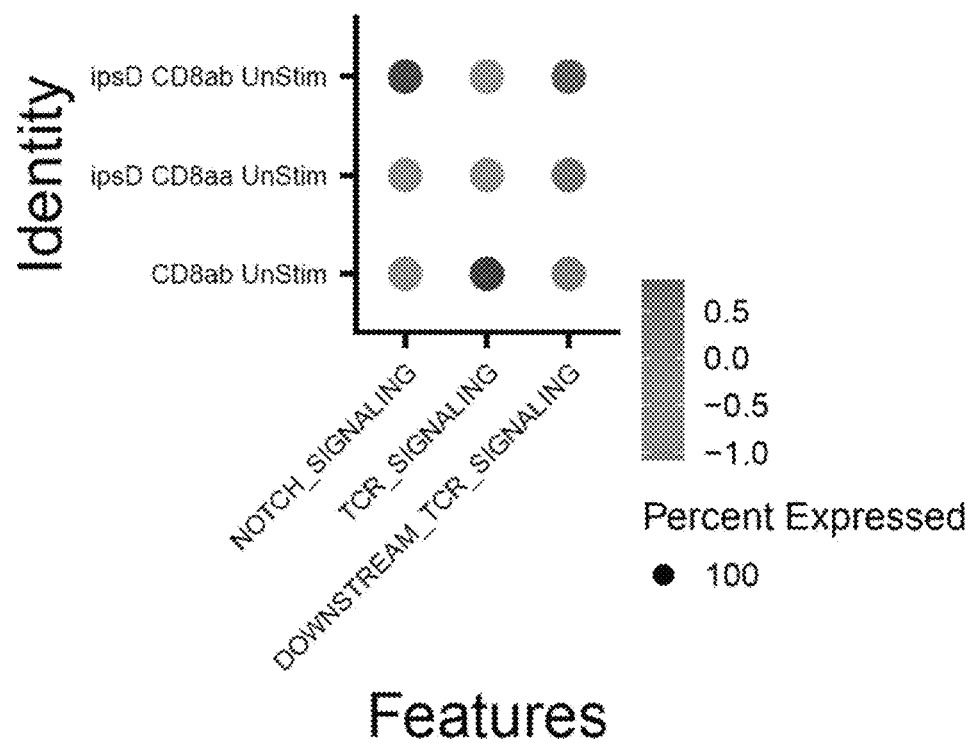
FIG. 18B is a graph depicting the enrichment of sets of genes related to Notch signalling, TCR signalling, and downstream TCR signalling in primary, unstimulated CD8αβ+ T cells (CD8ab UnStim) and iPSC-derived CD4−CD8+ cells cultured with 3D ETN bead concentration of $5.4 \times 10^7$ beads/mL (1× bead dose) (ipsD CD8ab UnStim), as determined by scRNAseq.
Figure 19A:
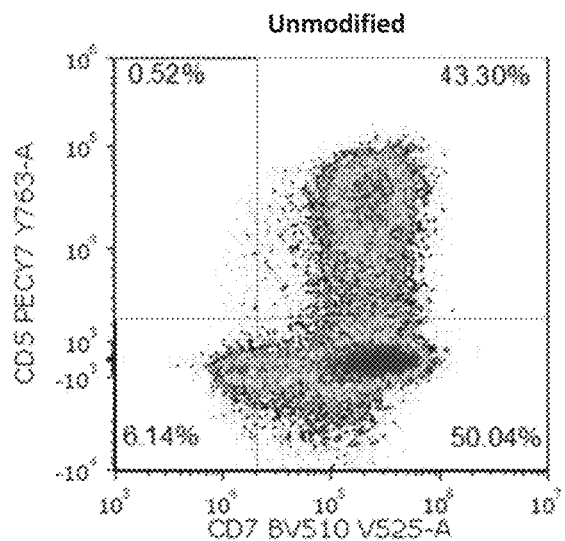
FIG. 19A is a flow cytometry plot of CD5 and CD7 expression, for unmodified iPSC-derived cells following 10 days of culture of an iPSC-derived hematopoietic stem/progenitor cell population comprising CD34+ cells with 3D ETN bead concentration of $2.7 \times 10^7$ beads/mL (0.5× bead dose).
Figure 19B:
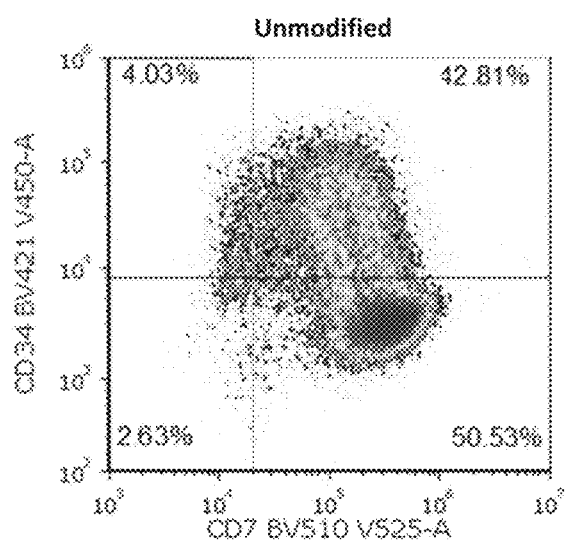
FIG. 19B is a flow cytometry plot of CD34 and CD7 expression, for unmodified iPSC-derived cells following 10 days of culture of an iPSC-derived hematopoietic stem/progenitor cell population comprising CD34+ cells with 3D ETN bead concentration of $2.7 \times 10^7$ beads/mL (0.5× bead dose).
Figure 19C:
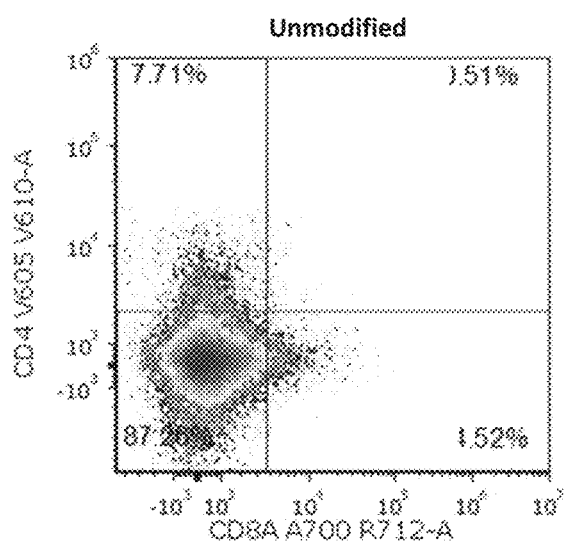
FIG. 19C is a flow cytometry plot of CD4 and CD8α (CD8A) expression, for unmodified iPSC-derived cells following 10 days of culture of an iPSC-derived hematopoietic stem/progenitor cell population comprising CD34+ cells with 3D ETN bead concentration of $2.7 \times 10^7$ beads/mL (0.5× bead dose).
Figure 19D:
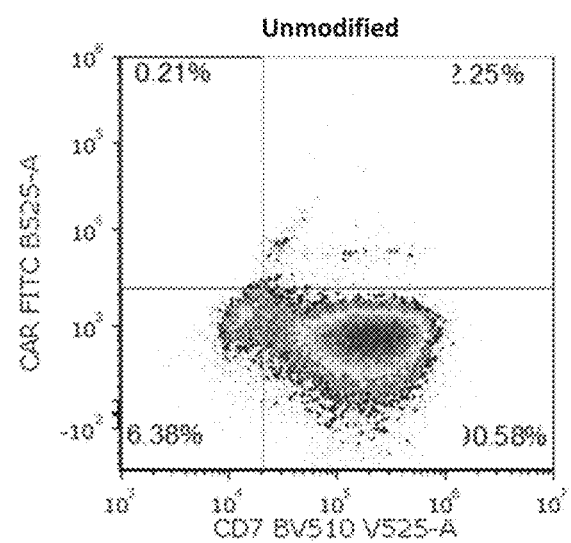
FIG. 19D is a flow cytometry plot of CAR and CD7 expression for unmodified iPSC-derived cells following 10 days of culture of an iPSC-derived hematopoietic stem/ progenitor cell population comprising CD34+ cells with 3D ETN bead concentration of $2.7 \times 10^7$ beads/mL (0.5× bead dose).

Using single sample GSEA, it was found that expression of CD8α(CD8A) was higher in primary CD8αβT cells compared to iPSC-derived cells, and expression of the CD3 subunits CD3γ (CD3G), CD3δ (CD3D) and CD3ε (CD3E) was lower (FIG. 18A). A subset of genes related to Notch signalling was more highly expressed in iPSC-derived CD4−CD8+ cells generated with the 3D ETN in comparison with primary CD8αβT cells, and expression of genes related to TCR signalling was reduced in iPSC-derived CD4−CD8+ cells (FIG. 18B).

Example 7: Generation of CD4−CD8+ Cells from CAR-Modified iPSC-Derived HSPCs To generate a progenitor T cell population, an iPSC-derived hematopoietic stem/progenitor cell population comprising CD34+ cells was cultured with 3D ETN beads (2.7×10$^7$ beads/mL (0.5× bead dose)) in a 24 well cell culture plate for 10 days. Two cell lines were investigated: unmodified (NTX4A1, (4A1)) and CAR-modified (NTX4B3, (4B3)). At day 10, cells exhibited a progenitor T cell phenotype as demonstrated by CD5+CD7+ expression, with both CD34+ and CD34− populations (FIG. 19, unmodified, 4A1; FIG. 20, CAR-modified, 4B3).

The progenitor T cells were then cultured for 7 days with Lymphoid Maturation Medium (LMM, STEMCELL Technologies) and 3D ETN (1.08×10$^8$ beads/mL (2× bead dose)) and following harvest re-cultured with new 3D ETN beads at the same bead concentration for a further 4 days. Two cell culturing densities were investigated: 2×10$^6$ cells/mL or 5×10$^5$ cells/mL. After 11 days of culture at 1.08×10$^8$ beads/mL (2× bead dose)) (21 days from differentiation of CD34+ cells), a CD8α enrichment step was also performed (EasySep™ Human CD8 Positive Selection Kit II, STEMCELL Technologies).

After 7 days of culturing the progenitor T cells with 3D ETN with bead concentration of 1.08×10$^8$ beads/mL (2× bead dose), CD4−CD8α+ (CD8SP) cells were observed in both unmodified and CAR cell lines (30-40%, FIG. 21A). Generation of CD8α+CD8β + cells was dependent on cell density, as cells cultured at 2×10$^6$ cells/mL had higher CD8β expression than cells cultured at 5×10$^5$ cells/mL (FIG. 21B). Cell viability was similar for both cell lines and cell densities tested (40-50%; FIG. 21C). CAR expression was ~50% for both cell densities in the 4B3 cell line (FIG. 21D). Cells were re-cultured after 7 days of culture with 3D ETN at a concentration of 1.08×10$^8$ beads/mL 3D ETN (2× bead dose) using the same conditions—5×10$^5$ cells/mL or 2×10$^6$ cells/mL with 3D ETN bead concentration of 1.08×10$^8$ beads/mL (2× bead dose). After a further 4 days, or a total of 11 days of culture with 3D ETN at a concentration of 1.08×10$^8$ beads/mL (2× bead dose), cells were harvested and CD8α enrichment was performed. The percentage of CD4−CD8α+ cells increased in all conditions following CD8α enrichment (FIG. 22A). Prior to enrichment, CD8β expression was higher in cells cultured at 2×10$^6$ cells/mL than in 5×10$^5$ cells/mL. CD8α enrichment increased the level of CD8β expression in all samples, though the higher cell density (2×10$^6$ cells/mL) retained higher CD8β expression after enrichment (FIG. 22B). Cell viability was higher at the lower cell density (5×10$^5$ cells/mL) for both the unmodified and CAR Cell lines, and both before and after CD8α enrichment (FIG. 22C). CD8α enrichment improved cell viability, though the improvement was more pronounced in the CAR cell line than the unmodified cell line. CAR expression was similar for the two cell densities tested (5×10$^5$ cells/mL and 2×10$^6$ cells/mL), and CD8α enrichment enhanced the percentage of CAR+ cells (FIG. 22D).

Cell viability was monitored over the complete 21 day differentiation time course (from CD34+ cells) for both the unmodified (4A1, FIG. 23A) and CAR (4B3, FIG. 23B) cell lines. At day 0, both cell lines were ~90% viable, and viability dropped to ~40% by day 10 during proT differentiation. At day 14 and 15 (4 and 5 days of culture with 3D ETN at a concentration of 1.08×10$^8$ beads/mL, respectively), 4A1 cell viability was cell density dependent, with lower cell density (5×10$^5$ cells/mL) displaying higher viability than higher cell density (2×10$^6$ cells/mL). At the day 17 harvest (after 7 days of culture with 3D ETN at a concentration of 1.08×10$^8$ beads/mL), cell viabilities were similar between the two cell lines (4A1 and 4B3) and cell densities (~40% for 5×10$^5$ cells/mL and 2×10$^6$ cells/mL). At day 21 (after 11 days of culture with 3D ETN at a concentration of 1.08×10$^8$ beads/mL), density dependent viabilities were observed again, as depicted in FIG. 22C.

Cell expansion was assessed relative to day 0 for 4A1 (FIG. 24A) and 4B3 (FIG. 24B) cells. The relative expansion between day 10 (before culture with 3D ETN at a concentration of 1.08×10$^8$ beads/mL) and day 17 (after 7 days culture with 3D ETN at a concentration of 1.08×10$^8$ beads/mL) was higher for cells cultured at 5×10$^5$ cells/mL than 2×10$^6$ cells/mL (7× vs. 2.5× for 4A1; 5.7× vs. 2.3× for 4B3). At day 21 (after 11 days of culture with 3D ETN at a concentration of 1.08×10$^8$ beads/mL), cumulative expansion remained higher for the lower cell culturing density (5×10$^5$ cells/mL).

Example 8: Generation and Function of CD4−CD8+ Cells

Reduction of Notch signalling via reduced ETN-dose specifies differentiation of ProTs through the canonical, thymic development pathway to CD4+CD8+ (Double Positive: DP) cells (schematic, FIG. 25). In vivo and in previously described methods, these require TCR rearrangement (B-selection) and CD3/TCR for differentiation to cytotoxic, CD4−CD8+ (Single Positive: SP) T cells (FIG. 25). In contrast, in vitro sustained, supra-physiological Notch signalling mediated by high ETN-dose culture, in the absence of CD3/TCR stimulation, yields a population of functional CD8-SP T cells from ProTs after just 7 days, bypassing intermediate differentiation stages and the necessity of TCR/CD3 signalling (FIG. 25).

iPSC-derived, CD34+ HSPCs were cultured with a range of ETN bead-doses for 10-days in serum-free suspension media. T cell lineage induction from iPSC-derived HSPCs was shown to be dependent upon ETN-mediated Notch signalling intensity. Progenitor T (ProT; CD5+CD7+) vs. Myeloid (CD33+CD7−) cell generation from iPSC-derived HSPCs at Day-10 of culture was observed to be dose-responsive to ETN bead dose (FIG. 26A). ETN bead doses are normalized to tissue culture plate surface area. Representative flow cytometry plots of CD5, CD7, and CD33 expression are shown for 0.1 and 1 ETN bead doses (FIG. 26B).

CD8-SP cell yield at Day-17 was found to be responsive to ETN dose in TRAC-deficient cell lines, in both CD19-CAR engineered cells and lines lacking CD19-CAR (FIG. 27A). High ETN doses yielded CD8-SP cells, while low (physiological) levels yield CD8+CD4+ (DP) cells. Representative flow cytometry plots of CD4 vs. CD8α expression are shown for 0.1, 1, and 3 ETN bead doses (FIG. 27B, n=3 technical triplicates/cell line).

Gene expression changes dose-responsive to ETN at Day+2 were found to be quantitative surrogates for Notch signal intensity. Transcripts were measured using a custom NanoString® panel. A machine learning workflow was used to predict CD8-SP phenotype at Day-17 based on Notch-responsive gene expression at Day-12 and identified the Notch-responsive genes (FIG. 28A) that are associated with CD8-SP phenotype. In the workflow, the gene-expression data following 2 days of culture and flow cytometry for CD4−CD8+ phenotype following 7 days of culture was randomly split into a 50-50 train-test split 1000 times. For each of the train-test splits, a regularized linear regression model was fitted with 5-fold cross-validation to predict CD4−CD8+ cell phenotype from the gene expression data. The model accuracy was measured by the coefficient of determination $R^2$ on the test data. A weighted linear average of the regression coefficients with the weights corresponding to the frequency of a gene appearing in the ensemble of models revealed the top 6 positively and top 6 negatively associated genes with CD8 SP phenotype (weighted averages shown in FIG. 28A). All models were highly accurate (average $R^2$=0.92 on the test data, FIG. 28B). DTX1 was identified as the most positively predictive feature and was tightly correlated with CD8-SP (FIG. 28C). ETN-responsive gene-expression trends were observed to be similar for both cell lines (FIG. 28D, z-score normalized mean expression shown, n=3).

The gene expression analysis was extended to additional cell lines. As above, transcriptional responses to ETN were measured at 2 and 7 days after ETN dosing the Progenitor T cell population (ProT) with a custom 43-gene NanoString® panel. Data was segregated into 1000 50-50 train-test splits, and a regularized linear model trained and assessed using 5-fold cross validation. Mean weighted regression coefficients for the top 12 predictive features are shown in FIG. 28E. Positive predictors (NOTCH1, HES1, DTX1) are known Notch signaling response elements, while negative predictors (RAG2, SPN) are known markers of canonical DP-stage differentiation. CD8α SP phenotype at day-17 (7 days after ETN dosing of progenitor T cell population) was predicted with good accuracy (85% cross-validation) independent of cell line using a machine learning workflow trained on gene expression at day-12 (FIG. 28F). NOTCH1 was identified as the most positively predictive feature and increases with increasing bead dose (FIG. 28G). ETN-responsive gene-expression trends were observed to be similar for TRAC-deficient (TRAC−/−) and TRAC-deficient, CD19-CAR-engineered (TRAC−/− CD19-CAR+) cell lines (FIG. 28H). Transcriptional profiles of WT, TRAC-knockout and CAR-engineered/TRAC-deficient cell lines were assessed using a more comprehensive 770-gene NanoString® panel, following culture with low (0.1× bead dose) vs. high (3× bead dose) ETN-doses. Variance partition analysis revealed that ETN bead-dose and day:line interaction effects accounted for the majority of transcriptional variance (FIG. 28I). That is, the three cell lines differentiate with different trajectories, yet responded similarly to Notch exposure. Differentiability expressed pathways (ssGSEA scores) were plotted by bead dose and culture time in the CAR-engineered TRAC-deficient cell line (FIG. 28J). The pathway subset shown was filtered based on a statistical cut-off of Padj<0.05 (ranks-sum test). High-ETN dose engaged transcriptional programs associated with T cell differentiation and functional activity. Note multiple pathways associated with T cell differentiation and function (interferon signalling, JAK-STAT, cytotoxicity) are both induced by heightened Notch signaling and increased with culture time (FIG. 28J).

Single cell transcriptome characterization of iPSC-derived CD8-SP cells was performed in comparison to CD8+ T cells derived from peripheral blood and cord blood. A UMAP of single cell transcriptomes for iPSC-derived T cells, CD8+ T cells from peripheral blood (PBMC) & cord blood (CB) identified these cell populations as transcriptionally distinct (FIG. 29A). An algorithm sourced from ProjecTILs (Haradhvala et al., 2022) was used to classify the cells and identified iPSC-derived cells as predominantly T-naïve, similar to cord blood-derived T cells (FIG. 29B). Select expression of canonical markers for T cells, Notch response-genes, Innate lymphoid cells (ILCs), T cell activation and exhaustion transcripts were evaluated (FIG. 29C). Single-sample GSEA (ssGSEA) was applied at single cell resolution, means computed for each cluster, and represented via hierarchical clustered z-scores. Select gene signatures were found to be differentially enriched in each cell cluster. iPSC-T cell clusters were observed to have distinct signalling profiles, as labelled and annotated from the UMAP projection (FIG. 29D). 1473 gene signatures were found to be variable across the cell clusters (with a coefficient of variation (CV), the ratio of the standard deviation and the mean ssGSEA scores over the clusters, >0.1 for these signatures). (FIG. 29E). Three of the iPSC-T cell clusters were observed to share signalling similarity with PBMC cells, and one with CB cells (FIG. 29E).

Additionally, a UMAP plot of single cell transcriptomes (scRNASeq) was generated for iPSC-derived T cells through differentiation (CD34+, ProT, CD8+SP stage, and following CD19-antigen stimulation) vs. primary lymphocytes (CD4+ T cells, CD8+ T cells, CD56+NK cells, and T cells activated by Dynabeads® (CD3/CD28-stimulated). A Cell*Gene expression matrix from single cell RNASeq sequencing data was calculated with CellRanger (Zheng et al., 2017). Cells with less than 500 UMI and mitochondrial ratio less than 0.2 were removed. The expression value of each transcript was normalized at single cell resolution with SCTransfor (Hafemeister and Satija, 2019) which applies regularized negative binomial regression model to adjust confounding effect of sequencing depth at cell level. Further scaling and UMAP (Uniform Manifold Approximation and projection) dimensionality reduction was implemented with Seurat (Satja et al., 2015). It was observed that the iPSC-derived cell populations were transcriptionally unique, but the CD19-stimulated subset was most similar to the activated primary cells (FIG. 29F). A bubble plot was generated for select genes associated with blood progenitors, T cell lineage commitment, canonical T cell function, innate lymphocytes, cytotoxic T cells, exhausted T cells, and Notch-response elements. In additional to internally generated samples, single cell transcriptomes of the autologous CAR-T products Yescarta® and Kymriah® were included for reference (Bai et al., 2022, and Haradhvala et al., 2022). iPSC-derived CD8+ cells acquired a canonical T cell expression pattern, with heightened CD3 expression, limited expression of ILC or exhausted markers, and extremely heightened Notch signaling.

A single-sample gene set enrichment analysis (ssGSEA) was implemented with gene set variation analysis (GSVA) package (Hanzelmann et al., 2013) to calculate an enrichment score for select gene signatures at single cell resolution from an internal database of approximately 2500 compiled pathways (Kirouac et al., 2023) (FIG. 29G). In addition to supra-Notch signaling, iPSC-derived CD8+ cells expressed pathways associated with T cell functional activity (JAK-STAT, IFNG) and TCR signaling, despite being TRAC-deficient. Post-CD19-stimulated iPSC-CD8+ cells upregulated transcriptional signature associated with CAR-antigen response and exhaustion (though limited in comparison to Yescarta® and Kymriah®), indicative of functional T cell response.

A UMAP of single cell transcriptomes focused on iPSC-CD8+ cells, iPSC-CD8+ cells post antigen stimulation, and activated T cells was annotated by transcriptional similarity to developing thymocytes (DN-proliferation, DN-early, DN-quiescent, CD8+T, NKT, gamma-delta T (GDT), and DP-proliferating, and Treg; Park et al., 2020). The iPSC-derived cells were annotated as a mixed composition of DN, CD8+T and NKT, and transitioned to NKT-like cells following antigen stimulation (FIG. 29I). A pseudo time analysis was implemented with Slingshot (Street et al., 2018). CD8+ T cells emerged directly from a quiescent-DN population, then transited to NKT-like cells (FIG. 29J). Expression of transcriptional pathways predictive of cell-population order via an ordinal regression model shown at single-cell resolution (ssGSEA, FIG. 29K). Cell cycle associated pathways gradually gave rise to pathways associated with T cell function (FIG. 29K).

The target-mediated cell killing, proliferation and cytokine secretion of iPSC-derived, CD19-CAR expressing CD8SP cells were assessed in in vitro serial assays in comparison to primary, adult donor-derived CAR-T cells. Target cell (CD19-expressing A549 cell) dynamics were assessed over 4 rounds of in vitro killing assay, with primary CARTs and iPSC-CD8 cells demonstrating cell killing over each round (FIG. 30A). Cell density was measured using Incucyte® live cell imaging, wherein effector T cells (iPSC-derived or primary) were added at 2:1 effector to target (E:T) ratios (FIG. 30A, mean±standard deviation, n=3). In vitro cytotoxicity vs. effector cell expansion of primary CAR-Ts and iPSC-CARTs were comparable (FIG. 30B, n=2 replicates). Cumulative cytotoxicity was reported as the sum of relative change in the area under the curve (AUC) from a target cell-only control on each stimulation (not shown). iPSC-CARTs secreted inflammatory cytokines upon co-culture with antigen expressing target cells at levels comparable to Primary CARTs (FIG. 30C). iPSC-derived, CD19-CAR expressing CD8SP cells were capable of in vitro serial target-mediated cell killing, proliferation and cytokine secretion comparable to Primary CARTs.

Example 9: Generation of CD4−CD8+ Cells from STR-Derived HPCs

Lymphoid potential of iPSC-derived CD34+ cells generated in a STR system was analyzed. An overview of the 3D Engineered Thymic Niche (ETN) platform for scalable T-cell manufacturing using iPSC derived CD34+ HPCs is shown in FIG. 31A. The ETN was shown to be amenable for use in STR to differentiate CD34+ HPCs to CD8 single positive T cells. iPSC-derived CD34+ HPCs from 3 different STR runs were differentiated to CD8 cells using microplate culture with HPCs generated in microplate culture as a reference. HPCs were cultured with ETN at $2.70\times10^7$ beads/mL (0.5× bead dose) for 10 days, followed by culture at $1.35\times10^8$ beads/mL (2.5× bead dose) for 6 days, and $1.89\times10^8$ beads/mL (3.5× bead dose) for a subsequent 5 days. STR-derived HPCs were equivalent to microplate culture-derived cells and generated 58.7±3.7% CD8+ cells compared to 59.99% CD8 positive cells from the research platform HPCs (FIG. 31B). The expression pattern for the CD8αβ+ T cells was equivalent across all 3 STR runs (mean±SEM, 3 independent STR runs, n=6 bioreactors) (FIG. 31C).

Example 10: Generation and Function of CD4−CD8+ Cells in STR Culture iPSC-derived ProT cells were cultured in microplates for 7 days with 30-fold range of ETN dose (from 0.1× to 3× bead dose ($5.40\times10^7$ beads/mL to $1.62\times10^8$ beads/mL)). The resulting cell phenotype was assessed by flow cytometry. High bead doses produced more CD8 SP cells than lower bead doses, while low bead doses produced more CD4 ISPs and double positive cells (DP) (FIG. 32A). Expression of CD8A, IL7R, CD4, and BCL11A measured at ETN Dose 2 and 3 by Nanostring® over 7 days, show CD8A and ILR7 expression increasing over time and CD4 and BCL11A decreasing over time (FIG. 32B). T cell phenotype was found to be modulated by ETN bead dose.

iPSC-derived CD34+ cells were differentiated into ProT cells for 10 days in microplates and STR using ETN at $2.70\times10^7$ beads/mL (0.5× bead dose). Two (2) CD34+ cell banks were seeded in duplicate at $1\times10^4$ and $5\times10^4$ cells/mL in DASbox® bioreactors (Eppendorf) and in 24-well plates. The percentage of CD5+CD7+ ProT cells at D10 was equivalent in STR and microplates for both cell banks, with higher percentage of ProT cells for conditions seeded at $5\times10^4$ cells/mL (FIG. 33A). The number of ProT produced per input CD34+ cell was higher for STR culture (FIG. 33A). STR culture with ETN generated an equivalent proportion of progenitor T cells as 24-well plate culture and was highly reproducible.

Eight (8) bioreactors were seeded with one CD34+ cell bank at $5\times10^4$ cells/mL. Differentiation and expansion were reproducible with 28±4% CD5+CD7+ cells at D10 and a yield of 23±6 ProT cells generated per input CD34+ cell (mean±1 SD) (FIG. 33B).

The STR generated ProT cells (FIG. 33) were re-seeded at $1\times10^6$ cells/mL and cultured for 11 days with ETN at $1.35\times10^8$ beads/mL (2.5× relative bead dose), based on the optimal conditions (FIG. 32) in microplate culture. The maximum CD8+ cell yield occurred after 8 days of maturation with an average percentage CD8+ of 41±1.5% across all 8 bioreactors (FIG. 34A). The number of CD8+ cells produced per input CD34+ cell was 35±5 (FIG. 33A). This expression pattern was equivalent to that seen in FIG. 32 for microplate culture. The proportion of CD8αβ+ cells at Day 8 of maturation was consistent across all 8 STR at 28±1% (FIG. 34B). In microplate culture an increasing proportion of CD8αβ+ cells has been observed up to Day 14 of maturation.

Gene expression dynamics (as assessed by Nanostring®) revealed similar trends in CD8A, IL7R, CD4 and BCL11A expression between STR and microplate cultures (FIG. 35A, FIG. 32). Gene expression dynamics were quantified by the sign of the regression coefficient of a linear model fit to each gene's expression over time and the logarithm of the Benjamini/Hochberg adjusted p-values. Microwell and STR gene expression dynamics were found to be significantly correlated (Pearson's r=0.71, p<0.001) for a panel of 24 genes related to leukocyte development (FIG. 35B).

A functional comparison of STR culture-generated iPSC-derived CD8+ CAR-T cells and donor peripheral blood CD8+ CAR-T (primary CD8+ CAR-T cells) was performed. A serial restimulation assay was developed to measure cytotoxic activity using an Incucyte® (Sartorius) live-cell imaging assay, with GFP-expressing CD19+ cells as target cells (n=3 technical replicates). T cells were co-cultured at a 2:1 effector cell to target cell (E:T) ratio every 5 days with target cells and exogenous cytokine support. Target clearance was measured by GFP surface area reduction. iPSC-derived CD8+ CAR-T cells showed comparable activity to primary CD8+ CAR-T cells over 4 rounds of antigen exposure (FIG. 36A). Fold-expansion of cells was calculated by performing a count at the end of each round of target exposure. iPSC-derived CAR-T cells proliferated 57,000-fold over 4 rounds of antigen exposure at levels comparable to primary CD8+ CAR-T cells (FIG. 36B).

The secretion of effector molecules perforin, interferon-γ (IFNγ), granzyme B, and tumour necrosis factor α (TNFα) was also assessed. iPSC-derived CD8+ CAR-T cells secreted effector molecules in a target specific manner at levels comparable to primary CD8+ CAR-T cells (FIG. 36C).

T-cell subsets in the iPSC-derived CD8+ CAR-T cells and primary CAR-T cells were classified based on expression of CD45RA, CD62L and CD95. Stem cell memory (TSCM) and central memory (TCM) subsets that have been previously shown to be associated with better performance in vivo were found to be enriched in iPSC-derived CD8+ CAR-T cells at baseline and chronic antigen exposures (FIG. 36D). Expression of exhaustion markers were also assessed in both cell populations. Co-expression of multiple exhaustion markers (PD1, TIM3, LAG3, TIGIT and CD39) that have been reported as a hallmark for T-cell exhaustion was observed to be lower in iPSC-derived CD8+ CAR-T cells in comparison to primary CD8+ CAR-T cells (FIG. 36E).

STR culture-generated iPSC-derived CD8+ CAR-T cells were also further enriched by CD8α or CD8β selection and analyzed by flow cytometry. Following CD8α enrichment, both CD8αα+ and CD8αβ+ cells were present (FIG. 37A). Lower CD8α was detected due to blocking of the CD8α epitope by the enrichment process. The majority of CD8β-enriched cells were CD8αβ+ (FIG. 37B) and both CD8α-enriched and CD8β-enriched cells lacked surface CD3 expression (FIG. 37A, B).

Example 11: Generation and Function of Exogenous TCR+ Cells

Two independent iPSC lines ("172", "174") were generated with site-specific integration (SSI) of a MAGE-A4 TCR at the TRAC locus under the ubiquitin C (UBC) promoter. These cell lines, along with an unmodified cell line control ("6A1") were differentiated to CD34+ cells as described above. The CD34+ cells were then seeded in well-plates at $5 \times 10^4$ cells/mL and differentiated to progenitor T cells for 10 days, with $2.70 \times 10^7$ beads/mL (0.5× bead dose) of the 3D ETN added at day 1, and half-media exchanges at days 4 and 7. Cells were then re-seeded at $1.5 \times 10^6$ cells/mL and cultured with 3D ETN at $1.62 \times 10^8$ beads/mL (3× bead dose) for a further 11 days (for a total of 21 days from CD34+ cells); half-media exchanges were performed at days 12, 14, 16, and 19, and cells were re-seeded at $1.5 \times 10^6$ cells/mL with 3D ETN at $1.62 \times 10^8$ beads/mL (3× bead dose) on day 17. At day 21 (from the CD34+ stage) cells were harvested and enriched for CD8 using the EasySep™ Human CD8 Positive Enrichment II kit (STEMCELL Technologies).

For all cell lines, decreased viability was observed at the end of differentiation, and was improved following CD8α enrichment (FIG. 38A, B). Cumulative fold expansion was highest in one of the TCR-modified cell lines ("174") at the end of differentiation (FIG. 38C).

As determined by flow cytometry, in all cell lines CD5+ CD7+ cells were observed on day 10 of differentiation, and expression of CD5 and CD7 further increased from day 17 onwards (FIG. 39A). CD8 expression was observed by day 17, and the CD8+ population was increased following CD8 enrichment at day 21 (FIG. 39B). Both CD8αα+ and CD8αβ+ cells were present in all cell lines following enrichment, with a greater proportion of CD8αβ+ cells observed for TCR SSI lines ("172", "174") (FIG. 39C). In all cell lines, a large proportion of the CD8αβ+ cells were CD4–CD8+ cells (FIG. 40).

For the TCR SSI lines, cells maintained high expression of the MAGE-A4 TCR over the course of differentiation (FIG. 41A, B).

Cell characteristics following differentiation with 3D ETN and CD8 enrichment are shown in Table 9 below.

TABLE 9

| Sample | Viability at frozen (%) | TCR (%) | CD8αβ (%) | Total cells frozen post-enrichment | Yield/Input CD34 |
|---|---|---|---|---|---|
| 6A1 | 63 | N/A | 32.7 | 1.98E+07 | 21 |
| 172 | 82 | 97 | 62.2 | 3.00E+07 | 25 |
| 174 | 84 | 92.1 | 49.2 | 4.68E+07 | 39 |

Next, the in vitro function of the TCR-iPSC-derived CD4–CD8+ cells described above was evaluated using a serial restimulation assay against A375 human malignant melanoma target cells. Both TCR-modified iPSC-derived CD8+ cells and TCR-modified primary CD8+ cells proliferated over the course of the assay, with the "174" line showing increased proliferation in comparison to the "172" line (FIG. 42A, B). After the first round of stimulation, cytotoxicity was similar for the two TCR-modified iPSC-derived CD8+ cell lines at multiple effector:target ratios (FIG. 43). In two independent experiments, the TCR-modified iPSC-derived CD8+ cells were functional through four rounds of serial killing, similarly to TCR-modified primary CD8+ cell controls (FIG. 44A,B and FIG. 44C,D).

The specificity of the cells was analyzed by comparing cytotoxicity against wild-type A375 target cells (A375 WT, presenting the antigen of interest), β2-microglobulin (B2M) knock-out A375 cells (A375 B2M KO, lacking antigen presentation), MC-38 murine colon adenocarcinoma cells, and human umbilical vein endothelial cells (HUVEC). MC-38 and HUVEC cells were labelled with Cytolight Orange (Incucyte®), and therefore showed loss of fluorescent labelling over time due to cell division, whereas A375 WT and A375 B2M KO cells were labelled with Nuclight Green (Incucyte®) for stable expression. Upon initial activation, the TCR-modified iPSC-derived CD8+ cells were specific to A375 targets (FIG. 45).

Example 12: Intracellular TCRβ Analysis

CAR-modified, TRAC–/– iPSCs-derived cells were differentiated using the 3D ETN as described in Example 11 above. Cells were analyzed for intracellular CD3 and intracellular TCRβ (TCR Vβ F1) at day 0 (CD34+ stage), day 10 (progenitor T cell stage), day 17, day 21, and day 24. A high proportion of cells were positive for intracellular CD3 by day 10 (FIG. 46A), and intracellular CD3 continued to be detected through to day 24 (FIG. 46A, B). In contrast, intracellular TCRβ was not detected at any of the timepoints (FIG. 46A, B). Cell viability decreased over time, and the proportion of CD4–CD8α+ cells increased (FIG. 46C, FIG. 47). The CD8α+β+ population also increased over time (FIG. 47). A small number of CD3+TCRγδ– and CD3+TCRγδ+ cells were observed at days 21 and 24 (FIG. 48).

Example 13: Generation and Function of Exogenous TCR+ and CAR+ Cells

Four cell lines were generated and compared: iPSC-derived CD34+ cells ("Unmodified"), iPSC-derived CD34+ cells transduced with TCR at day 7 ("Unmodified TCR transduced"), TRAC–/– CD19 CAR SSI iPSC-derived CD34+ cells ("CAR SSI") and TCR SSI iPSC-derived CD34+ cells ("TCR SSI"). Cells were differentiated with 3D ETN as described in Example 11 above. Viability was comparable among the lines over time (FIG. 49A), and fold-expansion was higher for the TCR SSI line (FIG. 49B).

Expression of the CAR or TCR was analyzed over the course of the differentiation. The TCRαβ expression levels on day 10 ranged between 20-30% for the different cell lines (FIG. 49C).

Cells were further characterized for expression of CD5, CD7, CD56, CD4, CD8α and CD8β by flow cytometry. TCR-transduced cells showed a higher percentage of CD5+ CD7+ and lower percentage of CD56+CD7+ populations during late-stage differentiation compared to untransduced counterparts (FIG. 50A, B). TCR-transduced cells showed higher CD4 expression at day 21, resulting in a lower percentage of CD4−CD8α+ cells compared to untransduced counterparts (FIG. 51A). However, the proportion of CD8α+CD8β + cells within this fraction was higher compared to CD8αα+ cells (FIG. 51B, sub-gated on CD4− CD8α+). Further, higher expression of CD8α+CD8β + in the overall cell population was observed for TCR-transduced cells at day 21 compared to untransduced controls (FIG. 52A). However, the composition of this subpopulation was attributed to both CD4−CD8+ cells (CD8SPs) and CD4+CD8+ cells (DPs) (FIG. 52B, sub-gated on CD8α+ CD8β +).

Next, CD8α-enriched cells modified with CAR ("CAR SSI") were cryopreserved before exposure to target cells in an in vitro serial restimulation assay. Post-thaw, cells retained expression of key markers (FIG. 53). In both the first and second rounds of stimulation, CAR SSI cells expanded in the presence of Raji target cells (FIG. 54A). However, loss of CD8β + expression was observed (FIG. 54B). Cells retained cytotoxicity over multiple rounds of stimulation, with activity observed against CD19−/− target cells (FIG. 55C).

In a subsequent in vitro serial restimulation assay, CAR SSI cells expanded in the presence of A549 target cells over three rounds of target cell co-culture (FIG. 55A,B). As reported above for co-culture with Raji target cells, loss of CD8β+ expression was observed over the course of the assay with A549 target cells (FIG. 55C). Cytokine secretion was antigen-dependent in iPSC-derived CAR SSI cells, with greater cytokine secretion observed in co-culture with A549 target cells in comparison to Raji target cells (FIG. 56). Viability of iPSC-derived CAR SSI cells declined following the first round of stimulation with both Raji or A549 target cells and continued to decline in co-culture with Raji cells and remained stable in subsequent rounds of stimulation with A549 target cells (FIG. 57).

Example 14: In Vivo Delivery of CAR+ Cells

Cells expressing a CD19 CAR were generated from iPSCs using the 3D ETN as described above. Cells were characterized at harvest and post-CD8 enrichment (Table 10, FIG. 58 post-enrichment).

TABLE 10

| | At harvest (pre-enrichment) | Post CD8+ enrichment |
|---|---|---|
| % Viability | 29 | 92 |
| % CD7+/CD5+ | 81 | 80 |
| % CD8 SP | 59 | 79 |
| % CD8ab | 31 | 53 |
| % CAR+ | 81 | 89 |

The in vivo function of CAR+ iPSC-derived CD8 cells was evaluated in a Raji tumor implant model. Raji cells were delivered intravenously (i.v.) to immunocompromised NOD-scid IL2Rg$^{null}$ (NSG) mice, and exogenous cytokine support was provided 3 times per week for four weeks by intraperitoneal (i.p.) injection. Two days following tumor implantation, CAR+ iPSC-derived CD8+ cells (3 doses of $1 \times 10^7$ cells, 3 days apart (Q3Dx3), i.v.) or primary CAR+ CD8+ T cells (single dose of $3 \times 10^6$ cells, i.v.) were administered. Repeat dosing of CAR+ iPSC-derived CD8+ cells significantly delayed Raji tumor growth compared to untreated control, resulting in extended median survival (FIG. 59A, B). Change in animal body weight was monitored as a surrogate metric for toxicity (FIG. 59C). In peripheral blood, lower numbers of CAR+ iPSC-derived CD8+ cells were detected in comparison to primary CAR+ CD8+ T cells (FIG. 60A). At day 8 post-infusion, CAR+ iPSC-derived CD8+ cells were highly CD3− CAR+ (FIG. 60B).

In a separate study, the in vivo function of CAR+ iPSC-derived CD8 cells was evaluated in a disseminated A549–CD19 tumor model. A459–CD19 tumor cells were delivered intravenously to NSG mice, and exogenous cytokine support was provided 3 times per week for four weeks by intraperitoneal (i.p.) injection. Two days following tumor implantation, CAR+ iPSC-derived CD8+ cells (3 doses of $1 \times 10^7$ cells, 3 days apart (Q3Dx3), i.v.) or primary CAR+ CD8+ T cells (single dose of $3 \times 10^6$ cells, i.v.) were administered. Repeat dosing of CAR+ iPSC-derived CD8+ cells maintained complete remission comparable to primary CAR+ CD8+ T cells against A549–CD19+ disseminated tumors (FIG. 61A-C). Change in animal body weight was monitored as a surrogate metric for toxicity, with comparable increases in bodyweight observed across groups (FIG. 61D). In peripheral blood, lower numbers of CAR+ iPSC-derived CD8+ cells were detected in comparison to primary CAR+ CD8+ T cells (FIG. 61D). At day 15 post-infusion, retrieved CAR+ iPSC-derived CD8+ cells were highly CD3+ in comparison to pre-infusion analysis (FIG. 62A). Within the CAR+ population, iPSC-derived CD8+ cells were highly CD8αβ+ from day 15 onwards (FIG. 62B). Further, CAR+ iPSC-derived CD8+ cells retrieved at day 15 post-infusion secreted inflammatory cytokines and cytolytic molecules (FIG. 63).

The A549–CD19 study was opportunistically extended to investigate the ability of CAR+ iPSC-derived CD8+ cells to exert control over tumor rechallenge. At day 36, $2.5 \times 10^5$ A549–CD19 tumor cells were delivered i.v. to animals previously treated with CAR+ iPSC-derived CD8+ cells. Cytokine support was re-started until study termination at day 50. Study animals tolerated rechallenge with A549–CD19+ tumors, with extended complete survival and continued increase in body weight (FIG. 64A, B). The persistent CAR+ iPSC-derived CD8+ cells maintained tumor growth inhibition (FIG. 65A-C) and were detected at low levels in peripheral blood following the rechallenge (FIG. 65D). At day 50, CAR+ iPSC-derived CD8+ cells were also detected in the lungs, and these cells were highly CD3+(FIG. 66A, B). During the rechallenge, CAR+ iPSC-derived CD8+ cells retrieved from peripheral blood remained highly CD8αβ+ (FIG. 66C).

Example 15: Generation and Function of Exogenous TCR+ and CAR+ Cells in STR

CAR-modified (CD19 CAR) and TCR-modified (MAGE-A4 TCR) iPSC-derived CD34+ cells were differentiated in stirred-tank reactors with the 3D ETN. Cells were first seeded at day 0 and cultured with 3D ETN at $2.7 \times 10^7$ beads/mL (0.5× bead dose) starting at day 1 to generate progenitor T cells. Cells were re-seeded at day 10 with 3D ETN at 1.35×10⁸ beads/mL (2.5× relative bead dose), re-seeded at day 16 with 3D ETN at 1.89×10⁸ beads/mL (3.5× bead dose) and cultured for a further 5 days (21 days total). Viability at day 21 was lower for the CAR-modified cells in comparison with TCR-modified cells (FIG. 67A) and greater cell density was observed for TCR-modified cells (FIG. 67B). At day 21, the TCR-modified cell line also had a higher purity of CD8αβ+ cells compared to the CAR-modified cell (FIG. 68A, B).

An in vitro serial restimulation assay was used to investigate TCR-modified cells generated in both STR and well-plate (WP) culture systems with the 3D ETN. Similar cytotoxicity and fold expansion was observed for both groups (FIG. 69A, B). Further, comparable function at varying E:T ratios (FIG. 69C) and antigen specificity (FIG. 69D) was observed for both STR-generated and WP-generated cells.

It is contemplated that T cell lineage populations derived from culturing progenitor T cells with 3D ETN using the method provided herein may be contained in pharmaceutical compositions.

It is further contemplated that T cell lineage populations derived from culturing progenitor T cells with 3D ETN using the method provided herein may be used to treat a disease or condition in a subject. By "treat" we mean administering to the subject an effective amount of cells, as provided herein, under conditions suitable for increasing the number of T cells in the subject, which may result in prevention, inhibition and/or therapeutic treatment of a medical condition. By "effective amount" we mean a therapeutically effective amount such as, for example, the amount of cells that, upon administration to a subject, is sufficient to achieve the intended purpose (e.g., treatment). The amount may vary from one subject to another and may depend upon one or more factors, such as, for example, subject gender, age, body weight, subject's health history, and/or the underlying cause of the condition to be prevented, inhibited and/or treated.

For example, subjects afflicted with an oncological or autoimmune disease, condition or disorder may benefit from administration of T cell lineage populations, as described herein.

Although the disclosure has been described with reference to certain specific embodiments, various modifications thereof will be apparent to those skilled in the art. Any examples provided herein are included solely for the purpose of illustrating the disclosure and are not intended to limit the disclosure in any way. Any drawings provided herein are solely for the purpose of illustrating various aspects of the disclosure and are not intended to be drawn to scale or to limit the disclosure in any way. The scope of the claims appended hereto should not be limited by the preferred embodiments set forth in the above description, but should be given the broadest interpretation consistent with the present specification as a whole. The disclosures of all art recited herein are incorporated herein by reference in their entirety.

DOCUMENTS CITED

1. Andreatta et al. Interpretation of T cell states from single-cell transcriptomics data using reference atlases. Nat. Commun. 12, 2965 (2021). Doi: 10.1038/s41467-021-23324-4
2. Bai, Z. et al. Single-cell antigen-specific landscape of CAR T infusion product identifies determinants of CD19-positive relapse in patients with ALL. Sci Adv 8, (2022). Doi:10.1126/sciadv.abj2820
3. Baulu et al. TCR-engineered T cell therapy in solid tumors: State of the art and perspectives. Science Advances eadf3700 (2023). Doi: 10.1126/sciadv.adf3700
4. Blassberg. Genome Editing of Pluripotent Stem Cells for Adoptive and Regenerative Cell Therapies. GEN Biotechnology. 2022.77-90. Doi: 10.1089/genbio.2021.0010
5. Drougkas et al. Comprehensive clinical evaluation of CAR-T cell immunotherapy for solid tumors: a path moving forward or a dead end? J Cancer Res Clin Oncol 149: 2709-2734 (2023). Doi: 10.1007/s00432-022-04547-4
6. Guha et al. Assessing the Future of Solid Tumor Immunotherapy. Biomedicines 10: 655 (2022). Doi: 10.3390/biomedicines10030655
7. Hafemeister, C., Satija, R. Normalization and variance stabilization of single-cell RNA-seq data using regularized negative binomial regression. Genome Biol 20, 296 (2019). Doi: 10.1186/s13059-019-1874-1
8. Hanzelmann, S., Castelo, R. & Guinney, J. GSVA: gene set variation analysis for microarray and RNA-Seq data. BMC Bioinformatics 14, 7 (2013). Doi: 10.1186/1471-2105-14-7
9. Haradhvala, N. J. et al. Distinct cellular dynamics associated with response to CAR-T therapy for refractory B cell lymphoma. Nat Med 1-12 (2022). Doi: 10.1038/s41591-022-01959-0
10. Iriguchi et al. A clinically applicable and scalable method to regenerate T-cells from iPSCs for off-the-shelf T-cell immunotherapy. Nat. Commun. 12, 430 (2021). Doi: 10.1038/s41467-020-20658-3
11. Kirouac, D. C. et al. Deconvolution of clinical variance in CAR-T cell pharmacology and response. Nat Biotechnol 1-12 (2023). Doi:10.1038/s41587-023-01687-x.
12. Michaels et al. DLL4 and VCAM1 enhance the emergence of T cell-competent hematopoietic progenitors from human pluripotent stem cells. Science Advances 2022 8(34) doi: 10.1126/sciadv.abn5522
13. Montel-Hagen et al. Generation of artificial thymic organoids from human and murine hematopoietic stem and progenitor cells. Curr. Protoc. 2022 2(4):e403 doi: 10.1002/cpz1.403
14. Park et al. A cell atlas of human thymic development defines T cell repertoire formation. Science 2020 367 (6480): 1-11. Doi: 10.1126/science.aay3224
15. Qu et al. Tumor buster—where will the CAR-T cell therapy 'missile' go? Molecular Cancer 21: 201 (2022). Doi: 10.1186/s12943-022-01669-8
16. Satija, R., et al. Spatial reconstruction of single-cell gene expression data. Nat Biotechnol. 2015 33, 495-502. Doi: 10.1038/nbt.3192
17. Shukla et al. Progenitor T-cell differentiation from hematopoietic stem cells using Delta-like-4 and VCAM-1. Nat. Methods. 2017 14(5):531-538. Doi:10.1038/nmeth.4258
18. Sjoukje et al. Generation of T-cell-receptor-negative CD8αβ-positive CAR T cells from T-cell-derived induced pluripotent stem cells. Nature Biomedical Engineering 1-14 (2022). Doi: 10.1038/s41551-022-00915-0
19. Street, K., et al. Slingshot: cell lineage and pseudotime inference for single-cell transcriptomics. BMC Genomics 19, 477 (2018). Doi: 10.1186/s12864-018-4772-0

20. Sun et al. Evolution of CD8+ T Cell Receptor (TCR) Engineered Therapies for the Treatment of Cancer. Cells 10: 2379 (2021) Doi: 10.3390/cells10092379
21. Trotman-Grant et al. DL4-pbeads induce T cell lineage differentiation from stem cells in a stromal cell free system. Nat. Commun. 2021 12(5023) 1-11. Doi: 10.1038/s41467
22. Van Gassen et al. FlowSOM: Using self-organizing maps for visualization and interpretation of cytometry data. Cytometry Part A 87.7 2015 87(7):636-645. Doi: 10.1002/cyto.a.22625
23. Want et al. T Cell Based Immunotherapy for Cancer: Approaches and Strategies. Vaccines 11: 835 (2023). Doi: 10.3390/vaccines11040835
24. Weber et al. The Emerging Landscape of Immune Cell Therapies. Cell. 2020 181(1):46-62. Doi: 10.1016/j.cell.2020.03.001
25. Zheng et al. Massively parallel digital transcriptional profiling of single cells. Nat Commun. 2017 8(14049). Doi: 10.1038/ncomms14049
26. Zuniga-Pflucker et al. WO 2019/157597

We claim:

1. A method of generating a human T cell lineage cell population, the method comprising:
    a) providing a population of human progenitor T cells; and
    b) culturing the progenitor T cells in the presence of a surface-bound recombinant Notch ligand Delta-like-4 (DL4),
    wherein the recombinant DL4 is provided on a culture plate, one or more particles, or one or more beads;
    wherein the recombinant DL4 is provided on a surface area of between 7 square centimetres per millilitre culture volume (7 cm²/mL) and 56 cm²/mL;
    wherein the concentration of the recombinant DL4 is between $7.89 \times 10^{10}$ and $1.66 \times 10^{13}$ molecules/mL culture volume;
    wherein the culturing is for at least 3 days;
    wherein the progenitor T cells comprise $CD5^+$ $CD7^+$ cells;
    wherein the T cell lineage cell population comprises $CD4^-$ $CD8^+$ cells;
    and wherein the $CD4^-$ $CD8^+$ cells are generated from the $CD5^+$ $CD7^+$ progenitor T cells, bypassing a $CD4^+$ $CD8^+$ cell stage.

2. The method of claim 1, wherein increasing the recombinant DL4 surface area increases the absolute number of $CD4^-$ $CD8^+$ cells and/or the ratio of $CD4^-$ $CD8^+$ cells in the cell population.

3. The method of claim 1, wherein the recombinant DL4 is provided on the one or more beads.

4. The method of claim 1, wherein the step of culturing the progenitor T cells further comprises culturing in the presence of surface-bound vascular cell adhesion molecule 1 (VCAM-1).

5. The method of claim 4, wherein the concentration of the VCAM-1 is between $7.89 \times 10^{10}$ and $1.66 \times 10^{13}$ molecules/mL culture volume.

6. The method of claim 1, wherein a cell density of the progenitor T cells is between $5 \times 10^5$ and $2 \times 10^6$ cells/mL.

7. The method of claim 1, wherein the $CD4^-$ $CD8^+$ cells are $CD8\alpha\beta^+$ cells.

8. The method of claim 1, wherein the $CD4^-$ $CD8^+$ cells are surface CD3 negative ($sCD3^-$).

9. The method of claim 1, wherein the $CD4^-$ $CD8^+$ cells are endogenous T cell receptor negative ($TCR^-$) cells.

10. The method of claim 1, wherein the progenitor T cells are derived from pluripotent stem cells.

11. The method of claim 1, wherein the $CD4^-$ $CD8^+$ cells comprise a nucleic acid sequence encoding a chimeric antigen receptor (CAR) or an exogenous T cell receptor (TCR).

12. The method of claim 1, wherein the progenitor T cells are cultured in a culture vessel, wherein the recombinant DL4 is provided on the one or more particles or the one or more beads, and wherein the ratio of the surface area of the one or more particles or the one or more beads to a culturing surface area of the culture vessel is between 1.77 to 1 (1.77:1) and 14 to 1 (14:1).

13. The method of claim 1, wherein the concentration of the recombinant DL4 is between $3.06 \times 10^{11}$ and $1.66 \times 10^{13}$ molecules/mL culture volume.

14. A method of generating a human T cell lineage cell population, the method comprising:
    a) providing a population of human progenitor T cells; and
    b) culturing the progenitor T cells in a culture vessel in the presence of a recombinant DL4,
    wherein the recombinant DL4 is provided on a three-dimensional substrate, and wherein the ratio of the surface area of the substrate to a culturing surface area of the culture vessel is between 1.77 to 1 (1.77:1) and 14 to 1 (14:1);
    wherein the concentration of the recombinant DL4 is between $7.89 \times 10^{10}$ and $1.66 \times 10^{13}$ molecules/mL culture volume;
    wherein the culturing is for at least 3 days;
    wherein the progenitor T cells comprise $CD5^+$ $CD7^+$ cells;
    wherein the T cell lineage cell population comprises $CD4^-$ $CD8^+$ cells;
    and wherein the $CD4^-$ $CD8^+$ cells are generated from the $CD5^+$ $CD7^+$ progenitor T cells, bypassing a $CD4^+$ $CD8^+$ cell stage.

15. The method of claim 14, wherein the three-dimensional substrate is one or more beads.

16. The method of claim 15, wherein the recombinant DL4 is covalently conjugated to the one or more beads.

17. The method of claim 14, wherein the step of culturing the progenitor T cells further comprises culturing in the presence of surface-bound vascular cell adhesion molecule 1 (VCAM-1).

18. The method of claim 17, wherein the density of the VCAM-1 is between $7.89 \times 10^{10}$ and $1.66 \times 10^{13}$ molecules/mL culture volume.

19. The method of claim 14, wherein a cell density of the progenitor T cells is between $5 \times 10^5$ and $2 \times 10^6$ cells/mL.

20. The method of claim 14, wherein the $CD4^-$ $CD8^+$ cells are $CD8\alpha\beta^+$ cells.

21. The method of claim 14, wherein the $CD4^-$ $CD8^+$ cells are surface CD3 negative ($sCD3^-$).

22. The method of claim 14, wherein the $CD4^-$ $CD8^+$ cells are endogenous T cell receptor negative ($TCR^-$) cells.

23. The method of claim 14, wherein the progenitor T cells are derived from pluripotent stem cells.

24. The method of claim 14, wherein the $CD4^-$ $CD8^+$ cells comprise a nucleic acid encoding a chimeric antigen receptor (CAR) or an exogenous T cell receptor (TCR).

* * * * *